(12) United States Patent
Ido et al.

(10) Patent No.: US 9,772,332 B2
(45) Date of Patent: Sep. 26, 2017

(54) METHOD FOR DETECTING CAPRIN-1 IN A BIOLOGICAL SAMPLE

(71) Applicant: TORAY INDUSTRIES, INC., Tokyo (JP)

(72) Inventors: Takayoshi Ido, Kamakura (JP); Fumiyoshi Okano, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 14/415,520

(22) PCT Filed: Jul. 19, 2013

(86) PCT No.: PCT/JP2013/069642
§ 371 (c)(1),
(2) Date: Jan. 16, 2015

(87) PCT Pub. No.: WO2014/014082
PCT Pub. Date: Jan. 23, 2014

(65) Prior Publication Data
US 2015/0198603 A1 Jul. 16, 2015

(30) Foreign Application Priority Data

Jul. 19, 2012 (JP) ................................ 2012-160751

(51) Int. Cl.
*G01N 33/574* (2006.01)

(52) U.S. Cl.
CPC . *G01N 33/57496* (2013.01); *G01N 33/57415* (2013.01); *G01N 33/57484* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,698,396 A | 12/1997 | Pfreundschuh | |
| 6,335,170 B1 | 1/2002 | Orntoft | |
| 6,444,425 B1 | 9/2002 | Reed et al. | |
| 7,449,184 B2 | 11/2008 | Allison et al. | |
| 7,485,302 B2 | 2/2009 | Adams et al. | |
| 7,745,391 B2 | 6/2010 | Mintz et al. | |
| 8,211,634 B2 | 7/2012 | DePinho et al. | |
| 8,709,418 B2 | 4/2014 | Okano et al. | |
| 8,828,398 B2 | 9/2014 | Kobayashi et al. | |
| 8,911,740 B2 | 12/2014 | Saito et al. | |
| 9,175,074 B2 | 11/2015 | Okano et al. | |
| 9,180,188 B2 * | 11/2015 | Kobayashi | A61K 45/06 |
| 2002/0006404 A1 | 1/2002 | Hanna et al. | |
| 2003/0118599 A1 | 6/2003 | Algate et al. | |
| 2003/0190640 A1 | 10/2003 | Faris et al. | |
| 2004/0029114 A1 | 2/2004 | Mack et al. | |
| 2004/0236091 A1 | 11/2004 | Chicz et al. | |
| 2004/0258678 A1 | 12/2004 | Bodary et al. | |
| 2005/0003390 A1 * | 1/2005 | Axenovich | C12Q 1/6886 435/5 |
| 2005/0032113 A1 | 2/2005 | Tanaka et al. | |
| 2005/0129690 A1 | 6/2005 | Bowdish et al. | |
| 2005/0244413 A1 | 11/2005 | Adolf et al. | |
| 2006/0019256 A1 | 1/2006 | Clarke et al. | |
| 2006/0069054 A1 | 3/2006 | Houghton et al. | |
| 2006/0275305 A1 | 12/2006 | Bryant | |
| 2007/0048301 A1 | 3/2007 | Bodary-Winter et al. | |
| 2007/0083334 A1 | 4/2007 | Mintz et al. | |
| 2007/0154931 A1 | 7/2007 | Radich et al. | |
| 2007/0264253 A1 | 11/2007 | Liu et al. | |
| 2008/0075722 A1 | 3/2008 | DePinho et al. | |
| 2008/0107668 A1 | 5/2008 | Philip et al. | |
| 2008/0161293 A1 | 7/2008 | Yoshinaga et al. | |
| 2008/0306018 A1 | 12/2008 | Croce et al. | |
| 2010/0068724 A1 | 3/2010 | Fung et al. | |
| 2011/0123492 A1 | 5/2011 | Okano et al. | |
| 2011/0136121 A1 | 6/2011 | Okano et al. | |
| 2011/0189700 A1 | 8/2011 | Moses et al. | |
| 2011/0256144 A1 | 10/2011 | Okano et al. | |
| 2012/0171699 A1 | 7/2012 | Goodman et al. | |
| 2012/0214975 A1 | 8/2012 | Sandig et al. | |
| 2012/0294860 A1 | 11/2012 | Ido et al. | |
| 2012/0301471 A1 | 11/2012 | Kobayashi et al. | |
| 2012/0301476 A1 | 11/2012 | Okano et al. | |
| 2012/0321641 A1 | 12/2012 | Okano et al. | |
| 2013/0045210 A1 | 2/2013 | Kobayashi et al. | |
| 2013/0071398 A1 | 3/2013 | Saito et al. | |
| 2014/0154261 A1 | 6/2014 | Okano et al. | |
| 2014/0178373 A1 | 6/2014 | Kobayashi et al. | |
| 2014/0179558 A1 | 6/2014 | Ido et al. | |
| 2014/0186359 A1 | 7/2014 | Okano et al. | |
| 2014/0193434 A1 | 7/2014 | Kobayashi et al. | |
| 2014/0199311 A1 | 7/2014 | Kobayashi et al. | |
| 2014/0308283 A1 | 10/2014 | Minamida et al. | |
| 2015/0004171 A1 | 1/2015 | Kobayashi et al. | |
| 2015/0017172 A1 | 1/2015 | Kobayashi et al. | |
| 2015/0044221 A1 | 2/2015 | Kobayashi et al. | |
| 2015/0050283 A1 | 2/2015 | Okano et al. | |
| 2015/0218285 A1 | 8/2015 | Saito et al. | |
| 2015/0299314 A1 | 10/2015 | Saito et al. | |

FOREIGN PATENT DOCUMENTS

| | | |
|---|---|---|
| CN | 1705676 A | 12/2005 |
| CN | 101120252 A | 2/2008 |
| CN | 101189516 A | 5/2008 |
| CN | 101836116 A | 9/2010 |

(Continued)

OTHER PUBLICATIONS

Solomon et al (Mol. Cell. Biol., 20007, 27(6): 2324-2342, IDS).*
Gong et al.,"Caprin-1 is a novel microRNA-223 target for regulating the proliferation and invasion of human breast cancer cells", Biomedicine & Pharmacotherapy, vol. 67, 2013, pp. 629-636.

(Continued)

*Primary Examiner* — Laura B Goddard
(74) *Attorney, Agent, or Firm* — Birch, Stewart, Kolasch & Birch, LLP

(57) ABSTRACT

This invention provides: a method for detecting a cancer, comprising measuring the expression of a polypeptide having binding reactivity through antigen-antibody reaction with an antibody against CAPRIN-1 having an amino acid sequence shown in any even-numbered SEQ ID NO shown in SEQ ID NOs: 2 to 30 in the Sequence Listing in a biological sample; a method for detecting a cancer which involves determining the presence and the amount of CAPRIN-1 in a sample of a cancer patient in order to determine the administration of a therapeutic drug targeting CAPRIN-1 to the cancer patient; and a drug and a kit for the diagnosis of a cancer, comprising an anti-CAPRIN-1 antibody.

17 Claims, 1 Drawing Sheet

(56) References Cited

FOREIGN PATENT DOCUMENTS

| | | |
|---|---|---|
| CN | 102170907 A | 8/2011 |
| CN | 102171570 A | 8/2011 |
| EP | 2 207 037 A1 | 7/2010 |
| EP | 2 325 648 A1 | 5/2011 |
| EP | 2322221 A1 | 5/2011 |
| EP | 2 532 367 A1 | 12/2012 |
| EP | 2 532 743 A1 | 12/2012 |
| EP | 2 740 794 A1 | 6/2014 |
| EP | 2 832 365 A1 | 2/2015 |
| EP | 2 832 366 A1 | 2/2015 |
| JP | 2002-540790 A | 12/2002 |
| JP | 2003-528587 A | 9/2003 |
| JP | 2006-316040 A | 11/2006 |
| JP | 2013-502205 A | 1/2013 |
| JP | 2013-505028 A | 2/2013 |
| RU | 2161042 C2 | 12/2000 |
| RU | 2234942 C2 | 8/2004 |
| RU | 2244720 C2 | 1/2005 |
| RU | 2306952 C2 | 9/2007 |
| RU | 2319709 C2 | 3/2008 |
| RU | 2006137060 A | 4/2008 |
| RU | 2391982 C2 | 6/2010 |
| WO | WO 96/09551 A1 | 3/1996 |
| WO | WO 00/04149 A2 | 1/2000 |
| WO | WO 00/05268 A1 | 2/2000 |
| WO | WO 00/60077 A2 | 10/2000 |
| WO | WO 01/32910 A2 | 5/2001 |
| WO | WO 01/72295 A2 | 5/2001 |
| WO | WO 02/078524 A2 | 10/2002 |
| WO | WO 02/083070 A2 | 10/2002 |
| WO | WO 02/092001 A2 | 11/2002 |
| WO | WO 03/007889 A2 | 1/2003 |
| WO | WO 2004/076682 A2 | 9/2004 |
| WO | WO 2004/097051 A2 | 11/2004 |
| WO | WO 2005/007830 A2 | 1/2005 |
| WO | WO 2005/100998 A2 | 10/2005 |
| WO | WO 2005/116076 A2 | 12/2005 |
| WO | WO 2006/002378 A2 | 1/2006 |
| WO | WO 2007/150077 A2 | 12/2007 |
| WO | WO 2008/031041 A2 | 3/2008 |
| WO | WO 2008/059252 A2 | 5/2008 |
| WO | WO 2008/073162 A2 | 6/2008 |
| WO | WO 2008/088583 A2 | 7/2008 |
| WO | WO 2009/113742 A1 | 9/2009 |
| WO | WO 2009/117277 A2 | 9/2009 |
| WO | WO 2010/016525 A1 | 2/2010 |
| WO | WO 2010/016526 A1 | 2/2010 |
| WO | WO 2010/016527 A1 | 2/2010 |
| WO | WO 2011/096517 A1 | 8/2011 |
| WO | WO 2011/096519 A1 | 8/2011 |
| WO | WO 2011/096528 A1 | 8/2011 |
| WO | WO 2011/096533 A1 | 8/2011 |
| WO | WO 2011/096534 A1 | 8/2011 |
| WO | WO 2011/096535 A1 | 8/2011 |
| WO | WO 2012/005550 A2 | 1/2012 |
| WO | WO 2012/013609 A1 | 2/2012 |
| WO | WO 2013/018885 A1 | 2/2013 |
| WO | WO 2013/018886 A1 | 2/2013 |
| WO | WO 2013/018894 A1 | 2/2013 |
| WO | WO 2013/147169 A1 | 10/2013 |
| WO | WO 2013/147176 A1 | 10/2013 |

OTHER PUBLICATIONS

Qiu et al., "Targeting a ribonucleoprotein complex containing the caprin-1 protein and the c-Myc mRNA suppresses tumor growth in mice: an identification of a novel oncotarget", Oncotarget, vol. 6, No. 4, Dec. 10, 2014, pp. 2148-2163.

Sabile et al., "Caprin-1, a novel Cyr61-interacting protein, promotes osteosarcoma tumor growth and lung metastasis in mice", Biochimica et Biophysica Acta, vol. 1832, 2013 (available online Mar. 23, 2013), pp. 1173-1182.

U.S. Office Action for U.S. Appl. No. 13/576,950, dated Mar. 30, 2015.

Extended European Search Report issued Mar. 18, 2015, in European Patent Application No. 12820225.6.

Extended European Search Report issued Mar. 23, 2015, in European Patent Application No. 12820596.0.

Non-Final Office Action issued Apr. 14, 2015, in U.S. Appl. No. 14/236,793.

De Pascalis et al., "Grafting of "Abbreviated" Complementary-Determining Regions Containing Specificity-Determining Residues Essential for Ligand Contact to Engineer a Less Immunogenic Humanized Monoclonal Antibody," J. Immunol. (2002), vol. 169, pp. 3076-3084.

Extended European Search Report issued Mar. 2, 2015, in European Patent Application No. 12819759.7.

Riechmann et al., "Reshaping Human Antibodies for Therapy," Nature (Mar. 24, 1988), vol. 332, pp. 323-327.

Russian Office Action issued Jan. 28, 2015 in Russian Patent Application No. 2012137502, with partial English translation.

Vajdos et al., "Comprehensive Functional Maps of the Antigen-binining Site of an Anti-ErbB2 Antibody Obtained with Shotgun Scanning Mutagenesis," J. Mol. Biol. (2002), vol. 320, pp. 415-428.

Carter, Paul J., "Potent antibody therapeutics by design", Nature Reviews Immunology, vol. 6, May 2006, pp. 343-357.

Akiyoshi, "Cancer Vaccine Therapy Using Peptides Derived from Tumor-Rejection Antigens," Jpn J Cancer Chemother., vol. 24, No. 5, Mar. 1997, pp, 511-519, with English Abstract (p. 519).

Australian Patent Examination Report No. 1, dated Oct. 14, 2014, for Australian Application No. 2009278387.

Balmaña et al., "BRCA in breast cancer: ESMO Clinical Recommendations," Annals of Oncology, vol. 20, Supplement 4, May 2009, pp. iv19-iv20.

Bodey et al., "Failure of Cancer Vaccines: The Significant Limitations of this Approach to Immunotherapy," Anticancer Research, vol. 20, 2000, pp. 2665-2676.

Bodey et al., "MAGE-1, a Cancer/Testis-Antigen, Expression in Childhood Astrocytomas as an Indicator of Tumor Progression," in vivo, vol. 16, 2002, pp. 583-588.

Brand et al., "Prospect or Anti-HER2 Receptor Therapy in Breast Cancer," Anticancer Research, vol. 26, 2006, pp. 463-470.

Brass et al., "Translation initiation factor eIF-4gamma is encoded by an amplified gene and induces an immune response in squamous cell lung carcinoma," Human Molecular Genetics, vol. 6, No. 1, 1997, pp. 33-39.

Chamberlain et al., "Innovations and strategies for the development of anticancer vaccines," Expert Opinion on Pharmacotherapy, vol. 1, No. 4, 2000, pp. 603-614.

Chinese Office Action and Search Report, dated Mar. 29, 2013, for Chinese Application No. 200980139037.X.

Chinese Office Action and Search Report, dated May 9, 2013, for Chinese Application No. 201180016730.5, with an English translation.

Chinese Office Action and Search Report, dated Sep. 28, 2014, for Chinese Application No. 201280038464.0.

Chinese Office Action and Search Report, dated Sep. 29, 2014, for Chinese Application No. 201280038490.3.

Comtesse et al., "Probing the human natural autoantibody repertoire using an immunoscreening approach," Clinical and Experimental Immunology, vol. 121, 2000, pp. 430-436.

Ellis et al., "Identification and Characterization of a Novel Protein (p137) Which Transcytoses Bidirectionally in Caco-2 Cells", The Journal of Biological Chemistry, Sep. 1, 1995, vol. 270, No. 35, pp. 20717-20723.

Evans et al., "Vaccine therapy for cancer—fact or fiction?", Q J Med, vol. 92, 1999, pp. 299-307.

Extended European Search Report, dated Aug. 13, 2013, for European Application No. 11739882.6.

Extended European Search Report, dated Aug. 26, 2011, for European Application No. 09805010.7.

Extended European Search Report, dated Jan. 30, 2013, for European Application No. 09805009.9.

Extended European Search Report, dated Nov. 6, 2013, for European Application No. 11739876.8.

(56) References Cited

OTHER PUBLICATIONS

GenBank Accession No. AAU93399, Sep. 22, 2005.
GenBank Accession No. BAF96513, Jan. 5, 2008.
GenBank Accession No. NM_001031365, Sep. 25, 2007.
GenBank Accession No. NM_001076062, Feb. 9, 2008.
GenBank Accession No. NM_001111289, Feb. 11, 2008.
GenBank Accession No. NM_001111290, Feb. 11, 2008.
GenBank Accession No. NM_001111291, Feb. 10, 2008.
GenBank Accession No. NM_001111292, Feb. 11, 2008.
GenBank Accession No. NM_005898, Feb. 11, 2008.
GenBank Accession No. NM_016739, Feb. 10, 2008.
GenBank Accession No. NM_203364, Feb. 10, 2008.
GenBank Accession No. Q14444, Jun. 10, 2008.
GenBank Accession No. Q1LZB6, Jun. 10, 2008.
GenBank Accession No. XM_853016, Aug. 30, 2005.
GeneCards, "Cell Cycle Associated Protein 1—Biological research products for CAPRIN 1," updated Mar. 19, 2013, 10 pages.
Grill et al., "Activation/Division of Lymphocytes Results in Increased Levels of Cytoplasmic Activation/Proliferation-Associated Protein-1: Prototype of a New Family of Proteins," The Journal of Immunology, vol. 172, 2004, pp. 2389-2400.
Güre et al., "Human Lung Cancer Antigens Recognized by Autologous Antibodies: Definition of a Novel cDNA Derived from the Tumor Suppressor Gene Locus on Chromosome 3p21.3," Cancer Research, vol. 58, Mar. 1, 1998, pp. 1034-1041.
Gure et al., "SSX: A Multigene Family with Several Members Transcribed in Normal Testis and Human Cancer," International Journal of Cancer, vol. 72, 1997, pp. 965-971.
Harlow et al., "Antibodies a Laboratory Manual", Cold Spring Harbor Laboratory, Chapter 3, 1988, pp. 23-34.
Hugo Gene Nomenclature Committee, Gene Symbol Report, CAPRIN1, Approved Name: Cell Cycle Associated Protein 1, HGNC ID: HGNC:6743, Nov. 3, 2012, 2 pages.
International Search Report and Written Opinion of the International Searching Authority (PCT/ISA/210 and PCT/ISA/237), dated Mar. 1, 2011, for International Application No. PCT/JP2011/052413, with an English translation of the International Search Report only.
International Search Report and Written Opinion of the International Searching Authority (PCT/ISA/210 and PCT/ISA/237), dated Mar. 15, 2011, for International Application No. PCT/JP2011/052384, with an English translation of the International Search Report only.
International Search Report and Written Opinion of the International Searching Authority (PCT/ISA/210 and PCT/ISA/237), dated Mar. 8, 2011, for International Application No. PCT/JP2011/052403, with an English translation of the International Search Report only.
International Search Report and Written Opinion of the International Searching Authority (PCT/ISA/210 and PCT/ISA/237), dated Mar. 8, 2011, for International Application No. PCT/JP2011/052414, with an English translation of the International Search Report only.
International Search Report and Written Opinion of the International Searching Authority (PCT/ISA/210 and PCT/ISA/237), dated Oct. 6, 2009, for International Application No. PCT/JP2009/063882, with an English translation of the International Search Report only.
International Search Report and Written Opinion of the International Searching Authority (PCT/ISA/210 and PCT/ISA/237), dated Sep. 8, 2009, for International Application No. PCT/JP2009/063883, with an English translation of the International Search Report only.
International Search Report and Written Opinion of the International Searching Authority (PCT/ISA/220, PCT/ISA/210 and PCT/ISA/237), dated Nov. 18, 2014, for International Application No. PCT/JP2014/071094.

Itoh et al., "HUB1 is an autoantigen frequently eliciting humoral immune response in patients with adult T cell leukemia," International Journal of Oncology, vol. 14, No. 4, Apr. 1999, pp. 703-708 (Abstract only provided).
Jang et al., "Antihypertensive Angiotensin I-Converting Enzyme Inhibitory Activity and Antioxidant Activity of Vitis hybrid-Vitis coignetiae Red Wine Made with *Saccharomyces cerevisiae*," Mycobiology, vol. 39, No. 2, 2011, pp. 137-139.
Jungbluth et al., "Immunohistochemical Analysis of NY-ESO-1 Antigen Expression in Normal and Malignant Human Tissues," International Journal of Cancer, vol. 92, 2001, pp. 856-860.
Jäger et al., "Identification of a Tissue-specitic Putative Transcription Factor in Breast Tissue by Serological Screening of a Breast Cancer Library," Cancer Research, vol. 61, Mar. 1, 2001, pp. 2055-2061.
Kaddar et al., "Two new miR-16 targets: caprin-1 and HMGA1, proteins implicated in cell proliferation," Biology of the Cell, vol. 101, No. 9, Feb. 27, 2009, pp. 511-524.
Kajiji et al., "Six Monoclonal Antibodies to Human Pancreatic Cancer Antigens," Cancer Research, vol. 47, Mar. 1, 1987, pp. 1367-1376.
Karauzum et al., "Caprin 1 is Frequently Overexpressed in Human Lymphomas," American Society of Human Genetics, Cancer Genetics, Program No. 1190W, Oct. 12, 2011, One page (Abstract only provided).
Kataja et al., "Primary breast cancer: ESMO Clinical Recommendations for diagnosis, treatment and follow-up," Annals of Oncology, vol. 20, Supplement 4, May 2009, pp. iv10-iv14.
Katsafanas et al., "Colocalization of Transcription and Translation within Cytoplasmic Poxvirus Factories Coordinates Viral Expression and Subjugates Host Functions," Cell Host & Microbe, vol. 2, Oct. 2007, pp. 221-228.
Katsafanas et al., "Vaccinia Virus Intermediate Stage Transcription Is Complemented by Ras-GTPase-activating Protein SH3 Domain-binding Protein (G3BP) . . . ," Journal of Biological Chemistry, vol. 279, No. 50, Dec. 10, 2004, pp. 52210-52217.
Kohler et al., "Tumor antigen analysis in neuroblastoma by serological interrogation of bioinformatic data," Cancer Science, vol. 101, No. 11, Nov. 2010 (first published online Aug. 17, 2010), pp. 2316-2324.
Kolobova et al., "Microtubule-dependent association of AKAP350A and CCAR1 with RNA stress granules," Experimental Cell Research, vol. 315, 2009 (Available online Dec. 3, 2008), pp. 542-555.
Lu et al., "Identification of an immunological signature of tumor rejection in the neu transgenic mouse," 2007 AACR Annual Meeting, Apr. 14-18, 2007 (Presentation conducted on Apr. 17, 2007), One page (Abstract only provided).
Lu et al., "Targeting serum antibody for cancer diagnosis: a focus on colorectal cancer," Expert Opinion on Therapeutic Targets, vol. 11, No. 2, 2007, pp. 235-244.
Müller-Pillasch et al., "Identification of a new tumour-associated antigen TM4SF5 and its expression in human cancer," Gene, vol. 208, 1998, pp. 25-30.
Munodzana et al., "Conformational Dependence of Anaplasma marginale Major Surface Protein 5 Surface-Exposed B-Cell Epitopes", Infection and Immunity, vol. 66, No. 6, Jun. 1998, pp. 2619-2624.
Nakamura et al. "Gene Expression Profile of Metastatic Human Pancreatic Cancer Cells Depends on the Organ Microenvironment," Cancer Research, vol. 67, No. 1, Jan. 1, 2007, pp. 139-148.
NCBI Reference Sequence, caprin-1 [Bos taurus], 2009, Accession No. NP_001069530, XP_615677, 1 page.
NCBI Reference Sequence, caprin-1 [Gallus gallus], 2005, Accession No. NP_001026536, XP_423820, 1 page.
NCBI Reference Sequence, caprin-1 isoform 1 [*Homo sapiens*], 1995, Accession No. NP_005889, 3 pages.
NCBI Reference Sequence, caprin-1 isoform 2 [*Homo sapiens*], 1995, Accession No. NP_976240, 3 pages.
NCBI Reference Sequence, caprin-1 isoform a [Mus musculus], 1996, Accession No. NP_058019, 3 pages.
NCBI Reference Sequence, caprin-1 isoform b [Mus musculus], 1996, Accession No. NP_001104760, 3 pages.

(56) References Cited

OTHER PUBLICATIONS

NCBI Reference Sequence, caprin-1 isoform c [Mus musculus], 1996, Accession No. NP_001104761, 4 pages.
NCBI Reference Sequence, Predicted: caprin-1 [Equus caballus], 2008, Accession No. XP_001492799, 1 page.
NCBI Reference Sequence, Predicted: caprin-1 isoform 2 [Canis lupus familiaris], Dec. 2, 2011, Accession No. XP_858109, 1 page.
Nelson et al., "Screening for Breast Cancer: An Update for the U.S. Preventive Services Task Force," Annals of Internal Medicine, vol. 151, No. 10, Nov. 17, 2009, pp. 727-737.
Okano et al., "Abstract 519: Identification of a novel target for antibody therapy of breast cancer", Cancer Research, vol. 72, Issue 8, Supplement 1, Apr. 15, 2012, XP-002700046, 2 pages.
Pegram et al., "Rational Combinations of Trastuzumab with Chemotherapeutic Drugs Used in the Treatment of Breast Cancer," Journal of the National Cancer Institute, vol. 96, No. 10, May 19, 2004, pp. 739-749.
Polyak et al., "Alanine-170 and proline-172 are critical determinants for extracellular CD20 epitopes; heterogeneity in the fine specificity of CD20 monoclonal antibodies is defined by additional requirements imposed by both amino acid . . . ", Blood, vol. 99, No. 9, May 1, 2002, pp. 3256-3262.
Punt et al., "Edrecolomab alone or in combination with fluorouracil and folinic acid in the adjuvant treatment of stage III colon cancer: a randomised study," Lancet, vol. 360, No. 9334, Aug. 31, 2002, pp. 671-677 (Abstract only provided).
R & D Systems, "IHC Products & Protocol Guide," printed Jan. 9, 2014, pp. 1-112.
Russian Notice of Allowance, dated Jan. 24, 2014, for Russian Application No. 2011108258/15.
Russian Notice of Allowance, dated Jun. 7, 2013, for Russian Application No. 2011108260/10, with an English translation.
Sahin et al., "Human neoplasms elicit multiple specific immune responses in the autologous host," Proceedings of the National Academy of Sciences USA, vol. 92, Dec. 1995, pp, 11810-11813.
Scanlan et al., "Cancer-related Serological Recognition of Human Colon Cancer: Identification of Potential Diagnostic and Immunotherapeutic Targets," Cancer Research, vol. 62, Jul. 15, 2002, pp. 4041-4047.
Scanlan et al., "Characterization of Human Colon Cancer Antigens Recognized by Autologous Antibodies," International Journal of Cancer, vol. 76, 1998, pp. 652-658.
Solomon et al., "Distinct Structural Features of Caprin-1 Mediate Its Interaction with G3BP-1 and Its Induction of Phosphorylation of Eukaryotic Translation Initiation Factor 2α, Entry to Cytoplasmic Stress . . . ," Molecular and Cellular Biology, vol. 27, No. 6, Mar. 2007, XP_002690351, pp. 2324-2342.
Strome et al.,"A Mechanistic Perspective of Monoclonal Antibodies in Cancer Therapy Beyond Target-Related Effects," The Oncologist, vol. 12, 2007, pp. 1084-1095.
Türeci et al., "The SSX-2 Gene, Which Is Involved in the t(X; 18) Translocation of Synovial Sarcomas, Codes for the Human Tumor Antigen HOM-MEL-40," Cancer Research, vol. 56, Oct. 15, 1996, pp. 4766-4772.
U.S. Notice of Allowance, dated Aug. 11, 2014, for U.S. Appl. No. 13/577,028.
U.S. Notice of Allowance, dated Dec. 2, 2013, for U.S. Appl. No. 13/576,955.
U.S. Notice of Allowance, dated Jul. 3, 2014, for U.S. Appl. No. 13/576,953 (Corrected Notice of Allowability).
U.S. Notice of Allowance, dated May 7, 2014, for U.S. Appl. No. 13/576,953.
U.S. Notice of Allowance, dated Sep. 12, 2014, for U.S. Appl. No. 13/577,212.
U.S. Office Action, dated Apr. 4, 2014, for U.S. Appl. No. 13/577,028.
U.S. Office Action, dated Apr. 7, 2014, for U.S. Appl. No. 13/576,950.
U.S. Office Action, dated Aug. 19, 2013, for U.S. Appl. No. 13/576,955.
U.S. Office Action, dated Aug. 26, 2013, for U.S. Appl. No. 13/576,950.
U.S. Office Action, dated Dec. 19, 2014, for U.S. Appl. No. 13/057,709.
U.S. Office Action, dated Dec. 21, 2012, for U.S. Appl. No. 13/057,515.
U.S. Office Action, dated Dec. 21, 2012, for U.S. Appl. No. 13/057,709.
U.S. Office Action, dated Dec. 29, 2014, for U.S. Appl. No. 13/576,969.
U.S. Office Action, dated Jan. 16, 2014, for U.S. Appl. No. 13/057,515.
U.S. Office Action, dated Jul. 1, 2013, for U.S. Appl. No. 13/057,515.
U.S. Office Action, dated Jul. 1, 2013, for U.S. Appl. No. 13/577,212.
U.S. Office Action, dated Jul. 16, 2013, for U.S. Appl. No. 13/057,709.
U.S. Office Action, dated Jul. 16, 2014, for U.S. Appl. No. 13/576,950.
U.S. Office Action, dated Jun. 14, 2013, for U.S. Appl. No. 13/576,969.
U.S. Office Action, dated Jun. 19, 2014, for U.S. Appl. No. 13/057,515.
U.S. Office Action, dated Mar. 13, 2013, for U.S. Appl. No. 13/576,955.
U.S. Office Action, dated Mar. 24, 2014, for U.S. Appl. No. 13/576,969.
U.S. Office Action, dated May 5, 2014, for U.S. Appl. No. 13/577,212.
U.S. Office Action, dated Nov. 15, 2013, for U.S. Appl. No. 13/576,950.
U.S. Office Action, dated Nov. 15, 2013, for U.S. Appl. No. 13/576,953.
U.S. Office Action, dated Nov. 15, 2013, for U.S. Appl. No. 13/577,028.
U.S. Office Action, dated Nov. 2, 2012, for U.S. Appl. No. 13/057,709.
U.S. Office Action, dated Nov. 6, 2014, for U.S. Appl. No. 13/576,950.
U.S. Office Action, dated Nov. 9, 2012, for U.S. Appl. No. 13/057,515.
U.S. Office Action, dated Oct. 1, 2014, for U.S. Appl. No. 13/057,515.
U.S. Office Action, dated Oct. 15, 2013, for U.S. Appl. No. 13/576,969.
U.S. Office Action, dated Oct. 2, 2013, for U.S. Appl. No. 13/057,709.
U.S. Office Action, dated Oct. 21, 2013, for U.S. Appl. No. 13/577,212.
U.S. Office Action, dated Oct. 9, 2013, for U.S. Appl. No. 13/057,515.
U.S. Office Action, dated Sep. 19, 2013, for U.S. Appl. No. 13/577,028.
U.S. Office Action, dated Sep. 3, 2014, for U.S. Appl. No. 13/576,969.
U.S. Office Action, dated Sep. 6, 2013, for U.S. Appl. No. 13/576,953.
Van Der Bruggen et al., "A Gene Encoding an Antigen Recognized by Cytolytic T Lymphocytes on a Human Melanoma," Science, vol. 254, Dec. 13, 1991, pp. 1643-1647 (Also published in Journal of Immunology, vol. 178, 2007, pp. 2617-2621).
Wang et al., "Absence of Caprin-1 Results in Defects in Cellular Proliferation", The Journal of Immunology, vol. 175, 2005, pp. 4274-4282.
Yanai et al., "Dlk-1, a cell surface antigen on foetal hepatic stem/progenitor cells, is expressed in hepatocellular, colon, pancreas and breast carcinomas at a high frequency," The Journal of Biochemistry, vol. 148, No. 1, 2010 (Published online Mar. 30, 2010), pp. 85-92.
Extended European Search Report for European Application No. 13767612.8, dated Sep. 22, 2015.

(56) References Cited

OTHER PUBLICATIONS

Extended European Search Report for European Application No. 13769665.4, dated Sep. 22, 2015.
Corada et al., "Monoclonal antibodies directed to different regions of vascular endothelial cadherin extracellular domain affect adhesion and clustering of the protein and modulate endothelial permeability," Blood (Mar. 15, 2001), vol. 97, No. 6, pp. 1679-1684.
Office Action issued Aug. 14, 2015, in U.S. Appl. No. 14/236,818.
Office Action issued Aug. 20, 2015, in U.S. Appl. No. 14/452,746.
Office Action issued Jul. 27, 2015, in Chinese Patent Application No. 201380038386.9.
Office Action issued Jul. 3, 2015, in Russian Patent Application No. 2012137503.
Office Action issued Sep. 15, 2015, in U.S. Appl. No. 14/389,266.
Padlan, E. A., "X-Ray Crystallography of Antibodies," Adv. Prot. Chem. (1996), vol. 49, pp. 57-133.
Saffari et al., "Identification of novel p53 target genes by cDNA AFLP in glioblastoma cells", Cancer Letters, 2009, No. 273, pp. 316-322.
U.S. Office Action for U.S. Appl. No. 14/379,867, dated Jun. 24, 2015.
"*Homo sapiens* cell cycle associated protein 1, mRNA (cDNA clone MGC:1378 IMAGE:3355481), complete cds", Genebank database, NCBI Accession No. BC001731, Sep. 11, 2007.
Extended European Search Report for Appl. No. 13820574.5 dated Jan. 11, 2016.
Huang, J. et al, "IgG Isotype Conversion of a Novel Human Anti-carcinoembryonic Antigen Antibody to Increase its Biological Activity," Anticancer Research, 2006, vol. 26, No. 2A, pp. 1057-1063.
Japanese Office Action for Appl. No. 2014-225640 dated Nov. 4, 2015.
Shibaguchi, H. et al, "New Human Antibody IgG Subclass Conversion for Enhancement of Tumor-Cytotoxic Activity," Research, 2006, vol. 11, No. 3, pp. 15-16.
Buchsbaum et al., "Treatment of Pancreatic Cancer Xenografts with Erbitux (IMC-C225) Anti-EGFR Antibody, Gemcitabine, and Radiation," Int. J. Radiation Oncology Biol. Phys. (2002), vol. 54, No. 4, pp. 1180-1193.
Chames et al., "Therapeutic Antibodies for the Treatment of Pancreatic Cancer," The Scientific World Journal (Jan. 1, 2010), vol. 10, pp. 1107-1120.
Eccleston et al., "Pancreatic Tumor Marker Anti-Mucin Antibody CAM 17.1 Reacts with a Sialyl Blood Group Antigen, Probably-I, Which is Expressed throughout the Human Gastrointestinal Tract," Digestion (1998), vol. 59, pp. 665-670.
Esteva et al., "Chemotheraphy of Metastatic Breast Cancer: What to Expect in 2001 and Beyond," The Oncologist (2001), vol. 6, pp. 133-146.
Extended European Search Report issued Feb. 2, 2015, in European Patent Application No. 12819473.5.
Extended European Search Report issued Jan. 29, 2015, in European Patent Application No. 12819899.1.
Houghton, P. J. and J. A. Houghton, "Evaluation of Single-Agent Therapy in Human Colorectal Tumour Xenografts," Br. J. Cancer (1978), vol. 37, pp. 833-840.
Office Action issued Jan. 27, 2015, in Japanese Patent Application No. 2011-510197.
Russian Notice of Allowance for Russian Application No. 2014108049/10, dated May 16, 2016, with an English translation.
U.S. Office Action for U.S. Appl. No. 14/415,090, dated May 19, 2016.
Russian Decision on Grant for Russian Application No. 2012137504/10, dated Jun. 22, 2016, with an English translation.
Russian Office Action for Russian Application No. 2014138041/10, dated Jul. 5, 2016, with an English translation.
Russian Office Action and Search Report for Russian Application No. 2014143784, dated Jan. 19, 2017, including a partial English translation.
Extended European Search Report issued Feb. 27, 2017, in European Patent Application No. 14834828.7.
Indian Examination Report issued Feb. 23, 2017, in Indian Patent Application No. 960/KOLNP/2011.
NCBI Reference Sequence:NP_005889 for human CAPRIN-1, printed Apr. 2017.
Russian Decision on Grant of Patent for Invention issued Mar. 13, 2017, in Russian Patent Application No. 2012137503, with English translation.
Russian Decision on Grant of Patent for Invention issued Mar. 29, 2017, in Russian Patent Application No. 2014108048, with English translation.
U.S. Non-Final Office Action issued Apr. 26, 2017, in U.S. Appl. No. 13/057,515.

* cited by examiner

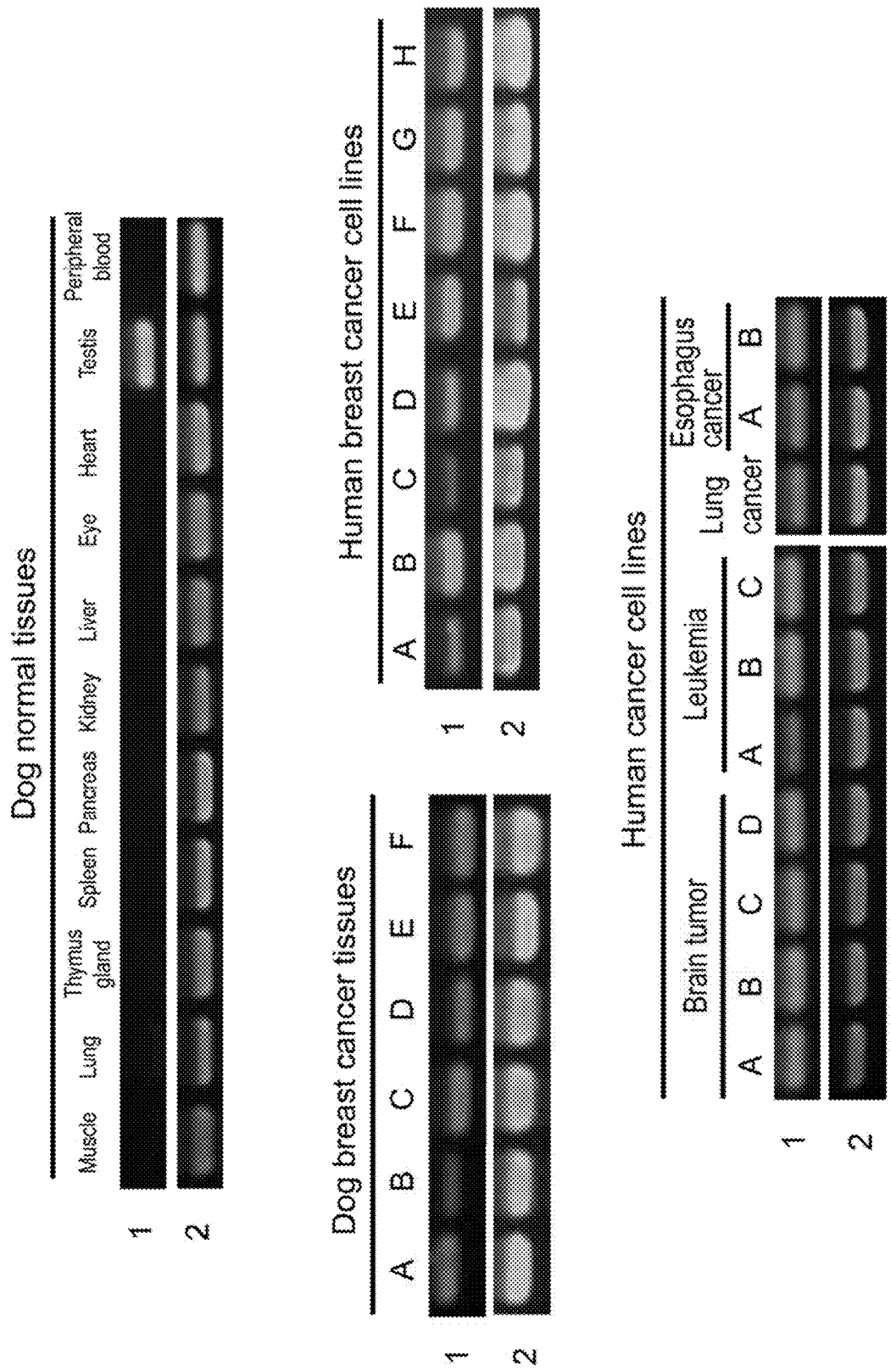

METHOD FOR DETECTING CAPRIN-1 IN A BIOLOGICAL SAMPLE

TECHNICAL FIELD

The present invention relates to a method for detecting a cancer with CAPRIN-1 as a tumor marker.

BACKGROUND ART

Cancer is the leading cause of death. This disease is currently treated principally by surgical therapy in combination with radiation therapy and/or chemotherapy. Owing to previous advances in medical technology, cancer is now a disease highly curable by early detection, depending on its type. Therefore, there is a demand for a method for detecting a cancer which places neither physical nor economic burdens on cancer patients and can be achieved by convenient tests.

Recently, methods for assaying tumor products such as tumor markers have been widely available. The tumor products refer to, for example, tumor-related antigens, enzymes, particular proteins, metabolites, oncogenes, oncogene products, and tumor suppressor genes. Carcinoembryonic antigen CEA, glycoprotein CA19-9, prostate-specific antigen PSA, calcitonin (peptide hormone produced in the thyroid gland), and the like are exploited as tumor markers in cancer diagnosis for some cancers. For many other types of cancers, however, tumor markers useful in cancer diagnosis have not yet been found. In addition, a large majority of currently known tumor markers is present only in very small amounts (of the order of pg/mL) in body fluids and requires highly sensitive assay methods or special techniques for detecting these markers. Under such circumstances, it can be expected that doors will be opened for diagnostic use for various types of cancers if a novel cancer testing approach capable of highly sensitively detecting various types of cancers by convenient operation can be provided.

Meanwhile, in spite of recent development of novel surgical techniques or discovery of novel anticancer agents, an effective cancer diagnosis technique has not been established for many cancers, except for some cancers. Hence, these cancers cannot be detected early, and the existing cancer treatment has an insufficiently improved outcome.

With recent advances in molecular biology or cancer immunology, antibodies specifically reacting with cancer, molecular targeting drugs for cancer antigens related to malignant transformation or cancer exacerbation, and the like have been identified, raising expectations on specific cancer therapy targeting cancer antigens. Among others, a plurality of antibody drugs for cancer treatment targeting antigenic proteins on cancer cells have been launched and used in the cancer treatment. These antibody drugs have received attention because of their certain efficacy as cancer-specific therapeutic agents. A large majority of antigenic proteins targeted by the drugs, however, is also expressed in normal cells. As a result of administering the antibodies, cancer cells as well as normal cells expressing the antigens are damaged, resulting in undesired adverse reactions. In addition, the effects of cancer treatment differ very largely among individuals due to various etiologies depending on the cancer patients. For example, surgery, chemotherapy, or radiation therapy largely varies in the treatment and prognosis depending on the stages of cancers. Different persons are known to have distinctive sensitivities to the same therapeutic drug for cancers due to the diversity of individuals. Thus, a certain drug is effective for some patients but ineffective for others.

Thus, their administration to cancer patients is determined by preliminarily measuring the expression of disease-related genes or proteins in the patients and evaluating whether a particular drug is effective for a cancer patient expressing a particular gene or protein. Specifically, the presence of a cancer antigen in a sample, for example, serum or tissue, derived from a cancer patient is tested in clinical practice by use of a detection method for assaying a disease-related gene or protein of a certain kind of cancer. Then, the administration of a cancer antigen-specific therapeutic drug is determined. For example, cancer tissues from a large bowel cancer patient are evaluated by an immunohistochemical staining EGFR detection method "EGFR pharm (Dako, an Agilent Technologies Company)" to predict the effectiveness of Erbitux for the large bowel cancer. Then, the administration of Erbitux is determined. Alternatively, cancer tissues from a breast cancer patient are evaluated by an immunohistochemical staining Her2 detection method "HercepTest" to predict the effectiveness of Herceptin for the breast cancer. Then, the application of Herceptin is determined.

Incidentally, companion animals have been raised as family members and often have lifestyles similar to those of their owners. For this reason, from the occurrence of cancers in companion animals, it can reportedly be predicted that their owners have the high risk of developing cancers in the future.

Dogs which are typical companion animals are known to age 7 times more quickly than humans. Reportedly, the number of dogs currently raised is approximately 6.7 million in Japan and approximately 17.64 million in the USA. Rabies shots as well as combined vaccines such as quintuple, septuple, or octuple combination shots are generally available, leading to decreased rates of highly lethal infections including canine parvovirus infection, canine distemper infection, canine parainfluenza virus infection (kennel cough), canine adenovirus type 2 infection (kennel cough), canine infectious hepatitis, canine coronavirus infection, and leptospirosis. An average dog life-span has therefore been increased, and 7-year-old or older dogs account for 35.5% of the total number of pet dogs. The causes of death such as cancer, hypertension, and heart disease are ever increasing in dogs, as in humans. In the USA, approximately 4 million dogs are yearly diagnosed with cancers. Also in Japan, approximately 1.6 million dogs allegedly have some potential tumor. Checkup examination, however, is not very common in companion animals, unlike humans. This leads to the late detection of disease. In most cases, their owners notice pets' symptoms for the first time after tumors have already become large, and then visit animal hospitals. If such large tumors are malignant, even surgical therapy (e.g., surgical operation) or medication using anticancer agents or the like is often too late to cure the tumors. Tumors confirmed by veterinarians to be malignant are generally treated with anticancer agents without surgery. Even in the case of performing surgery, it is required to secure surgical margins or to take stringent measures for surgery such as measures against the spread of blood or cells during surgery. Desirably, treatment with anticancer agents is initiated immediately after surgery, and a follow-up is also performed at short intervals. Thus, the medication using therapeutic drugs for cancers is also essential for the cancer-affected companion animals. A detection method, if any, for assaying a disease-related gene or protein of a certain kind of cancer permits more effective treatment than ever and is advantageous both for owners and for veterinarians.

Cytoplasmic- and proliferation-associated protein 1 (CAPRIN-1) is an intracellular protein known to be expressed upon activation or cell division of resting normal cells and to form cytoplasmic stress granules with intracellular RNAs to participate in the regulation of transport and translation of mRNAs. Meanwhile, the present inventors have revealed that: CAPRIN-1 is highly expressed on the membrane surface of breast cancer cells; and an antibody against CAPRIN-1 exerts strong antitumor effects on breast cancer cells (Patent Literature 1). According to another report, the expression of CAPRIN-1 in a patient-derived sample can be measured using an antibody binding to CAPRIN-1 expressed on cell surface to thereby detect a cancer and to evaluate the grade of the cancer (Patent Literature 2). Specifically; the report states that a plasma membrane protein CAPRIN-1 may serve as a target for cancer treatment or the like. As mentioned above, due to the diversity of cancer patients, it is required to test the expression of CAPRIN-1 in a cancer patient-derived sample for determining the administration of a CAPRIN-1-targeting therapeutic drug, for example, an antibody. Nonetheless, there exists no report on a method for detecting CAPRIN-1 for the application of such a specific therapeutic drug, or there exists no reagent for detecting a cancer using a cancer patient-derived sample.

CITATION LIST

Patent Literature

Patent Literature 1: WO2010/016526
Patent Literature 2: WO2010/016527

SUMMARY OF INVENTION

Technical Problem

An object of the present invention is to provide a cancer detection approach useful in the diagnosis of a cancer. Another object of the present invention is to provide a method for detecting a cancer which involves detecting CAPRIN-1 in a sample of a cancer patient and determining the expression level thereof in order to determine the administration of a therapeutic drug targeting CAPRIN-1 to the cancer patient, and a drug and a kit for the diagnosis of a cancer.

Solution to Problem

As a result of conducting diligent studies, the present inventors have obtained cDNAs encoding proteins to which antibodies present in cancer-bearing organism-derived serum bind by SEREX using a dog testis-derived cDNA library and the serum of cancer-bearing dogs. Dog CAPRIN-1 having any of the amino acid sequences shown in SEQ ID NOs: 6, 8, 10, 12, and 14 was prepared on the basis of the cDNAs. The present inventors have also prepared human CAPRIN-1 having any of the amino acid sequences shown in SEQ ID NOs: 2 and 4 on the basis of human homologous genes of the obtained genes. Consequently, the present inventors have found that: genes encoding CAPRIN-1 are specifically expressed in dog and human-testis, respectively, and in malignant cancer cells (see Example 1 mentioned later); and monoclonal antibodies prepared using, as antigens, recombinant polypeptides prepared on the basis of the amino acid sequences of CAPRIN-1 can bind to CAPRIN-1 in various cancer tissues and damage cancer cells having CAPRIN-1 on their surface. As a result, the present inventors have gained the finding that CAPRIN-1 can be used as a target for cancer treatment. The present inventors have further found that CAPRIN-1 can be specifically detected from cancer patient-derived samples by use of the monoclonal antibodies mentioned above. Specifically, the present invention provides a method for detecting a cancer in a biological sample, comprising measuring the expression of CAPRIN-1. In addition, the present invention has established a method for detecting CAPRIN-1 in a cancer patient-derived sample and evaluating the expression level thereof by an immunological assay method using any of the monoclonal antibodies mentioned above, i.e., by ELISA for cancer patient-derived serum and/or an immunohistochemical staining method for cancer tissues, etc. As a result of evaluating a cancer-derived sample by use of this method, a therapeutic drug targeting CAPRIN-1 has also be found to be applicable to a patient in which CAPRIN-1 is expressed at a high level. On the basis of these findings, the present invention has been completed.

The present invention provides a method for detecting a cancer in a biological sample, comprising detecting CAPRIN-1 in the sample and measuring the expression level thereof. The present invention also provides a diagnosis method for determining the applicability of a therapeutic drug against CAPRIN-1, comprising measuring the expression level of CAPRIN-1 in a tissue before administration of the therapeutic drug against CAPRIN-1 to a cancer patient to thereby predict whether a therapeutic drug targeting CAPRIN-1, for example, an antibody, can be applied to the cancer patient and also predict the effectiveness thereof. The present invention further provides a drug or kit for the diagnosis of a cancer, comprising an antibody capable of antigen-antibody reaction with CAPRIN-1, or an antigen-binding fragment thereof.

Specifically, the present invention has the following aspects:

(1) A method for detecting a cancer, comprising measuring the expression level of CAPRIN-1 in a biological sample through antigen-antibody reaction using an antibody having immunological reactivity with a polypeptide having the amino acid sequence shown in SEQ ID NO: 63.

(2) The method for detecting a cancer according to (1), wherein CAPRIN-1 to be measured is (a) a polypeptide having an amino acid sequence shown in any even-numbered SEQ ID NO shown in SEQ ID NOs: 2 to 30 in the Sequence Listing, or (b) a polypeptide having 85% or higher sequence identity to the CAPRIN-1.

(3) The method for detecting a cancer according to (1) or (2), wherein the biological sample is derived from a human, a dog, or a cat.

(4) The method for detecting a cancer according to any of (1) to (3), wherein the biological sample is derived from a dog, and CAPRIN-1 to be measured has an amino acid sequence shown in SEQ ID NO: 6, 8, 10, 12, or 14.

(5) The method for detecting a cancer according to any of (1) to (3), wherein the biological sample is derived from a human, and CAPRIN-1 to be measured has an amino acid sequence shown in SEQ ID NO: 2 or 4.

(6) The method for detecting a cancer according to any of (1) to (5), wherein a measured CAPRIN-1 expression level which is significantly higher than that of a healthy individual indicates the presence of the cancer targeted by the antibody as a therapeutic drug for the cancer.

(7) The method for detecting a cancer according to any of (1) to (6), wherein the measurement of the expression of CAPRIN-1 employs an immunological assay method.

(8) The method for detecting a cancer according to (7), wherein the immunological assay method is ELISA and/or an immunohistochemical staining method.

(9) The method for detecting a cancer according to any of (1) to (8), wherein the sample is a body fluid, a tissue, or a cell.

(10) The method for detecting a cancer according to any of (1) to (9), wherein the cancer is at least one cancer selected from the group consisting of breast cancer, brain tumor, esophagus cancer, stomach cancer, lung cancer, liver cancer, kidney cancer, thyroid gland cancer, spleen cancer, pancreas cancer, large bowel cancer, skin cancer, ovary cancer, uterus cancer, prostate cancer, bladder cancer, testis cancer, osteosarcoma, and fibrosarcoma.

(11) The method for detecting a cancer according to any of (1) to (10), wherein the antibody or the antigen-binding fragment thereof is a monoclonal antibody having a heavy chain variable region comprising the amino acid sequence shown in SEQ ID NO: 70 and a light chain variable region comprising the amino acid sequence shown in SEQ ID NO: 71, or an antigen-binding fragment thereof.

(12) A drug or kit for the diagnosis of a cancer, comprising an antibody having immunological reactivity with a polypeptide having the amino acid sequence shown in SEQ ID NO: 63, or an antigen-binding fragment thereof.

(13) The drug or kit for the diagnosis of a cancer according to (12), wherein the antibody or the antigen-binding fragment thereof is a monoclonal antibody having a heavy chain variable region comprising the amino acid sequence shown in SEQ ID NO: 70 and a light chain variable region comprising the amino acid sequence shown in SEQ ID NO: 71, or an antigen-binding fragment thereof.

(14) A method for selecting an individual-specific therapeutic drug for a cancer, comprising: measuring the expression level of CAPRIN-1 in a biological sample using an antibody having immunological reactivity with a polypeptide having the amino acid sequence shown in SEQ ID NO: 63, or an antigen-binding fragment thereof; and, when the expression level is statistically significantly higher than that of a healthy individual, determining selecting a CAPRIN-1-targeting drug as a therapeutic drug for a cancer suitable for administration to the individual from which the biological sample is derived.

(15) The method for selecting an individual-specific therapeutic drug for a cancer according to (14), wherein the CAPRIN-1-targeting drug is an antibody having immunological reactivity with CAPRIN-1, or an antigen-binding fragment thereof.

The present specification encompasses the contents described in the specification and/or drawings of Japanese Patent Application No. 2012-160751, on which the priority of the present application is based.

Advantageous Effects of Invention

The present invention provides a novel method for detecting a cancer to measure the expression level of CAPRIN-1 in a sample separated from a cancer patient. As specifically shown in Examples mentioned later, antibodies prepared using, as antigens, recombinant polypeptides prepared on the basis of the amino acid sequence of CAPRIN-1 (also referred to as Caprin-1) specifically react with CAPRIN-1 in the serum or tissues of cancer patients. As also described later in Examples, CAPRIN-1 itself is specifically expressed at high levels in various cancer tissues. The presence and the expression level of CAPRIN-1 in a sample separated from a cancer patient can therefore be measured to thereby detect a cancer. In addition, the presence or absence of sensitivity to a CAPRIN-1-targeting drug such as an antibody drug, can be preliminarily determined to thereby select a patient to which this therapeutic drug is applicable. Specifically, the presence and the expression level of CAPRIN-1 can be preliminarily measured by the application of the present invention to a cancer patient to thereby provide more efficient treatment using an anti-CAPRIN-1 antibody.

BRIEF DESCRIPTION OF DRAWING

FIG. 1 is a diagram showing the expression patterns of a CAPRIN-1-encoding gene in normal tissues and tumor cell lines. Reference number 1 depicts the expression patterns of the gene encoding the CAPRIN-1 protein. Reference number 2 depicts the expression patterns of the GAPDH gene. The uppermost panel shows the results about dog normal tissues. The left middle panel shows the results about dog breast cancer tissues. The right middle panel shows the results about human breast cancer cell lines. The lowermost panel shows the results about various human cancer cell lines.

DESCRIPTION OF EMBODIMENTS

The method for detecting a cancer according to the present invention comprises detecting CAPRIN-1 in a biological sample and measuring the expression level thereof. The expression level of CAPRIN-1 in a sample of a cancer patient can be measured by an analysis method based on, for example, an immunological assay method using an anti-CAPRIN-1 antibody. Most of such methods are known in the art, and any of immunological assay methods using the antibody, such as immunohistochemical analysis, Western blot analysis, immunoprecipitation, molecular binding assay, ELISA, and biochemical enzyme activity assay, can be used. In this context, the "expression level" used herein includes the intracellular accumulation and abundance of the protein.

The expression of CAPRIN-1 in the sample can be differentiated by classification into scores shown in Examples. A higher score indicates that CAPRIN-1 to be measured is contained in a larger amount in the cancer tissue or cancer serum of a cancer patient. In the present invention, the term "measurement" or "assay" encompasses all of detection and qualitative, quantitative, and semiquantitative approaches.

The amino acid sequence shown in SEQ ID NO: 6, 8, 10, 12, or 14 is the amino acid sequence of dog CAPRIN-1. The dog CAPRIN-1 having this amino acid sequence has been found by SEREX using a dog testis-derived cDNA library and serum derived from cancer-bearing dogs, and identified as a polypeptide binding to an antibody specifically present in the serum derived from cancer-bearing dogs (see Example 1). CAPRIN-1 itself having the amino acid sequence shown in SEQ ID NO: 6, 8, 10, 12, or 14 can be assayed as an antigen in dog tissues by the method mentioned above to thereby diagnose the presence or absence of sensitivity of the patient to a therapeutic drug targeting CAPRIN-1 (see Examples). In this context, the phrase "having an (the) amino acid sequence" used herein means that amino acid residues are arranged in the order presented in predetermined amino acid sequence information. Thus, for example, the "polypeptide having the amino acid sequence shown in SEQ ID NO: 2" means a polypeptide of 709 amino acid residues in size in which the amino acid residues are linked in the order presented in the amino acid sequence Met Pro Ser Ala . . . (snip) . . . Gln Gln Val Asn as shown in SEQ. ID NO: 2. In the present specification, the "polypeptide having the amino acid sequence shown in SEQ ID NO: 2" is abbreviated to the "polypeptide shown in SEQ ID NO: 2". The same holds true for the phrase "having a (the) nucleotide sequence". In this case, the term "having" may be used interchangeably with the term "comprising" or "consisting of".

The "polypeptide" used herein refers to a molecule that is formed through the peptide bonds of a plurality of amino acids, and encompasses not only a polypeptide molecule constituted by a large number of amino acids but a low-molecular-weight molecule having a small number of amino acids (oligopeptide) and a full-length protein. The polypeptide according to the present invention also encompasses the full-length protein of CAPRIN-1 having an amino acid sequence represented by any even-numbered SEQ ID NO shown in SEQ ID NOs: 2 to 30.

In the method of the present invention, additional mammalian CAPRIN-1 other than the dog CAPRIN-1 shown in SEQ ID NO: 6, 8, 10, 12, or 14 can also be used as an analyte. In the present specification, such non-dog mammalian CAPRIN-1 is also referred to as a "homolog" of dog CAPRIN-1. The term "CAPRIN-1" encompasses CAPRIN-1 derived from not only dogs but other mammals. Examples of the additional mammalian CAPRIN-1 that may be used as an analyte in the method of the present invention include, but not limited to, human CAPRIN-1 and cat CAPRIN-1. As specifically described below in Examples, mRNA encoding human CAPRIN-1 is significantly expressed at high levels in human testis and cancer cells, as with the dog CAPRIN-1 shown in SEQ ID NO: 6, 8, 10, 12, or 14. An anti-human CAPRIN-1 antibody, however, is not detected in the bodies of healthy humans. An anti-cat CAPRIN-1 antibody is not detected in the bodies of healthy cats, but is detected only in cancer-bearing cats. Thus, the applicability of a therapeutic drug targeting CAPRIN-1 to a non-dog mammal can also be determined by the measurement of the expression level of CAPRIN-1 derived from the non-dog mammal.

The nucleotide sequence encoding human CAPRIN-1 and the amino acid sequence thereof are as shown in SEQ ID NO: 1 and 3 and SEQ ID NO: 2 and 4, respectively, in the Sequence Listing. The sequence identity of human CAPRIN-1 to dog CAPRIN-1 is 94% for the nucleotide sequence and 98% for the amino acid sequence. Since the amino acid sequence of CAPRIN-1 is as very high as 98% even between dogs and humans, which are the genetically distantly related mammals, the amino acid sequence of CAPRIN-1 probably has high (approximately 85% or higher) sequence between non-human mammalian CAPRIN-1 and the dog CAPRIN-1. In the method of the present invention, the CAPRIN-1 whose expression level is to be measured is not particularly limited and is one having preferably 85% or higher, more preferably 95% or higher sequence identity to the amino acid sequence of the dog CAPRIN-1 shown in SEQ ID NO: 6, 8, 10, 12, or 14.

An antigenic substance, such as a protein, which has a complicated structure with a large molecular weight, usually contains a plurality of epitopes differing in structure on its molecule. Thus, plural types of antibodies that respectively recognize and bind to a plurality of epitopes on such an antigenic substance are produced in vivo. In other words, antibodies produced in vivo against the antigenic substance (e.g., protein) are polyclonal antibodies, which are mixtures of plural types of antibodies. The antibodies found by the present inventors to be specifically present in serum derived from cancer-affected organisms and to specifically bind to recombinant CAPRIN-1 through antigen-antibody reaction are also polyclonal antibodies. The term "polyclonal antibody" used in the present invention refers to an antibody that is found in serum derived from an organism containing an antigenic substance in the body, and has been induced in the organism against the antigenic substance.

Specific examples of a preferred polypeptide for use as an antigen include polypeptides of even-numbered SEQ ID NOs of SEQ ID NOs: 2 to 30 and fragments thereof.

The nucleotide sequences of polynucleotides encoding polypeptides consisting of the amino acid sequences shown in even-numbered SEQ ID NOs of SEQ ID NOs: 2 to 30 (i.e., SEQ ID NOs: 2, 4, 6, . . . 28, and 30) are shown in odd-numbered SEQ ID NOs of SEQ ID NOs: 1 to 29 (i.e., SEQ ID NOs: 1, 3, 5, . . . 27, and 29), respectively.

It is widely known to those skilled in the art that even a protein derived from a protein antigen by the substitution, deletion, addition, or insertion of a small number of amino acid residues in the amino acid sequence constituting the protein may generally have almost the same antigenicity as that of the original protein. Thus, a polypeptide having a sequence derived from the amino acid sequence of CAPRIN-1 by the substitution, deletion, addition and/or insertion of a small number of (preferably 1 or several) amino acid residues can also be used in the detection of the cancer, as with the polypeptides consisting of the amino acid sequences shown in even-numbered SEQ ID NOs of SEQ ID NOs: 2 to 30 above, as long as the polypeptide has 80% or higher or 85% or higher, preferably 90% or higher, more preferably 95% or higher, further preferably 98% or higher sequence identity to the original sequence and specifically binds to a polyclonal antibody against CAPRIN-1 through antigen-antibody reaction (hereinafter, this polypeptide is also referred to as a "specifically-reactive modified polypeptide" for the sake of convenience). Preferably, the specifically-reactive modified polypeptide has an amino acid sequence derived from the amino acid sequence of CAPRIN-1 by the substitution, deletion, addition, and/or insertion of 1 or several amino acid residues. The term "several" used herein refers to an integer of 2 to 10, preferably an integer of 2 to 6, more preferably an integer of 2 to 4.

The "sequence identity" used herein for the amino acid sequence refers to the percentage of a value determined by dividing the number of identical amino acid residues by the total number of amino acid residues in the best-matching alignments of the amino acid residues in two amino acid sequences to be compared. For the alignments, if necessary, one or both of these two sequences to be compared can be gapped. Such sequence alignments can be carried out using a well-known program, for example, BLAST, FASTA, or CLUSTAL W (Karlin and Altschul, Proc. Natl. Acad. Sci. U.S.A., 87: 2264-2268, 1993; and Altschul et al., Nucleic Acids Res., 25: 3389-3402, 1997).

Twenty types of amino acids constituting a natural protein can be divided according to similar properties into the following groups: neutral amino acids having a low polar side chain (Gly, Ile, Val, Leu, Ala, Met, and Pro); neutral amino acids having a hydrophilic side chain (Asn, Gln, Thr, Ser, Tyr, and Cys); acidic amino acids (Asp and Glu); basic amino acids (Arg, Lys, and His); and aromatic amino acids (Phe, Tyr, Trp, and His). It is known that substitution within each of these groups, i.e., conservative substitution, does not change the properties of the polypeptide in most cases. Thus, in the case of substituting the amino acid residues of CAPRIN-1, a member in each of these groups can be substituted by another member in the same group so that the binding activity against the appropriate antibody is likely to be maintained. In the present invention, however, the modified form may have non-conservative substitution as long as the modified form is provided with immunity-inducing activity equivalent to or substantially equivalent to that of the unmodified form.

The polypeptide used in the present invention can be synthesized according to chemical synthesis methods, for example, Fmoc (fluorenylmethyloxycarbonyl) and tBoc (t-butyloxycarbonyl) methods (Seikagaku Jikken Koza (Biochemical Experimentation Course in English) 1, the Japanese Biochemical Society ed., Protein Chemistry IV, Chemical Modification and Peptide Synthesis, Tokyo Kagaku Dojin Co., Ltd. (Japan), 1981). Also, the polypeptide can be synthesized by routine methods using various commercially available peptide synthesizers. Alternatively, the polypeptide can be easily prepared using genetic engineering approaches known in the art (Sambrook et al., Molecular Cloning, the 2nd edition, Current Protocols in Molecular Biology (1989), Cold Spring Harbor Laboratory Press; Ausubel et al., Short Protocols in Molecular Biology, the 3rd edition, A compendium of Methods from Current Protocols in Molecular Biology (1995), John Wiley & Sons; etc.). For example, RNA is extracted from a tissue expressing a gene encoding the human CAPRIN-1 shown in SEQ ID NO: 2 or a homologous factor thereof. From this RNA, cDNA of the gene is prepared by RT-PCR. The full-length cDNA or a desired partial fragment thereof is incorporated into expression vectors, which can then be transferred to host cells to obtain the polypeptide of interest. The nucleotide sequences of cDNAs encoding the dog CAPRIN-1 proteins shown in SEQ ID NOs: 6, 8, 10, 12, and 14 are shown in SEQ ID NOs: 5, 7, 9, 11, and 13, respectively. The nucleotide sequences of cDNAs encoding the human CAPRIN-1 proteins shown in SEQ ID NOs: 2 and 4 as human homologous factors thereof are shown in SEQ ID NOs: 1 and 3, respectively. Primers for use in RT-PCR can therefore be easily designed with reference to these nucleotide sequences. As mentioned later, a gene encoding non-human mammalian CAPRIN-1 can be amplified with primers designed with reference to the nucleotide sequence shown in any odd-numbered SEQ ID NO of SEQ ID NOs: 5 to 29. Thus, cDNA encoding, for example, cat CAPRIN-1, can also be easily prepared by the same approach as above. The RNA extraction, RT-PCR, the incorporation of cDNA into vectors, and the transfer of the vectors to host cells can be carried out, for example, by well-known methods as described below. Also, the vectors or host cells used are well known, and various products are commercially available.

The host cells may be any cell capable of expressing the above polypeptide. Examples of prokaryotic cells include *E. coli*. Examples of eukaryotic cells include: cultured mammalian cells such as monkey kidney cells COS1, Chinese hamster ovary cells CHO, a human embryonic kidney cell line HEK293, and mouse embryonic skin cell line NIH3T3; and budding yeast, fission yeast cells, silkworm cells, and *Xenopus* egg cells.

In the case of using prokaryotic cells as the host cells, the expression vectors used have an origin that permits replication in the prokaryotic cells, a promoter, a ribosomal binding site, a multicloning site, a terminator, a drug resistance gene, an auxotrophic complementary gene, etc. Examples of expression vectors for *E. coli* can include pUC series, pBluescript II, pET expression systems, and pGEX expression systems. DNA encoding the above polypeptide can be incorporated into such expression vectors, with which prokaryotic host cells are then transformed, followed by the culture of the obtained transformants so that the polypeptide encoded by the DNA is expressed in the prokaryotic host cells. In this respect, the polypeptide may be expressed as a fusion protein with an additional protein. In this context, the DNA encoding the above polypeptide can be obtained, for example, by the preparation of cDNA by RT-PCR as mentioned above. Alternatively, the DNA may be synthesized by routine methods using commercially available nucleic acid synthesizers as mentioned later. The nucleotide sequences of cDNAs of genes encoding the CAPRIN-1 proteins shown in SEQ ID NOs: 2 and 4 are shown in SEQ ID NOs: 1 and 3, respectively, in the Sequence Listing.

In the case of using eukaryotic cells as the host cells, expression vectors for eukaryotic cells having a promoter, a splicing region, a poly(A) addition site, etc. are used as the expression vectors. Examples of such expression vectors can include pKA1, pCDM8, pSVK3, pMSG, pSVL, pBK-CMV, pBK-RSV, EBV vector, pRS, pcDNA3, and pYES2 vectors. In the same way as above, the DNA encoding the above polypeptide used in the present invention can be incorporated into such expression vectors, with which eukaryotic host cells are then transformed, followed by the culture of the obtained transformants so that the polypeptide encoded by the DNA is expressed in the eukaryotic host cells. In the case of using expression vectors such as pIND/V5-His, pFLAG-CMV-2, pEGFP-N1, or pEGFP-C1, the polypeptide may be expressed as various fusion proteins tagged with His tag (e.g., $(His)_6$ to $(His)_{10}$), FLAG tag, myc tag, HA tag, GFP, or the like.

The expression vectors can be transferred to the host cells using well-known methods such as electroporation, a calcium phosphate method, a liposome method, a DEAE dextran method, microinjection, viral infection, lipofection, and binding with cell-penetrating peptides.

The polypeptide of interest can be isolated and purified from the host cells by a combination of separation operations known in the art. Examples thereof include treatment with a denaturant (e.g., urea) or a surfactant, ultrasonication, enzymatic digestion, salting-out, solvent fractionation and precipitation, dialysis, centrifugation, ultrafiltration, gel filtration, SDS-PAGE, isoelectric focusing electrophoresis, ion-exchange chromatography, hydrophobic chromatography, affinity chromatography, and reverse-phase chromatography.

The polypeptides obtained by these methods also include their forms of fusion proteins with other arbitrary proteins. Examples thereof can include fusion proteins with glutathione-S-transferase (GST) or His tag. The polypeptides expressed in transformed cells may undergo various intracellular modifications after translation. Such posttranslationally modified polypeptides may be used as long as these polypeptides have binding activity against the polyclonal antibody against CAPRIN-1. Examples of such posttranslational modifications can include N-terminal methionine elimination, N-terminal acetylation, glycosylation, intracellular protease-mediated limited degradation, myristoylation, isoprenylation, and phosphorylation.

In the method of the present invention, CAPRIN-1 that may be contained in the biological sample is assayed. As mentioned above, cancer cells have been found to have a significantly high expression level of CAPRIN-1 as an antigen. As specifically described below in Examples, CAPRIN-1 itself can be assayed in cancer cells or cancer tissues to thereby determine the applicability of a therapeutic drug targeting CAPRIN-1 to the patient having a high expression level of CAPRIN-1.

The polypeptide in the sample can be easily assayed by a well-known immunological assay method. Specifically, CAPRIN-1 that may be present in the sample can be assayed by immunoassay using, for example, a prepared antibody capable of antigen-antibody reaction with CAPRIN-1 or a prepared antigen-binding fragment thereof. Not only the dog CAPRIN-1 shown in SEQ ID NO: 6 but its homologous factors in other mammals, for example, human CAPRIN-1 shown in SEQ ID NO: 2 or 4 or cat CAPRIN-1, can be assayed using an antibody capable of antigen-antibody reaction with, for example, the dog CAPRIN-1 shown in SEQ ID NO: 6, or an antigen-binding fragment thereof, because the antibody has cross-reactivity.

Such an immunoassay method itself is a well-known routine method, as mentioned above. The antibody that recognizes CAPRIN-1 may be immunohistochemically tested for its reactivity with CAPRIN-1 by a method well known to those skilled in the art using a paraformaldehyde- or acetone-fixed frozen section or paraformaldehyde-fixed paraffin-embedded section of a tissue obtained from a patient during surgical operation or from an animal carrying a xenograft tissue inoculated with a cell line expressing CAPRIN-1 either spontaneously or after transfection.

The expression level of CAPRIN-1 in the sample thus immunohistochemically stained can be quantitatively determined by numerical scoring reflecting staining patterns. Two or more scores are preferably set. In the most preferred aspect, the staining patterns are classified into 4 scores. For example, CAPRIN-1 expressed on the surface of cancer cells is stained by a usual immunohistochemical staining method, and the amount thereof is given any of 4 scores reflecting its staining pattern. In such a case, each score is set as follows:

Score 0 (without CAPRIN-1 overexpression): Positive staining of the cell membrane is not observed or is observed in less than 10% of the cancer cells.

Score 1 (without CAPRIN-1 overexpression): Faint, almost unperceivable staining of the cell membrane is observed in 10% or more of the cancer cells, and these cancer cells are partially stained only at their cell membranes.

Score 2 (with CAPRIN-1 overexpression): Weak to moderate complete positive staining of the cell membrane is observed in 10% or more of the cancer cells, or strong complete positive staining of the cell membrane is observed in 10% or more and 30% or less of the cancer cells.

Score 3 (with CAPRIN-1 overexpression): Strong complete positive staining of the cell membrane is observed in 30% or more of the cancer cells.

Such a score system is specified by American Society of Clinical Oncology (USA) and approved by The Japanese Society of Pathology (Japan). A similar scoring system is also exploited in "HercepTest" for quantitatively determining the abundance of a cancer antigen Her2 in samples of patients. The quantification of Her2 is specified by the ASCO/CAP Her2 testing guidelines. In Japan, a guideline for Her2 testing including this scoring system is also specified by the pathological committee for trastuzumab.

The ratio of stained cancer cells after immunohistochemical staining described in each score can be determined by: counting at least 500 cells in the field of view using a light microscope with sensitivity increased to 4 times, 10 times, or 20 times; measuring cells that exhibit stain images of their cell membranes as described in each score; and making a trial calculation according to the following expression:

The number of positive cells/The total number of cells(approximately 500 cells)×100

For the immunohistochemical staining, the antibody having reactivity with CAPRIN-1 can be stained by various methods. For example, the antibody can be visualized through reaction with a horseradish peroxidase-conjugated goat anti-mouse antibody or goat anti-chicken antibody.

The antibody capable of antigen-antibody reaction with CAPRIN-1 or an antigen-binding fragment thereof for use in the immunoassay of CAPRIN-1 itself can also be provided as a drug or kit for the diagnosis of a cancer. In this case, the drug or kit for the diagnosis of a cancer may also consist of the antibody or the antigen-binding fragment or may further comprise, for example, various additives useful in the stabilization or the like of the antibody or the antigen-binding fragment. The antibody or the antigen-binding fragment may be conjugated with a metal such as manganese or iron. Such a metal-conjugated antibody or antigen-binding fragment, when administered to the body, accumulates to a site containing the antigenic protein. Accordingly, the presence of cancer cells producing the antigenic protein can be detected by the MRI measurement or the like of the metal.

CAPRIN-1 has been found to be a plasma membrane protein that is expressed on the surface of cancer cells. Since the bodies of cancer patients contain many proteolytic enzymes, the extracellular region in the CAPRIN-1 sequence on cancer cells is separated from the cancer cells upon degradation. The extracellular region thus separated is therefore present in larger amounts in blood, compared with the intracellular region in the CAPRIN-1 sequence on the cancer cells. Accordingly, CAPRIN-1 present not only in cancer tissues fixed on slide glass but in the serum of cancer patients can be detected by the assay according to the present invention using an anti-CAPRIN-1 antibody or an antigen-binding fragment thereof capable of binding more strongly to the extracellular region of CAPRIN-1. In addition, this detection method, which employs such an antibody binding to the extracellular region of CAPRIN-1, is capable of accurately identifying a cancer patient that can be expected to get therapeutic effects by the administration of a therapeutic drug targeting CAPRIN-1, particularly, an anti-CAPRIN-1 antibody drug, and can thus provide more effective cancer treatment. Thus, in the present invention, an antibody binding to the extracellular region of CAPRIN-1 on cancer cells is preferably used. Examples of the partial peptide of the CAPRIN-1 protein containing an epitope recognized by such an antibody include peptides corresponding to extracellular regions in the amino acid sequences shown in even-numbered SEQ ID NOs of SEQ ID NOs: 2 to 30 in the Sequence Listing except for SEQ ID NOs: 6 and 18. Specific examples thereof include peptides comprising a sequence of 7 or more consecutive amino acids in the region of amino acid residues 50 to 98 or amino acid residues 233 to 344 in SEQ ID NO: 2, and peptides comprising a sequence of 7 or more consecutive amino acids in a region homologous to these amino acid residues in an amino acid sequence shown in any even-numbered SEQ ID NO of SEQ ID NOs: 4 to 30 except for SEQ ID NOs: 6 and 18. More specific examples thereof include the amino acid sequence shown in SEQ ID NO: 43 or 61, preferably the amino acid sequence shown in SEQ ID NO: 62 in the amino acid sequence shown in SEQ ID NO: 61, and amino acid sequences having 80% or higher, preferably 85% or higher, more preferably 90% or higher, further preferably 95% or higher sequence identity to the amino acid sequence. The antibody used in the present invention encompasses all of antibodies binding to any of these peptides. Specific examples thereof include antibodies binding to the amino acid sequence shown in SEQ ID NO: 63 or antigen-binding fragments thereof, and monoclonal antibodies or antigen-binding fragments having the amino acid sequence of a monoclonal antibody having the amino acid sequences shown in SEQ ID NOs: 70 and 71 or an antigen-binding fragment thereof.

The "antigen-binding fragment" used herein means any antibody fragment having the ability to bind to the antigen, such as a Fab or F(ab')2 fragment contained in an antibody molecule. The antibody may be a polyclonal antibody or may be a monoclonal antibody. A highly reproducible monoclonal antibody is preferred for immunoassay or the like. These polyclonal and monoclonal antibodies can be prepared by a well-known method using a peptide as an immunogen and can be easily obtained by a routine method. The immunization method involves immunizing the animal with, for example, CAPRIN-1 conjugated with a carrier protein such as keyhole limpet hemocyanin (KLH), casein, or serum albumin as an immunogen together with an adjuvant to thereby induce an antibody against CAPRIN-1. The antibody-producing cells (e.g., spleen cells or lymphocytes) collected from the immunized animal are fused with myeloma cells to prepare hybridomas. Then, hybridomas producing antibodies binding to CAPRIN-1 are selected and proliferated. Monoclonal antibodies adaptable to CAPRIN-1 as an antigen can be obtained from the culture supernatant. This method is a well-known routine method.

The cancer to be detected by the method of the present invention is a cancer overexpressing CAPRIN-1. Examples thereof include breast cancer, brain tumor, esophagus cancer, stomach cancer, lung cancer, liver cancer, kidney cancer, thyroid gland cancer, spleen cancer, pancreas cancer, large bowel cancer, skin cancer, ovary cancer, uterus cancer (uterine cervix cancer and uterine body cancer), prostate cancer, bladder cancer, testis cancer, and osteosarcoma. Other examples thereof can include, but not limited to, squamous cell cancer of the head and neck, melanoma, various types of adenocarcinomas, hepatocellular cancer, basal cell cancer, acanthoma-like gingival tumor, tumor mass in the oral cavity, perianal gland cancer, tumor mass of the anal sac, anal sac apocrine adenocarcinoma, Sertoli cell carcinoma, vaginal vestibule cancer, sebaceous cancer, sebaceous epithelioma, sebaceous adenoma, sweat gland cancer, adenocarcinoma in the nasal cavity, adenocarcinoma of the nose, bronchial adenocarcinoma, ducal cancer, mammary gland cancer, mammary complex carcinoma, malignant mixed tumor of the mammary gland, intraductal papillary adenocarcinoma, fibrosarcoma, hemangiopericytoma, chondrosarcoma, soft tissue sarcoma, histiocytic sarcoma, myxosarcoma, primitive sarcoma, mastocytoma, cutaneous leiomyoma, intraperitoneal leiomyoma, leiomyoma, lymphoma, chronic lymphocytic leukemia, gastrointestinal lymphoma, lymphoma of the digestive organ, small/medium cell lymphoma, adrenal medullary tumor, granulosa cell tumor, and pheochromocytoma.

The biological sample to which the method of the present invention is applied is derived from a mammal and preferably from a human, a dog, or a cat.

Examples of the sample that is subjected to the method of the present invention include body fluids, tissues, and cells. The "body fluid" used herein refers to a biological sample in a liquid state. Examples thereof include blood (including serum, plasma, and interstitial fluid), lymph, ascites, pleural effusion, spinal fluid, sputum, lacrimal fluid, nasal discharge, saliva, urine, vaginal fluid, and semen. The body fluid may include, for example, peritoneal washings with saline. Serum, plasma, ascites, or pleural effusion is preferred.

In the method of the present invention, when the measured CAPRIN-1 expression level in the biological sample is higher (preferably, statistically significantly higher) than that of a healthy individual, the presence of a cancer that can be specifically bound by the anti-CAPRIN-1 antibody used in the measurement (i.e., a cancer that can be targeted by the antibody as a therapeutic drug for the cancer) is determined in the organism (individual) from which the biological sample is derived. By use of this, the expression level of CAPRIN-1 in a cancer patient-derived biological sample can be measured by the method of the present invention and compared with that of a healthy individual to confirm whether or not a therapeutic drug against CAPRIN-1 is applicable to the cancer in the patient (e.g., whether or not the cancer in the patient can be targeted by the antibody as a therapeutic drug for the cancer).

Thus, the method of the present invention can identify a cancer patient that can be expected to get therapeutic effects by the administration of a therapeutic drug including a CAPRIN-1-targeting antibody, and thus provide more effective cancer treatment.

According to one embodiment, the present invention relates to a method for selecting an individual-specific therapeutic drug for a cancer, comprising: measuring the expression level of CAPRIN-1 in a biological sample using an antibody having immunological reactivity with a polypeptide having the amino acid sequence shown in SEQ ID NO: 63; and, when the expression level is higher (preferably, statistically significantly higher) than that of a healthy individual, selecting a CAPRIN-1-targeting drug, preferably an antibody having immunological reactivity with CAPRIN-1 or an antigen-binding fragment thereof, as a CAPRIN-1-targeting therapeutic drug for a cancer suitable for administration to the individual from which the biological sample is derived. This selection of the individual-specific therapeutic drug for a cancer realizes so-called tailor-made medicine, which offers cancer therapy optimized for an individual patient.

The term "statistically significantly" used herein means that statistically treated quantitative difference between the two is a significant difference. Specifically, examples thereof include the case where a significance level is smaller than 5%, 1%, or 0.1%. The method of verification is not particularly limited as long as the method is known in the art and is capable of determining the presence or absence of significance. For example, a Student's t test or multiple comparison test method can be used.

EXAMPLES

Hereinafter, the present invention will be described more specifically with reference to Examples. However, the scope of the present invention is not intended to be limited by these Examples.

Example 1

Analysis of CAPRIN-1 Expression in Each Tissue

The expression of the CAPRIN-1 gene in dog and human normal tissues and various cancer tissues or cancer cell lines was examined by RT-PCR according to Example 1(4) of WO2010/016526. The result is shown in FIG. 1. As a result, its strong expression was observed in the testis among the normal tissues of the healthy dog. Also, the expression was observed in dog breast cancer. Further, the expression of the gene was also confirmed using human tissues. As a result, the expression was confirmed only in the testis among the normal tissues, as with the dog CAPRIN-1 gene, but was detected in many types of cancer cell lines such as 8 human breast cancer cell lines (ZR75-1, MCF7, T47D, SK-BR-3, MDA-MB-157, BT-20, MDA-MB-231V, and MRK-nu-1) as well as 4 brain tumor cell line, 3 leukemia-derived cell line, 1 lung cancer cell line, and 2 esophagus cancer cell line. These results demonstrated that CAPRIN-1 is not expressed in normal tissues except for the testis, but is expressed in many cancer cells including breast cancer cells.

Example 2

Preparation of Anti-CAPRIN-1 Antibody (1) Preparation of Mouse Anti-human CAPRIN-1 Monoclonal Antibody 100 µg of human CAPRIN-1 having the amino acid sequence shown in SEQ ID NO: 2 as prepared in Example 3 of WO2010/016526 was mixed with an equal amount of MPL+TDM adjuvant (Sigma-Aldrich Corp.). This mixture was used as an antigen solution per mouse. Said antigen solution was intraperitoneally administered to each 6-week-old Balb/c mouse (Japan SLC, Inc.). Then, 3 boosters were performed every 1 week. Three days after the final shot, the spleen of the mouse was excised and ground between two sterilized glass slides. Procedures of washing with PBS(−) (Nissui Pharmaceutical Co., Ltd.) and removing the supernatant by centrifugation at 1500 rpm for 10 minutes were repeated three times to obtain spleen cells. The obtained spleen cells were mixed with mouse myeloma cells SP2/0 (purchased from ATCC) at a ratio of 10:1. 200 µL of an RPMI1640 medium containing 10% FBS was heated to 37° C. and mixed with 800 µL of PEG1500 (Boehringer Ingelheim GmbH), and the PEG solution thus prepared was added to the cell mixture, which was then left standing for 5 minutes for cell fusion. After removal of the supernatant by centrifugation at 1700 rpm for 5 minutes, the cells were suspended in 150 mL of an RPMI1640 medium containing 15% FBS supplemented with 2% equivalent of a HAT solution (Gibco) (HAT selective medium). This suspension was inoculated to fifteen 96-well plates (Nunc) at 100 µL/well. The spleen cells and the myeloma cells were fused by culture under conditions at 37° C. for 7 days in 5% $CO_2$ to obtain hybridomas.

The prepared hybridomas were screened with the binding affinity of antibodies produced by the hybridomas against CAPRIN-1 as an indicator. The 1 µg/mL CAPRIN-1 solution was added to a 96-well plate at 100 µL/well and left standing at 4° C. for 18 hours. Each well was washed three times with PBS-T. Then, a 0.5% bovine serum albumin (BSA) solution (Sigma-Aldrich Corp.) was added thereto at 400 µL/well and left standing at room temperature for 3 hours. The solution in each well was discarded, and each well was washed three times with 400 µL of PBS-T. Then, the culture supernatant of each hybridoma obtained above was added thereto at 100 µL/well and left standing at room temperature for 2 hours. Each well was washed three times with PBS-T. Then, HRP-labeled anti-mouse IgG (H+L) antibodies (Life Technologies, Inc.) diluted 5000-fold with PBS were added thereto at 100 µL/well and left standing at room temperature for 1 hour. Each well was washed three times with PBS-T. Then, a TMB substrate solution (Thermo Fisher Scientific Inc.) was added thereto at 100 µL/well and left standing for 15 to 30 minutes to cause color reaction. After the color development, the reaction was terminated by the addition of 1 N sulfuric acid at 100 µL/well. The absorbance was measured at 450 nm and 595 nm using an absorption spectrometer. As a result, several hybridomas producing antibodies having high absorbance were selected as candidate lines of the hybridoma of interest.

The selected hybridomas were added to a 96-well plate at a density of 0.5 cells/well and cultured in the plate. One week later, hybridomas forming single colonies in the wells were observed. The cells in these wells were further cultured, and the cloned hybridomas were screened in the same way as above with the binding affinity of antibodies produced by the hybridomas against CAPRIN-1 as an indicator. A plurality of hybridoma lines producing monoclonal antibodies reactive with CAPRIN-1 protein was obtained. The culture supernatants of these hybridomas were purified using a protein G carrier to obtain 150 monoclonal antibodies binding to CAPRIN-1.

Next, monoclonal antibodies above were screened for antibodies reactive with the surface of breast cancer cells expressing CAPRIN-1. Specifically, $10^6$ cells of a human breast cancer cell line MDA-MB-231V were centrifuged in a 1.5-mL microcentrifuge tube. 100 µL of the supernatant of each hybridoma obtained above was added thereto and left standing for 1 hour on ice. After washing with PBS, FITC-labeled goat anti-mouse IgG antibodies (Invitrogen) diluted 500-fold with PBS containing 0.1% fetal bovine serum were added thereto and left standing for 1 hour on ice. After washing with PBS, the fluorescence intensity was measured using FACSCalibur (Becton, Dickinson and Company). On the other hand, the same operation as above was performed by the addition of a medium instead of the antibodies to prepare a control. As a result, 10 monoclonal antibodies (#1 to #10) having stronger fluorescence intensity than that of the control, i.e., reactive with the surface of breast cancer cells, were selected. The respective amino sequences of the heavy chain and light chain variable regions of these monoclonal antibodies are shown in SEQ ID NOs: 44 to 60. The monoclonal antibody #1 comprises the heavy chain variable region shown in SEQ ID NO: 44 and the light chain variable region shown in SEQ ID NO: 45; the monoclonal antibody #2 comprises the heavy chain variable region shown in SEQ ID NO: 44 and the light chain variable region shown in SEQ ID NO: 46; the monoclonal antibody #3 comprises the heavy chain variable region shown in SEQ ID NO: 44 and the light chain variable region shown in SEQ ID NO: 47; the monoclonal antibody #4 comprises the heavy chain variable region shown in SEQ ID NO: 44 and the light chain variable region shown in SEQ ID NO: 48; the monoclonal antibody #5 comprises the heavy chain variable region shown in SEQ ID NO: 49 and the light chain variable region shown in SEQ ID NO: 50; the monoclonal antibody #6 comprises the heavy chain variable region shown in SEQ ID NO: 51 and the light chain variable region shown in SEQ ID NO: 52; the monoclonal antibody #7 comprises the heavy chain variable region shown in SEQ ID NO: 53 and the light chain variable region shown in SEQ ID NO: 54; the monoclonal antibody #8 comprises the heavy chain variable region shown in SEQ ID NO: 55 and the light chain variable region shown in SEQ ID NO: 56; the monoclonal antibody #9 comprises the heavy chain variable region shown in SEQ ID NO: 57 and the light chain variable region shown in SEQ ID NO: 58; and the monoclonal antibody #10 comprises the heavy chain variable region shown in SEQ ID NO: 59 and the light chain variable region shown in SEQ ID NO: 60.

(2) Identification of Peptide in CAPRIN-1 to which Mouse Anti-Human CAPRIN-1 Antibody Reactive with Cancer Cell Surface Binds The cancer cell surface-reactive mouse anti-human CAPRIN-1 monoclonal antibodies #1 to #10 obtained above were used to identify partial sequences in CAPRIN-1 recognized thereby.

First, DTT (Fluka) was added at a final concentration of 10 mM to 100 μL of a 1 μg/μL solution containing recombinant CAPRIN-1 dissolved in PBS, and reacted at 95° C. for 5 minutes to reduce disulfide bonds in the CAPRIN-1. Next, 20 mM (final concentration) iodoacetamide (Wako Pure Chemical Industries, Ltd.) was added thereto, followed by the alkylation reaction of thiol groups at 37° C. for 30 minutes under shading conditions. 50 μg each of the mouse anti-human CAPRIN-1 monoclonal antibodies #1 to #10 was added to 40 μg of the obtained reduced alkylated CAPRIN-1. The total amount of each mixture was adjusted to 1 mL with a 20 mM phosphate buffer solution (pH 7.0). The resulting mixture was reacted overnight at 4° C. while mixed by stirring.

Next, trypsin (Promega K.K.) was added at a final concentration of 0.2 μg to each reaction mixture and reacted at 37° C. for 1 hour, 2 hours, 4 hours, and 12 hours. Then, the reaction mixture was mixed with protein A-glass beads (GE Healthcare Bio-Sciences Ltd.) blocked with PBS containing 1% BSA (Sigma-Aldrich Corp.) and washed with PBS in advance, 1 mM calcium carbonate, and NP-40 buffer solution (20 mM phosphate buffer solution (pH 7.4), 5 mM EDTA, 150 mM NaCl, 1% NP-40) and reacted for 30 minutes.

Each reaction solution was washed with a 25 mM ammonium carbonate buffer solution (pH 8.0), followed by the elution of antigen-antibody complexes using 100 μL of 0.1% formic acid. The eluate was analyzed by LC-MS using Q-TOF Premier (Waters-MicroMass). This analysis followed the protocol attached to the instrument.

As a result, the polypeptide shown in SEQ ID NO: 61 was identified as a partial CAPRIN-1 sequence recognized by all of the mouse anti-human CAPRIN-1 monoclonal antibodies #1 to #10. In the polypeptide shown in SEQ ID NO: 61, the peptide shown in SEQ ID NO: 62 was further identified as a partial amino sequence recognized by the monoclonal antibodies #1 to #4, #5 to #7, and #9. The peptide shown in SEQ ID NO: 63 was further found to be recognized by the monoclonal antibody #10.

(3) Preparation of Chicken Anti-human CAPRIN-1 Monoclonal Antibody

300 μg of human CAPRIN-1 having the amino acid sequence shown in SEQ ID NO: 2 as prepared in Example 3 of WO2010/016526 was mixed with an equal amount of a complete Freund's adjuvant. This mixture was used as an antigen solution per chicken. The antigen solution was intraperitoneally administered to each 7-week-old chicken. Then, 7 boosters were performed every 4 weeks to complete immunization. Four days after the final shot, the spleen of each chicken was excised and ground between two sterilized glass slides. Procedures of washing with PBS(−) (Nissui Pharmaceutical Co., Ltd.) and removing the supernatant by centrifugation at 1500 rpm for 10 minutes were repeated three times to obtain spleen cells. The obtained spleen cells were mixed with light chain-deficient chicken myeloma cells established from chickens by transformation using avian reticuloendotheliosis virus, at a ratio of 5:1. 200 μL of an IMDM medium containing 10% FBS was heated to 37° C. and mixed with 800 μL of PEG1500 (Boehringer Ingelheim GmbH), and the PEG solution thus prepared was added to the cell mixture, which was then left standing for 5 minutes for cell fusion. After removal of the supernatant by centrifugation at 1700 rpm for 5 minutes, the cells were suspended in 300 mL of an IMDM medium containing 10% FBS supplemented with 2% equivalent of a HAT solution (Gibco) (HAT selective medium). This suspension was inoculated to thirty 96-well plates (Nunc) at 100 μL/well. The spleen cells and the chicken myeloma cells were fused by culture at 37° C. for 7 days under conditions of 5% $CO_2$ to obtain hybridomas.

The prepared hybridomas were screened with the binding affinity of antibodies produced by the hybridomas against CAPRIN-1 as an indicator. The 1 μg/mL CAPRIN-1 solution was added to a 96-well plate at 100 μL/well and left standing at 4° C. for 18 hours. Each well was washed three times with PBS-T. Then, a 0.5% bovine serum albumin (BSA) solution (Sigma-Aldrich Corp.) was added thereto at 400 μL/well and left standing at room temperature for 3 hours. The solution in each well was discarded, and each well was washed three times with 400 μL of PBS-T. Then, the culture supernatant of each hybridoma obtained above was added thereto at 100 μL/well and left standing at room temperature for 2 hours. Each well was washed three times with PBS-T. Then, HRP-labeled anti-chicken IgY antibodies (Sigma-Aldrich Corp.) diluted 5000-fold with PBS were added thereto at 100 μL/well and left standing at room temperature for 1 hour. Each well was washed three times with PBS-T. Then, a TMB substrate solution (Thermo Fisher Scientific Inc.) was added thereto at 100 μL/well and left standing for 15 to 30 minutes to cause color reaction. After the color development, the reaction was terminated by the addition of 1 N sulfuric acid at 100 μL/well. The absorbance was measured at 450 nm and 595 nm using an absorption spectrometer. As a result, several hybridomas producing antibodies having high absorbance were selected as candidate lines of the hybridoma of interest.

The selected hybridomas were added to a 96-well plate at a density of 0.5 cells/well and cultured in the plate. One week later, hybridomas forming single colonies in the wells were observed. The cells in these wells were further cultured, and the cloned hybridomas were screened with the binding affinity of antibodies produced by the hybridomas against CAPRIN-1 proteins as an indicator. As a result, a plurality of hybridoma lines producing monoclonal antibodies reactive with CAPRIN-1 proteins was obtained.

Next, these monoclonal antibodies were screened for antibodies reactive with the surface of breast cancer cells expressing CAPRIN-1. Specifically, $5 \times 10^5$ cells of a human breast cancer cell line MDA-MB-231V were centrifuged in a 1.5-mL microcentrifuge tube. 100 μL of the culture supernatant of each hybridoma obtained above was added thereto and left standing for 1 hour on ice. After washing with PBS, FITC-labeled goat anti-chicken IgG (H+L) antibodies (SouthernBiotech) diluted 30-fold with PBS containing 0.1% FBS were added thereto and left standing for 1 hour on ice. After washing with PBS, the fluorescence intensity was measured using FACSCalibur (Becton, Dickinson and Company). On the other hand, the same operation as above was performed using a medium for hybridoma culture to prepare a control sample. As a result, 1 monoclonal antibody (chicken anti-human CAPRIN-1 monoclonal antibody #11) having stronger fluorescence intensity than that of the control, i.e., reactive with the surface of breast cancer cells expressing CAPRIN-1, was selected.

(4) Preparation of Mouse-Chicken Chimeric Recombinant Antibody

The gene amplification fragment of the heavy chain variable region (SEQ ID NO: 64) of the chicken anti-human CAPRIN-1 monoclonal antibody #11 obtained in the preceding paragraph (3) was treated at both ends with restriction enzymes, then purified, and inserted according to a routine method into a pcDNA4/myc-His (life Technologies, Inc.) vector already having gene inserts of a chicken antibody-derived leader sequence and a mouse IgG1 H chain constant region. Also, the gene amplification fragment of the light chain variable region (SEQ ID NO: 65) of the chicken anti-human CAPRIN-1 monoclonal antibody #11 was treated at both ends with restriction enzymes, then purified, and inserted according to a routine method into a pcDNA3.1/myc-His (life Technologies, Inc.) vector already having gene inserts of a chicken antibody-derived leader sequence and a mouse IgG1 L chain constant region.

Next, the recombinant vector having the gene insert of the heavy chain variable region of the chicken anti-human CAPRIN-1 monoclonal antibody #11 and the recombinant vector having the gene insert of the light chain variable region of the chicken anti-human CAPRIN-1 monoclonal antibody #11 were introduced into CHO-K1 cells (obtained from Riken Cell Bank). Specifically, $2 \times 10^5$ CHO-K1 cells were cultured in 1 mL of a Ham's F12 medium (life Technologies, Inc.) containing of 10% FBS per well of a 12-well culture plate, and washed with PBS(−). Then, a fresh Ham's F12 medium containing 1 mL of 10% FBS per well was added thereto. 250 ng each of the vectors dissolved in 30 μL of OptiMEM (life Technologies, Inc.) was mixed with 30 μL of Polyfect transfection reagent (Qiagen N.V.), and this mixture was added to each well. The CHO-K1 cells cotransfected with the recombinant vectors were cultured in a Ham's F12 medium containing 10% FBS supplemented with 200 μg/mL Zeocin (life Technologies, Inc.) and 200 μg/mL Geneticin (Roche Diagnostics K.K.) and then inoculated to a 96-well plate at a density of 0.5 cells/well to prepare a cell line stably producing a mouse-chicken chimeric anti-human CAPRIN-1 monoclonal antibody #12 having the variable regions of the chicken monoclonal antibody #11 and the constant regions of mouse IgG1. The prepared cell line was cultured for 5 days in a 150-cm² flask at a density of $5 \times 10^5$ cells/mL using 30 mL of a serum-free OptiCHO medium (life Technologies, Inc.) to obtain a culture supernatant containing #12.

(5) Identification of CAPRIN-1 Epitope Recognized by Mouse-chicken Chimeric Anti-Human CAPRIN-1 Monoclonal Antibody #12

The cancer cell surface-reactive mouse-chicken chimeric anti-human CAPRIN-1 monoclonal antibody #12 obtained in the paragraph (4) was used to identify a CAPRIN-1 epitope region recognized thereby. 100 μg of recombinant CAPRIN-1 proteins was dissolved in a protein inhibitor-free dissolving buffer and reacted with the monoclonal antibody #12. To this solution, a digestive enzyme trypsin or chymotrypsin was added, followed by digestion reaction at a proper temperature. After the reaction, a protein G Sepharose carrier was added thereto, then reacted, and precipitated by centrifugation operation. After removal of the supernatant, the carrier was washed with a dissolving buffer and PBS and dissolved in 0.1% formic acid, and the supernatant was recovered. The recovered supernatant sample was applied to a reverse-phase column (HLB Extraction Cartridge (Waters-OASIS)) to obtain an antibody-free sample solution. The obtained sample was subjected to reverse-phase liquid chromatography (Chromatography Nanosytem (KYA Technologies Corp.)) to recover a solution containing only peptides. The solution was introduced to a tandem-type mass spectrometer Quadrupole-TOF Mass Spectrometer (Waters-MicroMass) and analyzed by MS/MS to detect the peptides contained in the sample. As a result, a peptide consisting of the amino acid sequence shown in SEQ ID NO: 66 was identified as a partial CAPRIN-1 sequence recognized by the mouse-chicken chimeric anti-human CAPRIN-1 monoclonal antibody #12. Also, this peptide refers to a partial CAPRIN-1 sequence recognized by the chicken anti-human CAPRIN-1 monoclonal antibody #11 constituting the variable regions of the antibody #12.

(6) Preparation of Human-chicken Chimeric Anti-human CAPRIN-1 Antibody

The gene amplification fragment of the heavy chain variable region (SEQ ID NO: 64) of the chicken anti-human CAPRIN-1 monoclonal antibody #11 obtained in the preceding paragraph (3) was treated at both ends with restriction enzymes, then purified, and inserted according to a routine method into a pcDNA4/myc-His (life Technologies, Inc.) vector already having gene inserts of a chicken antibody-derived leader sequence comprising SEQ ID NO: 67 and a human IgG1 H chain constant region comprising SEQ ID NO: 68. Also, the gene amplification fragment of the light chain variable region (SEQ ID NO: 65) of the chicken anti-human CAPRIN-1 monoclonal antibody #11 was treated at both ends with restriction enzymes, then purified, and inserted according to a routine method into a pcDNA3.1/myc-His (life Technologies, Inc.) vector already having gene inserts of a chicken antibody-derived leader sequence comprising SEQ ID NO: 68 and a human IgG1 L chain constant region comprising SEQ ID NO: 69.

Next, the recombinant vector having the gene insert of the heavy chain variable region of the antibody #11 above and the recombinant vector having the gene insert of the light chain variable region of the antibody #11 above were introduced into CHO-K1 cells (obtained from Riken Cell Bank). Specifically, $2 \times 10^5$ CHO-K1 cells were cultured in 1 mL of a Ham's F12 medium (life Technologies, Inc.) containing 10% FBS per well of a 12-well culture plate, and washed with PBS(−). Then, a fresh Ham's F12 medium containing 1 mL of 10% FBS per well was added thereto. 250 ng each of the vectors dissolved in 30 μL of OptiMEM (life Technologies, Inc.) was mixed with 30 μL of Polyfect transfection reagent (Qiagen N.V.), and this mixture was added to each well. The CHO-K1 cells cotransfected with the recombinant vectors were cultured in a Ham's F12 medium containing 10% FBS supplemented with 200 μg/mL Zeocin (life Technologies, Inc.) and 200 μg/mL Geneticin (Roche Diagnostics K.K.) and then inoculated to a 96-well plate at a density of 0.5 cells/well to prepare a cell line stably producing a human-chicken chimeric anti-human CAPRIN-1 antibody #13 having the variable regions of the chicken anti-human CAPRIN-1 monoclonal antibody #11 and the constant regions of human IgG1. The prepared cell line was cultured for 5 days in a 150-cm² flask at a density of $5 \times 10^5$ cells/mL using 30 mL of a serum-free OptiCHO medium (life Technologies, Inc.) to obtain a culture supernatant containing the antibody #13 above.

(7) Preparation of Mouse Anti-human CAPRIN-1 Monoclonal Antibody #14

In the same way as in the paragraph (1), a fusion protein of the amino acid sequence shown in SEQ ID NO: 63 identified in the paragraph (2) and a carrier protein KLH (keyhole limpet hemocyanin) was mixed as an immunogen with an equal amount of an adjuvant TiterMax Gold® (CytRx Corp.), and this mixture was subcutaneously administered at a dose of 20 μg/shot to each mouse at 7-day intervals. After administration with four shots in total, spleen cells were obtained from the mouse 3 days after the final immunization and fused with mouse myeloma cells in the same way as in the paragraph (1) to prepare hybridomas. Then, antibodies were screened using, as an indicator, the reactivity of each antibody contained in the culture supernatants of the prepared hybridomas with a 1 μg/mL solution of CAPRIN-1 prepared in Example 3 of WO2010/016526 or a fusion protein of the amino acid sequence shown in SEQ ID NO: 63 used as an immunogen and a carrier protein KLH. The 1 μg/mL CAPRIN-1 solution prepared in Example 3 of WO2010/016526 and the fusion protein (30 μg/mL) of the amino acid sequence shown in SEQ ID NO: 63 and a carrier protein BSA were separately added at 100 μL/well to 96-well plates and left standing at 4° C. for 18 hours. Each well was washed with PBS-T. Then, a Block Ace (DS Pharma Biomedical Co., Ltd.) solution was added thereto at 400 μL/well and left standing at room temperature for 3 hours. The solution in each well was removed, and each well was washed with PBS-T. Then, the culture supernatant of each hybridoma obtained above was added thereto at 100 μL/well and left standing at room temperature for 2 hours. Each well was washed with PBS-T. Then, HRP-labeled anti-mouse IgG (H+L) antibodies (life Technologies, Inc.) diluted 5000-fold with PBS were added thereto at 100 μL/well and left standing at room temperature for 1 hour. Each well was washed with PBS-T. Then, a TMB substrate solution (Thermo Fisher Scientific Inc.) was added thereto at 100 μL/well and left standing for 5 to 30 minutes to cause color reaction. After the color development, the reaction was terminated by the addition of 1 N sulfuric acid at 100 μL/well. The absorbance was measured at 450 nm and 595 nm using an absorption spectrometer. As a result, hybridomas producing antibodies having high absorbance were selected.

The selected hybridomas were added to a 96-well plate at a density of 0.3 cells/well and cultured in the plate. One week later, hybridomas forming single colonies in the wells were observed. The cells in these wells were further cultured, and the cloned hybridomas were screened in the same way as above with the binding affinity of antibodies produced by the hybridomas against the amino acid sequence shown in SEQ ID NO: 63 as a partial CAPRIN-1 sequence as an indicator to obtain hybridomas producing antibodies against the amino acid of SEQ ID NO: 63.

Monoclonal antibodies produced by the obtained hybridomas were screened for antibodies reactive with the surface of breast cancer cells expressing CAPRIN-1. Specifically, $10^6$ cells of a human breast cancer cell line MDA-MB-231V were centrifuged in a 1.5-mL microcentrifuge tube. 100 μL of the culture supernatant of each hybridoma obtained above was added thereto and left standing for 1 hour on ice. After washing with PBS, FITC-labeled goat anti-mouse IgG antibodies (Life Technologies, Inc.) diluted 500-fold with PBS containing 0.1% FBS were added thereto and left standing for 1 hour on ice. After washing with PBS, the fluorescence intensity was measured using FACSCalibur (Becton, Dickinson and Company). On the other hand, the same operation as above was performed using instead of the antibodies a sample composed of the serum of each untreated 6-week-old Balb/c mouse diluted 500-fold with a medium for hybridoma culture and a negative control sample composed of cells reacted only with secondary antibodies. As a result, a mouse anti-human CAPRIN-1 monoclonal antibody #14 having stronger fluorescence intensity than that of the negative control, i.e., reactive with the surface of breast cancer cells, was obtained. The antibody #14 consists of the heavy chain variable region shown in SEQ ID NO: 70 and the light chain variable region shown in SEQ ID NO: 71.

The obtained mouse anti-human CAPRIN-1 monoclonal antibody #14 was examined for its specific reaction with the amino acid sequence shown in SEQ ID NO: 63 as a partial CAPRIN-1 sequence used as an immunogen. A 30 μg/mL solution consisting of the amino acid sequence shown in SEQ ID NO: 63 prepared with a 0.1 M aqueous sodium carbonate solution and a similar 30 μg/mL consisting of a partial CAPRIN-1 sequence free from the amino acid sequence shown in SEQ ID NO: 63 were separately added to 96-well plates Immobilizer Amino for ELISA (Thermo Fisher Scientific Inc./Nunc) at 100 μg/mL and reacted all night and all day at 4° C. to bind the peptides to the wells. A 0.1 M aqueous sodium carbonate solution containing 10 mM ethanolamine was added to each peptide-bound well and left standing at room temperature for 1 hour. The solution in each well was removed, and each well was then washed with PBS-T. Then, a Block Ace solution was added thereto at 400 μL/well and left standing at room temperature for 3 hours. The solution in each well was removed, and each well was washed with PBS-T. Then, the culture supernatant containing the mouse monoclonal antibody #14 was added thereto at 50 μL/well and reacted at room temperature for 1 hour. Then, each well was washed with PBS-T, and HRP-labeled anti-mouse IgG (H+L) antibodies (life Technologies, Inc.) diluted 5000-fold with a Block Ace solution were added thereto at 50 μL/well and left standing at room temperature for 1 hour. Each well was fully washed with PBS-T. Then, a TMB substrate solution (Thermo Fisher Scientific Inc.) was added thereto at 100 μL/well and left standing for 5 to 30 minutes to cause color reaction. After the color development, the reaction was terminated by the addition of 1 N sulfuric acid at 100 μL/well. The absorbance was measured at 450 nm and 595 nm using an absorption spectrometer. As a result, the mouse monoclonal antibody #14 did not react with the partial CAPRIN-1 sequence free from the amino acid sequence shown in SEQ ID NO: 63, but specifically reacted only with the amino acid sequence shown in SEQ ID NO: 63. Thus, the polypeptide shown in SEQ ID NO: 63 was confirmed to contain an epitope region recognized by the anti CAPRIN-1 antibody #14.

Example 3

Selection of Optimum Antibody for CAPRIN-1 Detection (1) Selection of Antibody Using Human Breast Cancer Tissue 31 breast cancer tissue samples of paraffin-embedded human breast cancer tissue arrays (Medical & Biological Laboratories Co., Ltd.) were used in immunohistochemical staining. Each human breast cancer tissue array was treated at 60° C. for 3 hours and then placed in a staining bottle filled with said xylene, and procedures of replacing xylene with a fresh one every 5 minutes were performed three times. Subsequently, the same operation as in xylene was performed using ethanol and PBS-T. The human breast cancer tissue array was placed in a staining bottle filled with a 10 mM citrate buffer solution (pH 6.0) containing 0.05% Tween 20, treated at 125° C. for 5 minutes, and then left standing at room temperature for 40 minutes or longer. Excess water around sections was wiped off with Kimwipe. The section on each glass slide was encircled with a Dako pen (Dako, an Agilent Technologies Company), and an appropriate amount of Peroxidase Block (Dako, an Agilent Technologies Company) was added dropwise thereto. The glass slide was left standing at room temperature for 5 minutes and then placed in a staining bottle filled with PBS-T, and procedures of replacing PBS-T with a fresh one every 5 minutes were performed three times. A PBS-T solution containing 10% FBS was applied thereto as a blocking solution, and the glass slide was left standing at room temperature for 1 hour in a moist chamber. Next, 10 μg/mL of the mouse anti-human CAPRIN-1 monoclonal antibody #8 or #14 prepared in Example 2 in a PBS-T solution containing 5% FBS was applied thereto. The glass slide was left standing overnight at 4° C. in a moist chamber. After washing with PBS-T for 10 minutes three times, an appropriate amount of Peroxidase Labelled Polymer Conjugated (Dako, an Agilent Technologies Company) was added dropwise thereto, and the glass slide was left standing at room temperature for 30 minutes in a moist chamber. After washing with PBS-T for 10 minutes three times, a DAB staining solution (Dako, an Agilent Technologies Company) was applied thereto, and the glass slide was left standing at room temperature for approximately 10 minutes. Then, the staining solution was discarded, and the glass slide was washed with PBS-T for 10 minutes three times. After rinsing with distilled water, the glass slide was placed in 70%, 80%, 90%, 95%, and 100% ethanol solutions in this order for 1 minute per solution, and finally left standing overnight in xylene. The glass slide was taken out and the section was embedded in Glycergel Mounting Medium (Dako, an Agilent Technologies Company), followed by observation. The expression level of CAPRIN-1 in the tissues was evaluated according to the criteria given below. A slide that exhibited positive results was selected, and its CAPRIN-1 stain image was observed. First, the CAPRIN-1 stain image of cancer cells in the tissues, the intensity of positive staining, and the ratio of positive cells were observed by use of a ×4 objective lens of a light microscope. Next, the objective lens was changed to a ×10 or ×20 lens, and examination was made on whether the positive results were localized to the cell membrane or the cytoplasm. The detection results were evaluated by these methods and classified into scores 0 to 3. The details of the scores are as follows:

Score 0 (without CAPRIN-1 overexpression): Positive staining of the cell membrane is not observed or is observed in less than 10% of the cancer cells.

Score 1 (without CAPRIN-1 overexpression): Faint, almost unperceivable staining of the cell membrane is observed in 10% or more of the cancer cells, and these cancer cells are partially stained only at their cell membranes.

Score 2 (with CAPRIN-1 overexpression): Weak to moderate complete positive staining of the cell membrane is observed in 10% or more of the cancer cells, or strong complete positive staining of the cell membrane is observed in 10% or more and 30% or less of the cancer cells.

Score 3 (with CAPRIN-1 overexpression): Strong complete positive staining of the cell membrane is observed in 30% or more of the cancer cells.

A tissue is determined as CAPRIN-1-positive cancer tissue, when its assay results are given score 2 and 3.

As a result, the expression of CAPRIN-1 in the breast cancer tissues was successfully observed using both of the antibodies. The results of immunohistochemical staining using the antibody #8 exhibited score 2 for 14 samples and score 3 for 1 sample, and the number of CAPRIN-1-positive samples was 15 samples. By contrast, the result of immunohistochemical staining using the antibody #14 exhibited score 2 for 12 samples and score 3 for 8 samples, and the number of CAPRIN-1-positive samples was 20 samples. Thus, the more highly sensitive antibody #14 was selected for the detection of CAPRIN-1 using human cancer tissues.

(2) Detection of CAPRIN-1 on Various Human Normal Tissues by Immunohistochemical Staining Method Using Antibody #14

Human normal tissue array (US Biomax, Inc.) (including brain, thyroid gland, lung, spleen, kidney, esophagus, stomach, large bowel, pancreas, muscle, skin, salivary gland, ovary, uterus, mammary gland, placenta, bone marrow, testis, and prostate tissues) was used in immunohistochemical staining. Excess water around a section was wiped off with Kimwipe. The section on the glass slide was encircled with a Dako pen (Dako, an Agilent Technologies Company), and an appropriate amount of Peroxidase Block (Dako, an Agilent Technologies Company) was added dropwise thereto. The glass slide was left standing at room temperature for 5 minutes and then placed in a staining bottle filled with PBS-T, and procedures of replacing PBS-T with a fresh one every 5 minutes were performed three times. A PBS-T solution containing 10% FBS was applied thereto as a blocking solution, and the glass slide was left standing at room temperature for 1 hour in a moist chamber. Next, 10 μg/mL of the mouse anti-human CAPRIN-1 monoclonal antibody #14 prepared in Example 2 in a PBS-T solution containing 5% FBS, and this solution was applied thereto. The glass slide was left standing overnight at 4° C. in a moist chamber. After washing with PBS-T for 10 minutes three times, an appropriate amount of Peroxidase Labelled Polymer Conjugated (Dako, an Agilent Technologies Company) was added dropwise thereto, and the glass slide was left standing at room temperature for 30 minutes in a moist chamber. After washing with PBS-T for 10 minutes three times, a DAB staining solution (Dako, an Agilent Technologies Company) was applied thereto, and the glass slide was left standing at room temperature for approximately 10 minutes. Then, the staining solution was discarded, and the glass slide was washed with PBS-T for 10 minutes three times. After rinsing with distilled water, the glass slide was placed in 70%, 80%, 90%, 95%, and 100% ethanol solutions in this order for 1 minute per solution, and finally left standing overnight in xylene. The glass slide was taken out and enclosed in Glycergel Mounting Medium (Dako, an Agilent Technologies Company), followed by observation.

The expression level of CAPRIN-1 in the tissues was evaluated according to the criteria given below. A slide that exhibited positive results was selected, and its CAPRIN-1 stain image was confirmed. First, the CAPRIN-1 stain image of cancer cells in the tissues, the intensity of positive staining, and the ratio of positive cells were observed by use of a ×4 objective lens of a light microscope. Next, the objective lens was changed to a ×10 or ×20 lens, and examination was made on whether the positive results were derived from the cell membrane or localized to the cytoplasm. The detection results were evaluated by these methods and classified into scores 0 to 3. The details of the scores are as follows:

Score 0 (without CAPRIN-1 overexpression): Positive staining of the cell membrane is not observed or is observed in less than 10% of the cancer cells.

Score 1 (without CAPRIN-1 overexpression): Faint, almost unperceivable staining of the cell membrane is observed in 10% or more of the cancer cells, and these cancer cells are partially stained only at their cell membranes.

Score 2 (with CAPRIN-1 overexpression): Weak to moderate complete positive staining of the cell membrane is observed in 10% or more of the cancer cells, or strong complete positive staining of the cell membrane is observed in 10% or more and 30% or less of the cancer cells.

Score 3 (with CAPRIN-1 overexpression): Strong complete positive staining of the cell membrane is observed in 30% or more of the cancer cells.

A tissue was determined as CAPRIN-1-positive cancer tissue, when its detection results were given score 2 or 3.

The uterus and prostate tissues were given score 1, whereas the other tissues were all given score 0. Thus, the expression of CAPRIN-1 was not observed in the human normal tissues.

(3) Detection of CAPRIN-1 on Various Human Cancer Tissues by Immunohistochemical Staining Method Using Mouse Anti-human CAPRIN-1 Antibody #14

Various cancer tissues of paraffin-embedded human cancer tissue arrays (US Biomax, Inc.) were used in immunohistochemical staining. Each human cancer tissue array was treated at 60° C. for 3 hours and then placed in a staining bottle filled with xylene, and procedures of replacing said xylene with a fresh one every 5 minutes were performed three times. Subsequently, the same operation as in xylene was performed using ethanol and PBS-T. The human cancer tissue array was placed in a staining bottle filled with a 10 mM citrate buffer solution (pH 6.0) containing 0.05% Tween 20, treated at 125° C. for 5 minutes, and then left standing at room temperature for 40 minutes or longer. Excess water around sections was wiped off with Kimwipe. The section on each glass slide was encircled with a Dako pen (Dako, an Agilent Technologies Company), and an appropriate amount of Peroxidase Block (Dako, an Agilent Technologies Company) was added dropwise thereto. The glass slide was left standing at room temperature for 5 minutes and then placed in a staining bottle filled with PBS-T, and procedures of replacing PBS-T with a fresh one every 5 minutes were performed three times. A PBS-T solution containing 10% FBS was applied thereto as a blocking solution, and the glass slide was left standing at room temperature for 1 hour in a moist chamber. Next, 10 µg/mL of the monoclonal antibody #14 prepared in Example 2 in a PBS-T solution containing 5% FBS, and this solution was applied thereto. The glass slide was left standing overnight at 4° C. in a moist chamber. After washing with PBS-T for 10 minutes three times, an appropriate amount of Peroxidase Labelled Polymer Conjugated (Dako, an Agilent Technologies Company) was added dropwise thereto, and the glass slide was left standing at room temperature for 30 minutes in a moist chamber. After washing with PBS-T for 10 minutes three times, a DAB staining solution (Dako, an Agilent Technologies Company) was applied thereto, and the glass slide was left standing at room temperature for approximately 10 minutes. Then, the staining solution was discarded, and the glass slide was washed with PBS-T for 10 minutes three times. The glass slide was rinsed with distilled water and placed in 70%, 80%, 90%, 95%, and 100% ethanol solutions in this order for 1 minute per solution, and finally left standing overnight in xylene. The glass slide was taken out and enclosed in Glycergel Mounting Medium (Dako, an Agilent Technologies Company), followed by observation.

The expression level of CAPRIN-1 in the tissues was evaluated according to the criteria given below. A slide that exhibited positive results was selected, and its CAPRIN-1 stain image was confirmed. First, the CAPRIN-1 stain image of cancer cells in the tissues, the intensity of positive staining, and the ratio of positive cells were observed by use of a ×4 objective lens of a light microscope. Next, the objective lens was changed to a ×10 or ×20 lens, and examination was made on whether the positive results were derived from the cell membrane or localized to the cytoplasm. The detection results were evaluated by these methods and classified into scores 0 to 3. The details of the scores are as follows:

Score 0 (without CAPRIN-1 overexpression): Positive staining of the cell membrane is not observed or is observed in less than 10% of the cancer cells.

Score 1 (without CAPRIN-1 overexpression): Faint, almost unperceivable staining of the cell membrane is observed in 10% or more of the cancer cells, and these cancer cells are partially stained only at their cell membranes.

Score 2 (with CAPRIN-1 overexpression): Weak to moderate complete positive staining of the cell membrane is observed in 10% or more of the cancer cells, or strong complete positive staining of the cell membrane is observed in 10% or more and 30% or less of the cancer cells.

Score 3 (with CAPRIN-1 overexpression): Strong complete positive staining of the cell membrane is observed in 30% or more of the cancer cells.

A tissue is determined as CAPRIN-1-positive cancer tissue, when its assay results are given score 2 or 3.

As a result, CAPRIN-1 was confirmed to be positive in each of 16 out of 22 brain tumor tissue samples (64%), 19 out of 32 lung cancer tissue samples (59%), 18 out of 21 uterus cancer tissue samples (86%), 10 out of 16 esophagus cancer tissue samples (63%), 27 out of 30 kidney cancer tissue samples (90%), 14 out of 17 liver cancer tissue samples (82%), 11 out of 15 thyroid gland cancer tissue samples (73%), 10 out of 14 stomach cancer tissue samples (71%), 17 out of 19 pancreas cancer tissue samples (89%), 13 out of 13 prostate cancer tissue samples (100%), 12 out of 14 bladder cancer tissue samples (86%), 11 out of 14 large bowel cancer tissue samples (79%), 24 out of 30 skin cancer tissue samples (80%), and 16 out of 21 breast cancer tissue samples (76%).

(4) Detection of CAPRIN-1 Protein on Dog Breast Cancer Tissue by Immunohistochemical Staining Method Using Mouse Anti-human CAPRIN-1 Antibody #14

100 frozen breast cancer tissue samples of dogs pathologically diagnosed as malignant breast cancer were used in immunohistochemical staining. Each frozen dog breast cancer tissue was sliced into 10 to 20 µm using Cryostat (Leica Biosystems), placed on a glass slide, and dried in air, together with the glass slide, for 30 minutes using a hair dryer to prepare a glass slide with a tissue slice placed thereon. Next, the glass slide was placed in a staining bottle filled with PBS-T (saline containing 0.05% Tween 20), and procedures of replacing PBS-T with a fresh one every 5 minutes were performed three times. Excess water around sections was wiped off with Kimwipe. The section on the glass slide was encircled with a Dako pen (Dako, an Agilent Technologies Company). Then, a PBS-T solution containing 10% fetal bovine serum was applied thereto as a blocking solution, and the glass slide was left standing at room temperature for 1 hour in a moist chamber. Next, 10 µg/mL of the mouse anti-human CAPRIN-1 monoclonal antibody #8 or #14 prepared in Example 2 in a blocking solution, and this solution was applied thereto. The glass slide was left standing overnight at 4° C. in a moist chamber. After washing with PBS-T for 10 minutes three times, MOM biotin-labeled anti-IgG antibodies (Vectastain) diluted 250-fold with a blocking solution were applied thereto, and the glass slide was left standing at room temperature for 1 hour in a moist chamber. After washing with PBS-T for 10 minutes three times, avidin-biotin ABC reagent (Vectastain) was applied thereto, and the glass slide was left standing at room temperature for 5 minutes in a moist chamber. After washing with PBS-T for 10 minutes three times, a DAB staining solution (10 mg of DAB+10 µL of 30% $H_2O_2$/50 mL of 0.05 M Tris-HCl (pH 7.6)) was applied thereto, and the glass slide was left standing at room temperature for 30 minutes in a moist chamber. The glass slide was rinsed with distilled water. A hematoxylin reagent (Dako, an Agilent Technologies Company) was applied thereto, and the glass slide was left standing at room temperature for 1 minute and then rinsed with distilled water. The glass slide was placed in 70%, 80%, 90%, 95%, and 100% ethanol solutions in this order for 1 minute per solution, and finally left standing overnight in xylene. The glass slide was taken out and enclosed in Glycergel Mounting Medium (Dako, an Agilent Technologies Company), followed by observation. The expression level of CAPRIN-1 in the tissues was evaluated according to the criteria given below. A slide that exhibited positive results was selected, and its CAPRIN-1 stain image was confirmed. First, the CAPRIN-1 stain image of cancer cells in the tissues, the intensity of positive staining, and the ratio of positive cells were observed by use of a ×4 objective lens of a light microscope. Next, the objective lens was changed to a ×10 or ×20 lens, and examination was made on whether the positive results were derived from the cell membrane or localized to the cytoplasm. The detection results were evaluated by these methods and classified into scores 0 to 3. The details of the scores are as follows:

Score 0 (without CAPRIN-1 overexpression): Positive staining of the cell membrane is not observed or is observed in less than 10% of the cancer cells.

Score 1 (without CAPRIN-1 overexpression): Faint, almost unperceivable staining of the cell membrane is observed in 10% or more of the cancer cells, and these cancer cells are partially stained only at their cell membranes.

Score 2 (with CAPRIN-1 overexpression): Weak to moderate complete positive staining of the cell membrane is observed in 10% or more of the cancer cells, or strong complete positive staining of the cell membrane is observed in 10% or more and 30% or less of the cancer cells.

Score 3 (with CAPRIN-1 overexpression): Strong complete positive staining of the cell membrane is observed in 30% or more of the cancer cells.

A cancer-bearing dog tissue was confirmed to be CAPRIN-1-positive and to get effective therapeutic effects by the administration of a therapeutic drug targeting CAPRIN-1, when its assay results were given score 2 or 3.

As a result, the expression of CAPRIN-1 in the dog breast cancer tissues was successfully observed using both of the antibodies. Specifically, the results of immunohistochemical staining using the antibody #8 exhibited score 2 for 69 samples and score 3 for 11 samples, and the number of CAPRIN-1-positive samples was 80 samples (80%). By contrast, the result of immunohistochemical staining using the antibody #14 exhibited score 2 for 50 samples and score 3 for 32 samples, and the number of CAPRIN-1-positive samples was 82 samples (82%).

(5) Detection of CAPRIN-1 on Cat Breast Cancer Tissue by Immunohistochemical Staining Method Using Mouse Anti-human CAPRIN-1 Monoclonal Antibody #14

30 frozen breast cancer tissue samples of cats pathologically diagnosed as malignant breast cancer were used in immunohistochemical staining. Each frozen cat cancer tissue was sliced into 10 to 20 µm using Cryostat (Leica Biosystems), placed on a glass slide, and dried in air, together with the glass slide, for 30 minutes using a hair dryer to prepare a glass slide with a tissue slice placed thereon. Next, the glass slide was placed in a staining bottle filled with PBS-T (saline containing 0.05% Tween 20), and procedures of replacing PBS-T with a fresh one every 5 minutes were performed three times. Excess water around sections was wiped off with Kimwipe. The section on the glass slide was encircled with a Dako pen (Dako, an Agilent Technologies Company). Then, a PBS-T solution containing 10% fetal bovine serum was applied thereto as a blocking solution, and the glass slide was left standing at room temperature for 1 hour in a moist chamber. Next, 10 µg/mL of the mouse anti-human CAPRIN-1 monoclonal antibody #8 or #14 prepared in Example 2 in a blocking solution, and this solution was applied thereto. The glass slide was left standing overnight at 4° C. in a moist chamber. After washing with PBS-T for 10 minutes three times, MOM biotin-labeled anti-IgG antibodies (Vectastain) diluted 250-fold with a blocking solution were applied thereto, and the glass slide was left standing at room temperature for 1 hour in a moist chamber. After washing with PBS-T for 10 minutes three times, avidin-biotin ABC reagent (Vectastain) was applied thereto, and the glass slide was left standing at room temperature for 5 minutes in a moist chamber. After washing with PBS-T for 10 minutes three times, a DAB staining solution (10 mg of DAB+10 µL of 30% $H_2O_2$/50 ml of 0.05 M Tris-HCl (pH 7.6)) was applied thereto, and the glass slide was left standing at room temperature for 30 minutes in a moist chamber. The glass slide was rinsed with distilled water. A hematoxylin reagent (Dako, an Agilent Technologies Company) was applied thereto, and the glass slide was left standing at room temperature for 1 minute and then rinsed with distilled water. The glass slide was placed in 70%, 80%, 90%, 95%, and 100% ethanol solutions in this order for 1 minute per solution, and finally left standing overnight in xylene. The glass slide was taken out and enclosed in Glycergel Mounting Medium (Dako, an Agilent Technologies Company), followed by observation. The expression level of CAPRIN-1 in the tissues was evaluated according to the criteria given below. A slide that exhibited positive results was selected, and its CAPRIN-1 stain image was confirmed. First, the CAPRIN-1 stain image of cancer cells in the tissues, the intensity of positive staining, and the ratio of positive cells were observed by use of a ×4 objective lens of a light microscope. Next, the objective lens was changed to a ×10 or ×20 lens, and examination was made on whether the positive results were derived from the cell membrane or localized to the cytoplasm. The detection results were evaluated by these methods and classified into scores 0 to 3. The details of the scores are as follows:

Score 0 (without CAPRIN-1 overexpression): Positive staining of the cell membrane is not observed or is observed in less than 10% of the cancer cells.

Score 1 (without CAPRIN-1 overexpression): Faint, almost unperceivable staining of the cell membrane is observed in 10% or more of the cancer cells, and these cancer cells are partially stained only at their cell membranes.

Score 2 (with CAPRIN-1 overexpression): Weak to moderate complete positive staining of the cell membrane is observed in 10% or more of the cancer cells, or strong complete positive staining of the cell membrane is observed in 10% or more and 30% or less of the cancer cells.

Score 3 (with CAPRIN-1 overexpression): Strong complete positive staining of the cell membrane is observed in 30% or more of the cancer cells.

A cancer-bearing cat tissue was confirmed to be CAPRIN-1-positive and to get effective therapeutic effects by the administration of a therapeutic drug targeting CAPRIN-1, when its assay results were given score 2 or 3.

As a result, the expression of CAPRIN-1 in the cat breast cancer tissues was successfully observed using both of the antibodies. Specifically, the results of immunohistochemical staining using the antibody #8 exhibited score 2 for 20 samples and score 3 for 4 samples, and the number of CAPRIN-1-positive samples was 24 samples (80%). By contrast, the result of immunohistochemical staining using the antibody #14 exhibited score 2 for 18 samples and score 3 for 6 samples, and the number of CAPRIN-1-positive samples was 27 samples (90%).

Example 4

Correlation of CAPRIN-1 Expression Evaluated Using Cancer Sample with Antitumor Effect of Anti-CAPRIN-1 Antibody (1) Detection of CAPRIN-1 by Immunohistochemical Staining Method Using Cancer Tissue Derived from Cancer-bearing Mouse in which Mouse Cancer Cell was Transplanted Two mouse-derived cancer cell lines (B16F10 and EMT-6) were subcutaneously transplanted (each for 5 mice) into the dorsal regions of 26 Balb/c mice (Japan SLC, Inc.) and grown until the size of tumor became approximately 7 mm in diameter. Three subjects were selected from each of these two mouse groups respectively having the 2 types of cancer cell transplants. A tumor mass was excised from each mouse, cut open in PBS, and perfusion-fixed overnight in a 0.1 M phosphate buffer solution (pH 7.4) containing 4% paraformaldehyde (PFA). The perfusate was discarded, and the tissue surface of each organ was rinsed with PBS. A PBS solution containing 10% sucrose was added to a 50-mL centrifuge tube, in which each cancer tissue was then placed and shaken at 4° C. for 2 hours using a rotor. The solution was replaced with a PBS solution containing 20% sucrose, and again, the resulting solution was left standing at 4° C. until the cancer tissue was precipitated. Then, the solution was replaced with a PBS solution containing 30% sucrose, and the resulting solution was left standing at 4° C. until the cancer tissue was precipitated. The cancer tissue was taken out, and necessary portions were cut off with a surgical knife. Next, OCT compound (Tissue Tek) was poured onto the tissue surface and spread over the surface. Then, the tissue was disposed on Cryomold. The Cryomold was placed on dry ice, and the tissue was quickly frozen, then sliced into 10 to 20 μm using Cryostat (Leica Biosystems), placed on a glass slide, and dried in air, together with the glass slide, for 30 minutes using a hair dryer to prepare a glass slide with a tissue slice placed thereon. On the next day, the glass slide was washed with PBS(−) three times. PBS(−) containing 5% goat serum was applied thereto as a blocking solution, and the glass slide was left standing at room temperature for 1 hour in a moist chamber. Next, 10 μg/mL of the mouse anti-human CAPRIN-1 monoclonal antibody #8 or #14 prepared in Example 2 in a PBS(−) solution, and this solution was applied thereto. The glass slide was left standing overnight at 4° C. in a moist chamber. After washing with PBS(−) for 5 minutes five times, an appropriate amount of Peroxidase Labelled Polymer Conjugated (Dako, an Agilent Technologies Company) was added dropwise thereto, and the glass slide was left standing at room temperature for 30 minutes in a moist chamber. After washing with PBS-T for 5 minutes six times, a DAB staining solution (Dako, an Agilent Technologies Company) was applied thereto, and the glass slide was left standing at room temperature for approximately 10 minutes. Then, the staining solution was discarded, and the glass slide was washed with PBS(−) for 5 minutes three times. Then, the glass slide was enclosed in Glycergel Mounting Medium (Dako, an Agilent Technologies Company), followed by observation. As a result of scoring as described in Example 3, the results of immunohistochemical staining using the antibody #8 exhibited score 1 both for the melanoma-derived cancer cells B16F10 and for the breast cancer-derived cells EMT-6. Thus, CAPRIN-1 expression was not detected. On the other hand, the results of immunohistochemical staining using the antibody #14 exhibited score 1 for the cancer cells B16F10, as with the antibody #8, but exhibited score 3 for the cancer cells EMT-6.

(2) Antitumor Effect of Anti-CAPRIN-1 Antibody

The human-chicken chimeric anti-human CAPRIN-1 antibody #13 was studied for its antitumor effect using the cancer-bearing mice prepared in the preceding paragraph (1). Of 10 cancer-bearing mice in which each cancer cell line (B16F10 and EMT-6) was transplanted, 5 cancer-bearing mice in each group underwent the intraperitoneal administration of the antibody #13 at a dose of 200 μg (200 μL) per mouse. Then, the antibody was intraperitoneally administered at the same dose as above to each cancer-bearing mouse a total of 3 times for 2 days to prepare a study group. The size of tumor was measured every day, and the antitumor effect of the antibody #13 was observed. On the other hand, PBS(−) was administered instead of the antibody to the remaining 5 cancer-bearing mice, which were in turn used as a control group.

As a result of observing the antitumor effect, the tumor volumes of the B16F10-transplanted study group receiving the antibody #13 were increased to approximately 150%, 200%, 370%, and 630% at days 4, 6, 8, and 11, respectively, with the tumor volume at the start of antibody administration defined as 100%. On the other hand, the tumor volumes of the EMT-6-transplanted study group receiving the antibody #13 were reduced to 51% at day 4, approximately 31% at day 6, and 9% at day 8 with the tumor volume at the start of antibody administration defined as 100%, and their tumors were almost completely regressed by days 10 to 14. The tumor volumes of both of the B16F10-transplanted study group and the EMT-6-transplanted study group in the control group receiving PBS(−) were increased to approximately 230%, 290%, 470%, and 800% at days 4, 6, 8, and 11, respectively.

From the results mentioned above, the results of detection of CAPRIN-1 using the antibody #8 were not observed to correlate with cancer therapeutic effects based on the antitumor activity of the antibody, whereas the results of detection of CAPRIN-1 using the antibody #14 were observed to correlate with cancer therapeutic effects based on the antitumor activity of the antibody. Specifically, the results of detecting CAPRIN-1 using the antibody #14 exhibited score 3 for the EMT-6 transplant-derived cancer tissues, demonstrating CAPRIN-1 overexpression and pharmacological effects based on the antitumor activity of the administered antibody.

On the other hand, the results of detection of the expression of CAPRIN-1 using the antibody #14 exhibited score 1 for the B16F10 transplant-derived cancer tissues. Thus, the expression of CAPRIN-1 was not detected. In addition, the antibody #13 having antitumor activity did not produce pharmacological effects when administered to the cancer-bearing mice in which B16F10 were transplanted.

From these results, it can be predicted that a cancer or an individual determined as having a high expression level of CAPRIN-1 by detecting CAPRIN-1 in a cancer tissue using the antibody #14 of the present invention specifically binding to CAPRIN-1 can get high therapeutic effects by administering an anti-CAPRIN-1 antibody having antitumor effects.

INDUSTRIAL APPLICABILITY

The present invention is industrially useful for the diagnosis of cancers.

All publications, patents, and patent applications cited herein are incorporated herein by reference in their entirety.

FREE TEXT OF SEQUENCE LISTING

SEQ ID NOs: 31 to 36, and 38 to 42: Primer

The invention claimed is:

1. A method for detecting a cancer in an individual, comprising: detecting an expression level of CAPRIN-1 in a biological sample from the individual above that of a healthy subject through an antigen-antibody reaction comprising contacting the sample with a monoclonal antibody having a heavy chain variable region comprising the amino acid sequence shown in SEQ ID NO:70 and a light chain variable region comprising the amino acid sequence shown in SEQ ID NO:71, or an antigen-binding fragment thereof.

2. The method according to claim 1, wherein CAPRIN-1 to be detected is
   (a) a polypeptide having the amino acid sequence shown in any even-numbered SEQ ID NO shown in SEQ ID NOs: 2 to 30 in the Sequence Listing, or
   (b) a polypeptide having 85% or higher sequence identity to the polypeptide.

3. The method according to claim 1, wherein the biological sample is derived from a human, a dog, or a cat.

4. The method according to claim 1, wherein the biological sample is derived from a dog, and CAPRIN-1 to be detected has an amino acid sequence shown in SEQ ID NO: 6, 8, 10, 12, or 14.

5. The method according to claim 1, wherein the biological sample is derived from a human, and CAPRIN-1 to be detected has an amino acid sequence shown in SEQ ID NO: 2 or 4.

6. The method according to claim 1, wherein the detection of the expression level of CAPRIN-1 is carried out using an immunological assay method.

7. The method according to claim 6, wherein the immunological assay method is ELISA and/or an immunohistochemical staining method.

8. The method according to claim 1, wherein the biological sample is a body fluid, a tissue, or a cell.

9. The method according to claim 1, wherein the cancer is at least one cancer selected from the group consisting of breast cancer, brain tumor, esophagus cancer, stomach cancer, lung cancer, liver cancer, kidney cancer, thyroid gland cancer, spleen cancer, pancreas cancer, large bowel cancer, skin cancer, ovary cancer, uterus cancer, prostate cancer, bladder cancer, testis cancer, osteosarcoma, and fibrosarcoma.

10. The method according to claim 2, wherein the biological sample is derived from a human, a dog, or a cat.

11. The method according to claim 2, wherein the biological sample is derived from a dog, and CAPRIN-1 to be detected has an amino acid sequence shown in SEQ ID NO: 6, 8, 10, 12, or 14.

12. The method according to claim 3, wherein the biological sample is derived from a dog, and CAPRIN-1 to be detected has an amino acid sequence shown in SEQ ID NO: 6, 8, 10, 12, or 14.

13. The method according to claim 2, wherein the biological sample is derived from a human, and CAPRIN-1 to be detected has an amino acid sequence shown in SEQ ID NO: 2 or 4.

14. The method according to claim 3, wherein the biological sample is derived from a human, and CAPRIN-1 to be detected has an amino acid sequence shown in SEQ ID NO: 2 or 4.

15. A method for selecting an individual-specific therapeutic drug for a cancer, comprising: detecting an expression level of CAPRIN-1 in a biological sample from the individual comprising contacting the sample with a monoclonal antibody having a heavy chain variable region comprising the amino acid sequence shown in SEQ ID NO:70 and a light chain variable region comprising the amino acid sequence shown in SEQ ID NO:71, or an antigen-binding fragment thereof; and, when the expression level is statistically significantly higher than that of a healthy individual, selecting a CAPRIN-1-targeting drug as a therapeutic drug for the cancer suitable for administration to the individual from which the biological sample was derived.

16. The method for selecting an individual-specific therapeutic drug for a cancer according to claim 15, wherein the CAPRIN-1-targeting drug is a monoclonal antibody having immunological reactivity with CAPRIN-1, or an antigen-binding fragment thereof.

17. A method for detecting CAPRIN-1 in an individual, comprising: detecting CAPRIN-1 in a biological sample from the individual through an antigen-antibody reaction comprising contacting the sample with a monoclonal antibody having a heavy chain variable region comprising the amino acid sequence shown in SEQ ID NO:70 and a light chain variable region comprising the amino acid sequence shown in SEQ ID NO:71, or an antigen-binding fragment thereof.

* * * * *

SEQUENCE LISTING

```
<160> NUMBER OF SEQ ID NOS: 71

<210> SEQ ID NO 1
<211> LENGTH: 5562
<212> TYPE: DNA
<213> ORGANISM: Homo sapiens
<220> FEATURE:
<221> NAME/KEY: CDS
<222> LOCATION: (190)..(2319)

<400> SEQUENCE: 1
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccaccttg ccccctcagc tgcccactcg tgatttccag cggcctccgc      180 gcgcgcacg atg ccc tcg gcc acc agc cac agc ggg agc ggc agc aag tcg    231
            Met Pro Ser Ala Thr Ser His Ser Gly Ser Gly Ser Lys Ser
            1               5                   10 tcc gga ccg cca ccg ccg tcg ggt tcc tcc ggg agt gag gcg gcc gcg       279
Ser Gly Pro Pro Pro Pro Ser Gly Ser Ser Gly Ser Glu Ala Ala Ala
15                  20                  25                  30 gga gcc ggg gcc gcc gcg ccg gct tct cag cac ccc gca acc ggc acc       327
Gly Ala Gly Ala Ala Ala Pro Ala Ser Gln His Pro Ala Thr Gly Thr
                35                  40                  45 ggc gct gtc cag acc gag gcc atg aag cag att ctc ggg gtg atc gac       375
Gly Ala Val Gln Thr Glu Ala Met Lys Gln Ile Leu Gly Val Ile Asp
            50                  55                  60 aag aaa ctt cgg aac ctg gag aag aaa aag ggt aag ctt gat gat tac       423
Lys Lys Leu Arg Asn Leu Glu Lys Lys Lys Gly Lys Leu Asp Asp Tyr
65                  70                  75 cag gaa cga atg aac aaa ggg gaa agg ctt aat caa gat cag ctg gat       471
Gln Glu Arg Met Asn Lys Gly Glu Arg Leu Asn Gln Asp Gln Leu Asp
    80                  85                  90 gcc gtt tct aag tac cag gaa gtc aca aat aat ttg gag ttt gca aaa       519
Ala Val Ser Lys Tyr Gln Glu Val Thr Asn Asn Leu Glu Phe Ala Lys
95                  100                 105                 110 gaa tta cag agg agt ttc atg gca cta agt caa gat att cag aaa aca       567
Glu Leu Gln Arg Ser Phe Met Ala Leu Ser Gln Asp Ile Gln Lys Thr
                115                 120                 125 ata aag aag aca gca cgt cgg gag cag ctt atg aga gaa gaa gct gaa       615
Ile Lys Lys Thr Ala Arg Arg Glu Gln Leu Met Arg Glu Glu Ala Glu
            130                 135                 140 cag aaa cgt tta aaa act gta ctt gag cta cag tat gtt ttg gac aaa       663
Gln Lys Arg Leu Lys Thr Val Leu Glu Leu Gln Tyr Val Leu Asp Lys
            145                 150                 155
```

-continued

| | | |
|---|---|---|
| ttg gga gat gat gaa gtg cgg act gac ctg aaa caa ggt ttg aat gga<br>Leu Gly Asp Asp Glu Val Arg Thr Asp Leu Lys Gln Gly Leu Asn Gly<br>160                       165                  170 | | 711 |
| gtg cca ata ttg tcc gaa gag gag ttg tca ttg ttg gat gaa ttc tat<br>Val Pro Ile Leu Ser Glu Glu Glu Leu Ser Leu Leu Asp Glu Phe Tyr<br>175                    180                    185                    190 | | 759 |
| aag cta gta gac cct gaa cgg gac atg agc ttg agg ttg aat gaa cag<br>Lys Leu Val Asp Pro Glu Arg Asp Met Ser Leu Arg Leu Asn Glu Gln<br>                        195                    200                    205 | | 807 |
| tat gaa cat gcc tcc att cac ctg tgg gac ctg ctg gaa ggg aag gaa<br>Tyr Glu His Ala Ser Ile His Leu Trp Asp Leu Leu Glu Gly Lys Glu<br>                        210                    215                    220 | | 855 |
| aaa cct gta tgt gga acc acc tat aaa gtt cta aag gaa att gtt gag<br>Lys Pro Val Cys Gly Thr Thr Tyr Lys Val Leu Lys Glu Ile Val Glu<br>              225                    230                    235 | | 903 |
| cgt gtt ttt cag tca aac tac ttt gac agc acc cac aac cac cag aat<br>Arg Val Phe Gln Ser Asn Tyr Phe Asp Ser Thr His Asn His Gln Asn<br>240                       245                    250 | | 951 |
| ggg ctg tgt gag gaa gaa gag gca gcc tca gca cct gca gtt gaa gac<br>Gly Leu Cys Glu Glu Glu Glu Ala Ala Ser Ala Pro Ala Val Glu Asp<br>255                       260                    265                    270 | | 999 |
| cag gta cct gaa gct gaa cct gag cca gca gaa gag tac act gag caa<br>Gln Val Pro Glu Ala Glu Pro Glu Pro Ala Glu Glu Tyr Thr Glu Gln<br>                        275                    280                    285 | | 1047 |
| agt gaa gtt gaa tca aca gag tat gta aat aga cag ttc atg gca gaa<br>Ser Glu Val Glu Ser Thr Glu Tyr Val Asn Arg Gln Phe Met Ala Glu<br>              290                    295                    300 | | 1095 |
| aca cag ttc acc agt ggt gaa aag gag cag gta gat gag tgg aca gtt<br>Thr Gln Phe Thr Ser Gly Glu Lys Glu Gln Val Asp Glu Trp Thr Val<br>              305                    310                    315 | | 1143 |
| gaa acg gtt gag gtg gta aat tca ctc cag cag caa cct cag gct gca<br>Glu Thr Val Glu Val Val Asn Ser Leu Gln Gln Gln Pro Gln Ala Ala<br>320                       325                    330 | | 1191 |
| tcc cct tca gta cca gag ccc cac tct ttg act cca gtg gct cag gca<br>Ser Pro Ser Val Pro Glu Pro His Ser Leu Thr Pro Val Ala Gln Ala<br>335                       340                    345                    350 | | 1239 |
| gat ccc ctt gtg aga aga cag cga gta caa gac ctt atg gca caa atg<br>Asp Pro Leu Val Arg Arg Gln Arg Val Gln Asp Leu Met Ala Gln Met<br>                        355                    360                    365 | | 1287 |
| cag ggt ccc tat aat ttc ata cag gat tca atg ctg gat ttt gaa aat<br>Gln Gly Pro Tyr Asn Phe Ile Gln Asp Ser Met Leu Asp Phe Glu Asn<br>              370                    375                    380 | | 1335 |
| cag aca ctt gat cct gcc att gta tct gca cag cct atg aat cca aca<br>Gln Thr Leu Asp Pro Ala Ile Val Ser Ala Gln Pro Met Asn Pro Thr<br>385                       390                    395 | | 1383 |
| caa aac atg gac atg ccc cag ctg gtt tgc cct cca gtt cat tct gaa<br>Gln Asn Met Asp Met Pro Gln Leu Val Cys Pro Pro Val His Ser Glu<br>400                       405                    410 | | 1431 |
| tct aga ctt gct cag cct aat caa gtt cct gta caa cca gaa gcg aca<br>Ser Arg Leu Ala Gln Pro Asn Gln Val Pro Val Gln Pro Glu Ala Thr<br>415                       420                    425                    430 | | 1479 |
| cag gtt cct ttg gta tca tcc aca agt gag ggg tac aca gca tct caa<br>Gln Val Pro Leu Val Ser Ser Thr Ser Glu Gly Tyr Thr Ala Ser Gln<br>                        435                    440                    445 | | 1527 |
| ccc ttg tac cag cct tct cat gct aca gag caa cga cca cag aag gaa<br>Pro Leu Tyr Gln Pro Ser His Ala Thr Glu Gln Arg Pro Gln Lys Glu<br>              450                    455                    460 | | 1575 |
| cca att gat cag att cag gca aca atc tct tta aat aca gac cag act<br>Pro Ile Asp Gln Ile Gln Ala Thr Ile Ser Leu Asn Thr Asp Gln Thr<br>              465                    470                    475 | | 1623 |

```
aca gca tca tca tcc ctt cct gct gcg tct cag cct caa gta ttt cag    1671
Thr Ala Ser Ser Ser Leu Pro Ala Ala Ser Gln Pro Gln Val Phe Gln
        480                 485                 490 gct ggg aca agc aaa cct tta cat agc agt gga atc aat gta aat gca    1719
Ala Gly Thr Ser Lys Pro Leu His Ser Ser Gly Ile Asn Val Asn Ala
495                 500                 505                 510 gct cca ttc caa tcc atg caa acg gtg ttc aat atg aat gcc cca gtt    1767
Ala Pro Phe Gln Ser Met Gln Thr Val Phe Asn Met Asn Ala Pro Val
                515                 520                 525 cct cct gtt aat gaa cca gaa act tta aaa cag caa aat cag tac cag    1815
Pro Pro Val Asn Glu Pro Glu Thr Leu Lys Gln Gln Asn Gln Tyr Gln
            530                 535                 540 gcc agt tat aac cag agc ttt tct agt cag cct cac caa gta gaa caa    1863
Ala Ser Tyr Asn Gln Ser Phe Ser Ser Gln Pro His Gln Val Glu Gln
        545                 550                 555 aca gag ctt cag caa gaa cag ctt caa aca gtg gtt ggc act tac cat    1911
Thr Glu Leu Gln Gln Glu Gln Leu Gln Thr Val Val Gly Thr Tyr His
    560                 565                 570 ggt tcc cca gac cag tcc cat caa gtg act ggt aac cac cag cag cct    1959
Gly Ser Pro Asp Gln Ser His Gln Val Thr Gly Asn His Gln Gln Pro
575                 580                 585                 590 cct cag cag aac act gga ttt cca cgt agc aat cag ccc tat tac aat    2007
Pro Gln Gln Asn Thr Gly Phe Pro Arg Ser Asn Gln Pro Tyr Tyr Asn
                595                 600                 605 agt cgt ggt gtg tct cgt gga ggc tcc cgt ggt gct aga ggc ttg atg    2055
Ser Arg Gly Val Ser Arg Gly Gly Ser Arg Gly Ala Arg Gly Leu Met
            610                 615                 620 aat gga tac cgg ggc cct gcc aat gga ttc aga gga gga tat gat ggt    2103
Asn Gly Tyr Arg Gly Pro Ala Asn Gly Phe Arg Gly Gly Tyr Asp Gly
        625                 630                 635 tac cgc cct tca ttc tct aac act cca aac agt ggt tat aca cag tct    2151
Tyr Arg Pro Ser Phe Ser Asn Thr Pro Asn Ser Gly Tyr Thr Gln Ser
    640                 645                 650 cag ttc agt gct ccc cgg gat tac tct ggc tat caa cgg gat gga tat    2199
Gln Phe Ser Ala Pro Arg Asp Tyr Ser Gly Tyr Gln Arg Asp Gly Tyr
655                 660                 665                 670 cag cag aat ttc aag cga ggc tct ggg cag agt gga cca cgg gga gcc    2247
Gln Gln Asn Phe Lys Arg Gly Ser Gly Gln Ser Gly Pro Arg Gly Ala
                675                 680                 685 cca cga ggt cgt gga ggg ccc cca aga ccc aac aga ggg atg ccg caa    2295
Pro Arg Gly Arg Gly Gly Pro Pro Arg Pro Asn Arg Gly Met Pro Gln
            690                 695                 700 atg aac act cag caa gtg aat taa tctgattcac aggattatgt ttaatcgcca   2349
Met Asn Thr Gln Gln Val Asn
        705 aaaacacact ggccagtgta ccataatatg ttaccagaag agttattatc tatttgttct   2409 cccctttcagg aaacttattg taaagggact gttttcatcc cataaagaca ggactacaat  2469 tgtcagcttt ctattacctg gatatggaag gaaactattt ttactctgca tgttctgtcc   2529 taagcgtcat cttgagcctt gcacatgata ctcagattcc tcacccttgc ttaggagtaa   2589 aacaatatac tttacagggt gataataatc tccatagtta tttgaagtgg cttgaaaaag   2649 gcaagattga cttttatgac attggataaa atctacaaat cagccctcga gttattcaat   2709 gataactgac aaactaaatt atttccctag aaaggaagat gaaaggagtg gagtgtggtt   2769 tggcagaaca actgcatttc acagcttttc cagttaaatt ggagcactga acgttcagat   2829 gcataccaaa ttatgcatgg gtcctaatca cacatataag gctggctacc agcttttgaca  2889
```

```
cagcactgtt catctggcca acaactgtg gttaaaaaca catgtaaaat gcttttaac      2949 agctgatact gtataagaca aagccaagat gcaaaattag gctttgattg cactttttg      3009 aaaaatatgc aacaaatatg ggatgtaatc cggatggccg cttctgtact taatgtgaaa    3069
tatttagata cctttttgaa cacttaacag tttcttgag acaatgactt ttgtaaggat      3129
tggtactatc tatcattcct tatgacatgt acattgtctg tcactaatcc ttggattttg    3189
ctgtattgtc acctaaattg gtacaggtac tgatgaaaat ctctagtgga taatcataac    3249
actctcggtc acatgttttt ccttcagctt gaaagctttt ttttaaaagg aaaagatacc    3309
aaatgcctgc tgctaccacc cttttcaatt gctatctttt gaaaggcacc agtatgtgtt    3369
ttagattgat ttccctgttt cagggaaatc acggacagta gtttcagttc tgatggtata    3429
agcaaaacaa ataaaacgtt tataaaagtt gtatctgaa acactggtgt tcaacagcta     3489
gcagcttatg tgattcaccc catgccacgt tagtgtcaca aattttatgg tttatctcca    3549
gcaacatttc tctagtactt gcacttatta tcttttgtct aatttaacct taactgaatt    3609
ctccgtttct cctggaggca tttatattca gtgataattc cttcccttag atgcataggg    3669
agagtctcta aatttgatgg aaatggacac ttgagtagtg acttagcctt atgtactctg    3729
ttggaatttg tgctagcagt ttgagcacta gttctgtgtg cctaggaagt taatgctgct    3789
tattgtctca ttctgacttc atggagaatt aatcccacct ttaagcaaag gctactaagt    3849
taatggtatt ttctgtgcag aaattaaatt ttattttcag catttagccc aggaattctt    3909
ccagtaggtg ctcagctatt taaaaacaaa actattctca acattcatc attagacaac     3969 tggagttttt gctggttttg taacctacca aaatggatag gctgttgaac attccacatt    4029
caaaagtttt gtagggtggt gggaaatggg ggatcttcaa tgtttatttt aaaataaaat    4089
aaaataagtt cttgactttt ctcatgtgtg gttgtggtac atcatattgg aagggttaac    4149
ctgttacttt ggcaaatgag tatttttttg ctagcacctc cccttgcgtg ctttaaatga    4209
catctgcctg ggatgtacca caaccatatg ttacctgtat cttaggggaa tggataaaat    4269
atttgtggtt tactgggtaa tccctagatg atgtatgctt gcagtcctat ataaaactaa    4329
atttgctatc tgtgtagaaa ataatttcat gacatttaca atcaggactg aagtaagttc    4389
ttcacacagt gacctctgaa tcagtttcag agaagggatg ggggagaaaa tgccttctag    4449
gttttgaact tctatgcatt agtgcagatg ttgtgaatgt gtaaaggtgt tcatagtttg    4509
actgtttcta tgtatgtttt ttcaaagaat tgttcctttt tttgaactat aattttttctt   4569 tttttggtta tttaccatc acagtttaaa tgtatatctt ttatgtctct actcagacca     4629
tatttttaaa ggggtgcctc attatggggc agagaacttt tcaataagtc tcattaagat    4689
ctgaatcttg gttctaagca ttctgtataa tatgtgattg cttgtcctag ctgcagaagg    4749
ccttttgttt ggtcaaatgc atattttagc agagtttcaa ggaaatgatt gtcacacatg    4809
tcactgtagc ctcttggtgt agcaagctca catacaaaat actttgtat atgcataata     4869 taaatcatct catgtggata tgaaacttct ttttaaaac ttaaaaggt agaatgttat       4929 tgattacctt gattagggca gttttatttc cagatcctaa taattcctaa aaaatatgga    4989
aaagtttttt ttcaatcatt gtaccttgat attaaaacaa atatcccttta agtatttcta   5049 atcagttagc ttctacagtt cttttgtctc cttttatatg cagctcttac gtgggagact    5109
tttccactta aaggagacat agaatgtgtg cttattctca gaaggttcat taactgaggt    5169
gatgagttaa caactagttg agcagtcagc ttcctaagtg ttttaggaca tttgttcatt    5229
atattttccg tcatataact agaggaagtg gaatgcagat aagtgccgaa ttcaaaccct    5289
```

```
tcattttatg tttaagctcc tgaatctgca ttccacttgg gttgttttta agcattctaa    5349
attttagttg attataagtt agatttcaca gaatcagtat tgcccttgat cttgtccttt    5409
ttatggagtt aacggggagg aagacccctc aggaaaacga aagtaaattg ttaaggctca    5469
tcttcatacc tttttccatt ttgaatccta caaaaatact gcaaaagact agtgaatgtt    5529
taaaattaca ctagattaaa taatatgaaa gtc                                5562
```

<210> SEQ ID NO 2
<211> LENGTH: 709
<212> TYPE: PRT
<213> ORGANISM: Homo sapiens

<400> SEQUENCE: 2

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320
```

```
Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
            405                 410                 415

Leu Ala Gln Pro Asn Gln Val Pro Val Gln Pro Glu Ala Thr Gln Val
        420                 425                 430

Pro Leu Val Ser Ser Thr Ser Glu Gly Tyr Thr Ala Ser Gln Pro Leu
    435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
            485                 490                 495

Thr Ser Lys Pro Leu His Ser Ser Gly Ile Asn Val Asn Ala Ala Pro
        500                 505                 510

Phe Gln Ser Met Gln Thr Val Phe Asn Met Asn Ala Pro Val Pro Pro
    515                 520                 525

Val Asn Glu Pro Glu Thr Leu Lys Gln Gln Asn Gln Tyr Gln Ala Ser
530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
            565                 570                 575

Pro Asp Gln Ser His Gln Val Thr Gly Asn His Gln Gln Pro Pro Gln
        580                 585                 590

Gln Asn Thr Gly Phe Pro Arg Ser Asn Gln Pro Tyr Tyr Asn Ser Arg
    595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
            645                 650                 655

Ser Ala Pro Arg Asp Tyr Ser Gly Tyr Gln Arg Asp Gly Tyr Gln Gln
        660                 665                 670

Asn Phe Lys Arg Gly Ser Gly Gln Ser Gly Pro Arg Gly Ala Pro Arg
    675                 680                 685

Gly Arg Gly Gly Pro Pro Arg Pro Asn Arg Gly Met Pro Gln Met Asn
    690                 695                 700

Thr Gln Gln Val Asn
705

<210> SEQ ID NO 3
<211> LENGTH: 3553
<212> TYPE: DNA
```

<213> ORGANISM: Homo sapiens
<220> FEATURE:
<221> NAME/KEY: CDS
<222> LOCATION: (190)..(2274)

<400> SEQUENCE: 3

```
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccaccccttg cccctcagc tgcccactcg tgatttccag cggcctccgc     180
```

| | | | | | | | | | | | | | | | | |
|---|---|---|---|---|---|---|---|---|---|---|---|---|---|---|---|---|
| gcgcgcacg | atg | ccc | tcg | gcc | acc | agc | cac | agc | ggg | agc | ggc | agc | aag | tcg | | 231 |
| | Met | Pro | Ser | Ala | Thr | Ser | His | Ser | Gly | Ser | Gly | Ser | Lys | Ser | | |
| | 1 | | | 5 | | | | | 10 | | | | | | | |
| tcc | gga | ccg | cca | ccg | ccg | tcg | ggt | tcc | tcc | ggg | agt | gag | gcg | gcc | gcg | 279 |
| Ser | Gly | Pro | Pro | Pro | Pro | Ser | Gly | Ser | Ser | Gly | Ser | Glu | Ala | Ala | Ala | |
| 15 | | | | 20 | | | | | 25 | | | | | 30 | | |
| gga | gcc | ggg | gcc | gcc | gcg | ccg | gct | tct | cag | cac | ccc | gca | acc | ggc | acc | 327 |
| Gly | Ala | Gly | Ala | Ala | Ala | Pro | Ala | Ser | Gln | His | Pro | Ala | Thr | Gly | Thr | |
| | | | 35 | | | | | 40 | | | | | 45 | | | |
| ggc | gct | gtc | cag | acc | gag | gcc | atg | aag | cag | att | ctc | ggg | gtg | atc | gac | 375 |
| Gly | Ala | Val | Gln | Thr | Glu | Ala | Met | Lys | Gln | Ile | Leu | Gly | Val | Ile | Asp | |
| | 50 | | | | | 55 | | | | | 60 | | | | | |
| aag | aaa | ctt | cgg | aac | ctg | gag | aag | aaa | aag | ggt | aag | ctt | gat | gat | tac | 423 |
| Lys | Lys | Leu | Arg | Asn | Leu | Glu | Lys | Lys | Lys | Gly | Lys | Leu | Asp | Asp | Tyr | |
| 65 | | | | | 70 | | | | | 75 | | | | | | |
| cag | gaa | cga | atg | aac | aaa | ggg | gaa | agg | ctt | aat | caa | gat | cag | ctg | gat | 471 |
| Gln | Glu | Arg | Met | Asn | Lys | Gly | Glu | Arg | Leu | Asn | Gln | Asp | Gln | Leu | Asp | |
| | 80 | | | | | 85 | | | | | 90 | | | | | |
| gcc | gtt | tct | aag | tac | cag | gaa | gtc | aca | aat | aat | ttg | gag | ttt | gca | aaa | 519 |
| Ala | Val | Ser | Lys | Tyr | Gln | Glu | Val | Thr | Asn | Asn | Leu | Glu | Phe | Ala | Lys | |
| 95 | | | | 100 | | | | | 105 | | | | | 110 | | |
| gaa | tta | cag | agg | agt | ttc | atg | gca | cta | agt | caa | gat | att | cag | aaa | aca | 567 |
| Glu | Leu | Gln | Arg | Ser | Phe | Met | Ala | Leu | Ser | Gln | Asp | Ile | Gln | Lys | Thr | |
| | | | 115 | | | | | 120 | | | | | 125 | | | |
| ata | aag | aag | aca | gca | cgt | cgg | gag | cag | ctt | atg | aga | gaa | gaa | gct | gaa | 615 |
| Ile | Lys | Lys | Thr | Ala | Arg | Arg | Glu | Gln | Leu | Met | Arg | Glu | Glu | Ala | Glu | |
| | | 130 | | | | | 135 | | | | | 140 | | | | |
| cag | aaa | cgt | tta | aaa | act | gta | ctt | gag | cta | cag | tat | gtt | ttg | gac | aaa | 663 |
| Gln | Lys | Arg | Leu | Lys | Thr | Val | Leu | Glu | Leu | Gln | Tyr | Val | Leu | Asp | Lys | |
| | 145 | | | | | 150 | | | | | 155 | | | | | |
| ttg | gga | gat | gat | gaa | gtg | cgg | act | gac | ctg | aaa | caa | ggt | ttg | aat | gga | 711 |
| Leu | Gly | Asp | Asp | Glu | Val | Arg | Thr | Asp | Leu | Lys | Gln | Gly | Leu | Asn | Gly | |
| 160 | | | | | 165 | | | | | 170 | | | | | | |
| gtg | cca | ata | ttg | tcc | gaa | gag | gag | ttg | tca | ttg | gat | gaa | ttc | tat | | 759 |
| Val | Pro | Ile | Leu | Ser | Glu | Glu | Glu | Leu | Ser | Leu | Leu | Asp | Glu | Phe | Tyr | |
| 175 | | | | 180 | | | | | 185 | | | | | 190 | | |
| aag | cta | gta | gac | cct | gaa | cgg | gac | atg | agc | ttg | agg | ttg | aat | gaa | cag | 807 |
| Lys | Leu | Val | Asp | Pro | Glu | Arg | Asp | Met | Ser | Leu | Arg | Leu | Asn | Glu | Gln | |
| | | | 195 | | | | | 200 | | | | | 205 | | | |
| tat | gaa | cat | gcc | tcc | att | cac | ctg | tgg | gac | ctg | ctg | gaa | ggg | aag | gaa | 855 |
| Tyr | Glu | His | Ala | Ser | Ile | His | Leu | Trp | Asp | Leu | Leu | Glu | Gly | Lys | Glu | |
| | | 210 | | | | | 215 | | | | | 220 | | | | |
| aaa | cct | gta | tgt | gga | acc | acc | tat | aaa | gtt | cta | aag | gaa | att | gtt | gag | 903 |
| Lys | Pro | Val | Cys | Gly | Thr | Thr | Tyr | Lys | Val | Leu | Lys | Glu | Ile | Val | Glu | |
| | 225 | | | | | 230 | | | | | 235 | | | | | |
| cgt | gtt | ttt | cag | tca | aac | tac | ttt | gac | agc | acc | cac | aac | cac | cag | aat | 951 |
| Arg | Val | Phe | Gln | Ser | Asn | Tyr | Phe | Asp | Ser | Thr | His | Asn | His | Gln | Asn | |
| 240 | | | | 245 | | | | | 250 | | | | | | | |
| ggg | ctg | tgt | gag | gaa | gaa | gag | gca | gcc | tca | gca | cct | gca | gtt | gaa | gac | 999 |
| Gly | Leu | Cys | Glu | Glu | Glu | Glu | Ala | Ala | Ser | Ala | Pro | Ala | Val | Glu | Asp | |

-continued

```
                255                 260                 265                 270 cag gta cct gaa gct gaa cct gag cca gca gaa gag tac act gag caa    1047
     Gln Val Pro Glu Ala Glu Pro Glu Pro Ala Glu Glu Tyr Thr Glu Gln
                     275                 280                 285 agt gaa gtt gaa tca aca gag tat gta aat aga cag ttc atg gca gaa    1095
     Ser Glu Val Glu Ser Thr Glu Tyr Val Asn Arg Gln Phe Met Ala Glu
                         290                 295                 300 aca cag ttc acc agt ggt gaa aag gag cag gta gat gag tgg aca gtt    1143
     Thr Gln Phe Thr Ser Gly Glu Lys Glu Gln Val Asp Glu Trp Thr Val
                 305                 310                 315 gaa acg gtt gag gtg gta aat tca ctc cag cag caa cct cag gct gca    1191
     Glu Thr Val Glu Val Val Asn Ser Leu Gln Gln Gln Pro Gln Ala Ala
                     320                 325                 330 tcc cct tca gta cca gag ccc cac tct ttg act cca gtg gct cag gca    1239
     Ser Pro Ser Val Pro Glu Pro His Ser Leu Thr Pro Val Ala Gln Ala
     335                 340                 345                 350 gat ccc ctt gtg aga aga cag cga gta caa gac ctt atg gca caa atg    1287
     Asp Pro Leu Val Arg Arg Gln Arg Val Gln Asp Leu Met Ala Gln Met
                         355                 360                 365 cag ggt ccc tat aat ttc ata cag gat tca atg ctg gat ttt gaa aat    1335
     Gln Gly Pro Tyr Asn Phe Ile Gln Asp Ser Met Leu Asp Phe Glu Asn
                 370                 375                 380 cag aca ctt gat cct gcc att gta tct gca cag cct atg aat cca aca    1383
     Gln Thr Leu Asp Pro Ala Ile Val Ser Ala Gln Pro Met Asn Pro Thr
             385                 390                 395 caa aac atg gac atg ccc cag ctg gtt tgc cct cca gtt cat tct gaa    1431
     Gln Asn Met Asp Met Pro Gln Leu Val Cys Pro Pro Val His Ser Glu
                 400                 405                 410 tct aga ctt gct cag cct aat caa gtt cct gta caa cca gaa gcg aca    1479
     Ser Arg Leu Ala Gln Pro Asn Gln Val Pro Val Gln Pro Glu Ala Thr
     415                 420                 425                 430 cag gtt cct ttg gta tca tcc aca agt gag ggg tac aca gca tct caa    1527
     Gln Val Pro Leu Val Ser Ser Thr Ser Glu Gly Tyr Thr Ala Ser Gln
                         435                 440                 445 ccc ttg tac cag cct tct cat gct aca gag caa cga cca cag aag gaa    1575
     Pro Leu Tyr Gln Pro Ser His Ala Thr Glu Gln Arg Pro Gln Lys Glu
                 450                 455                 460 cca att gat cag att cag gca aca atc tct tta aat aca gac cag act    1623
     Pro Ile Asp Gln Ile Gln Ala Thr Ile Ser Leu Asn Thr Asp Gln Thr
                     465                 470                 475 aca gca tca tca tcc ctt cct gct gcg tct cag cct caa gta ttt cag    1671
     Thr Ala Ser Ser Ser Leu Pro Ala Ala Ser Gln Pro Gln Val Phe Gln
     480                 485                 490 gct ggg aca agc aaa cct tta cat agc agt gga atc aat gta aat gca    1719
     Ala Gly Thr Ser Lys Pro Leu His Ser Ser Gly Ile Asn Val Asn Ala
     495                 500                 505                 510 gct cca ttc caa tcc atg caa acg gtg ttc aat atg aat gcc cca gtt    1767
     Ala Pro Phe Gln Ser Met Gln Thr Val Phe Asn Met Asn Ala Pro Val
                         515                 520                 525 cct cct gtt aat gaa cca gaa act tta aaa cag caa aat cag tac cag    1815
     Pro Pro Val Asn Glu Pro Glu Thr Leu Lys Gln Gln Asn Gln Tyr Gln
                 530                 535                 540 gcc agt tat aac cag agc ttt tct agt cag cct cac caa gta gaa caa    1863
     Ala Ser Tyr Asn Gln Ser Phe Ser Ser Gln Pro His Gln Val Glu Gln
                     545                 550                 555 aca gag ctt cag caa gaa cag ctt caa aca gtg gtt ggc act tac cat    1911
     Thr Glu Leu Gln Gln Glu Gln Leu Gln Thr Val Val Gly Thr Tyr His
                 560                 565                 570 ggt tcc cca gac cag tcc cat caa gtg act ggt aac cac cag cag cct    1959
```

```
Gly Ser Pro Asp Gln Ser His Gln Val Thr Gly Asn His Gln Gln Pro
575                 580                 585                 590 cct cag cag aac act gga ttt cca cgt agc aat cag ccc tat tac aat      2007
Pro Gln Gln Asn Thr Gly Phe Pro Arg Ser Asn Gln Pro Tyr Tyr Asn
                    595                 600                 605 agt cgt ggt gtg tct cgt gga ggc tcc cgt ggt gct aga ggc ttg atg      2055
Ser Arg Gly Val Ser Arg Gly Gly Ser Arg Gly Ala Arg Gly Leu Met
                610                 615                 620 aat gga tac cgg ggc cct gcc aat gga ttc aga gga gga tat gat ggt      2103
Asn Gly Tyr Arg Gly Pro Ala Asn Gly Phe Arg Gly Gly Tyr Asp Gly
            625                 630                 635 tac cgc cct tca ttc tct aac act cca aac agt ggt tat aca cag tct      2151
Tyr Arg Pro Ser Phe Ser Asn Thr Pro Asn Ser Gly Tyr Thr Gln Ser
        640                 645                 650 cag ttc agt gct ccc cgg gat tac tct ggc tat caa cgg gat gga tat      2199
Gln Phe Ser Ala Pro Arg Asp Tyr Ser Gly Tyr Gln Arg Asp Gly Tyr
655                 660                 665                 670 cag cag aat ttc aag cga ggc tct ggg cag agt gga cca cgg gga gcc      2247
Gln Gln Asn Phe Lys Arg Gly Ser Gly Gln Ser Gly Pro Arg Gly Ala
                    675                 680                 685 cca cga ggt aat att ttg tgg tgg tga tcctagctcc taagtggagc            2294
Pro Arg Gly Asn Ile Leu Trp Trp
                690 ttctgttctg gccttggaag agctgttaat agtctgcatg ttaggaatac atttatcctt    2354 tccagacttg ttgctaggga ttaaatgaaa tgctctgttt ctaaaactta atcttggacc    2414 caaattttaa ttttttgaatg atttaatttt ccctgttact atataaactg tcttgaaaac   2474 tagaacatat tctcttctca gaaaaagtgt ttttccaact gaaaattatt tttcaggtcc    2534 taaaacctgc taaatgtttt taggaagtac ttactgaaac attttttgtaa gacatttttg   2594 gaatgagatt gaacatttat ataaatttat tattcctctt tcattttttt gaaacatgcc    2654 tattatattt tagggccaga caccctttaa tggccggata agccatagtt aacatttaga    2714 gaaccattta gaagtgatag aactaatgga atttgcaatg ccttttggac ctctattagt    2774 gatataaata tcaagttatt tctgactttt aaacaaaact cccaaattcc taacttattg    2834 agctatactt aaaaaaaatt acaggtttag agagtttttt gttttctttt tactgttgga    2894 aaactacttc ccattttggc aggaagttaa cctatttaac aattagagct agcatttcat    2954 gtagtctgaa attctaaatg gttctctgat ttgagggagg ttaaacatca acaggtttc     3014 ctctattggc cataacatgt ataaaatgtg tgttaaggag gaattacaac gtactttgat    3074 ttgaatacta gtagaaactg gccaggaaaa aggtacattt ttctaaaaat taatggatca    3134 cttgggaatt actgacttga ctagaagtat caaaggatgt tgcatgtga atgtgggtta     3194 tgttctttcc caccttgtag catattcgat gaaagttgag ttaactgata gctaaaaatc    3254 tgttttaaca gcatgtaaaa agttatttta tctgttaaaa gtcattatac agttttgaat    3314 gttatgtagt ttcttttttaa cagtttaggt aataaggtct gttttcattc tggtgctttt   3374 attaattttg atagtatgat gttacttact actgaaatgt aagctagagt gtacactaga    3434 atgtaagctc catgagagca ggtaccttgt ctgtcttctc tgctgtatct attcccaacg    3494 cttgatgatg gtgcctggca catagtaggc actcaataaa tatttgttga atgaatgaa     3553
```

<210> SEQ ID NO 4
<211> LENGTH: 694
<212> TYPE: PRT
<213> ORGANISM: Homo sapiens

<400> SEQUENCE: 4

```
Met Pro Ser Ala Thr Ser His Ser Gly Ser Gly Ser Lys Ser Gly
1               5                   10                  15

Pro Pro Pro Pro Ser Gly Ser Gly Ser Glu Ala Ala Gly Ala
            20                  25                  30

Gly Ala Ala Ala Pro Ala Ser Gln His Pro Ala Thr Gly Thr Gly Ala
                35                  40                  45

Val Gln Thr Glu Ala Met Lys Gln Ile Leu Gly Val Ile Asp Lys Lys
    50                  55                  60

Leu Arg Asn Leu Glu Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
            115                 120                 125

Lys Thr Ala Arg Arg Glu Gln Leu Met Arg Glu Ala Glu Gln Lys
130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
            195                 200                 205

His Ala Ser Ile His Leu Trp Asp Leu Leu Glu Gly Lys Glu Lys Pro
210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Ala Ala Ser Ala Pro Ala Val Glu Asp Gln Val
            260                 265                 270

Pro Glu Ala Glu Pro Glu Pro Ala Glu Tyr Thr Glu Gln Ser Glu
            275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Pro Gln Ala Ala Ser Pro
            325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
            355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415
```

-continued

```
Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
610                 615                 620

Tyr Arg Gly Pro Ala Asn Gly Phe Arg Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Asn Ile Leu Trp Trp
    690

<210> SEQ ID NO 5
<211> LENGTH: 1605
<212> TYPE: DNA
<213> ORGANISM: Canis familiaris
<220> FEATURE:
<221> NAME/KEY: CDS
<222> LOCATION: (46)..(1392)

<400> SEQUENCE: 5
gtcacaaata acttggagtt tgcaaaagaa ttacagagga gtttc atg gca tta agt         57
                                                  Met Ala Leu Ser
                                                    1 caa gat att cag aaa aca ata aag aag act gca cgt cgg gag cag ctt         105
Gln Asp Ile Gln Lys Thr Ile Lys Lys Thr Ala Arg Arg Glu Gln Leu
 5                  10                  15                  20 atg aga gag gaa gcg gaa caa aaa cgt tta aaa act gta ctt gag ctc        153
Met Arg Glu Glu Ala Glu Gln Lys Arg Leu Lys Thr Val Leu Glu Leu
                25                  30                  35 cag tat gtt ttg gac aaa ttg gga gat gat gaa gtg aga act gac ctg        201
```

```
                Gln Tyr Val Leu Asp Lys Leu Gly Asp Glu Val Arg Thr Asp Leu
                            40                  45                  50 aag caa ggt ttg aat gga gtg cca ata ttg tct gaa gaa gaa ttg tcg         249
Lys Gln Gly Leu Asn Gly Val Pro Ile Leu Ser Glu Glu Glu Leu Ser
            55                  60                  65 ttg ttg gat gaa ttc tac aaa tta gca gac cct gaa cgg gac atg agc         297
Leu Leu Asp Glu Phe Tyr Lys Leu Ala Asp Pro Glu Arg Asp Met Ser
    70                  75                  80 ttg agg ttg aat gag cag tat gaa cat gct tcc att cac ctg tgg gac         345
Leu Arg Leu Asn Glu Gln Tyr Glu His Ala Ser Ile His Leu Trp Asp
85                  90                  95                  100 ttg ctg gaa gga aag gaa aag tct gta tgt gga aca acc tat aaa gca         393
Leu Leu Glu Gly Lys Glu Lys Ser Val Cys Gly Thr Thr Tyr Lys Ala
                105                 110                 115 cta aag gaa att gtt gag cgt gtt ttc cag tca aat tac ttt gac agc         441
Leu Lys Glu Ile Val Glu Arg Val Phe Gln Ser Asn Tyr Phe Asp Ser
            120                 125                 130 act cac aac cac cag aat ggg cta tgt gag gaa gaa gag gca gcc tca         489
Thr His Asn His Gln Asn Gly Leu Cys Glu Glu Glu Glu Ala Ala Ser
    135                 140                 145 gca cct aca gtt gaa gac cag gta gct gaa gct gag cct gag cca gca         537
Ala Pro Thr Val Glu Asp Gln Val Ala Glu Ala Glu Pro Glu Pro Ala
150                 155                 160 gaa gaa tac act gaa caa agt gaa gtt gaa tca aca gag tat gta aat         585
Glu Glu Tyr Thr Glu Gln Ser Glu Val Glu Ser Thr Glu Tyr Val Asn
165                 170                 175                 180 aga caa ttt atg gca gaa aca cag ttc agc agt ggt gaa aag gag cag         633
Arg Gln Phe Met Ala Glu Thr Gln Phe Ser Ser Gly Glu Lys Glu Gln
                185                 190                 195 gta gat gag tgg acg gtc gaa aca gtg gag gtg gtg aat tca ctc cag         681
Val Asp Glu Trp Thr Val Glu Thr Val Glu Val Val Asn Ser Leu Gln
            200                 205                 210 cag caa cct cag gct gcg tct cct tca gta cca gag ccc cac tct ttg         729
Gln Gln Pro Gln Ala Ala Ser Pro Ser Val Pro Glu Pro His Ser Leu
    215                 220                 225 act ccg gtg gct cag gca gat ccc ctt gtg aga aga cag cga gtc cag         777
Thr Pro Val Ala Gln Ala Asp Pro Leu Val Arg Arg Gln Arg Val Gln
230                 235                 240 gac ctt atg gcg cag atg cag ggg ccc tat aat ttc ata cag gat tca         825
Asp Leu Met Ala Gln Met Gln Gly Pro Tyr Asn Phe Ile Gln Asp Ser
245                 250                 255                 260 atg ctg gat ttt gaa aac cag aca ctc gat cct gcc att gta tct gca         873
Met Leu Asp Phe Glu Asn Gln Thr Leu Asp Pro Ala Ile Val Ser Ala
                265                 270                 275 cag cct atg aat ccg aca caa aac atg gac atg ccc cag ctg gtt tgc         921
Gln Pro Met Asn Pro Thr Gln Asn Met Asp Met Pro Gln Leu Val Cys
            280                 285                 290 cct cca gtt cat tct gaa tct aga ctt gct caa cct aat caa gtt cct         969
Pro Pro Val His Ser Glu Ser Arg Leu Ala Gln Pro Asn Gln Val Pro
    295                 300                 305 gta caa cca gaa gct aca cag gtt cct ttg gtt tca tcc aca agt gag        1017
Val Gln Pro Glu Ala Thr Gln Val Pro Leu Val Ser Ser Thr Ser Glu
310                 315                 320 ggg tat aca gca tct caa ccc ttg tac cag cct tct cat gct aca gag        1065
Gly Tyr Thr Ala Ser Gln Pro Leu Tyr Gln Pro Ser His Ala Thr Glu
325                 330                 335                 340 caa cga cca caa aag gaa cca att gac cag att cag gca aca atc tct        1113
Gln Arg Pro Gln Lys Glu Pro Ile Asp Gln Ile Gln Ala Thr Ile Ser
                345                 350                 355
```

```
tta aat aca gac cag act aca gcg tca tca tcc ctt ccg gct gct tct    1161
Leu Asn Thr Asp Gln Thr Thr Ala Ser Ser Ser Leu Pro Ala Ala Ser
        360                 365                 370 cag cct cag gta ttc cag gct ggg aca agc aaa cca tta cat agc agt    1209
Gln Pro Gln Val Phe Gln Ala Gly Thr Ser Lys Pro Leu His Ser Ser
        375                 380                 385 gga atc aat gta aat gca gct cca ttc caa tcc atg caa acg gtg ttc    1257
Gly Ile Asn Val Asn Ala Ala Pro Phe Gln Ser Met Gln Thr Val Phe
        390                 395                 400 aat atg aat gcc cca gtt cct cct gtt aat gaa cca gaa act ttg aaa    1305
Asn Met Asn Ala Pro Val Pro Pro Val Asn Glu Pro Glu Thr Leu Lys
405                 410                 415                 420 caa caa aat cag tac cag gcc agt tat aac cag agc ttt tct agt cag    1353
Gln Gln Asn Gln Tyr Gln Ala Ser Tyr Asn Gln Ser Phe Ser Ser Gln
                425                 430                 435 cct cac caa gta gaa caa aca gag gga tgc cgc aaa tga acactcagca     1402
Pro His Gln Val Glu Gln Thr Glu Gly Cys Arg Lys
            440                 445 agtgaattaa tctgattcac aggattatgt ttaaacgcca aaacacact ggccagtgta    1462 ccataatatg ttaccagaag agttattatc tatttgttct cccttttcagg aaacttattg  1522 taaagggact gttttcatcc cataaagaca ggactacaat tgtcagcttt atattacctg   1582
gaaaaaaaaa aaaaaaaaaa aaa                                          1605

<210> SEQ ID NO 6
<211> LENGTH: 448
<212> TYPE: PRT
<213> ORGANISM: Canis familiaris

<400> SEQUENCE: 6

Met Ala Leu Ser Gln Asp Ile Gln Lys Thr Ile Lys Lys Thr Ala Arg
1               5                   10                  15

Arg Glu Gln Leu Met Arg Glu Glu Ala Glu Gln Lys Arg Leu Lys Thr
            20                  25                  30

Val Leu Glu Leu Gln Tyr Val Leu Asp Lys Leu Gly Asp Asp Glu Val
        35                  40                  45

Arg Thr Asp Leu Lys Gln Gly Leu Asn Gly Val Pro Ile Leu Ser Glu
    50                  55                  60

Glu Glu Leu Ser Leu Leu Asp Glu Phe Tyr Lys Leu Ala Asp Pro Glu
65                  70                  75                  80

Arg Asp Met Ser Leu Arg Leu Asn Glu Gln Tyr Glu His Ala Ser Ile
                85                  90                  95

His Leu Trp Asp Leu Leu Glu Gly Lys Glu Lys Ser Val Cys Gly Thr
            100                 105                 110

Thr Tyr Lys Ala Leu Lys Glu Ile Val Glu Arg Val Phe Gln Ser Asn
        115                 120                 125

Tyr Phe Asp Ser Thr His Asn His Gln Asn Gly Leu Cys Glu Glu Glu
    130                 135                 140

Glu Ala Ala Ser Ala Pro Thr Val Glu Asp Gln Val Ala Glu Ala Glu
145                 150                 155                 160

Pro Glu Pro Ala Glu Glu Tyr Thr Glu Gln Ser Glu Val Glu Ser Thr
                165                 170                 175

Glu Tyr Val Asn Arg Gln Phe Met Ala Glu Thr Gln Phe Ser Ser Gly
            180                 185                 190

Glu Lys Glu Gln Val Asp Glu Trp Thr Val Glu Thr Val Glu Val Val
        195                 200                 205
```

```
Asn Ser Leu Gln Gln Gln Pro Gln Ala Ala Ser Pro Ser Val Pro Glu
    210                 215                 220

Pro His Ser Leu Thr Pro Val Ala Gln Ala Asp Pro Leu Val Arg Arg
225                 230                 235                 240

Gln Arg Val Gln Asp Leu Met Ala Gln Met Gln Gly Pro Tyr Asn Phe
                245                 250                 255

Ile Gln Asp Ser Met Leu Asp Phe Glu Asn Gln Thr Leu Asp Pro Ala
                260                 265                 270

Ile Val Ser Ala Gln Pro Met Asn Pro Thr Gln Asn Met Asp Met Pro
            275                 280                 285

Gln Leu Val Cys Pro Pro Val His Ser Glu Ser Arg Leu Ala Gln Pro
290                 295                 300

Asn Gln Val Pro Val Gln Pro Glu Ala Thr Gln Val Pro Leu Val Ser
305                 310                 315                 320

Ser Thr Ser Glu Gly Tyr Thr Ala Ser Gln Pro Leu Tyr Gln Pro Ser
                325                 330                 335

His Ala Thr Glu Gln Arg Pro Gln Lys Glu Pro Ile Asp Gln Ile Gln
                340                 345                 350

Ala Thr Ile Ser Leu Asn Thr Asp Gln Thr Thr Ala Ser Ser Ser Leu
            355                 360                 365

Pro Ala Ala Ser Gln Pro Gln Val Phe Gln Ala Gly Thr Ser Lys Pro
370                 375                 380

Leu His Ser Ser Gly Ile Asn Val Asn Ala Ala Pro Phe Gln Ser Met
385                 390                 395                 400

Gln Thr Val Phe Asn Met Asn Ala Pro Val Pro Pro Val Asn Glu Pro
                405                 410                 415

Glu Thr Leu Lys Gln Gln Asn Gln Tyr Gln Ala Ser Tyr Asn Gln Ser
                420                 425                 430

Phe Ser Ser Gln Pro His Gln Val Glu Gln Thr Glu Gly Cys Arg Lys
            435                 440                 445

<210> SEQ ID NO 7
<211> LENGTH: 4154
<212> TYPE: DNA
<213> ORGANISM: Canis familiaris
<220> FEATURE:
<221> NAME/KEY: CDS
<222> LOCATION: (1)..(2154)

<400> SEQUENCE: 7 atg ccg tcg gcc acc agc ctc agc gga agc ggc agc aag tcg tcg ggc    48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg    96
Pro Pro Pro Pro Ser Gly Ser Ser Gly Ser Glu Ala Ala Ala Ala Ala
                20                  25                  30 ggg gcg gcg ggg gcg gcg ggg gcc ggg gcg gct gcg ccc gcc tcc cag   144
Gly Ala Ala Gly Ala Ala Gly Ala Gly Ala Ala Pro Ala Ser Gln
            35                  40                  45 cac ccc gcg acc ggc acc ggc gct gtc cag acc gag gcc atg aag cag   192
His Pro Ala Thr Gly Thr Gly Ala Val Gln Thr Glu Ala Met Lys Gln
50                  55                  60 atc ctc ggg gtg atc gac aag aaa ctc cgg aac ctg gag aag aaa aag   240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt   288
Gly Lys Leu Asp Asp Tyr Gln Glu Arg Met Asn Lys Gly Glu Arg Leu
                85                  90                  95
```

```
aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110 aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125 caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140 atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175 aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190 ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205 ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220 ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240 cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255 act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270 gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285 gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300 aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350 act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365 gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380 atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400 cag cct atg aat ccg aca caa aac atg gac atg ccc cag ctg gtt tgc     1248
Gln Pro Met Asn Pro Thr Gln Asn Met Asp Met Pro Gln Leu Val Cys
```

```
                    405                410                415
cct cca gtt cat tct gaa tct aga ctt gct caa cct aat caa gtt cct    1296
Pro Pro Val His Ser Glu Ser Arg Leu Ala Gln Pro Asn Gln Val Pro
            420                425                430 gta caa cca gaa gct aca cag gtt cct ttg gtt tca tcc aca agt gag    1344
Val Gln Pro Glu Ala Thr Gln Val Pro Leu Val Ser Ser Thr Ser Glu
        435                440                445 ggg tat aca gca tct caa ccc ttg tac cag cct tct cat gct aca gag    1392
Gly Tyr Thr Ala Ser Gln Pro Leu Tyr Gln Pro Ser His Ala Thr Glu
    450                455                460 caa cga cca caa aag gaa cca att gac cag att cag gca aca atc tct    1440
Gln Arg Pro Gln Lys Glu Pro Ile Asp Gln Ile Gln Ala Thr Ile Ser
465                470                475                480 tta aat aca gac cag act aca gcg tca tca tcc ctt ccg gct gct tct    1488
Leu Asn Thr Asp Gln Thr Thr Ala Ser Ser Ser Leu Pro Ala Ala Ser
            485                490                495 cag cct cag gta ttc cag gct ggg aca agc aaa cca tta cat agc agt    1536
Gln Pro Gln Val Phe Gln Ala Gly Thr Ser Lys Pro Leu His Ser Ser
        500                505                510 gga atc aat gta aat gca gct cca ttc caa tcc atg caa acg gtg ttc    1584
Gly Ile Asn Val Asn Ala Ala Pro Phe Gln Ser Met Gln Thr Val Phe
    515                520                525 aat atg aat gcc cca gtt cct cct gtt aat gaa cca gaa act ttg aaa    1632
Asn Met Asn Ala Pro Val Pro Pro Val Asn Glu Pro Glu Thr Leu Lys
530                535                540 caa caa aat cag tac cag gcc agt tat aac cag agc ttt tct agt cag    1680
Gln Gln Asn Gln Tyr Gln Ala Ser Tyr Asn Gln Ser Phe Ser Ser Gln
545                550                555                560 cct cac caa gta gaa caa aca gac ctt cag caa gaa cag ctt caa aca    1728
Pro His Gln Val Glu Gln Thr Asp Leu Gln Gln Glu Gln Leu Gln Thr
            565                570                575 gtg gtt ggc act tac cat ggt tcc cag gac cag ccc cac caa gtg act    1776
Val Val Gly Thr Tyr His Gly Ser Gln Asp Gln Pro His Gln Val Thr
        580                585                590 ggt aac cat cag cag cct ccc cag cag aac act gga ttt cca cgt agc    1824
Gly Asn His Gln Gln Pro Pro Gln Gln Asn Thr Gly Phe Pro Arg Ser
    595                600                605 agt cag ccc tat tac aat agt cgt ggt gtg tct cgt ggt ggt tcc cgt    1872
Ser Gln Pro Tyr Tyr Asn Ser Arg Gly Val Ser Arg Gly Gly Ser Arg
610                615                620 ggt gct aga ggc tta atg aat gga tac agg ggc cct gcc aat gga ttc    1920
Gly Ala Arg Gly Leu Met Asn Gly Tyr Arg Gly Pro Ala Asn Gly Phe
625                630                635                640 aga gga gga tat gat ggt tac cgc cct tca ttc tct aac act cca aac    1968
Arg Gly Gly Tyr Asp Gly Tyr Arg Pro Ser Phe Ser Asn Thr Pro Asn
            645                650                655 agt ggt tat aca cag tct cag ttc agt gct ccc cgg gac tac tct ggc    2016
Ser Gly Tyr Thr Gln Ser Gln Phe Ser Ala Pro Arg Asp Tyr Ser Gly
        660                665                670 tat cag cgg gat gga tat cag cag aat ttc aag cga ggc tct ggg cag    2064
Tyr Gln Arg Asp Gly Tyr Gln Gln Asn Phe Lys Arg Gly Ser Gly Gln
    675                680                685 agt gga cca cgg gga gcc cca cga ggt cgt gga ggg ccc cca aga ccc    2112
Ser Gly Pro Arg Gly Ala Pro Arg Gly Arg Gly Gly Pro Pro Arg Pro
690                695                700 aac aga ggg atg ccg caa atg aac act cag caa gtg aat taa             2154
Asn Arg Gly Met Pro Gln Met Asn Thr Gln Gln Val Asn
705                710                715 tctgattcac aggattatgt ttaaacgcca aaaacacact ggccagtgta ccataatatg   2214
```

```
ttaccagaag agttattatc tatttgttct cccttttcagg aaacttattg taaagggact    2274
gttttcatcc cataaagaca ggactacaat tgtcagcttt atattacctg gatatggaag    2334
gaaactattt ttattctgca tgttcttcct aagcgtcatc ttgagccttg cacatgatac    2394
tcagattcct cacccttgct taggagtaaa acataataca ctttacaggg tgatatctcc    2454
atagttattt gaagtggctt ggaaaaagca agattaactt ctgacattgg ataaaaatca    2514
acaaatcagc cctagagtta ttcaaatggt aattgacaaa actaaaata tttcccttcg    2574
agaaggagtg gaatgtggtt tggcagaaca actgcatttc acagcttttc cggttaaatt    2634
ggagcactaa acgtttagat gcataccaaa ttatgcatgg gcccttaata taaaaggctg    2694
gctaccagct ttgacacagc actattcatc ctctggccaa acaactgtgg ttaaacaaca    2754
catgtaaatt gcttttttaac agctgatact ataataagac aaagccaaaa tgcaaaaatt    2814
gggctttgat tggcactttt tgaaaaatat gcaacaaata tgggatgtaa tctggatggc    2874
cgcttctgta cttaatgtga agtatttaga taccttttg aacacttaac agtttcttct    2934
gacaatgact tttgtaagga ttggtactat ctatcattcc ttataatgta cattgtctgt    2994
cactaatcct cagatcttgc tgtattgtca cctaaattgg tacaggtact gatgaaaata    3054
tctaatggat aatcataaca ctcttggtca catgtttttc ctgcagcctg aaggttttta    3114
aaagaaaaag atatcaaatg cctgctgcta ccacccttt aaattgctat cttttgaaaa    3174
gcaccagtat gtgttttaga ttgatttccc tatttaggg aaatgacaga cagtagtttc    3234
agttctgatg gtataagcaa aacaaataaa acatgtttat aaaagttgta tcttgaaaca    3294
ctggtgttca acagctagca gcttatgtgg ttcaccccat gcattgttag tgtttcagat    3354
tttatggtta tctccagcag ctgtttctgt agtacttgca tttatctttt gtctaaccct    3414
aatattctca cggaggcatt tatattcaaa gtggtgatcc cttcacttag acgcataggg    3474
agagtcacaa gtttgatgaa gaggacagtg tagtaattta tatgctgttg gaatttgtgc    3534
tagcagtttg agcactagtt ctgtgtgcct atgaacttaa tgctgcttgt catattccac    3594
tttgacttca tggagaatta atcccatcta ctcagcaaag gctatactaa tactaagtta    3654
atggtatttt ctgtgcagaa attgaatttt gttttattag catttagcta aggaattttt    3714
ccagtaggtg ctcagctact aaagaaaaac aaaaacaaga cacaaaacta ttctcaaaca    3774
ttcattgtta gacaactgga gttttgctg gttttgtaac ctactaaaat ggataggctg    3834
ttgaacattc cacattcaaa gttttttgt agggtggtgg ggaagggggg gtgtcttcaa    3894
tgtttatttt aaaataaaat aagttcttga cttttctcat gtgtggttgt ggtacatcat    3954
attggaaggg ttatctgttt acttttgcaa atgagtattt ctcttgctag cacctcccgt    4014
tgtgcgcttt aaatgacatc tgcctgggat gtaccacaac catatgttag ctgtattta    4074
tggggaatag ataaaatatt cgtggtttat tgggtaatcc ctagatgtgt atgcttacaa    4134
tcctatatat aaaactaaat                                                 4154
```

<210> SEQ ID NO 8
<211> LENGTH: 717
<212> TYPE: PRT
<213> ORGANISM: Canis familiaris

<400> SEQUENCE: 8

```
Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
```

```
                20                  25                  30
Gly Ala Ala Gly Ala Ala Gly Ala Ala Pro Ala Ser Gln
            35                  40                  45
His Pro Ala Thr Gly Thr Gly Ala Val Gln Thr Glu Ala Met Lys Gln
 50                  55                  60
Ile Leu Gly Val Ile Asp Lys Lys Leu Arg Asn Leu Glu Lys Lys Lys
 65                  70                  75                  80
Gly Lys Leu Asp Asp Tyr Gln Glu Arg Met Asn Lys Gly Glu Arg Leu
                85                  90                  95
Asn Gln Asp Gln Leu Asp Ala Val Ser Lys Tyr Gln Glu Val Thr Asn
                100                 105                 110
Asn Leu Glu Phe Ala Lys Glu Leu Gln Arg Ser Phe Met Ala Leu Ser
            115                 120                 125
Gln Asp Ile Gln Lys Thr Ile Lys Lys Thr Ala Arg Arg Glu Gln Leu
            130                 135                 140
Met Arg Glu Glu Ala Glu Gln Lys Arg Leu Lys Thr Val Leu Glu Leu
145                 150                 155                 160
Gln Tyr Val Leu Asp Lys Leu Gly Asp Asp Glu Val Arg Thr Asp Leu
                165                 170                 175
Lys Gln Gly Leu Asn Gly Val Pro Ile Leu Ser Glu Glu Leu Ser
            180                 185                 190
Leu Leu Asp Glu Phe Tyr Lys Leu Ala Asp Pro Glu Arg Asp Met Ser
            195                 200                 205
Leu Arg Leu Asn Glu Gln Tyr Glu His Ala Ser Ile His Leu Trp Asp
            210                 215                 220
Leu Leu Glu Gly Lys Glu Lys Ser Val Cys Gly Thr Thr Tyr Lys Ala
225                 230                 235                 240
Leu Lys Glu Ile Val Glu Arg Val Phe Gln Ser Asn Tyr Phe Asp Ser
                245                 250                 255
Thr His Asn His Gln Asn Gly Leu Cys Glu Glu Glu Ala Ala Ser
            260                 265                 270
Ala Pro Thr Val Glu Asp Gln Val Ala Glu Ala Glu Pro Glu Pro Ala
            275                 280                 285
Glu Glu Tyr Thr Glu Gln Ser Glu Val Glu Ser Thr Glu Tyr Val Asn
            290                 295                 300
Arg Gln Phe Met Ala Glu Thr Gln Phe Ser Ser Gly Glu Lys Glu Gln
305                 310                 315                 320
Val Asp Glu Trp Thr Val Glu Thr Val Glu Val Val Asn Ser Leu Gln
                325                 330                 335
Gln Gln Pro Gln Ala Ala Ser Pro Ser Val Pro Glu Pro His Ser Leu
            340                 345                 350
Thr Pro Val Ala Gln Ala Asp Pro Leu Val Arg Arg Gln Arg Val Gln
            355                 360                 365
Asp Leu Met Ala Gln Met Gln Gly Pro Tyr Asn Phe Ile Gln Asp Ser
            370                 375                 380
Met Leu Asp Phe Glu Asn Gln Thr Leu Asp Pro Ala Ile Val Ser Ala
385                 390                 395                 400
Gln Pro Met Asn Pro Thr Gln Asn Met Asp Met Pro Gln Leu Val Cys
                405                 410                 415
Pro Pro Val His Ser Glu Ser Arg Leu Ala Gln Pro Asn Gln Val Pro
                420                 425                 430
Val Gln Pro Glu Ala Thr Gln Val Pro Leu Val Ser Thr Ser Glu
            435                 440                 445
```

```
Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Val Asn Glu Pro Glu Thr Leu Lys
530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Gly Pro Pro Arg Pro
690                 695                 700

Asn Arg Gly Met Pro Gln Met Asn Thr Gln Gln Val Asn
705                 710                 715

<210> SEQ ID NO 9
<211> LENGTH: 4939
<212> TYPE: DNA
<213> ORGANISM: Canis familiaris
<220> FEATURE:
<221> NAME/KEY: CDS
<222> LOCATION: (1)..(2109)

<400> SEQUENCE: 9 atg ccg tcg gcc acc agc ctc agc gga agc ggc agc aag tcg tcg ggc      48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg      96
Pro Pro Pro Pro Ser Gly Ser Ser Gly Ser Glu Ala Ala Ala Ala Ala
            20                  25                  30 ggg gcg gcg ggg gcg gcg ggg gcc ggg gcg gct gcg ccc gcc tcc cag     144
Gly Ala Ala Gly Ala Ala Gly Ala Gly Ala Ala Pro Ala Ser Gln
            35                  40                  45 cac ccc gcg acc ggc acc ggc gct gtc cag acc gag gcc atg aag cag     192
His Pro Ala Thr Gly Thr Gly Ala Val Gln Thr Glu Ala Met Lys Gln
    50                  55                  60
```

```
atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95 aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110 aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125 caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140 atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175 aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190 ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205 ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220 ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240 cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255 act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270 gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285 gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300 aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350 act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365 gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380
```

-continued

| | |
|---|---|
| atg ctg gat ttt gaa aac cag aca ctc gat cct gcc att gta tct gca<br>Met Leu Asp Phe Glu Asn Gln Thr Leu Asp Pro Ala Ile Val Ser Ala<br>385                       390                   395                   400 | 1200 |
| cag cct atg aat ccg aca caa aac atg gac atg ccc cag ctg gtt tgc<br>Gln Pro Met Asn Pro Thr Gln Asn Met Asp Met Pro Gln Leu Val Cys<br>                   405                   410                   415 | 1248 |
| cct cca gtt cat tct gaa tct aga ctt gct caa cct aat caa gtt cct<br>Pro Pro Val His Ser Glu Ser Arg Leu Ala Gln Pro Asn Gln Val Pro<br>         420                   425                   430 | 1296 |
| gta caa cca gaa gct aca cag gtt cct ttg gtt tca tcc aca agt gag<br>Val Gln Pro Glu Ala Thr Gln Val Pro Leu Val Ser Ser Thr Ser Glu<br>435                       440                   445 | 1344 |
| ggg tat aca gca tct caa ccc ttg tac cag cct tct cat gct aca gag<br>Gly Tyr Thr Ala Ser Gln Pro Leu Tyr Gln Pro Ser His Ala Thr Glu<br>         450                   455                   460 | 1392 |
| caa cga cca caa aag gaa cca att gac cag att cag gca aca atc tct<br>Gln Arg Pro Gln Lys Glu Pro Ile Asp Gln Ile Gln Ala Thr Ile Ser<br>465                       470                   475                   480 | 1440 |
| tta aat aca gac cag act aca gcg tca tca tcc ctt ccg gct gct tct<br>Leu Asn Thr Asp Gln Thr Thr Ala Ser Ser Ser Leu Pro Ala Ala Ser<br>                       485                   490                   495 | 1488 |
| cag cct cag gta ttc cag gct ggg aca agc aaa cca tta cat agc agt<br>Gln Pro Gln Val Phe Gln Ala Gly Thr Ser Lys Pro Leu His Ser Ser<br>         500                   505                   510 | 1536 |
| gga atc aat gta aat gca gct cca ttc caa tcc atg caa acg gtg ttc<br>Gly Ile Asn Val Asn Ala Ala Pro Phe Gln Ser Met Gln Thr Val Phe<br>                   515                   520                   525 | 1584 |
| aat atg aat gcc cca gtt cct cct gtt aat gaa cca gaa act ttg aaa<br>Asn Met Asn Ala Pro Val Pro Pro Val Asn Glu Pro Glu Thr Leu Lys<br>530                       535                   540 | 1632 |
| caa caa aat cag tac cag gcc agt tat aac cag agc ttt tct agt cag<br>Gln Gln Asn Gln Tyr Gln Ala Ser Tyr Asn Gln Ser Phe Ser Ser Gln<br>545                       550                   555                   560 | 1680 |
| cct cac caa gta gaa caa aca gac ctt cag caa gaa cag ctt caa aca<br>Pro His Gln Val Glu Gln Thr Asp Leu Gln Gln Glu Gln Leu Gln Thr<br>                     565                   570                   575 | 1728 |
| gtg gtt ggc act tac cat ggt tcc cag gac cag ccc cac caa gtg act<br>Val Val Gly Thr Tyr His Gly Ser Gln Asp Gln Pro His Gln Val Thr<br>         580                   585                   590 | 1776 |
| ggt aac cat cag cag cct ccc cag cag aac act gga ttt cca cgt agc<br>Gly Asn His Gln Gln Pro Pro Gln Gln Asn Thr Gly Phe Pro Arg Ser<br>595                       600                   605 | 1824 |
| agt cag ccc tat tac aat agt cgt ggt gtg tct cgt ggt ggt tcc cgt<br>Ser Gln Pro Tyr Tyr Asn Ser Arg Gly Val Ser Arg Gly Gly Ser Arg<br>         610                   615                   620 | 1872 |
| ggt gct aga ggc tta atg aat gga tac agg ggc cct gcc aat gga ttc<br>Gly Ala Arg Gly Leu Met Asn Gly Tyr Arg Gly Pro Ala Asn Gly Phe<br>625                       630                   635                   640 | 1920 |
| aga gga gga tat gat ggt tac cgc cct tca ttc tct aac act cca aac<br>Arg Gly Gly Tyr Asp Gly Tyr Arg Pro Ser Phe Ser Asn Thr Pro Asn<br>                     645                   650                   655 | 1968 |
| agt ggt tat aca cag tct cag ttc agt gct ccc cgg gac tac tct ggc<br>Ser Gly Tyr Thr Gln Ser Gln Phe Ser Ala Pro Arg Asp Tyr Ser Gly<br>         660                   665                   670 | 2016 |
| tat cag cgg gat gga tat cag cag aat ttc aag cga ggc tct ggg cag<br>Tyr Gln Arg Asp Gly Tyr Gln Gln Asn Phe Lys Arg Gly Ser Gly Gln<br>                   675                   680                   685 | 2064 |
| agt gga cca cgg gga gcc cca cga ggt aat att ttg tgg tgg tga<br>Ser Gly Pro Arg Gly Ala Pro Arg Gly Asn Ile Leu Trp Trp | 2109 |

```
       690         695         700
tcctagctcc taagtggagc ttctgttctg gccttggaag agctgttcca tagtctgcat   2169
gtaggttaca tgttaggaat acatttatca ttaccagact tgttgctagg gattaaatga   2229
aatgctctgt ttctaaaact tctcttgaac ccaaatttaa ttttttgaat gactttccct   2289
gttactatat aaattgtctt gaaaactaga acatttctcc tcctcagaaa aagtgttttt   2349
ccaactgcaa attattttc aggtcctaaa acctgctaaa tgttttagg aagtacttac     2409
tgaaacattt ttgtaagaca ttttttggaat gagattgaac atttatataa atttattatt 2469
attcctcttt cattttttgaa catgcatatt atattttagg gtcagaaatc ctttaatggc 2529
caaataagcc atagttacat ttagagaacc atttagaagt gatagaacta actgaaattt 2589
caatgccttt ggatcattaa tagcgatata aatttcaaat tgtttctgac ttttaaataa 2649
aacatccaaa atcctaacta acttcctgaa ctatatttaa aaattacagg tttaaggagt 2709
ttctggtttt ttttctctta ccataggaaa actgttccct gtttggccag gaagtcaacc 2769
tgtgtaataa ttagaagtag catttcatat gatctgaagt tctaaatggt tctctgattt 2829
aagggaagtt aaattgaata ggtttcctct agttattggc cataacatgt ataaaatgta 2889
tattaaggag gaatacaaag tactttgatt tcaatgctag tagaaactgg ccagcaaaaa 2949
ggtgcatttt attttttaaat taatggatca cttgggaatt actgacttga agtatcaaag 3009
gatatttgca tgtgaatgtg ggttatgttc tttctcacct tgtagcatat tctatgaaag 3069
ttgagttgac tggtagctaa aaatctgttt taacagcatg taaaaagtta ttttatctgt 3129
tacaagtcat tatacaattt tgaatgttat gtagtttctt tttaacagtt taggtaacaa 3189
ggtctgttt tcattctggt gctttttatta attttgatag tatgatgtta cttactactg 3249
aaatgtaagc tagagtgtac actagaatgt aagctccatg agagcaggta ccttgtctgt 3309
cttcactgct gtatctattt ccaacgcctg atgacagtgc ctgacacata gtaggcactc 3369
aataaatact tgttgaatga atgaatgaat gagtactggt ggaatactcc attagctcta 3429
ctcttctttt agctagagaa catgagcaaa tttgcgcatg acaacttcca ggacaggtga 3489
acactgaaga attgacctct taaacctaat aatgtggtga caagctgccc acatgcttct 3549
tgacttcaga tgaaaatctg cttgaaggca aagcaaataa tatttgaaag aaaaaccaaa 3609
tgccatttt gtcttctagg tcgtggaggg cccccaagac ccaacagagg gatgccgcaa  3669
atgaacactc agcaagtgaa ttaatctgat tcacaggatt atgtttaaac gccaaaaaca 3729
cactggccag tgtaccataa tatgttacca gaagagttat tatctatttg ttctcccttt 3789
caggaaactt attgtaaagg gactgttttc atcccataaa gacaggacta caattgtcag 3849
ctttatatta cctggatatg gaaggaaact atttttattc tgcatgttct tcctaagcgt 3909
catcttgagc cttgcacatg atactcagat tcctcaccct tgcttaggag taaaacataa 3969
tacactttac agggtgatat ctccatagtt atttgaagtg gcttgaaaaa agcaagatta 4029
acttctgaca ttggataaaa atcaacaaat cagccctaga gttattcaaa tggtaattga 4089
caaaaactaa atatttccc ttcgagaagg agtggaatgt ggtttggcag aacaactgca  4149
tttcacagct tttccggtta aattggagca ctaaacgttt agatgcatac caattatgc   4209
atgggccctt aatataaaag gctggctacc agctttgaca cagcactatt catcctctgg 4269
ccaaacaact gtggttaaac aacacatgta aattgctttt taacagctga tactataata 4329
agacaaagcc aaaatgcaaa aattgggctt tgattggcac ttttttgaaaa atatgcaaca 4389
aatatgggat gtaatctgga tggccgcttc tgtacttaat gtgaagtatt tagataccct 4449
```

```
tttgaacact taacagtttc ttctgacaat gacttttgta aggattggta ctatctatca    4509
ttccttataa tgtacattgt ctgtcactaa tcctcagatc ttgctgtatt gtcacctaaa    4569
ttggtacagg tactgatgaa aatatctaat ggataatcat aacactcttg gtcacatgtt    4629
tttcctgcag cctgaaggtt tttaaaagaa aaagatatca aatgcctgct gctaccaccc    4689
ttttaaattg ctatcttttg aaaagcacca gtatgtgttt tagattgatt tccctatttt    4749
agggaaatga cagacagtag tttcagttct gatggtataa gcaaaacaaa taaaacatgt    4809
ttataaaagt tgtatcttga aacactggtg ttcaacagct agcagcttat gtggttcacc    4869
ccatgcattg ttagtgtttc agattttatg gttatctcca gcagctgttt ctgtagtact    4929
tgcatttatc                                                          4939
```

<210> SEQ ID NO 10
<211> LENGTH: 702
<212> TYPE: PRT
<213> ORGANISM: Canis familiaris

<400> SEQUENCE: 10

```
Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Ala Ala Ser
            260                 265                 270

Ala Pro Thr Val Glu Asp Gln Val Ala Glu Ala Glu Pro Glu Pro Ala
```

-continued

```
            275                 280                 285
Glu Glu Tyr Thr Glu Gln Ser Glu Val Glu Ser Thr Glu Tyr Val Asn
290                 295                 300
Arg Gln Phe Met Ala Glu Thr Gln Phe Ser Ser Gly Glu Lys Glu Gln
305                 310                 315                 320
Val Asp Glu Trp Thr Val Glu Thr Val Glu Val Val Asn Ser Leu Gln
                    325                 330                 335
Gln Gln Pro Gln Ala Ala Ser Pro Ser Val Pro Glu Pro His Ser Leu
            340                 345                 350
Thr Pro Val Ala Gln Ala Asp Pro Leu Val Arg Arg Gln Arg Val Gln
        355                 360                 365
Asp Leu Met Ala Gln Met Gln Gly Pro Tyr Asn Phe Ile Gln Asp Ser
    370                 375                 380
Met Leu Asp Phe Glu Asn Gln Thr Leu Asp Pro Ala Ile Val Ser Ala
385                 390                 395                 400
Gln Pro Met Asn Pro Thr Gln Asn Met Asp Met Pro Gln Leu Val Cys
                    405                 410                 415
Pro Pro Val His Ser Glu Ser Arg Leu Ala Gln Pro Asn Gln Val Pro
                420                 425                 430
Val Gln Pro Glu Ala Thr Gln Val Pro Leu Val Ser Ser Thr Ser Glu
            435                 440                 445
Gly Tyr Thr Ala Ser Gln Pro Leu Tyr Gln Pro Ser His Ala Thr Glu
        450                 455                 460
Gln Arg Pro Gln Lys Glu Pro Ile Asp Gln Ile Gln Ala Thr Ile Ser
465                 470                 475                 480
Leu Asn Thr Asp Gln Thr Thr Ala Ser Ser Ser Leu Pro Ala Ala Ser
                    485                 490                 495
Gln Pro Gln Val Phe Gln Ala Gly Thr Ser Lys Pro Leu His Ser Ser
                500                 505                 510
Gly Ile Asn Val Asn Ala Ala Pro Phe Gln Ser Met Gln Thr Val Phe
            515                 520                 525
Asn Met Asn Ala Pro Val Pro Pro Val Asn Glu Pro Glu Thr Leu Lys
        530                 535                 540
Gln Gln Asn Gln Tyr Gln Ala Ser Tyr Asn Gln Ser Phe Ser Ser Gln
545                 550                 555                 560
Pro His Gln Val Glu Gln Thr Asp Leu Gln Gln Glu Gln Leu Gln Thr
                    565                 570                 575
Val Val Gly Thr Tyr His Gly Ser Gln Asp Gln Pro His Gln Val Thr
                580                 585                 590
Gly Asn His Gln Gln Pro Pro Gln Gln Asn Thr Gly Phe Pro Arg Ser
            595                 600                 605
Ser Gln Pro Tyr Tyr Asn Ser Arg Gly Val Ser Arg Gly Gly Ser Arg
        610                 615                 620
Gly Ala Arg Gly Leu Met Asn Gly Tyr Arg Gly Pro Ala Asn Gly Phe
625                 630                 635                 640
Arg Gly Gly Tyr Asp Gly Tyr Arg Pro Ser Phe Ser Asn Thr Pro Asn
                    645                 650                 655
Ser Gly Tyr Thr Gln Ser Gln Phe Ser Ala Pro Arg Asp Tyr Ser Gly
                660                 665                 670
Tyr Gln Arg Asp Gly Tyr Gln Gln Asn Phe Lys Arg Gly Ser Gly Gln
            675                 680                 685
Ser Gly Pro Arg Gly Ala Pro Arg Gly Asn Ile Leu Trp Trp
        690                 695                 700
```

<210> SEQ ID NO 11
<211> LENGTH: 3306
<212> TYPE: DNA
<213> ORGANISM: Canis familiaris
<220> FEATURE:
<221> NAME/KEY: CDS
<222> LOCATION: (1)..(2040)

<400> SEQUENCE: 11

| | | | | | | | | | | | | | | | | |
|---|---|---|---|---|---|---|---|---|---|---|---|---|---|---|---|---|
| atg | ccg | tcg | gcc | acc | agc | ctc | agc | gga | agc | ggc | agc | aag | tcg | tcg | ggc | 48 |
| Met | Pro | Ser | Ala | Thr | Ser | Leu | Ser | Gly | Ser | Gly | Ser | Lys | Ser | Ser | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ccg | ccg | ccc | ccg | tcg | ggt | tcc | tcc | ggg | agc | gag | gcg | gcg | gcg | gcg | gcg | 96 |
| Pro | Pro | Pro | Pro | Ser | Gly | Ser | Ser | Gly | Ser | Glu | Ala | Ala | Ala | Ala | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| ggg | gcg | gcg | ggg | gcg | gcg | ggg | gcc | ggg | gcg | gct | gcg | ccc | gcc | tcc | cag | 144 |
| Gly | Ala | Ala | Gly | Ala | Ala | Gly | Ala | Gly | Ala | Ala | Ala | Pro | Ala | Ser | Gln | |
| | | 35 | | | | | 40 | | | | | 45 | | | | |

| | | | | | | | | | | | | | | | | |
|---|---|---|---|---|---|---|---|---|---|---|---|---|---|---|---|---|
| cac | ccc | gcg | acc | ggc | acc | ggc | gct | gtc | cag | acc | gag | gcc | atg | aag | cag | 192 |
| His | Pro | Ala | Thr | Gly | Thr | Gly | Ala | Val | Gln | Thr | Glu | Ala | Met | Lys | Gln | |
| | 50 | | | | | 55 | | | | | 60 | | | | | |

| | | | | | | | | | | | | | | | | |
|---|---|---|---|---|---|---|---|---|---|---|---|---|---|---|---|---|
| atc | ctc | ggg | gtg | atc | gac | aag | aaa | ctc | cgg | aac | ctg | gag | aag | aaa | aag | 240 |
| Ile | Leu | Gly | Val | Ile | Asp | Lys | Lys | Leu | Arg | Asn | Leu | Glu | Lys | Lys | Lys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggc | aag | ctt | gat | gat | tac | cag | gaa | cga | atg | aac | aaa | ggg | gaa | agg | ctt | 288 |
| Gly | Lys | Leu | Asp | Asp | Tyr | Gln | Glu | Arg | Met | Asn | Lys | Gly | Glu | Arg | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| aat | caa | gat | cag | ctg | gat | gcc | gta | tct | aag | tac | cag | gaa | gtc | aca | aat | 336 |
| Asn | Gln | Asp | Gln | Leu | Asp | Ala | Val | Ser | Lys | Tyr | Gln | Glu | Val | Thr | Asn | |
| | | | 100 | | | | | 105 | | | | | 110 | | | |

| | | | | | | | | | | | | | | | | |
|---|---|---|---|---|---|---|---|---|---|---|---|---|---|---|---|---|
| aac | ttg | gag | ttt | gca | aaa | gaa | tta | cag | agg | agt | ttc | atg | gca | tta | agt | 384 |
| Asn | Leu | Glu | Phe | Ala | Lys | Glu | Leu | Gln | Arg | Ser | Phe | Met | Ala | Leu | Ser | |
| | | 115 | | | | | 120 | | | | | 125 | | | | |

| | | | | | | | | | | | | | | | | |
|---|---|---|---|---|---|---|---|---|---|---|---|---|---|---|---|---|
| caa | gat | att | cag | aaa | aca | ata | aag | aag | act | gca | cgt | cgg | gag | cag | ctt | 432 |
| Gln | Asp | Ile | Gln | Lys | Thr | Ile | Lys | Lys | Thr | Ala | Arg | Arg | Glu | Gln | Leu | |
| | 130 | | | | | 135 | | | | | 140 | | | | | |

| | | | | | | | | | | | | | | | | |
|---|---|---|---|---|---|---|---|---|---|---|---|---|---|---|---|---|
| atg | aga | gag | gaa | gcg | gaa | caa | aaa | cgt | tta | aaa | act | gta | ctt | gag | ctc | 480 |
| Met | Arg | Glu | Glu | Ala | Glu | Gln | Lys | Arg | Leu | Lys | Thr | Val | Leu | Glu | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cag | tat | gtt | ttg | gac | aaa | ttg | gga | gat | gat | gaa | gtg | aga | act | gac | ctg | 528 |
| Gln | Tyr | Val | Leu | Asp | Lys | Leu | Gly | Asp | Asp | Glu | Val | Arg | Thr | Asp | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| aag | caa | ggt | ttg | aat | gga | gtg | cca | ata | ttg | tct | gaa | gaa | gaa | ttg | tcg | 576 |
| Lys | Gln | Gly | Leu | Asn | Gly | Val | Pro | Ile | Leu | Ser | Glu | Glu | Glu | Leu | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| ttg | ttg | gat | gaa | ttc | tac | aaa | tta | gca | gac | cct | gaa | cgg | gac | atg | agc | 624 |
| Leu | Leu | Asp | Glu | Phe | Tyr | Lys | Leu | Ala | Asp | Pro | Glu | Arg | Asp | Met | Ser | |
| | | 195 | | | | | 200 | | | | | 205 | | | | |

| | | | | | | | | | | | | | | | | |
|---|---|---|---|---|---|---|---|---|---|---|---|---|---|---|---|---|
| ttg | agg | ttg | aat | gag | cag | tat | gaa | cat | gct | tcc | att | cac | ctg | tgg | gac | 672 |
| Leu | Arg | Leu | Asn | Glu | Gln | Tyr | Glu | His | Ala | Ser | Ile | His | Leu | Trp | Asp | |
| | 210 | | | | | 215 | | | | | 220 | | | | | |

| | | | | | | | | | | | | | | | | |
|---|---|---|---|---|---|---|---|---|---|---|---|---|---|---|---|---|
| ttg | ctg | gaa | gga | aag | gaa | aag | tct | gta | tgt | gga | aca | acc | tat | aaa | gca | 720 |
| Leu | Leu | Glu | Gly | Lys | Glu | Lys | Ser | Val | Cys | Gly | Thr | Thr | Tyr | Lys | Ala | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cta | aag | gaa | att | gtt | gag | cgt | gtt | ttc | cag | tca | aat | tac | ttt | gac | agc | 768 |
| Leu | Lys | Glu | Ile | Val | Glu | Arg | Val | Phe | Gln | Ser | Asn | Tyr | Phe | Asp | Ser | |
| | | | | 245 | | | | | 250 | | | | | 255 | | |

| | | | | | | | | | | | | | | | | |
|---|---|---|---|---|---|---|---|---|---|---|---|---|---|---|---|---|
| act | cac | aac | cac | cag | aat | ggg | cta | tgt | gag | gaa | gaa | gag | gca | gcc | tca | 816 |
| Thr | His | Asn | His | Gln | Asn | Gly | Leu | Cys | Glu | Glu | Glu | Glu | Ala | Ala | Ser | |
| | | | 260 | | | | | 265 | | | | | 270 | | | |

|  |  |  |  |  |  |  |  |  |  |  |  |  |  |  |  |
|---|---|---|---|---|---|---|---|---|---|---|---|---|---|---|---|
| gca | cct | aca | gtt | gaa | gac | cag | gta | gct | gaa | gct | gag | cct | gag | cca | gca |
| Ala | Pro | Thr | Val | Glu | Asp | Gln | Val | Ala | Glu | Ala | Glu | Pro | Glu | Pro | Ala |
|  |  | 275 |  |  |  | 280 |  |  |  | 285 |  |  |  |  |  |

(864)

|  |  |  |  |  |  |  |  |  |  |  |  |  |  |  |  |
|---|---|---|---|---|---|---|---|---|---|---|---|---|---|---|---|
| gaa | gaa | tac | act | gaa | caa | agt | gaa | gtt | gaa | tca | aca | gag | tat | gta | aat |
| Glu | Glu | Tyr | Thr | Glu | Gln | Ser | Glu | Val | Glu | Ser | Thr | Glu | Tyr | Val | Asn |
| 290 |  |  |  |  | 295 |  |  |  |  | 300 |  |  |  |  |  |

(912)

|  |  |  |  |  |  |  |  |  |  |  |  |  |  |  |  |
|---|---|---|---|---|---|---|---|---|---|---|---|---|---|---|---|
| aga | caa | ttt | atg | gca | gaa | aca | cag | ttc | agc | agt | ggt | gaa | aag | gag | cag |
| Arg | Gln | Phe | Met | Ala | Glu | Thr | Gln | Phe | Ser | Ser | Gly | Glu | Lys | Glu | Gln |
| 305 |  |  |  | 310 |  |  |  |  | 315 |  |  |  |  | 320 |  |

(960)

|  |  |  |  |  |  |  |  |  |  |  |  |  |  |  |  |
|---|---|---|---|---|---|---|---|---|---|---|---|---|---|---|---|
| gta | gat | gag | tgg | acg | gtc | gaa | aca | gtg | gag | gtg | gtg | aat | tca | ctc | cag |
| Val | Asp | Glu | Trp | Thr | Val | Glu | Thr | Val | Glu | Val | Val | Asn | Ser | Leu | Gln |
|  |  |  |  | 325 |  |  |  |  | 330 |  |  |  |  | 335 |  |

(1008)

|  |  |  |  |  |  |  |  |  |  |  |  |  |  |  |  |
|---|---|---|---|---|---|---|---|---|---|---|---|---|---|---|---|
| cag | caa | cct | cag | gct | gcg | tct | cct | tca | gta | cca | gag | ccc | cac | tct | ttg |
| Gln | Gln | Pro | Gln | Ala | Ala | Ser | Pro | Ser | Val | Pro | Glu | Pro | His | Ser | Leu |
|  |  |  | 340 |  |  |  |  | 345 |  |  |  |  | 350 |  |  |

(1056)

|  |  |  |  |  |  |  |  |  |  |  |  |  |  |  |  |
|---|---|---|---|---|---|---|---|---|---|---|---|---|---|---|---|
| act | ccg | gtg | gct | cag | gca | gat | ccc | ctt | gtg | aga | aga | cag | cga | gtc | cag |
| Thr | Pro | Val | Ala | Gln | Ala | Asp | Pro | Leu | Val | Arg | Arg | Gln | Arg | Val | Gln |
|  |  | 355 |  |  |  |  | 360 |  |  |  |  | 365 |  |  |  |

(1104)

|  |  |  |  |  |  |  |  |  |  |  |  |  |  |  |  |
|---|---|---|---|---|---|---|---|---|---|---|---|---|---|---|---|
| gac | ctt | atg | gcg | cag | atg | cag | ggg | ccc | tat | aat | ttc | ata | cag | gat | tca |
| Asp | Leu | Met | Ala | Gln | Met | Gln | Gly | Pro | Tyr | Asn | Phe | Ile | Gln | Asp | Ser |
| 370 |  |  |  |  | 375 |  |  |  |  | 380 |  |  |  |  |  |

(1152)

|  |  |  |  |  |  |  |  |  |  |  |  |  |  |  |  |
|---|---|---|---|---|---|---|---|---|---|---|---|---|---|---|---|
| atg | ctg | gat | ttt | gaa | aac | cag | aca | ctc | gat | cct | gcc | att | gta | tct | gca |
| Met | Leu | Asp | Phe | Glu | Asn | Gln | Thr | Leu | Asp | Pro | Ala | Ile | Val | Ser | Ala |
| 385 |  |  |  | 390 |  |  |  |  | 395 |  |  |  |  | 400 |  |

(1200)

|  |  |  |  |  |  |  |  |  |  |  |  |  |  |  |  |
|---|---|---|---|---|---|---|---|---|---|---|---|---|---|---|---|
| cag | cct | atg | aat | ccg | aca | caa | aac | atg | gac | atg | ccc | cag | ctg | gtt | tgc |
| Gln | Pro | Met | Asn | Pro | Thr | Gln | Asn | Met | Asp | Met | Pro | Gln | Leu | Val | Cys |
|  |  |  |  | 405 |  |  |  |  | 410 |  |  |  |  | 415 |  |

(1248)

|  |  |  |  |  |  |  |  |  |  |  |  |  |  |  |  |
|---|---|---|---|---|---|---|---|---|---|---|---|---|---|---|---|
| cct | cca | gtt | cat | tct | gaa | tct | aga | ctt | gct | caa | cct | aat | caa | gtt | cct |
| Pro | Pro | Val | His | Ser | Glu | Ser | Arg | Leu | Ala | Gln | Pro | Asn | Gln | Val | Pro |
|  |  |  | 420 |  |  |  |  | 425 |  |  |  |  | 430 |  |  |

(1296)

|  |  |  |  |  |  |  |  |  |  |  |  |  |  |  |  |
|---|---|---|---|---|---|---|---|---|---|---|---|---|---|---|---|
| gta | caa | cca | gaa | gct | aca | cag | gtt | cct | ttg | gtt | tca | tcc | aca | agt | gag |
| Val | Gln | Pro | Glu | Ala | Thr | Gln | Val | Pro | Leu | Val | Ser | Ser | Thr | Ser | Glu |
|  |  | 435 |  |  |  |  | 440 |  |  |  |  | 445 |  |  |  |

(1344)

|  |  |  |  |  |  |  |  |  |  |  |  |  |  |  |  |
|---|---|---|---|---|---|---|---|---|---|---|---|---|---|---|---|
| ggg | tat | aca | gca | tct | caa | ccc | ttg | tac | cag | cct | tct | cat | gct | aca | gag |
| Gly | Tyr | Thr | Ala | Ser | Gln | Pro | Leu | Tyr | Gln | Pro | Ser | His | Ala | Thr | Glu |
|  | 450 |  |  |  |  | 455 |  |  |  |  | 460 |  |  |  |  |

(1392)

|  |  |  |  |  |  |  |  |  |  |  |  |  |  |  |  |
|---|---|---|---|---|---|---|---|---|---|---|---|---|---|---|---|
| caa | cga | cca | caa | aag | gaa | cca | att | gac | cag | att | cag | gca | aca | atc | tct |
| Gln | Arg | Pro | Gln | Lys | Glu | Pro | Ile | Asp | Gln | Ile | Gln | Ala | Thr | Ile | Ser |
| 465 |  |  |  | 470 |  |  |  |  | 475 |  |  |  |  | 480 |  |

(1440)

|  |  |  |  |  |  |  |  |  |  |  |  |  |  |  |  |
|---|---|---|---|---|---|---|---|---|---|---|---|---|---|---|---|
| tta | aat | aca | gac | cag | act | aca | gcg | tca | tca | tcc | ctt | ccg | gct | gct | tct |
| Leu | Asn | Thr | Asp | Gln | Thr | Thr | Ala | Ser | Ser | Ser | Leu | Pro | Ala | Ala | Ser |
|  |  |  | 485 |  |  |  |  | 490 |  |  |  |  | 495 |  |  |

(1488)

|  |  |  |  |  |  |  |  |  |  |  |  |  |  |  |  |
|---|---|---|---|---|---|---|---|---|---|---|---|---|---|---|---|
| cag | cct | cag | gta | ttc | cag | gct | ggg | aca | agc | aaa | cca | tta | cat | agc | agt |
| Gln | Pro | Gln | Val | Phe | Gln | Ala | Gly | Thr | Ser | Lys | Pro | Leu | His | Ser | Ser |
|  |  |  | 500 |  |  |  |  | 505 |  |  |  |  | 510 |  |  |

(1536)

|  |  |  |  |  |  |  |  |  |  |  |  |  |  |  |  |
|---|---|---|---|---|---|---|---|---|---|---|---|---|---|---|---|
| gga | atc | aat | gta | aat | gca | gct | cca | ttc | caa | tcc | atg | caa | acg | gtg | ttc |
| Gly | Ile | Asn | Val | Asn | Ala | Ala | Pro | Phe | Gln | Ser | Met | Gln | Thr | Val | Phe |
|  |  |  | 515 |  |  |  |  | 520 |  |  |  |  | 525 |  |  |

(1584)

|  |  |  |  |  |  |  |  |  |  |  |  |  |  |  |  |
|---|---|---|---|---|---|---|---|---|---|---|---|---|---|---|---|
| aat | atg | aat | gcc | cca | gtt | cct | cct | gtt | aat | gaa | cca | gaa | act | ttg | aaa |
| Asn | Met | Asn | Ala | Pro | Val | Pro | Pro | Val | Asn | Glu | Pro | Glu | Thr | Leu | Lys |
|  | 530 |  |  |  |  | 535 |  |  |  |  | 540 |  |  |  |  |

(1632)

|  |  |  |  |  |  |  |  |  |  |  |  |  |  |  |  |
|---|---|---|---|---|---|---|---|---|---|---|---|---|---|---|---|
| caa | caa | aat | cag | tac | cag | gcc | agt | tat | aac | cag | agc | ttt | tct | agt | cag |
| Gln | Gln | Asn | Gln | Tyr | Gln | Ala | Ser | Tyr | Asn | Gln | Ser | Phe | Ser | Ser | Gln |
| 545 |  |  |  | 550 |  |  |  |  | 555 |  |  |  |  | 560 |  |

(1680)

|  |  |  |  |  |  |  |  |  |  |  |  |  |  |  |  |
|---|---|---|---|---|---|---|---|---|---|---|---|---|---|---|---|
| cct | cac | caa | gta | gaa | caa | aca | gac | ctt | cag | caa | gaa | cag | ctt | caa | aca |
| Pro | His | Gln | Val | Glu | Gln | Thr | Asp | Leu | Gln | Gln | Glu | Gln | Leu | Gln | Thr |
|  |  |  | 565 |  |  |  |  | 570 |  |  |  |  | 575 |  |  |

(1728)

|  |  |  |  |  |  |  |  |  |  |  |  |  |  |  |  |
|---|---|---|---|---|---|---|---|---|---|---|---|---|---|---|---|
| gtg | gtt | ggc | act | tac | cat | ggt | tcc | cag | gac | cag | ccc | cac | caa | gtg | act |
| Val | Val | Gly | Thr | Tyr | His | Gly | Ser | Gln | Asp | Gln | Pro | His | Gln | Val | Thr |

(1776)

```
ggt aac cat cag cag cct ccc cag cag aac act gga ttt cca cgt agc      1824
Gly Asn His Gln Gln Pro Pro Gln Gln Asn Thr Gly Phe Pro Arg Ser
            595                 600                 605 agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
    610                 615                 620 ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac      1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc      2016
Ser Gly Tyr Thr Gln Ser Gln Phe Ser Ala Pro Arg Asp Tyr Ser Gly
            660                 665                 670 tat cag cgg gga tgc cgc aaa tga acactcagca agtgaattaa tctgattcac     2070
Tyr Gln Arg Gly Cys Arg Lys
            675
```

```
aggattatgt ttaaacgcca aaaacacact ggccagtgta ccataatatg ttaccagaag     2130
agttattatc tatttgttct cccttttcagg aaacttattg taaagggact gttttcatcc   2190
cataaagaca ggactacaat tgtcagcttt atattacctg gatatggaag gaaactattt    2250
ttattctgca tgttcttcct aagcgtcatc ttgagcctg cacatgatac tcagattcct    2310
cacccttgct taggagtaaa acataataca ctttacaggg tgatatctcc atagttattt    2370
gaagtggctt ggaaaagca agattaactt ctgacattgg ataaaaatca acaaatcagc    2430
cctagagtta ttcaaatggt aattgacaaa actaaaata tttcccttcg agaaggagtg    2490
gaatgtggtt tggcagaaca actgcatttc acagcttttc cggttaaatt ggagcactaa   2550
acgtttagat gcataccaaa ttatgcatgg gcccttaata taaaaggctg gctaccagct   2610
ttgacacagc actattcatc ctctggccaa acaactgtgg ttaaacaaca catgtaaatt   2670
gcttttaac agctgatact ataataagac aaagccaaaa tgcaaaaatt gggctttgat    2730
tggcactttt tgaaaaatat gcaacaaata tgggatgtaa tctggatggc cgcttctgta   2790
cttaatgtga agtatttaga taccttttg aacacttaac agtttcttct gacaatgact    2850
tttgtaagga ttggtactat ctatcattcc ttataatgta cattgtctgt cactaatcct   2910
cagatcttgc tgtattgtca cctaaattgg tacaggtact gatgaaaata tctaatggat   2970
aatcataaca ctcttggtca catgtttttc ctgcagcctg aaggttttta aaagaaaaag   3030
atatcaaatg cctgctgcta ccacccttt aaattgctat cttttgaaaa gcaccagtat   3090
gtgttttaga ttgatttccc tattttaggg aaatgacaga cagtagtttc agttctgatg   3150
gtataagcaa acaaataaa acatgtttat aaaagttgta tcttgaaaca ctggtgttca    3210
acagctagca gcttatgtgg ttcaccccat gcattgttag tgtttcagat tttatggtta   3270
tctccagcag ctgtttctgt agtacttgca tttatc                             3306
```

```
<210> SEQ ID NO 12
<211> LENGTH: 679
<212> TYPE: PRT
<213> ORGANISM: Canis familiaris

<400> SEQUENCE: 12

Met Pro Ser Ala Thr Ser Leu Ser Gly Ser Gly Ser Lys Ser Ser Gly
1               5                   10                  15
```

```
Pro Pro Pro Pro Ser Gly Ser Ser Gly Ser Glu Ala Ala Ala Ala
                20                  25                  30
Gly Ala Ala Gly Ala Ala Gly Ala Gly Ala Ala Pro Ala Ser Gln
        35                  40                  45
His Pro Ala Thr Gly Thr Gly Ala Val Gln Thr Glu Ala Met Lys Gln
 50                  55                  60
Ile Leu Gly Val Ile Asp Lys Lys Leu Arg Asn Leu Glu Lys Lys Lys
 65                  70                  75                  80
Gly Lys Leu Asp Asp Tyr Gln Glu Arg Met Asn Lys Gly Glu Arg Leu
                 85                  90                  95
Asn Gln Asp Gln Leu Asp Ala Val Ser Lys Tyr Gln Glu Val Thr Asn
            100                 105                 110
Asn Leu Glu Phe Ala Lys Glu Leu Gln Arg Ser Phe Met Ala Leu Ser
        115                 120                 125
Gln Asp Ile Gln Lys Thr Ile Lys Lys Thr Ala Arg Arg Glu Gln Leu
    130                 135                 140
Met Arg Glu Glu Ala Glu Gln Lys Arg Leu Lys Thr Val Leu Glu Leu
145                 150                 155                 160
Gln Tyr Val Leu Asp Lys Leu Gly Asp Asp Glu Val Arg Thr Asp Leu
                165                 170                 175
Lys Gln Gly Leu Asn Gly Val Pro Ile Leu Ser Glu Glu Leu Ser
            180                 185                 190
Leu Leu Asp Glu Phe Tyr Lys Leu Ala Asp Pro Glu Arg Asp Met Ser
        195                 200                 205
Leu Arg Leu Asn Glu Gln Tyr Glu His Ala Ser Ile His Leu Trp Asp
    210                 215                 220
Leu Leu Glu Gly Lys Glu Lys Ser Val Cys Gly Thr Thr Tyr Lys Ala
225                 230                 235                 240
Leu Lys Glu Ile Val Glu Arg Val Phe Gln Ser Asn Tyr Phe Asp Ser
                245                 250                 255
Thr His Asn His Gln Asn Gly Leu Cys Glu Glu Glu Ala Ala Ser
            260                 265                 270
Ala Pro Thr Val Glu Asp Gln Val Ala Glu Ala Glu Pro Glu Pro Ala
        275                 280                 285
Glu Glu Tyr Thr Glu Gln Ser Glu Val Glu Ser Thr Glu Tyr Val Asn
    290                 295                 300
Arg Gln Phe Met Ala Glu Thr Gln Phe Ser Ser Gly Glu Lys Glu Gln
305                 310                 315                 320
Val Asp Glu Trp Thr Val Glu Thr Val Glu Val Val Asn Ser Leu Gln
                325                 330                 335
Gln Gln Pro Gln Ala Ala Ser Pro Ser Val Pro Glu Pro His Ser Leu
            340                 345                 350
Thr Pro Val Ala Gln Ala Asp Pro Leu Val Arg Arg Gln Arg Val Gln
        355                 360                 365
Asp Leu Met Ala Gln Met Gln Gly Pro Tyr Asn Phe Ile Gln Asp Ser
    370                 375                 380
Met Leu Asp Phe Glu Asn Gln Thr Leu Asp Pro Ala Ile Val Ser Ala
385                 390                 395                 400
Gln Pro Met Asn Pro Thr Gln Asn Met Asp Met Pro Gln Leu Val Cys
                405                 410                 415
Pro Pro Val His Ser Glu Ser Arg Leu Ala Gln Pro Asn Gln Val Pro
            420                 425                 430
Val Gln Pro Glu Ala Thr Gln Val Pro Leu Val Ser Ser Thr Ser Glu
```

```
                    435                 440                 445
Gly Tyr Thr Ala Ser Gln Pro Leu Tyr Gln Pro Ser His Ala Thr Glu
        450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Gly Cys Arg Lys
        675

<210> SEQ ID NO 13
<211> LENGTH: 2281
<212> TYPE: DNA
<213> ORGANISM: Canis familiaris
<220> FEATURE:
<221> NAME/KEY: CDS
<222> LOCATION: (1)..(2154)

<400> SEQUENCE: 13 atg ccg tcg gcc acc agc ctc agc gga agc ggc agc aag tcg tcg ggc      48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg      96
Pro Pro Pro Pro Ser Gly Ser Ser Gly Ser Glu Ala Ala Ala Ala Ala
            20                  25                  30 ggg gcg gcg ggg gcg gcg ggg gcc ggg gcg gct gcg ccc gcc tcc cag     144
Gly Ala Ala Gly Ala Ala Gly Ala Gly Ala Ala Ala Pro Ala Ser Gln
        35                  40                  45 cac ccc gcg acc ggc acc ggc gct gtc cag acc gag gcc atg aag cag     192
His Pro Ala Thr Gly Thr Gly Ala Val Gln Thr Glu Ala Met Lys Gln
    50                  55                  60 atc ctc ggg gtg atc gac aag aaa ctc cgg aac ctg gag aag aaa aag     240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt     288
```

```
                Gly Lys Leu Asp Asp Tyr Gln Glu Arg Met Asn Lys Gly Glu Arg Leu
                             85                  90                  95 aat caa gat cag ctg gat gcc gta tct aag tac cag gaa gtc aca aat          336
Asn Gln Asp Gln Leu Asp Ala Val Ser Lys Tyr Gln Glu Val Thr Asn
            100                 105                 110 aac ttg gag ttt gca aaa gaa tta cag agg agt ttc atg gca tta agt          384
Asn Leu Glu Phe Ala Lys Glu Leu Gln Arg Ser Phe Met Ala Leu Ser
        115                 120                 125 caa gat att cag aaa aca ata aag aag act gca cgt cgg gag cag ctt          432
Gln Asp Ile Gln Lys Thr Ile Lys Lys Thr Ala Arg Arg Glu Gln Leu
    130                 135                 140 atg aga gag gaa gcg gaa caa aaa cgt tta aaa act gta ctt gag ctc          480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg          528
Gln Tyr Val Leu Asp Lys Leu Gly Asp Asp Glu Val Arg Thr Asp Leu
                165                 170                 175 aag caa ggt ttg aat gga gtg cca ata ttg tct gaa gaa gaa ttg tcg          576
Lys Gln Gly Leu Asn Gly Val Pro Ile Leu Ser Glu Glu Glu Leu Ser
            180                 185                 190 ttg ttg gat gaa ttc tac aaa tta gca gac cct gaa cgg gac atg agc          624
Leu Leu Asp Glu Phe Tyr Lys Leu Ala Asp Pro Glu Arg Asp Met Ser
        195                 200                 205 ttg agg ttg aat gag cag tat gaa cat gct tcc att cac ctg tgg gac          672
Leu Arg Leu Asn Glu Gln Tyr Glu His Ala Ser Ile His Leu Trp Asp
    210                 215                 220 ttg ctg gaa gga aag gaa aag tct gta tgt gga aca acc tat aaa gca          720
Leu Leu Glu Gly Lys Glu Lys Ser Val Cys Gly Thr Thr Tyr Lys Ala
225                 230                 235                 240 cta aag gaa att gtt gag cgt gtt ttc cag tca aat tac ttt gac agc          768
Leu Lys Glu Ile Val Glu Arg Val Phe Gln Ser Asn Tyr Phe Asp Ser
                245                 250                 255 act cac aac cac cag aat ggg cta tgt gag gaa gaa gag gca gcc tca          816
Thr His Asn His Gln Asn Gly Leu Cys Glu Glu Glu Glu Ala Ala Ser
            260                 265                 270 gca cct aca gtt gaa gac cag gta gct gaa gct gag cct gag cca gca          864
Ala Pro Thr Val Glu Asp Gln Val Ala Glu Ala Glu Pro Glu Pro Ala
        275                 280                 285 gaa gaa tac act gaa caa agt gaa gtt gaa tca aca gag tat gta aat          912
Glu Glu Tyr Thr Glu Gln Ser Glu Val Glu Ser Thr Glu Tyr Val Asn
    290                 295                 300 aga caa ttt atg gca gaa aca cag ttc agc agt ggt gaa aag gag cag          960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag         1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg         1056
Gln Gln Pro Gln Ala Ala Ser Pro Ser Val Pro Glu Pro His Ser Leu
            340                 345                 350 act ccg gtg gct cag gca gat ccc ctt gtg aga aga cag cga gtc cag         1104
Thr Pro Val Ala Gln Ala Asp Pro Leu Val Arg Arg Gln Arg Val Gln
        355                 360                 365 gac ctt atg gcg cag atg cag ggg ccc tat aat ttc ata cag gat tca         1152
Asp Leu Met Ala Gln Met Gln Gly Pro Tyr Asn Phe Ile Gln Asp Ser
    370                 375                 380 atg ctg gat ttt gaa aac cag aca ctc gat cct gcc att gta tct gca         1200
Met Leu Asp Phe Glu Asn Gln Thr Leu Asp Pro Ala Ile Val Ser Ala
385                 390                 395                 400
```

-continued

```
cag cct atg aat ccg aca caa aac atg gac atg ccc cag ctg gtt tgc    1248
Gln Pro Met Asn Pro Thr Gln Asn Met Asp Met Pro Gln Leu Val Cys
            405                 410                 415 cct cca gtt cat tct gaa tct aga ctt gct caa cct aat caa gtt cct    1296
Pro Pro Val His Ser Glu Ser Arg Leu Ala Gln Pro Asn Gln Val Pro
            420                 425                 430 gta caa cca gaa gct aca cag gtt cct ttg gtt tca tcc aca agt gag    1344
Val Gln Pro Glu Ala Thr Gln Val Pro Leu Val Ser Ser Thr Ser Glu
            435                 440                 445 ggg tat aca gca tct caa ccc ttg tac cag cct tct cat gct aca gag    1392
Gly Tyr Thr Ala Ser Gln Pro Leu Tyr Gln Pro Ser His Ala Thr Glu
        450                 455                 460 caa cga cca caa aag gaa cca att gac cag att cag gca aca atc tct    1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct    1488
Leu Asn Thr Asp Gln Thr Thr Ala Ser Ser Ser Leu Pro Ala Ala Ser
                485                 490                 495 cag cct cag gta ttc cag gct ggg aca agc aaa cca tta cat agc agt    1536
Gln Pro Gln Val Phe Gln Ala Gly Thr Ser Lys Pro Leu His Ser Ser
            500                 505                 510 gga atc aat gta aat gca gct cca ttc caa tcc atg caa acg gtg ttc    1584
Gly Ile Asn Val Asn Ala Ala Pro Phe Gln Ser Met Gln Thr Val Phe
            515                 520                 525 aat atg aat gcc cca gtt cct cct gtt aat gaa cca gaa act ttg aaa    1632
Asn Met Asn Ala Pro Val Pro Pro Val Asn Glu Pro Glu Thr Leu Lys
            530                 535                 540 caa caa aat cag tac cag gcc agt tat aac cag agc ttt tct agt cag    1680
Gln Gln Asn Gln Tyr Gln Ala Ser Tyr Asn Gln Ser Phe Ser Ser Gln
545                 550                 555                 560 cct cac caa gta gaa caa aca gac ctt cag caa gaa cag ctt caa aca    1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act    1776
Val Val Gly Thr Tyr His Gly Ser Gln Asp Gln Pro His Gln Val Thr
            580                 585                 590 ggt aac cat cag cag cct ccc cag cag aac act gga ttt cca cgt agc    1824
Gly Asn His Gln Gln Pro Pro Gln Gln Asn Thr Gly Phe Pro Arg Ser
            595                 600                 605 agt cag ccc tat tac aat agt cgt ggt gtg tct cgt ggt ggt tcc cgt    1872
Ser Gln Pro Tyr Tyr Asn Ser Arg Gly Val Ser Arg Gly Gly Ser Arg
            610                 615                 620 ggt gct aga ggc tta atg aat gga tac agg ggc cct gcc aat gga ttc    1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac    1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc    2016
Ser Gly Tyr Thr Gln Ser Gln Phe Ser Ala Pro Arg Asp Tyr Ser Gly
            660                 665                 670 tat cag cgg gat gga tat cag cag aat ttc aag cga ggc tct ggg cag    2064
Tyr Gln Arg Asp Gly Tyr Gln Gln Asn Phe Lys Arg Gly Ser Gly Gln
            675                 680                 685 agt gga cca cgg gga gcc cca cga ggt cgt gga ggg ccc cca aga ccc    2112
Ser Gly Pro Arg Gly Ala Pro Arg Gly Arg Gly Gly Pro Pro Arg Pro
            690                 695                 700 aac aga ggg atg ccg caa atg aac act cag caa gtg aat taa           2154
Asn Arg Gly Met Pro Gln Met Asn Thr Gln Gln Val Asn
705                 710                 715
```

```
tctgattcac aggattatgt ttaaacgcca aaaacacact ggccagtgta ccataatatg  2214
ttaccagaag agttattatc tatttggact gttttcatcc cataaagaca ggactacaat  2274
tgtcagc                                                             2281
```

<210> SEQ ID NO 14
<211> LENGTH: 717
<212> TYPE: PRT
<213> ORGANISM: Canis familiaris

<400> SEQUENCE: 14

```
Met Pro Ser Ala Thr Ser Leu Ser Gly Ser Gly Ser Lys Ser Gly
1               5                   10                  15

Pro Pro Pro Ser Gly Ser Ser Gly Ser Glu Ala Ala Ala Ala
                20                  25                  30

Gly Ala Ala Gly Ala Ala Gly Ala Ala Ala Pro Ala Ser Gln
            35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
                100                 105                 110

Asn Leu Glu Phe Ala Lys Glu Leu Gln Arg Ser Phe Met Ala Leu Ser
            115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Leu Ser
                180                 185                 190

Leu Leu Asp Glu Phe Tyr Lys Leu Ala Asp Pro Glu Arg Asp Met Ser
            195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Ala Ala Ser
                260                 265                 270

Ala Pro Thr Val Glu Asp Gln Val Ala Glu Ala Glu Pro Glu Pro Ala
            275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Gly Glu Lys Glu Gln
305                 310                 315                 320

Val Asp Glu Trp Thr Val Glu Thr Val Glu Val Asn Ser Leu Gln
                325                 330                 335

Gln Gln Pro Gln Ala Ala Ser Pro Ser Val Pro Glu Pro His Ser Leu
```

```
                340                 345                 350
Thr Pro Val Ala Gln Ala Asp Pro Leu Val Arg Arg Gln Arg Val Gln
            355                 360                 365

Asp Leu Met Ala Gln Met Gln Gly Pro Tyr Asn Phe Ile Gln Asp Ser
370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
            405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Thr Ser Ser Glu
            435                 440                 445

Gly Tyr Thr Ala Ser Gln Pro Leu Tyr Gln Pro Ser His Ala Thr Glu
            450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Leu Pro Ala Ala Ser
            485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
            515                 520                 525

Asn Met Asn Ala Pro Val Pro Pro Val Asn Glu Pro Glu Thr Leu Lys
530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
            565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
            595                 600                 605

Ser Gln Pro Tyr Tyr Asn Ser Arg Gly Val Ser Arg Gly Gly Ser Arg
            610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
            645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
            675                 680                 685

Ser Gly Pro Arg Gly Ala Pro Arg Gly Arg Gly Gly Pro Pro Arg Pro
            690                 695                 700

Asn Arg Gly Met Pro Gln Met Asn Thr Gln Gln Val Asn
705                 710                 715

<210> SEQ ID NO 15
<211> LENGTH: 3386
<212> TYPE: DNA
<213> ORGANISM: Bos taurus
<220> FEATURE:
<221> NAME/KEY: CDS
<222> LOCATION: (82)..(2208)
```

<400> SEQUENCE: 15

```
cgcgtctcgc cccgtccacc gattgactcg ccgctcttgt ccttcctccc gctctttctt      60
ctctccccTT acggtttcaa g atg cct tcg gcc acc agc cac agc gga agc       111
                        Met Pro Ser Ala Thr Ser His Ser Gly Ser
                        1               5                   10 ggc agc aag tcg tcc gga ccg cca ccg ccg tcg ggt tcc tcc ggg aat       159
Gly Ser Lys Ser Ser Gly Pro Pro Pro Pro Ser Gly Ser Ser Gly Asn
             15                  20                  25 gag gcg ggg gcc ggg gcc gcc gcg ccg gct tcc caa cac ccc atg acc       207
Glu Ala Gly Ala Gly Ala Ala Ala Pro Ala Ser Gln His Pro Met Thr
 30                  35                  40 ggc acc ggg gct gtc cag acc gag gcc atg aag cag att ctc ggg gtg       255
Gly Thr Gly Ala Val Gln Thr Glu Ala Met Lys Gln Ile Leu Gly Val
         45                  50                  55 atc gac aag aaa ctt cgg aac ctg gag aag aaa aag ggc aag ctt gat       303
Ile Asp Lys Lys Leu Arg Asn Leu Glu Lys Lys Lys Gly Lys Leu Asp
 60                  65                  70 gat tat cag gaa cga atg aac aaa ggg gaa agg ctt aat caa gat cag       351
Asp Tyr Gln Glu Arg Met Asn Lys Gly Glu Arg Leu Asn Gln Asp Gln
75                  80                  85                  90 ctg gat gcc gtg tct aag tac cag gaa gtc aca aat aac ttg gag ttt       399
Leu Asp Ala Val Ser Lys Tyr Gln Glu Val Thr Asn Asn Leu Glu Phe
                 95                 100                 105 gca aaa gaa tta cag agg agt ttc atg gca tta agc caa gat att cag       447
Ala Lys Glu Leu Gln Arg Ser Phe Met Ala Leu Ser Gln Asp Ile Gln
            110                 115                 120 aaa aca ata aag aag aca gca cgt cgg gag cag ctt atg aga gag gaa       495
Lys Thr Ile Lys Lys Thr Ala Arg Arg Glu Gln Leu Met Arg Glu Glu
        125                 130                 135 gct gaa cag aaa cgt tta aaa aca gta ctt gag ctg cag tat gtt ttg       543
Ala Glu Gln Lys Arg Leu Lys Thr Val Leu Glu Leu Gln Tyr Val Leu
    140                 145                 150 gac aaa cta gga gat gat gaa gtg aga act gac ctg aag caa ggt ttg       591
Asp Lys Leu Gly Asp Asp Glu Val Arg Thr Asp Leu Lys Gln Gly Leu
155                 160                 165                 170 aat gga gtg cca ata ttg tct gaa gag gag ttg tcg ttg tta gat gag       639
Asn Gly Val Pro Ile Leu Ser Glu Glu Glu Leu Ser Leu Leu Asp Glu
                175                 180                 185 ttc tac aaa tta gca gac cct gaa cga gac atg agc ttg agg ttg aat       687
Phe Tyr Lys Leu Ala Asp Pro Glu Arg Asp Met Ser Leu Arg Leu Asn
            190                 195                 200 gag cag tat gaa cat gcc tcc att cac ctg tgg gac ttg ctg gaa gga       735
Glu Gln Tyr Glu His Ala Ser Ile His Leu Trp Asp Leu Leu Glu Gly
        205                 210                 215 aag gaa aaa cct gta tgt gga aca act tat aaa gct cta aag gaa att       783
Lys Glu Lys Pro Val Cys Gly Thr Thr Tyr Lys Ala Leu Lys Glu Ile
    220                 225                 230 gtt gag cgt gtt ttc cag tca aac tac ttt gac agc acc cac aac cac       831
Val Glu Arg Val Phe Gln Ser Asn Tyr Phe Asp Ser Thr His Asn His
235                 240                 245                 250 cag aat ggt ctg tgt gag gaa gag gca gcc tca gca cct aca gtt           879
Gln Asn Gly Leu Cys Glu Glu Glu Ala Ala Ser Ala Pro Thr Val
                255                 260                 265 gaa gac cag gca gct gaa gct gaa cct gag cca gtg gaa gaa tat act       927
Glu Asp Gln Ala Ala Glu Ala Glu Pro Glu Pro Val Glu Glu Tyr Thr
            270                 275                 280 gaa caa aat gag gtt gaa tca aca gag tat gta aat aga caa ttt atg       975
Glu Gln Asn Glu Val Glu Ser Thr Glu Tyr Val Asn Arg Gln Phe Met
```

|                                                                                              |      |
|----------------------------------------------------------------------------------------------|------|
|            285                    290                    295 | |
| gca gaa aca cag ttc agc agt ggt gaa aag gag cag gta gat gat tgg<br>Ala Glu Thr Gln Phe Ser Ser Gly Glu Lys Glu Gln Val Asp Asp Trp<br> 300                               305                              310 | 1023 |
| aca gtt gaa aca gtt gag gtg gta aat tca ctc cag cag caa cct cag<br>Thr Val Glu Thr Val Glu Val Val Asn Ser Leu Gln Gln Gln Pro Gln<br>315                          320                          325                        330 | 1071 |
| gct gca tct cct tca gta cca gaa ccc cac tct ttg acc cca gtg gct<br>Ala Ala Ser Pro Ser Val Pro Glu Pro His Ser Leu Thr Pro Val Ala<br>                      335                              340                        345 | 1119 |
| caa gcc gat ccc ctc gtg aga aga cag cga gta cag gac ctt atg gca<br>Gln Ala Asp Pro Leu Val Arg Arg Gln Arg Val Gln Asp Leu Met Ala<br>              350                              355                              360 | 1167 |
| caa atg cag ggg ccc tat aat ttc ata cag gat tca atg ttg gat ttt<br>Gln Met Gln Gly Pro Tyr Asn Phe Ile Gln Asp Ser Met Leu Asp Phe<br>        365                            370                            375 | 1215 |
| gaa aac cag aca ctt gat cct gcc att gta tct gca cag ccg atg aat<br>Glu Asn Gln Thr Leu Asp Pro Ala Ile Val Ser Ala Gln Pro Met Asn<br>380                          385                          390 | 1263 |
| cca gca cag aac atg gac ata ccc cag ctg gtt tgc cct cca gtt cat<br>Pro Ala Gln Asn Met Asp Ile Pro Gln Leu Val Cys Pro Pro Val His<br>395                        400                        405                        410 | 1311 |
| tct gaa tct aga ctt gct caa cct aat caa gtt tct gta cag cca gaa<br>Ser Glu Ser Arg Leu Ala Gln Pro Asn Gln Val Ser Val Gln Pro Glu<br>              415                              420                              425 | 1359 |
| gct aca cag gtt cct ttg gtt tca tcc aca agt gag gga tat aca gca<br>Ala Thr Gln Val Pro Leu Val Ser Ser Thr Ser Glu Gly Tyr Thr Ala<br>                      430                              435                        440 | 1407 |
| tct caa ccc ttg tac caa cct tct cat gct act gac caa cga cca caa<br>Ser Gln Pro Leu Tyr Gln Pro Ser His Ala Thr Asp Gln Arg Pro Gln<br>        445                            450                            455 | 1455 |
| aag gaa ccg att gat cag att cag gcg acg atc tct tta aat aca gac<br>Lys Glu Pro Ile Asp Gln Ile Gln Ala Thr Ile Ser Leu Asn Thr Asp<br>460                          465                          470 | 1503 |
| cag act aca gca tca tca tcc ctt cct gct gct tct cag cct caa gtg<br>Gln Thr Thr Ala Ser Ser Ser Leu Pro Ala Ala Ser Gln Pro Gln Val<br>475                          480                        485                        490 | 1551 |
| ttc cag gct ggg aca agc aaa cct tta cat agc agt gga atc aat gta<br>Phe Gln Ala Gly Thr Ser Lys Pro Leu His Ser Ser Gly Ile Asn Val<br>                      495                              500                        505 | 1599 |
| aat gca gct cca ttc caa tcc atg caa acg gta ttc aat atg aat gcc<br>Asn Ala Ala Pro Phe Gln Ser Met Gln Thr Val Phe Asn Met Asn Ala<br>              510                              515                            520 | 1647 |
| cca gtt cct cct gtt aat gaa cca gaa act tta aaa cag caa aat cag<br>Pro Val Pro Pro Val Asn Glu Pro Glu Thr Leu Lys Gln Gln Asn Gln<br>        525                            530                            535 | 1695 |
| tac cag gcc agt tac aac cag agc ttt tcc agt cag cct cac caa gta<br>Tyr Gln Ala Ser Tyr Asn Gln Ser Phe Ser Ser Gln Pro His Gln Val<br>              540                              545                              550 | 1743 |
| gaa caa aca gag ctt cag caa gaa cag ctt caa aca gtg gtt ggc act<br>Glu Gln Thr Glu Leu Gln Gln Glu Gln Leu Gln Thr Val Val Gly Thr<br>555                          560                          565                        570 | 1791 |
| tat cat ggt tct cag gac cag ccc cat caa gtg act ggt aac cac cag<br>Tyr His Gly Ser Gln Asp Gln Pro His Gln Val Thr Gly Asn His Gln<br>                      575                              580                        585 | 1839 |
| cag cct cct cag cag aac act gga ttt cca cgt agc aat cag ccc tat<br>Gln Pro Pro Gln Gln Asn Thr Gly Phe Pro Arg Ser Asn Gln Pro Tyr<br>              590                              595                            600 | 1887 |
| tac aac agt cgt ggt gtg tct cgt gga ggt tcc cgt ggt gct aga ggc | 1935 |

```
                Tyr Asn Ser Arg Gly Val Ser Arg Gly Gly Ser Arg Gly Ala Arg Gly
                            605                 610                 615 ttg atg aat gga tac aga gga cct gct aat gga ttc aga gga gga tat          1983
Leu Met Asn Gly Tyr Arg Gly Pro Ala Asn Gly Phe Arg Gly Gly Tyr
        620                 625                 630 gat ggt tac cgc cct tca ttc tct act aac act cca aac agt ggt tat          2031
Asp Gly Tyr Arg Pro Ser Phe Ser Thr Asn Thr Pro Asn Ser Gly Tyr
635                 640                 645                 650 aca caa tct caa ttc agt gct ccc cgg gac tac tct ggc tat cag cgg          2079
Thr Gln Ser Gln Phe Ser Ala Pro Arg Asp Tyr Ser Gly Tyr Gln Arg
                655                 660                 665 gat gga tat cag cag aat ttc aag cga ggc tct ggg cag agt gga cca          2127
Asp Gly Tyr Gln Gln Asn Phe Lys Arg Gly Ser Gly Gln Ser Gly Pro
            670                 675                 680 cgg gga gcc cca cga ggt cgt gga ggg ccc cca aga ccc aac aga ggg          2175
Arg Gly Ala Pro Arg Gly Arg Gly Gly Pro Pro Arg Pro Asn Arg Gly
        685                 690                 695 atg ccg caa atg aac act cag caa gtg aat taa tctgattcac aggattatgt       2228
Met Pro Gln Met Asn Thr Gln Gln Val Asn
    700                 705 ttaatcgcca aaacacact  ggccagtgta  ccataaatatg  ttaccagaag  agttattatc   2288
tatttgttct ccctttcagg aaacttattg taaagggact gttttcatcc cataaagaca       2348
ggactacaat tgtcagcttt atattacctg gatatggaag gaaactattt ttactctgca       2408
tgttctgtcc taagcgtcat cttgagcctt gcacatgata ctcagattcc tcacccttgc       2468
ttaggagtaa aacataatat actttaatgg ggtgatatct ccatagttat ttgaagtggc       2528
ttggataaag caagactgac ttctgacatt ggataaaatc tacaaatcag ccctagagtc       2588
attcagtggt aactgacaaa actaaaatat ttcccttgaa aggaagatgg aaggagtgga       2648
gtgtggtttg gcagaacaac tgcatttcac agcttttcca cttaaattgg agcactgaac       2708
atttagatgc ataccgaatt atgcatgggc cctaatcaca cagacaaggc tggtgccagc       2768
cttaggcttg acacggcagt gttcaccctc tggccagacg actgtggttc aagacacatg       2828
taaattgctt tttaacagct gatactgtat aagacaaagc caaatgcaa aattaggctt       2888 tgattggcac ttttcgaaaa atatgcaaca attaagggat ataatctgga tggccgcttc       2948
tgtacttaat gtgaaatatt tagatacctt tcaaacactt aacagtttct ttgacaatga      3008
gttttgtaag gattggtagt aaatatcatt ccttatgacg tacattgtct gtcactaatc      3068
cttggatctt gctgtattgt cacctaaatt ggtacaggta ctgatgaaaa tctaatggat      3128
aatcataaca ctcttggtta catgtttttc ctgcagcctg aaagttttta taagaaaaag      3188
acatcaaatg cctgctgctg ccacccttttt aaattgctat cttttgaaaa gcaccagtat    3248
gtgttttaga ttgatttccc tattttaggg aaatgacagt cagtagtttc acttctgatg      3308
gtataagcaa acaaataaaa catgttata aaaaaaaaaa aaaaaaaaaa aaaaaaaaaa       3368 aaaaaaaaaaa aaaaaaaa                                                    3386

<210> SEQ ID NO 16
<211> LENGTH: 708
<212> TYPE: PRT
<213> ORGANISM: Bos taurus

<400> SEQUENCE: 16

Met Pro Ser Ala Thr Ser His Ser Gly Ser Gly Ser Lys Ser Ser Gly
1               5                   10                  15

Pro Pro Pro Pro Ser Gly Ser Ser Gly Asn Glu Ala Gly Ala Gly Ala
```

-continued

```
                20                  25                  30
Ala Ala Pro Ala Ser Gln His Pro Met Thr Gly Thr Gly Ala Val Gln
            35                  40                  45
Thr Glu Ala Met Lys Gln Ile Leu Gly Val Ile Asp Lys Lys Leu Arg
 50                  55                  60
Asn Leu Glu Lys Lys Gly Lys Leu Asp Asp Tyr Gln Glu Arg Met
 65                  70                  75                  80
Asn Lys Gly Glu Arg Leu Asn Gln Asp Gln Leu Asp Ala Val Ser Lys
                85                  90                  95
Tyr Gln Glu Val Thr Asn Asn Leu Glu Phe Ala Lys Glu Leu Gln Arg
            100                 105                 110
Ser Phe Met Ala Leu Ser Gln Asp Ile Gln Lys Thr Ile Lys Lys Thr
            115                 120                 125
Ala Arg Arg Glu Gln Leu Met Arg Glu Glu Ala Glu Gln Lys Arg Leu
            130                 135                 140
Lys Thr Val Leu Glu Leu Gln Tyr Val Leu Asp Lys Leu Gly Asp Asp
145                 150                 155                 160
Glu Val Arg Thr Asp Leu Lys Gln Gly Leu Asn Gly Val Pro Ile Leu
                165                 170                 175
Ser Glu Glu Glu Leu Ser Leu Leu Asp Glu Phe Tyr Lys Leu Ala Asp
            180                 185                 190
Pro Glu Arg Asp Met Ser Leu Arg Leu Asn Glu Gln Tyr Glu His Ala
            195                 200                 205
Ser Ile His Leu Trp Asp Leu Leu Glu Gly Lys Glu Lys Pro Val Cys
            210                 215                 220
Gly Thr Thr Tyr Lys Ala Leu Lys Glu Ile Val Glu Arg Val Phe Gln
225                 230                 235                 240
Ser Asn Tyr Phe Asp Ser Thr His Asn His Gln Asn Gly Leu Cys Glu
                245                 250                 255
Glu Glu Glu Ala Ala Ser Ala Pro Thr Val Glu Asp Gln Ala Ala Glu
            260                 265                 270
Ala Glu Pro Glu Pro Val Glu Glu Tyr Thr Glu Gln Asn Glu Val Glu
            275                 280                 285
Ser Thr Glu Tyr Val Asn Arg Gln Phe Met Ala Glu Thr Gln Phe Ser
            290                 295                 300
Ser Gly Glu Lys Glu Gln Val Asp Asp Trp Thr Val Glu Thr Val Glu
305                 310                 315                 320
Val Val Asn Ser Leu Gln Gln Gln Pro Gln Ala Ala Ser Pro Ser Val
                325                 330                 335
Pro Glu Pro His Ser Leu Thr Pro Val Ala Gln Ala Asp Pro Leu Val
            340                 345                 350
Arg Arg Gln Arg Val Gln Asp Leu Met Ala Gln Met Gln Gly Pro Tyr
            355                 360                 365
Asn Phe Ile Gln Asp Ser Met Leu Asp Phe Glu Asn Gln Thr Leu Asp
            370                 375                 380
Pro Ala Ile Val Ser Ala Gln Pro Met Asn Pro Ala Gln Asn Met Asp
385                 390                 395                 400
Ile Pro Gln Leu Val Cys Pro Pro Val His Ser Glu Ser Arg Leu Ala
                405                 410                 415
Gln Pro Asn Gln Val Ser Val Gln Pro Glu Ala Thr Gln Val Pro Leu
            420                 425                 430
Val Ser Ser Thr Ser Glu Gly Tyr Thr Ala Ser Gln Pro Leu Tyr Gln
            435                 440                 445
```

-continued

```
Pro Ser His Ala Thr Asp Gln Arg Pro Gln Lys Glu Pro Ile Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Val Asn
        515                 520                 525

Glu Pro Glu Thr Leu Lys Gln Gln Asn Gln Tyr Gln Ala Ser Tyr Asn
    530                 535                 540

Gln Ser Phe Ser Ser Gln Pro His Gln Val Glu Gln Thr Glu Leu Gln
545                 550                 555                 560

Gln Glu Gln Leu Gln Thr Val Val Gly Thr Tyr His Gly Ser Gln Asp
                565                 570                 575

Gln Pro His Gln Val Thr Gly Asn His Gln Gln Pro Pro Gln Gln Asn
            580                 585                 590

Thr Gly Phe Pro Arg Ser Asn Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Thr Asn Thr Pro Asn Ser Gly Tyr Thr Gln Ser Gln Phe Ser
                645                 650                 655

Ala Pro Arg Asp Tyr Ser Gly Tyr Gln Arg Asp Gly Tyr Gln Gln Asn
            660                 665                 670

Phe Lys Arg Gly Ser Gly Gln Ser Gly Pro Arg Gly Ala Pro Arg Gly
        675                 680                 685

Arg Gly Gly Pro Pro Arg Pro Asn Arg Gly Met Pro Gln Met Asn Thr
    690                 695                 700

Gln Gln Val Asn
705

<210> SEQ ID NO 17
<211> LENGTH: 3150
<212> TYPE: DNA
<213> ORGANISM: Equus caballus
<220> FEATURE:
<221> NAME/KEY: CDS
<222> LOCATION: (1)..(1917)

<400> SEQUENCE: 17 atg gag ggc aag ctc gat gat tac caa gag cga atg aac aaa gga gaa      48
Met Glu Gly Lys Leu Asp Asp Tyr Gln Glu Arg Met Asn Lys Gly Glu
1               5                   10                  15 agg ctt aat cag gat cag ctg gat gct gtg tct aag tac cag gaa gtc      96
Arg Leu Asn Gln Asp Gln Leu Asp Ala Val Ser Lys Tyr Gln Glu Val
            20                  25                  30 aca aat aac ttg gag ttt gcg aaa gaa ttg cag agg agt ttc atg gcg     144
Thr Asn Asn Leu Glu Phe Ala Lys Glu Leu Gln Arg Ser Phe Met Ala
        35                  40                  45 ttg agt cag gat att cag aaa aca ata aag aag acg gca cgt cgg gag     192
Leu Ser Gln Asp Ile Gln Lys Thr Ile Lys Lys Thr Ala Arg Arg Glu
    50                  55                  60
```

| | | | | | | | | | | | | | | | | |
|---|---|---|---|---|---|---|---|---|---|---|---|---|---|---|---|---|
| cag | ctt | atg | aga | gaa | gaa | gct | gaa | cag | aaa | cgt | tta | aaa | act | gta | ctt | 240 |
| Gln | Leu | Met | Arg | Glu | Glu | Ala | Glu | Gln | Lys | Arg | Leu | Lys | Thr | Val | Leu | |
| 65 | | | | 70 | | | | | 75 | | | | | 80 | | |
| gag | ctg | cag | tat | gtt | ttg | gac | aaa | ttg | gga | gat | gaa | gaa | gtg | cga | act | 288 |
| Glu | Leu | Gln | Tyr | Val | Leu | Asp | Lys | Leu | Gly | Asp | Glu | Glu | Val | Arg | Thr | |
| | | | | 85 | | | | | 90 | | | | | 95 | | |
| gac | ctg | aaa | caa | ggt | ttg | aat | gga | gtg | cca | ata | ctc | tct | gaa | gaa | gag | 336 |
| Asp | Leu | Lys | Gln | Gly | Leu | Asn | Gly | Val | Pro | Ile | Leu | Ser | Glu | Glu | Glu | |
| | | | 100 | | | | | 105 | | | | | 110 | | | |
| ttg | tcg | ctg | ttg | gat | gag | ttc | tac | aag | tta | gca | gac | cct | gta | cgg | gac | 384 |
| Leu | Ser | Leu | Leu | Asp | Glu | Phe | Tyr | Lys | Leu | Ala | Asp | Pro | Val | Arg | Asp | |
| | | | 115 | | | | | 120 | | | | | 125 | | | |
| atg | agc | ttg | agg | ttg | aat | gag | cag | tat | gag | cat | gcc | tcc | att | cac | ctg | 432 |
| Met | Ser | Leu | Arg | Leu | Asn | Glu | Gln | Tyr | Glu | His | Ala | Ser | Ile | His | Leu | |
| | | | 130 | | | | | 135 | | | | | 140 | | | |
| tgg | gac | ttg | ctg | gaa | ggg | aag | gaa | aaa | tct | gtc | tgt | gga | aca | acc | tat | 480 |
| Trp | Asp | Leu | Leu | Glu | Gly | Lys | Glu | Lys | Ser | Val | Cys | Gly | Thr | Thr | Tyr | |
| 145 | | | | 150 | | | | | 155 | | | | | 160 | | |
| aaa | gct | ctg | agg | gaa | att | gtt | gag | cgt | gtt | ttc | cag | tcc | aac | tac | ttt | 528 |
| Lys | Ala | Leu | Arg | Glu | Ile | Val | Glu | Arg | Val | Phe | Gln | Ser | Asn | Tyr | Phe | |
| | | | 165 | | | | | 170 | | | | | 175 | | | |
| gac | agc | acc | cac | aac | cac | cag | aat | ggg | ctc | tgt | gag | gag | gaa | gag | gct | 576 |
| Asp | Ser | Thr | His | Asn | His | Gln | Asn | Gly | Leu | Cys | Glu | Glu | Glu | Glu | Ala | |
| | | | 180 | | | | | 185 | | | | | 190 | | | |
| acc | tca | gct | cca | aca | gct | gaa | gac | cag | gga | gct | gaa | gct | gaa | cct | gag | 624 |
| Thr | Ser | Ala | Pro | Thr | Ala | Glu | Asp | Gln | Gly | Ala | Glu | Ala | Glu | Pro | Glu | |
| | | | 195 | | | | | 200 | | | | | 205 | | | |
| cca | gca | gaa | gaa | tac | act | gaa | caa | agt | gaa | gtt | gaa | tca | aca | gag | tat | 672 |
| Pro | Ala | Glu | Glu | Tyr | Thr | Glu | Gln | Ser | Glu | Val | Glu | Ser | Thr | Glu | Tyr | |
| 210 | | | | | 215 | | | | | 220 | | | | | | |
| gta | aat | aga | cag | ttt | atg | gca | gaa | gcg | cag | ttc | agt | ggt | gag | aag | gag | 720 |
| Val | Asn | Arg | Gln | Phe | Met | Ala | Glu | Ala | Gln | Phe | Ser | Gly | Glu | Lys | Glu | |
| 225 | | | | | 230 | | | | | 235 | | | | | 240 | |
| cag | gtg | gat | gag | tgg | aca | gtc | gag | acg | gtc | gag | gtg | gta | aat | tca | ctc | 768 |
| Gln | Val | Asp | Glu | Trp | Thr | Val | Glu | Thr | Val | Glu | Val | Val | Asn | Ser | Leu | |
| | | | | 245 | | | | | 250 | | | | | 255 | | |
| cag | cag | caa | cct | cag | gct | gca | tct | cct | tca | gta | ccg | gag | ccc | cac | tct | 816 |
| Gln | Gln | Gln | Pro | Gln | Ala | Ala | Ser | Pro | Ser | Val | Pro | Glu | Pro | His | Ser | |
| | | | 260 | | | | | 265 | | | | | 270 | | | |
| ttg | act | cca | gtg | gct | cag | gca | gat | ccc | ctt | gtg | aga | aga | cag | cga | gta | 864 |
| Leu | Thr | Pro | Val | Ala | Gln | Ala | Asp | Pro | Leu | Val | Arg | Arg | Gln | Arg | Val | |
| | | | 275 | | | | | 280 | | | | | 285 | | | |
| cag | gac | ctt | atg | gcg | caa | atg | cag | ggg | ccc | tat | aat | ttc | ata | cag | gat | 912 |
| Gln | Asp | Leu | Met | Ala | Gln | Met | Gln | Gly | Pro | Tyr | Asn | Phe | Ile | Gln | Asp | |
| | | | 290 | | | | | 295 | | | | | 300 | | | |
| tca | atg | ctg | gat | ttt | gaa | aac | cag | aca | ctt | gat | cct | gcc | att | gta | tct | 960 |
| Ser | Met | Leu | Asp | Phe | Glu | Asn | Gln | Thr | Leu | Asp | Pro | Ala | Ile | Val | Ser | |
| 305 | | | | | 310 | | | | | 315 | | | | | 320 | |
| gca | cag | cct | atg | aat | cca | gca | cag | aat | atg | gac | atg | ccc | cag | ctg | gtt | 1008 |
| Ala | Gln | Pro | Met | Asn | Pro | Ala | Gln | Asn | Met | Asp | Met | Pro | Gln | Leu | Val | |
| | | | | 325 | | | | | 330 | | | | | 335 | | |
| tgc | cct | cca | gtt | cat | gct | gaa | tct | aga | ctt | gct | caa | cct | aat | caa | gtt | 1056 |
| Cys | Pro | Pro | Val | His | Ala | Glu | Ser | Arg | Leu | Ala | Gln | Pro | Asn | Gln | Val | |
| | | | | 340 | | | | | 345 | | | | | 350 | | |
| cct | gta | caa | cca | gaa | gct | aca | cag | gtt | cct | ttg | gtt | tca | tcc | aca | agt | 1104 |
| Pro | Val | Gln | Pro | Glu | Ala | Thr | Gln | Val | Pro | Leu | Val | Ser | Ser | Thr | Ser | |
| | | | 355 | | | | | 360 | | | | | 365 | | | |
| gag | ggg | tat | aca | gca | tct | cag | ccc | ttg | tac | cag | cct | tct | cat | gct | aca | 1152 |
| Glu | Gly | Tyr | Thr | Ala | Ser | Gln | Pro | Leu | Tyr | Gln | Pro | Ser | His | Ala | Thr | |
| | | | 370 | | | | | 375 | | | | | 380 | | | |

```
gag caa cga ccg caa aag gaa ccg act gac cag atc cag gca aca atc      1200
Glu Gln Arg Pro Gln Lys Glu Pro Thr Asp Gln Ile Gln Ala Thr Ile
385                 390                 395                 400 tct tta aat aca gac cag act aca gca tca tca tcc ctt cct gct gct      1248
Ser Leu Asn Thr Asp Gln Thr Thr Ala Ser Ser Ser Leu Pro Ala Ala
                405                 410                 415 tct cag cct cag gtg ttc cag gct ggg aca agc aaa cct tta cac agc      1296
Ser Gln Pro Gln Val Phe Gln Ala Gly Thr Ser Lys Pro Leu His Ser
            420                 425                 430 agt ggg atc aat gta aat gca gcg cca ttc cag tcc atg caa acg gtg      1344
Ser Gly Ile Asn Val Asn Ala Ala Pro Phe Gln Ser Met Gln Thr Val
        435                 440                 445 ttc aac atg aat gcc ccg gtt cct cct gtt aat gaa cca gaa act tta      1392
Phe Asn Met Asn Ala Pro Val Pro Pro Val Asn Glu Pro Glu Thr Leu
    450                 455                 460 aaa cag caa aat cag tac cag gcc agc tat aac cag agc ttt tcc agt      1440
Lys Gln Gln Asn Gln Tyr Gln Ala Ser Tyr Asn Gln Ser Phe Ser Ser
465                 470                 475                 480 ccg cct cac caa gta gag cag aca gag ctt ccg caa gag cag ctt cag      1488
Pro Pro His Gln Val Glu Gln Thr Glu Leu Pro Gln Glu Gln Leu Gln
                485                 490                 495 acg gtg gtt ggt act tac cat gct tcc caa gac cag ccc cat caa gtg      1536
Thr Val Val Gly Thr Tyr His Ala Ser Gln Asp Gln Pro His Gln Val
            500                 505                 510 acc ggt aac cac cag cag cct ccc cag cag aac act ggg ttt cca cgt      1584
Thr Gly Asn His Gln Gln Pro Pro Gln Gln Asn Thr Gly Phe Pro Arg
        515                 520                 525 agc agt cag ccc tat tac aac agt cgt ggt gtg tct cgt gga ggc tcc      1632
Ser Ser Gln Pro Tyr Tyr Asn Ser Arg Gly Val Ser Arg Gly Gly Ser
    530                 535                 540 cgt ggt gct aga ggc ttg atg aat gga tac agg ggc cct gcc aat gga      1680
Arg Gly Ala Arg Gly Leu Met Asn Gly Tyr Arg Gly Pro Ala Asn Gly
545                 550                 555                 560 ttc aga gga gga tat gat ggt tac cgc cct tcg ttc tct aac act cca      1728
Phe Arg Gly Gly Tyr Asp Gly Tyr Arg Pro Ser Phe Ser Asn Thr Pro
                565                 570                 575 aac agc ggt tac aca cag tct cag ttc agt gct ccc cgg gac tac tct      1776
Asn Ser Gly Tyr Thr Gln Ser Gln Phe Ser Ala Pro Arg Asp Tyr Ser
            580                 585                 590 ggc tat cag cgg gat gga tat cag cag aat ttc aag cga ggc tct ggg      1824
Gly Tyr Gln Arg Asp Gly Tyr Gln Gln Asn Phe Lys Arg Gly Ser Gly
        595                 600                 605 cag agt gga ccc cgg gga gcc cca cga ggt cgt gga ggg ccc cca aga      1872
Gln Ser Gly Pro Arg Gly Ala Pro Arg Gly Arg Gly Gly Pro Pro Arg
    610                 615                 620 ccc aac aga ggg atg ccg caa atg aac act cag caa gtg aat taa          1917
Pro Asn Arg Gly Met Pro Gln Met Asn Thr Gln Gln Val Asn
625                 630                 635 tctgattcac aggattatct ttaatcgcca aaacacactg gccagtgtac cataatatgt   1977
taccagaaga gttattatct atttgttctc cctttcagga aacttattgt aaagggactg   2037
ttttcatccc ataaagacag gactacagtt gtcagcttta tattacctgg atatggaagg   2097
aaactatttt tactctgcat gttctgtcct aagcgtcatc ttgagccttg cacatgatac   2157
tcagattcct ttcccttgct taggagtaaa acataatata ctttatgggg tgataatatc   2217
tccatagtta tttgaagtgg cttggaaaaa gcaagattga cttttgacat tggataaaat   2277
ctacaaatca gccctagagt ttcatggtca ttcacaaaac taaatatttt cccttgaaag   2337
```

```
gaagatggaa ggactggagt gtggtttggc agaacaactg catttcacag cttttcctat   2397
taaattggag cactgaatgt taaatgcata ccaaattatg catgggccct taatcacaca   2457
tacatggcta ccagctttga cacagcacta ttcatcctct ggccaaacga ctgtggttaa   2517
aaacacgtgt aaattgcttt ttaacagctg atactgtaaa agacaaagct aaaatgcaaa   2577
attaggcttt cattggcact tttcgaaaaa tatgcaacaa atttgggatg taatctggat   2637
ggccacttct gtacttaatg tgaagtattt agatacctttt ttgaacactt aacagtttct   2697
tcgacaatga cttttgtaag gattggtagt atatatcatt ccttatgaca tacattgtct   2757
gttgctaatc cttggatctt gctgtattgt caccta aatt ggtacaggta ctgatgaaaa   2817
tctctcatgg ataaacctaa cactcttcgt cacatgtttt tcctgcagcc tgaaggtttt   2877
taaaaggaaa agatatcaaa tgcctgctgc taccacccct ttaaattgct atcttttgaa   2937
aagcaccagt atgtgttttt agattgattt ccctatttta gggaaatgac agtcagtagt   2997
ttcagttctg atggtataag caaagcaaat aaaacgtgtt tataaaagtt gtatcttgaa   3057
acactggtgt tcaacagcta gcagcttctg tggttcaccc cctgccttgt tagtgttacc   3117
catttatggt tatctccagc agcaatttct cta                                3150

<210> SEQ ID NO 18
<211> LENGTH: 638
<212> TYPE: PRT
<213> ORGANISM: Equus caballus

<400> SEQUENCE: 18

Met Glu Gly Lys Leu Asp Asp Tyr Gln Glu Arg Met Asn Lys Gly Glu
1               5                   10                  15

Arg Leu Asn Gln Asp Gln Leu Asp Ala Val Ser Lys Tyr Gln Glu Val
                20                  25                  30

Thr Asn Asn Leu Glu Phe Ala Lys Glu Leu Gln Arg Ser Phe Met Ala
            35                  40                  45

Leu Ser Gln Asp Ile Gln Lys Thr Ile Lys Lys Thr Ala Arg Arg Glu
        50                  55                  60

Gln Leu Met Arg Glu Glu Ala Glu Gln Lys Arg Leu Lys Thr Val Leu
65                  70                  75                  80

Glu Leu Gln Tyr Val Leu Asp Lys Leu Gly Asp Glu Glu Val Arg Thr
                85                  90                  95

Asp Leu Lys Gln Gly Leu Asn Gly Val Pro Ile Leu Ser Glu Glu Glu
                100                 105                 110

Leu Ser Leu Leu Asp Glu Phe Tyr Lys Leu Ala Asp Pro Val Arg Asp
            115                 120                 125

Met Ser Leu Arg Leu Asn Glu Gln Tyr Glu His Ala Ser Ile His Leu
        130                 135                 140

Trp Asp Leu Leu Glu Gly Lys Glu Lys Ser Val Cys Gly Thr Thr Tyr
145                 150                 155                 160

Lys Ala Leu Arg Glu Ile Val Glu Arg Val Phe Gln Ser Asn Tyr Phe
                165                 170                 175

Asp Ser Thr His Asn His Gln Asn Gly Leu Cys Glu Glu Glu Glu Ala
            180                 185                 190

Thr Ser Ala Pro Thr Ala Glu Asp Gln Gly Ala Glu Ala Glu Pro Glu
        195                 200                 205

Pro Ala Glu Glu Tyr Thr Glu Gln Ser Glu Val Glu Ser Thr Glu Tyr
    210                 215                 220

Val Asn Arg Gln Phe Met Ala Glu Ala Gln Phe Ser Gly Glu Lys Glu
```

```
            225                 230                 235                 240

Gln Val Asp Glu Trp Thr Val Glu Thr Val Glu Val Val Asn Ser Leu
                        245                 250                 255

Gln Gln Gln Pro Gln Ala Ala Ser Pro Ser Val Pro Glu Pro His Ser
                    260                 265                 270

Leu Thr Pro Val Ala Gln Ala Asp Pro Leu Val Arg Arg Gln Arg Val
                275                 280                 285

Gln Asp Leu Met Ala Gln Met Gln Gly Pro Tyr Asn Phe Ile Gln Asp
        290                 295                 300

Ser Met Leu Asp Phe Glu Asn Gln Thr Leu Asp Pro Ala Ile Val Ser
        305                 310                 315                 320

Ala Gln Pro Met Asn Pro Ala Gln Asn Met Asp Met Pro Gln Leu Val
                        325                 330                 335

Cys Pro Pro Val His Ala Glu Ser Arg Leu Ala Gln Pro Asn Gln Val
                        340                 345                 350

Pro Val Gln Pro Glu Ala Thr Gln Val Pro Leu Val Ser Ser Thr Ser
                    355                 360                 365

Glu Gly Tyr Thr Ala Ser Gln Pro Leu Tyr Gln Pro Ser His Ala Thr
                370                 375                 380

Glu Gln Arg Pro Gln Lys Glu Pro Thr Asp Gln Ile Gln Ala Thr Ile
        385                 390                 395                 400

Ser Leu Asn Thr Asp Gln Thr Thr Ala Ser Ser Ser Leu Pro Ala Ala
                        405                 410                 415

Ser Gln Pro Gln Val Phe Gln Ala Gly Thr Ser Lys Pro Leu His Ser
                        420                 425                 430

Ser Gly Ile Asn Val Asn Ala Ala Pro Phe Gln Ser Met Gln Thr Val
                    435                 440                 445

Phe Asn Met Asn Ala Pro Val Pro Pro Val Asn Glu Pro Glu Thr Leu
                450                 455                 460

Lys Gln Gln Asn Gln Tyr Gln Ala Ser Tyr Asn Gln Ser Phe Ser Ser
        465                 470                 475                 480

Pro Pro His Gln Val Glu Gln Thr Glu Leu Pro Gln Glu Gln Leu Gln
                        485                 490                 495

Thr Val Val Gly Thr Tyr His Ala Ser Gln Asp Gln Pro His Gln Val
                        500                 505                 510

Thr Gly Asn His Gln Gln Pro Pro Gln Gln Asn Thr Gly Phe Pro Arg
                    515                 520                 525

Ser Ser Gln Pro Tyr Tyr Asn Ser Arg Gly Val Ser Arg Gly Gly Ser
                530                 535                 540

Arg Gly Ala Arg Gly Leu Met Asn Gly Tyr Arg Gly Pro Ala Asn Gly
        545                 550                 555                 560

Phe Arg Gly Gly Tyr Asp Gly Tyr Arg Pro Ser Phe Ser Asn Thr Pro
                        565                 570                 575

Asn Ser Gly Tyr Thr Gln Ser Gln Phe Ser Ala Pro Arg Asp Tyr Ser
                        580                 585                 590

Gly Tyr Gln Arg Asp Gly Tyr Gln Gln Asn Phe Lys Arg Gly Ser Gly
                    595                 600                 605

Gln Ser Gly Pro Arg Gly Ala Pro Arg Gly Arg Gly Pro Pro Arg
                610                 615                 620

Pro Asn Arg Gly Met Pro Gln Met Asn Thr Gln Gln Val Asn
        625                 630                 635

<210> SEQ ID NO 19
```

```
<211> LENGTH: 6181
<212> TYPE: DNA
<213> ORGANISM: Mus musculus
<220> FEATURE:
<221> NAME/KEY: CDS
<222> LOCATION: (179)..(2302)

<400> SEQUENCE: 19
gctggctggc taagtccctc ccgcgccggc tcttgtccca ctaggagcag ctcagagccg      60
cggggacagg gcgaagcggc ctgcgcccac ggagcgcacg tctctgttct caacgcagca     120 ccaccctttgc cccctcggc tgcccactcc agacgtccag cggctccgcg cgcgcacg        178 atg ccc tcg gcc acc agc cac agc gga agc ggc agc aaa tcg tcg gga      226
Met Pro Ser Ala Thr Ser His Ser Gly Ser Gly Ser Lys Ser Ser Gly
1               5                  10                  15 ccg ccg ccg ccg tcc ggt tcc tcc ggg agt gag gcg gcg gcc ggg gca      274
Pro Pro Pro Pro Ser Gly Ser Ser Gly Ser Glu Ala Ala Ala Gly Ala
            20                  25                  30 gct gcg ccg gct tct cag cat ccg gca acc ggc acc ggc gcc gtc cag      322
Ala Ala Pro Ala Ser Gln His Pro Ala Thr Gly Thr Gly Ala Val Gln
        35                  40                  45 acc gag gcc atg aag cag att ctc ggc gta atc gac aag aaa ctt cgg      370
Thr Glu Ala Met Lys Gln Ile Leu Gly Val Ile Asp Lys Lys Leu Arg
50                  55                  60 aac ctg gag aag aaa aag ggt aaa ctt gat gat tac cag gaa cga atg      418
Asn Leu Glu Lys Lys Lys Gly Lys Leu Asp Asp Tyr Gln Glu Arg Met
65                  70                  75                  80 aat aaa ggg gaa agg ctc aat caa gac cag ctg gat gcc gta tct aag      466
Asn Lys Gly Glu Arg Leu Asn Gln Asp Gln Leu Asp Ala Val Ser Lys
                85                  90                  95 tac cag gaa gtc aca aat aat ttg gag ttt gca aag gaa tta cag agg      514
Tyr Gln Glu Val Thr Asn Asn Leu Glu Phe Ala Lys Glu Leu Gln Arg
            100                 105                 110 agt ttc atg gca tta agt caa gat att cag aaa aca ata aag aag aca      562
Ser Phe Met Ala Leu Ser Gln Asp Ile Gln Lys Thr Ile Lys Lys Thr
        115                 120                 125 gca cgt cgg gaa cag ctt atg aga gaa gaa gca gaa cag aag cgc tta      610
Ala Arg Arg Glu Gln Leu Met Arg Glu Glu Ala Glu Gln Lys Arg Leu
    130                 135                 140 aaa act gta ctt gag tta cag tat gta ttg gat aag ctg gga gat gat      658
Lys Thr Val Leu Glu Leu Gln Tyr Val Leu Asp Lys Leu Gly Asp Asp
145                 150                 155                 160 gat gtg aga aca gat ctg aaa caa ggt ttg agt gga gtg cca ata ttg      706
Asp Val Arg Thr Asp Leu Lys Gln Gly Leu Ser Gly Val Pro Ile Leu
                165                 170                 175 tct gag gag gag ttg tca ttg ctg gat gag ttc tac aag ctc gta gat      754
Ser Glu Glu Glu Leu Ser Leu Leu Asp Glu Phe Tyr Lys Leu Val Asp
            180                 185                 190 cct gag cgt gac atg agt tta agg tta aat gag cag tat gaa cat gcc      802
Pro Glu Arg Asp Met Ser Leu Arg Leu Asn Glu Gln Tyr Glu His Ala
        195                 200                 205 tca att cac ttg tgg gat ttg ctg aaa ggg aaa gaa aag cct gtg tgt      850
Ser Ile His Leu Trp Asp Leu Leu Lys Gly Lys Glu Lys Pro Val Cys
    210                 215                 220 gga aca acc tat aaa gct cta aag gaa att gtt gag cgt gtt ttc cag      898
Gly Thr Thr Tyr Lys Ala Leu Lys Glu Ile Val Glu Arg Val Phe Gln
225                 230                 235                 240 tca aac tac ttt gat agc act cac aat cat caa aat ggg ttg tgt gag      946
Ser Asn Tyr Phe Asp Ser Thr His Asn His Gln Asn Gly Leu Cys Glu
                245                 250                 255
```

| | | |
|---|---|---|
| gag gaa gag gcg gct tca gcg ccc aca gtg gag gac cag gta gct gaa<br>Glu Glu Glu Ala Ala Ser Ala Pro Thr Val Glu Asp Gln Val Ala Glu<br>260                       265                   270 | 994 |
| gct gaa cct gag cca gcg gaa gaa tac aca gag caa agt gag gtt gaa<br>Ala Glu Pro Glu Pro Ala Glu Glu Tyr Thr Glu Gln Ser Glu Val Glu<br>275                       280                   285 | 1042 |
| tca aca gag tat gtc aat agg cag ttc atg gca gaa aca cag ttc agc<br>Ser Thr Glu Tyr Val Asn Arg Gln Phe Met Ala Glu Thr Gln Phe Ser<br>290                       295                   300 | 1090 |
| agt ggt gag aag gag caa gtg gat gag tgg aca gtt gaa aca gtt gag<br>Ser Gly Glu Lys Glu Gln Val Asp Glu Trp Thr Val Glu Thr Val Glu<br>305                       310                   315                   320 | 1138 |
| gtt gta aac tca ctc cag cag caa cct cag gct gcg tcc cct tca gtc<br>Val Val Asn Ser Leu Gln Gln Gln Pro Gln Ala Ala Ser Pro Ser Val<br>                   325                   330                   335 | 1186 |
| cca gag ccc cac tct ttg act cca gtg gct cag tca gat cca ctt gtg<br>Pro Glu Pro His Ser Leu Thr Pro Val Ala Gln Ser Asp Pro Leu Val<br>                   340                   345                   350 | 1234 |
| aga agg cag cgt gta caa gat ctt atg gca caa atg caa ggg ccc tat<br>Arg Arg Gln Arg Val Gln Asp Leu Met Ala Gln Met Gln Gly Pro Tyr<br>               355                   360                   365 | 1282 |
| aat ttc ata cag gat tca atg ttg gat ttt gaa aat cag acg ctt gat<br>Asn Phe Ile Gln Asp Ser Met Leu Asp Phe Glu Asn Gln Thr Leu Asp<br>370                       375                   380 | 1330 |
| cct gcc att gta tcc gca cag cct atg aac cct acc cag aac atg gat<br>Pro Ala Ile Val Ser Ala Gln Pro Met Asn Pro Thr Gln Asn Met Asp<br>385                       390                   395                   400 | 1378 |
| atg cct cag ctg gtt tgc cct cag gtt cat tct gaa tct aga ctt gcc<br>Met Pro Gln Leu Val Cys Pro Gln Val His Ser Glu Ser Arg Leu Ala<br>                   405                   410                   415 | 1426 |
| caa tct aat caa gtt cct gta caa cca gaa gcc aca cag gtt cct ttg<br>Gln Ser Asn Gln Val Pro Val Gln Pro Glu Ala Thr Gln Val Pro Leu<br>                   420                   425                   430 | 1474 |
| gtt tca tcc aca agt gag ggg tat aca gca tct cag ccc ttg tac cag<br>Val Ser Ser Thr Ser Glu Gly Tyr Thr Ala Ser Gln Pro Leu Tyr Gln<br>               435                   440                   445 | 1522 |
| cca tct cat gct acg gag cag cgg ccg cag aaa gag cca atg gat cag<br>Pro Ser His Ala Thr Glu Gln Arg Pro Gln Lys Glu Pro Met Asp Gln<br>450                       455                   460 | 1570 |
| att cag gca aca ata tct ttg aat aca gac cag act aca gca tcc tca<br>Ile Gln Ala Thr Ile Ser Leu Asn Thr Asp Gln Thr Thr Ala Ser Ser<br>465                       470                   475                   480 | 1618 |
| tcc ctt cct gct gct tct cag cct caa gtg ttc cag gct ggg aca agt<br>Ser Leu Pro Ala Ala Ser Gln Pro Gln Val Phe Gln Ala Gly Thr Ser<br>                   485                   490                   495 | 1666 |
| aaa cct ttg cac agc agt gga atc aat gta aat gca gct cca ttc cag<br>Lys Pro Leu His Ser Ser Gly Ile Asn Val Asn Ala Ala Pro Phe Gln<br>               500                   505                   510 | 1714 |
| tcc atg caa acg gtg ttc aat atg aat gct cca gtc cct cct gct aat<br>Ser Met Gln Thr Val Phe Asn Met Asn Ala Pro Val Pro Pro Ala Asn<br>             515                   520                   525 | 1762 |
| gaa cca gaa acg tta aaa caa cag agt cag tac cag gcc act tat aac<br>Glu Pro Glu Thr Leu Lys Gln Gln Ser Gln Tyr Gln Ala Thr Tyr Asn<br>530                       535                   540 | 1810 |
| cag agt ttt tcc agt cag cct cac caa gtg gaa caa aca gag ctt caa<br>Gln Ser Phe Ser Ser Gln Pro His Gln Val Glu Gln Thr Glu Leu Gln<br>545                       550                   555                   560 | 1858 |
| caa gac caa ctg caa acg gtg gtt ggc act tac cat gga tcc cag gac<br>Gln Asp Gln Leu Gln Thr Val Val Gly Thr Tyr His Gly Ser Gln Asp<br>                   565                   570                   575 | 1906 |

```
cag cct cat caa gtg cct ggt aac cac cag caa ccc cca cag cag aac       1954
Gln Pro His Gln Val Pro Gly Asn His Gln Gln Pro Pro Gln Gln Asn
            580                 585                 590 act ggc ttt cca cgt agc agt cag cct tat tac aac agt cgt ggg gta       2002
Thr Gly Phe Pro Arg Ser Ser Gln Pro Tyr Tyr Asn Ser Arg Gly Val
        595                 600                 605 tct cga gga ggg tct cgt ggt gcc aga ggc ttg atg aat gga tac agg       2050
Ser Arg Gly Gly Ser Arg Gly Ala Arg Gly Leu Met Asn Gly Tyr Arg
    610                 615                 620 ggc cct gcc aat gga ttt aga gga gga tat gat ggt tac cgc cct tca       2098
Gly Pro Ala Asn Gly Phe Arg Gly Gly Tyr Asp Gly Tyr Arg Pro Ser
625                 630                 635                 640 ttc tcg aac act cca aac agt ggt tat tca cag tct cag ttc act gct       2146
Phe Ser Asn Thr Pro Asn Ser Gly Tyr Ser Gln Ser Gln Phe Thr Ala
                645                 650                 655 ccc cgg gac tac tct ggt tac cag cgg gat gga tat cag cag aat ttc       2194
Pro Arg Asp Tyr Ser Gly Tyr Gln Arg Asp Gly Tyr Gln Gln Asn Phe
            660                 665                 670 aag cga ggc tct ggg cag agt gga cca cgg gga gcc cca cga ggt cgt       2242
Lys Arg Gly Ser Gly Gln Ser Gly Pro Arg Gly Ala Pro Arg Gly Arg
        675                 680                 685 gga ggg ccc cca aga ccc aac aga ggg atg ccg caa atg aac act cag       2290
Gly Gly Pro Pro Arg Pro Asn Arg Gly Met Pro Gln Met Asn Thr Gln
    690                 695                 700 caa gtg aat taa tgtgatacac aggattatgt ttaatcgcca aaaacacact           2342
Gln Val Asn
705 ggccagtgta ccataatatg ttaccagaag agttattatc tatttgttct cccttttcagg    2402 aaacttattg taaagggact gttttcatcc cataaagaca ggactgcaat tgtcagcttt     2462 acattacctg gatatggaag gaaactattt ttattctgca tgttctgtcc taagcgtcat    2522 cttgagcctt gcacacaata caatactcag attcctcacc cttgcttagg agtaaaacat    2582 tatatactta tggggtgata atatctccat agttagttga agtggcttgg aaaaaaaatg    2642 caagattgaa ttttttgacct tggataaaat ctacaatcag ccctagaact attcagtggt   2702 aattgacaaa gttaaagcat tttctttgaa aggaagatgg aaggagtgga gtgtggttta    2762 gcaaaactgc atttcatagc tttcccatta aattggagca ccgacagatt aaaagcatac    2822 caaattatgc atgggtcctt actcacacaa gtgaggctgg ctaccagcct tgacatagca    2882 ctcactagtc ttctggccaa acgactgtga ttaaaacaca tgtaaattgc tctttagtag    2942 tggatactgt gtaagacaaa gccaaattgc aaatcaggct ttgattggct cttctggaaa    3002 atatgcatca aatatggggg ataatctgga tgggctgctg ctgtgctcaa tgtgaactat    3062 ttagatacct ttgaacact taacagtttc tctgaacaat gacttacatg gggattggtc     3122 ctgtttgtca ttcctcacca taattgcatt gtcatcacta atccttggat cttgctgtat    3182 tgttactcaa attggtaata ggtactgatg gaaatcgcta atggatggat aatcataaca    3242 cttttggtca catgttttct cctgcagcct gaaagttctt aaagaaaaag atatcaaatg    3302 cctgctgcta ccaccctttt aaattgctat ctttagaaaa gcaccggtat gtgttttaga    3362 ttcatttccc tgttttaggg aaatgacagg cagtagtttc agttctgatg gcaaaacaaa    3422 taaaaacatg tttctaaaag ttgtatcttg aaacactggt gttcaacagc tagcagctaa    3482 agtaattcaa cccatgcatt gctagtgtca cagcctttgg ttatgtctag tagctgtttc    3542 tgaagtattt tcatttatct tttgtcaaat ttaaccctgt tgaattctc tccttttcctc    3602
```

```
aaggagacac ttatgttcaa agtgttgatt ctttgcctta ggtgcataga gagtagacag    3662
tttggagatg gaaaggttag cagtgactta gccatatgtt ctgtgttgga atttgtgcta    3722
gcagtttgag cactagctct gcgtgcctat gaactgaatg ctgcttgtcc cattccattt    3782
tatgtcatgg agaaataatt ccacttggta acacaaaggc taagttaatg ttattttctg    3842
tacagaaatt aaattttact tttagccttt tgtaaacttt ttttttttttt ttccaagccg    3902 gtatcagcta ctcaaaacaa ttctcagata ttcatcatta gacaactgga gtttttgctg    3962
gttttgtagc ctactaaaac tgctgaggct gttgaacatt ccacattcaa aagttttgta    4022
gggtggtgga taatgggga gcttcaatgt ttatttttaaa ataaataaaa taagttcttg    4082
acttttctca tgtgtggtta tggtacatca tattggaagg gttatctgtt tacttttgcc    4142
aagactattt tgccagcacc tacacttgtg tgctttaaaa gacaactacc tgggatgtac    4202
cacaaccata tgttaattgt attttattgg gatggataaa atgtttgtgg tttattggat    4262
aatccctaga tggtgtgtta cgtgtgtaga atataatttt atgatagtaa gaaagcaaaa    4322
ttgaagaaaa taagtttagt attgaatttg agttctgaag tgaattcagg gaatgtctca    4382
cgtttcgggc ttctacccaa agtgtagggc agaaggtgta aaagttgttt gtagtttgac    4442
ttgtttattt tttaagttgc ttattccttt caacagcaac atatcattag ctgtcattct    4502
accattgcag ttctagtgag ttttaacgtc tgcattcaag actgttttaa aagcaacctc    4562
actggacaga gaactgctaa agtcttttcc ttaagatctg agtctttgtt actcagtatc    4622
ttctataata tgcaaatgct tgtctagagg cagaagacct tttgtttggt caagtgtgta    4682
ttttaccaga gtcagggaa ctgatggtcc tacatgtctc ttagtgtagt aagactataa     4742
aatcttttgt acatgcacaa ttcacagtat gtttagatac cacgtgtata atgcccccccc   4802 ctccccagg tagcatgcca ttgatgactt tttgcttagg gccatttta taccagggcc      4862 ttaatattcc taaaaagatg attttttttc atcctttctc ctcttttgat cattgtatct    4922
tgatattaaa aacatgacct tccaatgatt gtagtaaatt aacttctata gttcttttgt    4982
ctctatatgt attcatatat atgctattgt atagagactt caaggagaca tggagatgca    5042
tgcttattct caggttcatt cactaaggtg cttggcagac aaccagtttc taagtgcaga    5102
atgtagttaa gcagcttcat atatgtgcca ggcaatttgt tttgttaaat tttcatctac    5162
ttaaggaaat agggtattgt agcttaggct gatcataccc ttcatttcaa ccttaagctc    5222
tcaacctgca tccatccgac ttgagctatt aagtacttta gttttatcga gtataagtta    5282
acagaaaaag taaattaagc tttgccttta ctattttgaa tttatataca ttctggaaaa    5342
acttagaaac tgttgtatat ttcattagat taaattatat gaaaatgtga ttgtttatag    5402
caaagcctgt gagttgcata caccctaagg aaaactcctt aagtgctcct tgaagagaga    5462
agaaacaatt ctgggtctgg tctttttaag aacaaagcta gactactgta tgttagcact    5522
gtacattaat agtctgttgt gaagcttgag cagtttcctg catagccttg atccttcacc    5582
gttggcattg aaaatagcag tatccctgat gtacttaaaa cttaaagtca ggttttggta    5642
tatttatttg taagtcttaa tttcctctaa atactatatc tctttagcga gacaacctga    5702
aatttattag cacatttggg tatctcttgc ttggcattat ggccagtgtt aactattcag    5762
tggtgaaaaa attacccctc aagacactgg agtgaccccca gatgtgtgta gtaagtggca    5822
tggttcaact gtgtggttaa tgataaaatat atgactagt cggtatgatc tggaaagact    5882
tgattgaaag ataattcagc tgacataagg atgagtgagg agtggcaaac tggataaaag    5942
agtcaagaga cctgtattcc agtgactcct gttttgttta agcattagca agatctgtct    6002
```

```
ggggaaactg atagggcag ttttcttcca tgtttagttt ttgtctcaac atttggaagc    6062
tattgaaggt tttaaaatgg tgtgtattgt ttttttttgg ggggggggtg gccagaatag    6122
tgggtcatct aataaaactg ccatttaaaa gatcaaaaaa aaaaaaaaaa aaaaaaaa      6181
```

<210> SEQ ID NO 20
<211> LENGTH: 707
<212> TYPE: PRT
<213> ORGANISM: Mus musculus

<400> SEQUENCE: 20

```
Met Pro Ser Ala Thr Ser His Ser Gly Ser Gly Ser Lys Ser Gly
1               5                   10                  15

Pro Pro Pro Ser Gly Ser Ser Gly Ser Glu Ala Ala Gly Ala
            20                  25                  30

Ala Ala Pro Ala Ser Gln His Pro Ala Thr Gly Thr Gly Ala Val Gln
                35                  40                  45

Thr Glu Ala Met Lys Gln Ile Leu Gly Val Ile Asp Lys Lys Leu Arg
50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
                100                 105                 110

Ser Phe Met Ala Leu Ser Gln Asp Ile Gln Lys Thr Ile Lys Lys Thr
            115                 120                 125

Ala Arg Arg Glu Gln Leu Met Arg Glu Glu Ala Glu Gln Lys Arg Leu
            130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
            195                 200                 205

Ser Ile His Leu Trp Asp Leu Leu Glu Gly Lys Glu Lys Pro Val Cys
            210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Gln Ser Glu Val Glu
            275                 280                 285

Ser Thr Glu Tyr Val Asn Arg Gln Phe Met Ala Glu Thr Gln Phe Ser
290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
```

|     |     |     |     | 340 |     |     |     | 345 |     |     |     | 350 |     |     |
| --- | --- | --- | --- | --- | --- | --- | --- | --- | --- | --- | --- | --- | --- | --- |
| Arg | Arg | Gln | Arg | Val | Gln | Asp | Leu | Met | Ala | Gln | Met | Gln | Gly | Pro | Tyr |
|     |     |     | 355 |     |     |     |     | 360 |     |     |     |     | 365 |     |     |
| Asn | Phe | Ile | Gln | Asp | Ser | Met | Leu | Asp | Phe | Glu | Asn | Gln | Thr | Leu | Asp |
|     |     | 370 |     |     |     |     | 375 |     |     |     |     | 380 |     |     |     |
| Pro | Ala | Ile | Val | Ser | Ala | Gln | Pro | Met | Asn | Pro | Thr | Gln | Asn | Met | Asp |
| 385 |     |     |     |     | 390 |     |     |     |     | 395 |     |     |     |     | 400 |
| Met | Pro | Gln | Leu | Val | Cys | Pro | Gln | Val | His | Ser | Glu | Ser | Arg | Leu | Ala |
|     |     |     | 405 |     |     |     |     | 410 |     |     |     |     | 415 |     |     |
| Gln | Ser | Asn | Gln | Val | Pro | Val | Gln | Pro | Glu | Ala | Thr | Gln | Val | Pro | Leu |
|     |     | 420 |     |     |     |     | 425 |     |     |     |     | 430 |     |     |     |
| Val | Ser | Thr | Ser | Glu | Gly | Tyr | Thr | Ala | Ser | Gln | Pro | Leu | Tyr | Gln |
| 435 |     |     |     |     | 440 |     |     |     |     | 445 |     |     |     |     |
| Pro | Ser | His | Ala | Thr | Glu | Gln | Arg | Pro | Gln | Lys | Glu | Pro | Met | Asp | Gln |
|     |     |     | 450 |     |     |     |     | 455 |     |     |     |     | 460 |     |     |
| Ile | Gln | Ala | Thr | Ile | Ser | Leu | Asn | Thr | Asp | Gln | Thr | Thr | Ala | Ser | Ser |
| 465 |     |     |     |     | 470 |     |     |     |     | 475 |     |     |     |     | 480 |
| Ser | Leu | Pro | Ala | Ala | Ser | Gln | Pro | Gln | Val | Phe | Gln | Ala | Gly | Thr | Ser |
|     |     |     | 485 |     |     |     |     | 490 |     |     |     |     | 495 |     |     |
| Lys | Pro | Leu | His | Ser | Ser | Gly | Ile | Asn | Val | Asn | Ala | Ala | Pro | Phe | Gln |
|     |     |     | 500 |     |     |     |     | 505 |     |     |     |     | 510 |     |     |
| Ser | Met | Gln | Thr | Val | Phe | Asn | Met | Asn | Ala | Pro | Val | Pro | Pro | Ala | Asn |
|     |     |     | 515 |     |     |     |     | 520 |     |     |     |     | 525 |     |     |
| Glu | Pro | Glu | Thr | Leu | Lys | Gln | Gln | Ser | Gln | Tyr | Gln | Ala | Thr | Tyr | Asn |
|     |     |     | 530 |     |     |     |     | 535 |     |     |     |     | 540 |     |     |
| Gln | Ser | Phe | Ser | Ser | Gln | Pro | His | Gln | Val | Glu | Gln | Thr | Glu | Leu | Gln |
| 545 |     |     |     |     | 550 |     |     |     |     | 555 |     |     |     |     | 560 |
| Gln | Asp | Gln | Leu | Gln | Thr | Val | Val | Gly | Thr | Tyr | His | Gly | Ser | Gln | Asp |
|     |     |     | 565 |     |     |     |     | 570 |     |     |     |     | 575 |     |     |
| Gln | Pro | His | Gln | Val | Pro | Gly | Asn | His | Gln | Gln | Pro | Gln | Gln | Asn |
|     |     |     | 580 |     |     |     |     | 585 |     |     |     |     | 590 |     |     |
| Thr | Gly | Phe | Pro | Arg | Ser | Ser | Gln | Pro | Tyr | Tyr | Asn | Ser | Arg | Gly | Val |
|     |     |     | 595 |     |     |     |     | 600 |     |     |     |     | 605 |     |     |
| Ser | Arg | Gly | Gly | Ser | Arg | Gly | Ala | Arg | Gly | Leu | Met | Asn | Gly | Tyr | Arg |
|     | 610 |     |     |     |     | 615 |     |     |     |     | 620 |     |     |     |     |
| Gly | Pro | Ala | Asn | Gly | Phe | Arg | Gly | Gly | Tyr | Asp | Gly | Tyr | Arg | Pro | Ser |
| 625 |     |     |     |     | 630 |     |     |     |     | 635 |     |     |     |     | 640 |
| Phe | Ser | Asn | Thr | Pro | Asn | Ser | Gly | Tyr | Ser | Gln | Ser | Gln | Phe | Thr | Ala |
|     |     |     | 645 |     |     |     |     | 650 |     |     |     |     | 655 |     |     |
| Pro | Arg | Asp | Tyr | Ser | Gly | Tyr | Gln | Arg | Asp | Gly | Tyr | Gln | Gln | Asn | Phe |
|     |     |     | 660 |     |     |     |     | 665 |     |     |     |     | 670 |     |     |
| Lys | Arg | Gly | Ser | Gly | Gln | Ser | Gly | Pro | Arg | Gly | Ala | Pro | Arg | Gly | Arg |
|     |     |     | 675 |     |     |     |     | 680 |     |     |     |     | 685 |     |     |
| Gly | Gly | Pro | Pro | Arg | Pro | Asn | Arg | Gly | Met | Pro | Gln | Met | Asn | Thr | Gln |
|     | 690 |     |     |     |     | 695 |     |     |     |     | 700 |     |     |     |     |
| Gln | Val | Asn |
| 705 |     |     |

```
<210> SEQ ID NO 21
<211> LENGTH: 6141
<212> TYPE: DNA
<213> ORGANISM: Mus musculus
<220> FEATURE:
<221> NAME/KEY: CDS
<222> LOCATION: (139)..(2262)
```

<400> SEQUENCE: 21

```
cccaccgcgc gcgcgcgtag ccgcctgccc gcccgcccgc tgcgcgtttt gtcccgcgtc      60
tctccccgtc cgtctcctga cttgctggtc ttgtccttcc ctcccgcttt tttcctctcc     120
tctcttctcg gtctaaag atg ccc tcg gcc acc agc cac agc gga agc ggc       171
                    Met Pro Ser Ala Thr Ser His Ser Gly Ser Gly
                     1               5                  10 agc aaa tcg tcg gga ccg ccg ccg tcc ggt tcc tcc ggg agt gag           219
Ser Lys Ser Ser Gly Pro Pro Pro Ser Gly Ser Ser Gly Ser Glu
             15                  20                  25 gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
                 30                  35                  40 acc ggc gcc gtc cag acc gag gcc atg aag cag att ctc ggc gta atc       315
Thr Gly Ala Val Gln Thr Glu Ala Met Lys Gln Ile Leu Gly Val Ile
         45                  50                  55 gac aag aaa ctt cgg aac ctg gag aag aaa aag ggt aaa ctt gat gat       363
Asp Lys Lys Leu Arg Asn Leu Glu Lys Lys Lys Gly Lys Leu Asp Asp
 60                  65                  70                  75 tac cag gaa cga atg aat aaa ggg gaa agg ctc aat caa gac cag ctg       411
Tyr Gln Glu Arg Met Asn Lys Gly Glu Arg Leu Asn Gln Asp Gln Leu
                 80                  85                  90 gat gcc gta tct aag tac cag gaa gtc aca aat aat ttg gag ttt gca       459
Asp Ala Val Ser Lys Tyr Gln Glu Val Thr Asn Asn Leu Glu Phe Ala
             95                 100                 105 aag gaa tta cag agg agt ttc atg gca tta agt caa gat att cag aaa       507
Lys Glu Leu Gln Arg Ser Phe Met Ala Leu Ser Gln Asp Ile Gln Lys
        110                 115                 120 aca ata aag aag aca gca cgt cgg gaa cag ctt atg aga gaa gaa gca       555
Thr Ile Lys Lys Thr Ala Arg Arg Glu Gln Leu Met Arg Glu Glu Ala
    125                 130                 135 gaa cag aag cgc tta aaa act gta ctt gag tta cag tat gta ttg gat       603
Glu Gln Lys Arg Leu Lys Thr Val Leu Glu Leu Gln Tyr Val Leu Asp
140                 145                 150                 155 aag ctg gga gat gat gat gtg aga aca gat ctg aaa caa ggt ttg agt       651
Lys Leu Gly Asp Asp Asp Val Arg Thr Asp Leu Lys Gln Gly Leu Ser
                160                 165                 170 gga gtg cca ata ttg tct gag gag gag ttg tca ttg ctg gat gag ttc       699
Gly Val Pro Ile Leu Ser Glu Glu Glu Leu Ser Leu Leu Asp Glu Phe
            175                 180                 185 tac aag ctc gta gat cct gag cgt gac atg agt tta agg tta aat gag       747
Tyr Lys Leu Val Asp Pro Glu Arg Asp Met Ser Leu Arg Leu Asn Glu
        190                 195                 200 cag tat gaa cat gcc tca att cac ttg tgg gat ttg ctg gaa ggg aaa       795
Gln Tyr Glu His Ala Ser Ile His Leu Trp Asp Leu Leu Glu Gly Lys
    205                 210                 215 gaa aag cct gtg tgt gga aca acc tat aaa gct cta aag gaa att gtt       843
Glu Lys Pro Val Cys Gly Thr Thr Tyr Lys Ala Leu Lys Glu Ile Val
220                 225                 230                 235 gag cgt gtt ttc cag tca aac tac ttt gat agc act cac aat cat caa       891
Glu Arg Val Phe Gln Ser Asn Tyr Phe Asp Ser Thr His Asn His Gln
                240                 245                 250 aat ggg ttg tgt gag gag gaa gag gcg gct tca gcg ccc aca gtg gag       939
Asn Gly Leu Cys Glu Glu Glu Glu Ala Ala Ser Ala Pro Thr Val Glu
            255                 260                 265 gac cag gta gct gaa gct gaa cct gag cca gcg gaa gaa tac aca gag       987
Asp Gln Val Ala Glu Ala Glu Pro Glu Pro Ala Glu Glu Tyr Thr Glu
        270                 275                 280
```

```
caa agt gag gtt gaa tca aca gag tat gtc aat agg cag ttc atg gca      1035
Gln Ser Glu Val Glu Ser Thr Glu Tyr Val Asn Arg Gln Phe Met Ala
    285                 290                 295 gaa aca cag ttc agc agt ggt gag aag gag caa gtg gat gag tgg aca      1083
Glu Thr Gln Phe Ser Ser Gly Glu Lys Glu Gln Val Asp Glu Trp Thr
300                 305                 310                 315 gtt gaa aca gtt gag gtt gta aac tca ctc cag cag caa cct cag gct      1131
Val Glu Thr Val Glu Val Val Asn Ser Leu Gln Gln Gln Pro Gln Ala
            320                 325                 330 gcg tcc cct tca gtc cca gag ccc cac tct ttg act cca gtg gct cag      1179
Ala Ser Pro Ser Val Pro Glu Pro His Ser Leu Thr Pro Val Ala Gln
        335                 340                 345 tca gat cca ctt gtg aga agg cag cgt gta caa gat ctt atg gca caa      1227
Ser Asp Pro Leu Val Arg Arg Gln Arg Val Gln Asp Leu Met Ala Gln
    350                 355                 360 atg caa ggg ccc tat aat ttc ata cag gat tca atg ttg gat ttt gaa      1275
Met Gln Gly Pro Tyr Asn Phe Ile Gln Asp Ser Met Leu Asp Phe Glu
365                 370                 375 aat cag acg ctt gat cct gcc att gta tcc gca cag cct atg aac cct      1323
Asn Gln Thr Leu Asp Pro Ala Ile Val Ser Ala Gln Pro Met Asn Pro
380                 385                 390                 395 acc cag aac atg gat atg cct cag ctg gtt tgc cct cag gtt cat tct      1371
Thr Gln Asn Met Asp Met Pro Gln Leu Val Cys Pro Gln Val His Ser
            400                 405                 410 gaa tct aga ctt gcc caa tct aat caa gtt cct gta caa cca gaa gcc      1419
Glu Ser Arg Leu Ala Gln Ser Asn Gln Val Pro Val Gln Pro Glu Ala
        415                 420                 425 aca cag gtt cct ttg gtt tca tcc aca agt gag ggg tat aca gca tct      1467
Thr Gln Val Pro Leu Val Ser Ser Thr Ser Glu Gly Tyr Thr Ala Ser
    430                 435                 440 cag ccc ttg tac cag cca tct cat gct acg gag cag cgg ccg cag aaa      1515
Gln Pro Leu Tyr Gln Pro Ser His Ala Thr Glu Gln Arg Pro Gln Lys
445                 450                 455 gag cca atg gat cag att cag gca aca ata tct ttg aat aca gac cag      1563
Glu Pro Met Asp Gln Ile Gln Ala Thr Ile Ser Leu Asn Thr Asp Gln
460                 465                 470                 475 act aca gca tcc tca tcc ctt cct gct gct tct cag cct caa gtg ttc      1611
Thr Thr Ala Ser Ser Ser Leu Pro Ala Ala Ser Gln Pro Gln Val Phe
            480                 485                 490 cag gct ggg aca agt aaa cct ttg cac agc agt gga atc aat gta aat      1659
Gln Ala Gly Thr Ser Lys Pro Leu His Ser Ser Gly Ile Asn Val Asn
        495                 500                 505 gca gct cca ttc cag tcc atg caa acg gtg ttc aat atg aat gct cca      1707
Ala Ala Pro Phe Gln Ser Met Gln Thr Val Phe Asn Met Asn Ala Pro
    510                 515                 520 gtc cct cct gct aat gaa cca gaa acg tta aaa caa cag agt cag tac      1755
Val Pro Pro Ala Asn Glu Pro Glu Thr Leu Lys Gln Gln Ser Gln Tyr
525                 530                 535 cag gcc act tat aac cag agt ttt tcc agt cag cct cac caa gtg gaa      1803
Gln Ala Thr Tyr Asn Gln Ser Phe Ser Ser Gln Pro His Gln Val Glu
540                 545                 550                 555 caa aca gag ctt caa caa gac caa ctg caa acg gtg gtt ggc act tac      1851
Gln Thr Glu Leu Gln Gln Asp Gln Leu Gln Thr Val Val Gly Thr Tyr
            560                 565                 570 cat gga tcc cag gac cag cct cat caa gtg cct ggt aac cac cag caa      1899
His Gly Ser Gln Asp Gln Pro His Gln Val Pro Gly Asn His Gln Gln
        575                 580                 585 ccc cca cag cag aac act ggc ttt cca cgt agc agt cag cct tat tac      1947
Pro Pro Gln Gln Asn Thr Gly Phe Pro Arg Ser Ser Gln Pro Tyr Tyr
    590                 595                 600
```

```
aac agt cgt ggg gta tct cga gga ggg tct cgt ggt gcc aga ggc ttg      1995
Asn Ser Arg Gly Val Ser Arg Gly Gly Ser Arg Gly Ala Arg Gly Leu
        605                 610                 615 atg aat gga tac agg ggc cct gcc aat gga ttt aga gga gga tat gat      2043
Met Asn Gly Tyr Arg Gly Pro Ala Asn Gly Phe Arg Gly Gly Tyr Asp
620                 625                 630                 635 ggt tac cgc cct tca ttc tcg aac act cca aac agt ggt tat tca cag      2091
Gly Tyr Arg Pro Ser Phe Ser Asn Thr Pro Asn Ser Gly Tyr Ser Gln
                640                 645                 650 tct cag ttc act gct ccc cgg gac tac tct ggt tac cag cgg gat gga      2139
Ser Gln Phe Thr Ala Pro Arg Asp Tyr Ser Gly Tyr Gln Arg Asp Gly
            655                 660                 665 tat cag cag aat ttc aag cga ggc tct ggg cag agt gga cca cgg gga      2187
Tyr Gln Gln Asn Phe Lys Arg Gly Ser Gly Gln Ser Gly Pro Arg Gly
        670                 675                 680 gcc cca cga ggt cgt gga ggg ccc cca aga ccc aac aga ggg atg ccg      2235
Ala Pro Arg Gly Arg Gly Gly Pro Pro Arg Pro Asn Arg Gly Met Pro
685                 690                 695 caa atg aac act cag caa gtg aat taa tgtgatacac aggattatgt            2282
Gln Met Asn Thr Gln Gln Val Asn
700                 705 ttaatcgcca aaacacact ggccagtgta ccataatatg ttaccagaag agttattatc     2342
tatttgttct ccctttcagg aaacttattg taaaggact gttttcatcc cataaagaca     2402
ggactgcaat tgtcagcttt acattacctg gatatggaag gaaactattt ttattctgca    2462
tgttctgtcc taagcgtcat cttgagcctt gcacacaata caatactcag attcctcacc    2522
cttgcttagg agtaaaacat tatatactta tggggtgata atatctccat agttagttga    2582
agtggcttgg aaaaaaaatg caagattgaa ttttgacct tggataaaat ctacaatcag     2642
ccctagaact attcagtggt aattgacaaa gttaaagcat tttctttgaa aggaagatgg    2702
aaggagtgga gtgtggttta gcaaaactgc atttcatagc tttcccatta aattggagca    2762
ccgacagatt aaaagcatac caaattatgc atgggtcctt actcacacaa gtgaggctgg    2822
ctaccagcct tgacatagca ctcactagtc ttctggccaa acgactgtga ttaaaacaca    2882
tgtaaattgc tctttagtag tggatactgt gtaagacaaa gccaaattgc aaatcaggct    2942
ttgattggct cttctggaaa atatgcatca aatatggggg ataatctgga tgggctgctg    3002
ctgtgctcaa tgtgaactat ttagatacct ttggaacact taacagtttc tctgaacaat    3062
gacttacatg gggattggtc ctgtttgtca ttcctcacca taattgcatt gtcatcacta    3122
atccttggat cttgctgtat tgttactcaa attggtaata ggtactgatg gaaatcgcta    3182
atggatggat aatcataaca cttttggtca catgttttct cctgcagcct gaaagttctt    3242
aaagaaaaag atatcaaatg cctgctgcta ccaccctttt aaattgctat ctttagaaaa    3302
gcaccggtat gtgttttaga ttcatttccc tgtttaggg aaatgacagg cagtagtttc     3362
agttctgatg gcaaacaaa taaaaacatg tttctaaaag ttgtatcttg aaacactggt     3422
gttcaacagc tagcagctaa agtaattcaa cccatgcatt gctagtgtca cagcctttgg    3482
ttatgtctag tagctgtttc tgaagtattt tcatttatct tttgtcaaat ttaaccctgt    3542
ttgaattctc tcctttcctc aaggagacac ttatgttcaa agtgttgatt cttttgcctta   3602 ggtgcataga gagtagacag tttggagatg gaaaggttag cagtgactta gccatatgtt    3662
ctgtgttgga atttgtgcta gcagtttgag cactagctct gcgtgcctat gaactgaatg    3722
ctgcttgtcc cattccattt tatgtcatgg agaaataatt ccacttggta acacaaaggc    3782
```

```
taagttaatg ttattttctg tacagaaatt aaattttact tttagccttt tgtaaacttt    3842
tttttttttt ttccaagccg gtatcagcta ctcaaaacaa ttctcagata ttcatcatta    3902
gacaactgga gttttgctg gttttgtagc ctactaaaac tgctgaggct gttgaacatt     3962
ccacattcaa aagttttgta gggtggtgga taatggggaa gcttcaatgt ttattttaaa    4022
ataaataaaa taagttcttg acttttctca tgtgtggtta tggtacatca tattggaagg    4082
gttatctgtt tacttttgcc aagactattt tgccagcacc tacacttgtg tgctttaaaa    4142
gacaactacc tgggatgtac cacaaccata tgttaattgt atttttattgg gatggataaa   4202
atgtttgtgg tttattggat aatccctaga tggtgtgtta cgtgtgtaga atataatttt    4262
atgatagtaa gaaagcaaaa ttgaagaaaa taagtttagt attgaatttg agttctgaag    4322
tgaattcagg gaatgtctca cgtttcgggc ttctacccaa agtgtagggc agaaggtgta    4382
aaagttgttt gtagtttgac ttgtttattt tttaagttgc ttattccttt caacagcaac    4442
atatcattag ctgtcattct accattgcag ttctagtgag ttttaacgtc tgcattcaag    4502
actgttttaa aagcaacctc actggacaga gaactgctaa agtctttttcc ttaagatctg   4562
agtctttgtt actcagtatc ttctataata tgcaaatgct tgtctagagg cagaagacct    4622
tttgttggt caagtgtgta ttttaccaga gtacaggaa ctgatggtcc tacatgtctc      4682
ttagtgtagt aagactataa aatcttttgt acatgcacaa ttcacagtat gtttagatac    4742
cacgtgtata atgcccccc ctcccccagg tagcatgcca ttgatgactt tttgcttagg     4802
gccatttat taccagggcc ttaatattcc taaaaagatg atttttttc atcctttctc      4862
ctcttttgat cattgtatct tgatattaaa aacatgacct tccaatgatt gtagtaaatt    4922
aacttctata gttcttttgt ctctatatgt attcatatat atgctattgt atagagactt    4982
caaggagaca tggagatgca tgcttattct caggttcatt cactaaggtg cttggcagac    5042
aaccagtttc taagtgcaga atgtagttaa gcagcttcat atatgtgcca ggcaatttgt    5102
tttgttaaat tttcatctac ttaaggaaat agggtattgt agcttaggct gatcataccc    5162
ttcatttcaa ccttaagctc tcaacctgca tccatccgac ttgagctatt aagtacttta    5222
gttttatcga gtataagtta acagaaaaag taaattaagc tttgcctttta ctattttgaa   5282
tttatataca ttctggaaaa acttagaaac tgttgtatat ttcattagat taaattatat    5342
gaaaatgtga ttgtttatag caaagcctgt gagttgcata caccctaagg aaaactcctt    5402
aagtgctcct tgaagagaga agaaacaatt ctgggtctgg tcttttttaag aacaaagcta   5462
gactactgta tgttagcact gtacattaat agtctgttgt gaagcttgag cagtttcctg    5522
catagccttg atccttcacc gttggcattg aaaatagcag tatccctgat gtacttaaaa    5582
cttaaagtca ggttttggta tatttatttg taagtcttaa tttcctctaa atactatatc    5642
tctttagcga gacaacctga aatttattag cacatttggg tatctcttgc ttggcattat    5702
ggccagtgtt aactattcag tggtgaaaaa attacccctc aagacactgg agtgaccca    5762
gatgtgtgta gtaagtggca tggttcaact gtgtggttaa tgataaatat atgacttagt    5822
cggtatgatc tggaaagact tgattgaaag ataattcagc tgacataagg atgagtgagg    5882
agtggcaaac tggataaaag agtcaagaga cctgtattcc agtgactcct gttttgttta    5942
agcattagca agatctgtct ggggaaactg gatagggcag ttttcttcca tgtttagttt    6002
ttgtctcaac atttggaagc tattgaaggt tttaaaatgg tgtgtattgt ttttttttgg    6062
ggggggggtg gccagaatag tgggtcatct aataaaactg ccatttaaaa gatcaaaaaa    6122
aaaaaaaaaa aaaaaaaa                                                  6141
```

<210> SEQ ID NO 22
<211> LENGTH: 707
<212> TYPE: PRT
<213> ORGANISM: Mus musculus

<400> SEQUENCE: 22

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
                20                  25                  30

Ala Ala Pro Ala Ser Gln His Pro Ala Thr Gly Thr Gly Ala Val Gln
            35                  40                  45

Thr Glu Ala Met Lys Gln Ile Leu Gly Val Ile Asp Lys Lys Leu Arg
50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
                100                 105                 110

Ser Phe Met Ala Leu Ser Gln Asp Ile Gln Lys Thr Ile Lys Lys Thr
            115                 120                 125

Ala Arg Arg Glu Gln Leu Met Arg Glu Ala Glu Gln Lys Arg Leu
130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
                180                 185                 190

Pro Glu Arg Asp Met Ser Leu Arg Leu Asn Glu Gln Tyr Glu His Ala
            195                 200                 205

Ser Ile His Leu Trp Asp Leu Leu Glu Gly Lys Glu Lys Pro Val Cys
210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
            275                 280                 285

Ser Thr Glu Tyr Val Asn Arg Gln Phe Met Ala Glu Thr Gln Phe Ser
290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
                340                 345                 350

Arg Arg Gln Arg Val Gln Asp Leu Met Ala Gln Met Gln Gly Pro Tyr
            355                 360                 365

Asn Phe Ile Gln Asp Ser Met Leu Asp Phe Glu Asn Gln Thr Leu Asp
```

```
                370             375             380
Pro Ala Ile Val Ser Ala Gln Pro Met Asn Pro Thr Gln Asn Met Asp
385                 390             395                 400

Met Pro Gln Leu Val Cys Pro Gln Val His Ser Glu Ser Arg Leu Ala
            405                 410                 415

Gln Ser Asn Gln Val Pro Val Gln Pro Glu Ala Thr Gln Val Pro Leu
        420                 425                 430

Val Ser Ser Thr Ser Glu Gly Tyr Thr Ala Ser Gln Pro Leu Tyr Gln
    435                 440                 445

Pro Ser His Ala Thr Glu Gln Arg Pro Gln Lys Glu Pro Met Asp Gln
450                 455                 460

Ile Gln Ala Thr Ile Ser Leu Asn Thr Asp Gln Thr Thr Ala Ser Ser
465                 470             475                 480

Ser Leu Pro Ala Ala Ser Gln Pro Gln Val Phe Gln Ala Gly Thr Ser
            485                 490                 495

Lys Pro Leu His Ser Ser Gly Ile Asn Val Asn Ala Ala Pro Phe Gln
        500                 505                 510

Ser Met Gln Thr Val Phe Asn Met Asn Ala Pro Val Pro Pro Ala Asn
    515                 520                 525

Glu Pro Glu Thr Leu Lys Gln Gln Ser Gln Tyr Gln Ala Thr Tyr Asn
530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
            565                 570                 575

Gln Pro His Gln Val Pro Gly Asn His Gln Gln Pro Pro Gln Gln Asn
        580                 585                 590

Thr Gly Phe Pro Arg Ser Ser Gln Pro Tyr Tyr Asn Ser Arg Gly Val
    595                 600                 605

Ser Arg Gly Gly Ser Arg Gly Ala Arg Gly Leu Met Asn Gly Tyr Arg
610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
            645                 650                 655

Pro Arg Asp Tyr Ser Gly Tyr Gln Arg Asp Gly Tyr Gln Gln Asn Phe
        660                 665                 670

Lys Arg Gly Ser Gly Gln Ser Gly Pro Arg Gly Ala Pro Arg Gly Arg
    675                 680                 685

Gly Gly Pro Pro Arg Pro Asn Arg Gly Met Pro Gln Met Asn Thr Gln
690                 695                 700

Gln Val Asn
705

<210> SEQ ID NO 23
<211> LENGTH: 6114
<212> TYPE: DNA
<213> ORGANISM: Mus musculus
<220> FEATURE:
<221> NAME/KEY: CDS
<222> LOCATION: (139)..(2235)

<400> SEQUENCE: 23
cccaccgcgc gcgcgcgtag ccgcctgccc gcccgcccgc tgcgcgtttt gtcccgcgtc      60
tctccccgtc cgtctcctga cttgctggtc ttgtccttcc ctcccgcttt tttcctctcc     120
```

| | | |
|---|---|---|
| tctcttctcg gtctaaag atg ccc tcg gcc acc agc cac agc gga agc ggc<br>                               Met Pro Ser Ala Thr Ser His Ser Gly Ser Gly<br>                                1               5                       10 | 171 |
| agc aaa tcg tcg gga ccg ccg ccg tcc ggt tcc tcc ggg agt gag<br>Ser Lys Ser Ser Gly Pro Pro Pro Ser Gly Ser Ser Gly Ser Glu<br>             15                   20                   25 | 219 |
| gcg gcg gcc ggg gca gct gcg ccg gct tct cag cat ccg gca acc ggc<br>Ala Ala Ala Gly Ala Ala Ala Pro Ala Ser Gln His Pro Ala Thr Gly<br>         30                   35                    40 | 267 |
| acc ggc gcc gtc cag acc gag gcc atg aag cag att ctc ggc gta atc<br>Thr Gly Ala Val Gln Thr Glu Ala Met Lys Gln Ile Leu Gly Val Ile<br> 45                   50                   55 | 315 |
| gac aag aaa ctt cgg aac ctg gag aag aaa aag ggt aaa ctt gat gat<br>Asp Lys Lys Leu Arg Asn Leu Glu Lys Lys Lys Gly Lys Leu Asp Asp<br>60               65                   70                   75 | 363 |
| tac cag gaa cga atg aat aaa ggg gaa agg ctc aat caa gac cag ctg<br>Tyr Gln Glu Arg Met Asn Lys Gly Glu Arg Leu Asn Gln Asp Gln Leu<br>                  80                   85               90 | 411 |
| gat gcc gta tct aag tac cag gaa gtc aca aat aat ttg gag ttt gca<br>Asp Ala Val Ser Lys Tyr Gln Glu Val Thr Asn Asn Leu Glu Phe Ala<br>            95                   100               105 | 459 |
| aag gaa tta cag agg agt ttc atg gca tta agt caa gat att cag aaa<br>Lys Glu Leu Gln Arg Ser Phe Met Ala Leu Ser Gln Asp Ile Gln Lys<br>         110                 115                120 | 507 |
| aca ata aag aag aca gca cgt cgg gaa cag ctt atg aga gaa gaa gca<br>Thr Ile Lys Lys Thr Ala Arg Arg Glu Gln Leu Met Arg Glu Glu Ala<br>125                 130                135 | 555 |
| gaa cag aag cgc tta aaa act gta ctt gag tta cag tat gta ttg gat<br>Glu Gln Lys Arg Leu Lys Thr Val Leu Glu Leu Gln Tyr Val Leu Asp<br>140                 145               150             155 | 603 |
| aag ctg gga gat gat gat gtg aga aca gat ctg aaa caa ggt ttg agt<br>Lys Leu Gly Asp Asp Asp Val Arg Thr Asp Leu Lys Gln Gly Leu Ser<br>                160                165              170 | 651 |
| gga gtg cca ata ttg tct gag gag gag ttg tca ttg ctg gat gag ttc<br>Gly Val Pro Ile Leu Ser Glu Glu Glu Leu Ser Leu Leu Asp Glu Phe<br>            175                   180                185 | 699 |
| tac aag ctc gta gat cct gag cgt gac atg agt tta agg tta aat gag<br>Tyr Lys Leu Val Asp Pro Glu Arg Asp Met Ser Leu Arg Leu Asn Glu<br>         190                 195                200 | 747 |
| cag tat gaa cat gcc tca att cac ttg tgg gat ttg ctg gaa ggg aaa<br>Gln Tyr Glu His Ala Ser Ile His Leu Trp Asp Leu Leu Glu Gly Lys<br>         205                 210                215 | 795 |
| gaa aag cct gtg tgt gga aca acc tat aaa gct cta aag gaa att gtt<br>Glu Lys Pro Val Cys Gly Thr Thr Tyr Lys Ala Leu Lys Glu Ile Val<br>220                 225                230              235 | 843 |
| gag cgt gtt ttc cag tca aac tac ttt gat agc act cac aat cat caa<br>Glu Arg Val Phe Gln Ser Asn Tyr Phe Asp Ser Thr His Asn His Gln<br>         240                 245                250 | 891 |
| aat ggg ttg tgt gag gag gaa gag gcg gct tca gcg ccc aca gtg gag<br>Asn Gly Leu Cys Glu Glu Glu Glu Ala Ala Ser Ala Pro Thr Val Glu<br>         255                 260                265 | 939 |
| gac cag gta gct gaa gct gaa cct gag cca gcg gaa gaa tac aca gag<br>Asp Gln Val Ala Glu Ala Glu Pro Glu Pro Ala Glu Glu Tyr Thr Glu<br>         270                 275                280 | 987 |
| caa agt gag gtt gaa tca aca gag tat gtc aat agg cag ttc atg gca<br>Gln Ser Glu Val Glu Ser Thr Glu Tyr Val Asn Arg Gln Phe Met Ala<br>         285                 290                295 | 1035 |
| gaa aca cag ttc agc agt ggt gag aag gag caa gtg gat gag tgg aca<br>Glu Thr Gln Phe Ser Ser Gly Glu Lys Glu Gln Val Asp Glu Trp Thr | 1083 |

| | |
|---|---|
| gtt gaa aca gtt gag gtt gta aac tca ctc cag cag caa cct cag gct<br>Val Glu Thr Val Glu Val Val Asn Ser Leu Gln Gln Gln Pro Gln Ala<br>300               305             310             315<br>320             325             330 | 1131 |
| gcg tcc cct tca gtc cca gag ccc cac tct ttg act cca gtg gct cag<br>Ala Ser Pro Ser Val Pro Glu Pro His Ser Leu Thr Pro Val Ala Gln<br>           335               340             345 | 1179 |
| tca gat cca ctt gtg aga agg cag cgt gta caa gat ctt atg gca caa<br>Ser Asp Pro Leu Val Arg Arg Gln Arg Val Gln Asp Leu Met Ala Gln<br>350               355             360 | 1227 |
| atg caa ggg ccc tat aat ttc ata cag acg ctt gat cct gcc att gta<br>Met Gln Gly Pro Tyr Asn Phe Ile Gln Thr Leu Asp Pro Ala Ile Val<br>     365              370             375 | 1275 |
| tcc gca cag cct atg aac cct acc cag aac atg gat atg cct cag ctg<br>Ser Ala Gln Pro Met Asn Pro Thr Gln Asn Met Asp Met Pro Gln Leu<br>380               385             390             395 | 1323 |
| gtt tgc cct cag gtt cat tct gaa tct aga ctt gcc caa tct aat caa<br>Val Cys Pro Gln Val His Ser Glu Ser Arg Leu Ala Gln Ser Asn Gln<br>               400             405             410 | 1371 |
| gtt cct gta caa cca gaa gcc aca cag gtt cct ttg gtt tca tcc aca<br>Val Pro Val Gln Pro Glu Ala Thr Gln Val Pro Leu Val Ser Ser Thr<br>           415               420             425 | 1419 |
| agt gag ggg tat aca gca tct cag ccc ttg tac cag cca tct cat gct<br>Ser Glu Gly Tyr Thr Ala Ser Gln Pro Leu Tyr Gln Pro Ser His Ala<br>       430              435             440 | 1467 |
| acg gag cag cgg ccg cag aaa gag cca atg gat cag att cag gca aca<br>Thr Glu Gln Arg Pro Gln Lys Glu Pro Met Asp Gln Ile Gln Ala Thr<br>445               450             455 | 1515 |
| ata tct ttg aat aca gac cag act aca gca tcc tca tcc ctt cct gct<br>Ile Ser Leu Asn Thr Asp Gln Thr Thr Ala Ser Ser Ser Leu Pro Ala<br>460               465             470             475 | 1563 |
| gct tct cag cct caa gtg ttc cag gct ggg aca agt aaa cct ttg cac<br>Ala Ser Gln Pro Gln Val Phe Gln Ala Gly Thr Ser Lys Pro Leu His<br>               480             485             490 | 1611 |
| agc agt gga atc aat gta aat gca gct cca ttc cag tcc atg caa acg<br>Ser Ser Gly Ile Asn Val Asn Ala Ala Pro Phe Gln Ser Met Gln Thr<br>           495               500             505 | 1659 |
| gtg ttc aat atg aat gct cca gtc cct cct gct aat gaa cca gaa acg<br>Val Phe Asn Met Asn Ala Pro Val Pro Pro Ala Asn Glu Pro Glu Thr<br>       510              515             520 | 1707 |
| tta aaa caa cag agt cag tac cag gcc act tat aac cag agt ttt tcc<br>Leu Lys Gln Gln Ser Gln Tyr Gln Ala Thr Tyr Asn Gln Ser Phe Ser<br>525               530             535 | 1755 |
| agt cag cct cac caa gtg gaa caa aca gag ctt caa caa gac caa ctg<br>Ser Gln Pro His Gln Val Glu Gln Thr Glu Leu Gln Gln Asp Gln Leu<br>540               545             550             555 | 1803 |
| caa acg gtg gtt ggc act tac cat gga tcc cag gac cag cct cat caa<br>Gln Thr Val Val Gly Thr Tyr His Gly Ser Gln Asp Gln Pro His Gln<br>               560             565             570 | 1851 |
| gtg cct ggt aac cac cag caa ccc cca cag cag aac act ggc ttt cca<br>Val Pro Gly Asn His Gln Gln Pro Pro Gln Gln Asn Thr Gly Phe Pro<br>       575              580             585 | 1899 |
| cgt agc agt cag cct tat tac aac agt cgt ggg gta tct cga gga ggg<br>Arg Ser Ser Gln Pro Tyr Tyr Asn Ser Arg Gly Val Ser Arg Gly Gly<br>           590               595             600 | 1947 |
| tct cgt ggt gcc aga ggc ttg atg aat gga tac agg ggc cct gcc aat<br>Ser Arg Gly Ala Arg Gly Leu Met Asn Gly Tyr Arg Gly Pro Ala Asn<br>605               610             615 | 1995 |
| gga ttt aga gga gga tat gat ggt tac cgc cct tca ttc tcg aac act | 2043 |

```
Gly Phe Arg Gly Gly Tyr Asp Gly Tyr Arg Pro Ser Phe Ser Asn Thr
620                 625                 630                 635 cca aac agt ggt tat tca cag tct cag ttc act gct ccc cgg gac tac      2091
Pro Asn Ser Gly Tyr Ser Gln Ser Gln Phe Thr Ala Pro Arg Asp Tyr
                        640                 645                 650 tct ggt tac cag cgg gat gga tat cag cag aat ttc aag cga ggc tct      2139
Ser Gly Tyr Gln Arg Asp Gly Tyr Gln Gln Asn Phe Lys Arg Gly Ser
                655                 660                 665 ggg cag agt gga cca cgg gga gcc cca cga ggt cgt gga ggg ccc cca      2187
Gly Gln Ser Gly Pro Arg Gly Ala Pro Arg Gly Arg Gly Gly Pro Pro
            670                 675                 680 aga ccc aac aga ggg atg ccg caa atg aac act cag caa gtg aat taa      2235
Arg Pro Asn Arg Gly Met Pro Gln Met Asn Thr Gln Gln Val Asn
        685                 690                 695 tgtgatacac aggattatgt ttaatcgcca aaaacacact ggccagtgta ccataatatg    2295
ttaccagaag agttattatc tatttgttct ccctttcagg aaacttattg taaagggact    2355
gttttcatcc cataaagaca ggactgcaat tgtcagcttt acattacctg gatatggaag    2415
gaaactattt ttattctgca tgttctgtcc taagcgtcat cttgagcctt gcacacaata    2475
caatactcag attcctcacc cttgcttagg agtaaaacat tatatactta tggggtgata    2535
atatctccat agttagttga agtggcttgg aaaaaaaatg caagattgaa ttttttgacct   2595 tggataaaat ctacaatcag ccctagaact attcagtggt aattgacaaa gttaaagcat    2655
tttctttgaa aggaagatgg aaggagtgga gtgtggttta gcaaaactgc atttcatagc    2715
tttcccatta aattggagca ccgacagatt aaaagcatac caaattatgc atgggtcctt    2775
actcacacaa gtgaggctgg ctaccagcct tgacatagca ctcactagtc ttctggccaa    2835
acgactgtga ttaaaacaca gtaaattgc tctttagtag tggatactgt gtaagacaaa     2895
gccaaattgc aaatcaggct tgattggct cttctggaaa atatgcatca aatatggggg     2955
ataatctgga tgggctgctg ctgtgctcaa tgtgaactat ttagatacct ttggaacact    3015
taacagtttc tctgaacaat gacttacatg gggattggtc ctgtttgtca ttcctcacca    3075
taattgcatt gtcatcacta atccttggat cttgctgtat tgttactcaa attggtaata   3135
ggtactgatg gaaatcgcta atggatggat aatcataaca cttttggtca catgttttct   3195
cctgcagcct gaaagttctt aaagaaaaag atatcaaatg cctgctgcta ccacccttt    3255 aaattgctat ctttagaaaa gcaccggtat gtgtttaga ttcatttccc tgttttaggg    3315
aaatgacagg cagtagtttc agttctgatg gcaaaacaaa taaaaacatg tttctaaaag   3375
ttgtatcttg aaacactggt gttcaacagc tagcagctaa agtaattcaa cccatgcatt   3435
gctagtgtca cagcctttgg ttatgtctag tagctgtttc tgaagtattt tcatttatct   3495
tttgtcaaat ttaaccctgt ttgaattctc tcctttcctc aaggagacac ttatgttcaa   3555
agtgttgatt ctttgcctta ggtgcataga gagtagacag tttggagatg gaaaggttag   3615
cagtgactta gccatatgtt ctgtgttgga atttgtgcta gcagtttgag cactagctct   3675
gcgtgcctat gaactgaatg ctgcttgtcc cattccattt tatgtcatgg agaaataatt   3735
ccacttggta acacaaaggc taagttaatg ttattttctg tacagaaatt aaattttact   3795
tttagccttt tgtaaacttt tttttttttt tccaagccg gtatcagcta ctcaaaacaa    3855
ttctcagata ttcatcatta gacaactgga gttttgctg gttttgtagc ctactaaaac    3915
tgctgaggct gttgaacatt ccacattcaa aagtttgta gggtggtgga taatggggaa    3975
gcttcaatgt ttattttaaa ataaataaaa taagttcttg acttttctca tgtgtggtta   4035
```

```
tggtacatca tattggaagg gttatctgtt tacttttgcc aagactattt tgccagcacc    4095
tacacttgtg tgctttaaaa gacaactacc tgggatgtac cacaaccata tgttaattgt    4155
attttattgg gatggataaa atgtttgtgg tttattggat aatccctaga tggtgtgtta    4215
cgtgtgtaga atataatttt atgatagtaa gaaagcaaaa ttgaagaaaa taagtttagt    4275
attgaatttg agttctgaag tgaattcagg gaatgtctca cgtttcgggc ttctacccaa    4335
agtgtagggc agaaggtgta aaagttgttt gtagtttgac ttgtttatttt tttaagttgc    4395 ttattccttt caacagcaac atatcattag ctgtcattct accattgcag ttctagtgag    4455
ttttaacgtc tgcattcaag actgttttaa aagcaacctc actggacaga gaactgctaa    4515
agtcttttcc ttaagatctg agtctttgtt actcagtatc ttctataata tgcaaatgct    4575
tgtctagagg cagaagacct tttgtttggt caagtgtgta ttttaccaga gtacagggaa    4635
ctgatggtcc tacatgtctc ttagtgtagt aagactataa aatcttttgt acatgcacaa    4695
ttcacagtat gtttagatac cacgtgtata atgccccccc ctccccccagg tagcatgcca    4755 tgatgactt tttgcttagg gccatttat taccagggcc ttaatattcc taaaaagatg    4815 atttttttc atccttttctc ctcttttgat cattgtatct tgatattaaa aacatgacct    4875
tccaatgatt gtagtaaatt aacttctata gttcttttgt ctctatatgt attcatatat    4935
atgctattgt atagagactt caaggagaca tggagatgca tgcttattct caggttcatt    4995
cactaaggtg cttggcagac aaccagtttc taagtgcaga atgtagttaa gcagcttcat    5055
atatgtgcca ggcaatttgt tttgttaaat tttcatctac ttaaggaaat agggtattgt    5115
agcttaggct gatcataccc ttcatttcaa ccttaagctc tcaacctgca tccatccgac    5175
ttgagctatt aagtacttta gttttatcga gtataagtta acagaaaaag taaattaagc    5235
tttgccttta ctattttgaa tttatataca ttctggaaaa acttagaaac tgttgtatat    5295
ttcattagat taaattatat gaaaatgtga ttgtttatag caaagcctgt gagttgcata    5355
caccctaagg aaaactcctt aagtgctcct tgaagagaga agaaacaatt ctgggtctgg    5415 tcttttaag aacaaagcta gactactgta tgttagcact gtacattaat agtctgttgt    5475
gaagcttgag cagtttcctg catagccttg atccttcacc gttggcattg aaaatagcag    5535
tatccctgat gtacttaaaa cttaaagtca ggttttggta tatttatttg taagtcttaa    5595
tttcctctaa atactatatc tctttagcga gacaacctga aatttattag cacatttggg    5655
tatctcttgc ttggcattat ggccagtgtt aactattcag tggtgaaaaa attacccctc    5715 aagcactgg agtgacccca gatgtgtgta gtaagtggca tggttcaact gtgtggttaa    5775
tgataaatat atgacttagt cggtatgatc tggaaagact tgattgaaag ataattcagc    5835
tgacataagg atgagtgagg agtggcaaac tggataaaag agtcaagaga cctgtattcc    5895
agtgactcct gttttgttta agcattagca agatctgtct ggggaaactg gatagggcag    5955
ttttcttcca tgtttagttt ttgtctcaac atttggaagc tattgaaggt tttaaaatgg    6015
tgtgtattgt tttttttggg gggggggtg gccagaatag tgggtcatct aataaaactg    6075
ccatttaaaa gatcaaaaaa aaaaaaaaa aaaaaaaa                              6114
```

<210> SEQ ID NO 24
<211> LENGTH: 698
<212> TYPE: PRT
<213> ORGANISM: Mus musculus

<400> SEQUENCE: 24

Met Pro Ser Ala Thr Ser His Ser Gly Ser Gly Ser Lys Ser Ser Gly

-continued

```
1               5                   10                  15
Pro Pro Pro Pro Ser Gly Ser Ser Gly Ser Glu Ala Ala Gly Ala
                20                  25                  30

Ala Ala Pro Ala Ser Gln His Pro Ala Thr Gly Thr Gly Ala Val Gln
                35                  40                  45

Thr Glu Ala Met Lys Gln Ile Leu Gly Val Ile Asp Lys Lys Leu Arg
        50                  55                  60

Asn Leu Glu Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
                100                 105                 110

Ser Phe Met Ala Leu Ser Gln Asp Ile Gln Lys Thr Ile Lys Lys Thr
                115                 120                 125

Ala Arg Arg Glu Gln Leu Met Arg Glu Glu Ala Glu Gln Lys Arg Leu
            130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
                180                 185                 190

Pro Glu Arg Asp Met Ser Leu Arg Leu Asn Glu Gln Tyr Glu His Ala
                195                 200                 205

Ser Ile His Leu Trp Asp Leu Leu Glu Gly Lys Glu Lys Pro Val Cys
        210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
                260                 265                 270

Ala Glu Pro Glu Pro Ala Glu Glu Tyr Thr Glu Gln Ser Glu Val Glu
            275                 280                 285

Ser Thr Glu Tyr Val Asn Arg Gln Phe Met Ala Glu Thr Gln Phe Ser
        290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
            355                 360                 365

Asn Phe Ile Gln Thr Leu Asp Pro Ala Ile Val Ser Ala Gln Pro Met
            370                 375                 380

Asn Pro Thr Gln Asn Met Asp Met Pro Gln Leu Val Cys Pro Gln Val
385                 390                 395                 400

His Ser Glu Ser Arg Leu Ala Gln Ser Asn Gln Val Pro Val Gln Pro
                405                 410                 415

Glu Ala Thr Gln Val Pro Leu Val Ser Ser Thr Ser Glu Gly Tyr Thr
                420                 425                 430
```

```
Ala Ser Gln Pro Leu Tyr Gln Pro Ser His Ala Thr Glu Gln Arg Pro
        435                 440                 445

Gln Lys Glu Pro Met Asp Gln Ile Gln Ala Thr Ile Ser Leu Asn Thr
    450                 455                 460

Asp Gln Thr Thr Ala Ser Ser Leu Pro Ala Ser Gln Pro Gln
465                 470                 475                 480

Val Phe Gln Ala Gly Thr Ser Lys Pro Leu His Ser Ser Gly Ile Asn
                485                 490                 495

Val Asn Ala Ala Pro Phe Gln Ser Met Gln Thr Val Phe Asn Met Asn
            500                 505                 510

Ala Pro Val Pro Pro Ala Asn Glu Pro Glu Thr Leu Lys Gln Gln Ser
        515                 520                 525

Gln Tyr Gln Ala Thr Tyr Asn Gln Ser Phe Ser Gln Pro His Gln
    530                 535                 540

Val Glu Gln Thr Glu Leu Gln Gln Asp Gln Leu Gln Thr Val Val Gly
545                 550                 555                 560

Thr Tyr His Gly Ser Gln Asp Gln Pro His Gln Val Pro Gly Asn His
                565                 570                 575

Gln Gln Pro Pro Gln Asn Thr Gly Phe Pro Arg Ser Ser Gln Pro
        580                 585                 590

Tyr Tyr Asn Ser Arg Gly Val Ser Arg Gly Gly Ser Arg Gly Ala Arg
    595                 600                 605

Gly Leu Met Asn Gly Tyr Arg Gly Pro Ala Asn Gly Phe Arg Gly Gly
    610                 615                 620

Tyr Asp Gly Tyr Arg Pro Ser Phe Ser Asn Thr Pro Asn Ser Gly Tyr
625                 630                 635                 640

Ser Gln Ser Gln Phe Thr Ala Pro Arg Asp Tyr Ser Gly Tyr Gln Arg
                645                 650                 655

Asp Gly Tyr Gln Gln Asn Phe Lys Arg Gly Ser Gly Gln Ser Gly Pro
                660                 665                 670

Arg Gly Ala Pro Arg Gly Arg Gly Gly Pro Arg Pro Asn Arg Gly
        675                 680                 685

Met Pro Gln Met Asn Thr Gln Gln Val Asn
        690                 695

<210> SEQ ID NO 25
<211> LENGTH: 3548
<212> TYPE: DNA
<213> ORGANISM: Mus musculus
<220> FEATURE:
<221> NAME/KEY: CDS
<222> LOCATION: (179)..(2257)

<400> SEQUENCE: 25
gctggctggc taagtccctc ccgcgccggc tcttgtccca ctaggagcag ctcagagccg     60
cggggacagg gcgaagcggc ctgcgcccac ggagcgcacg tctctgttct caacgcagca    120
ccacccttgc ccccctcggc tgcccactcc agacgtccag cggctccgcg cgcgcacg     178 atg ccc tcg gcc acc agc cac agc gga agc ggc agc aaa tcg tcg gga    226
Met Pro Ser Ala Thr Ser His Ser Gly Ser Gly Ser Lys Ser Ser Gly
1               5                   10                  15 ccg ccg ccg ccg tcc ggt tcc tcc ggg agt gag gcg gcg gcc ggg gca    274
Pro Pro Pro Pro Ser Gly Ser Ser Gly Ser Glu Ala Ala Ala Gly Ala
            20                  25                  30 gct gcg ccg gct tct cag cat ccg gca acc ggc acc ggc gcc gtc cag    322
Ala Ala Pro Ala Ser Gln His Pro Ala Thr Gly Thr Gly Ala Val Gln
```

```
                35                  40                  45
acc gag gcc atg aag cag att ctc ggc gta atc gac aag aaa ctt cgg    370
Thr Glu Ala Met Lys Gln Ile Leu Gly Val Ile Asp Lys Lys Leu Arg
 50                  55                  60 aac ctg gag aag aaa aag ggt aaa ctt gat gat tac cag gaa cga atg    418
Asn Leu Glu Lys Lys Lys Gly Lys Leu Asp Asp Tyr Gln Glu Arg Met
 65                  70                  75                  80 aat aaa ggg gaa agg ctc aat caa gac cag ctg gat gcc gta tct aag    466
Asn Lys Gly Glu Arg Leu Asn Gln Asp Gln Leu Asp Ala Val Ser Lys
                     85                  90                  95 tac cag gaa gtc aca aat aat ttg gag ttt gca aag gaa tta cag agg    514
Tyr Gln Glu Val Thr Asn Asn Leu Glu Phe Ala Lys Glu Leu Gln Arg
                100                 105                 110 agt ttc atg gca tta agt caa gat att cag aaa aca ata aag aag aca    562
Ser Phe Met Ala Leu Ser Gln Asp Ile Gln Lys Thr Ile Lys Lys Thr
            115                 120                 125 gca cgt cgg gaa cag ctt atg aga gaa gaa gca gaa cag aag cgc tta    610
Ala Arg Arg Glu Gln Leu Met Arg Glu Glu Ala Glu Gln Lys Arg Leu
130                 135                 140 aaa act gta ctt gag tta cag tat gta ttg gat aag ctg gga gat gat    658
Lys Thr Val Leu Glu Leu Gln Tyr Val Leu Asp Lys Leu Gly Asp Asp
145                 150                 155                 160 gat gtg aga aca gat ctg aaa caa ggt ttg agt gga gtg cca ata ttg    706
Asp Val Arg Thr Asp Leu Lys Gln Gly Leu Ser Gly Val Pro Ile Leu
                165                 170                 175 tct gag gag gag ttg tca ttg ctg gat gag ttc tac aag ctc gta gat    754
Ser Glu Glu Glu Leu Ser Leu Leu Asp Glu Phe Tyr Lys Leu Val Asp
                180                 185                 190 cct gag cgt gac atg agt tta agg tta aat gag cag tat gaa cat gcc    802
Pro Glu Arg Asp Met Ser Leu Arg Leu Asn Glu Gln Tyr Glu His Ala
            195                 200                 205 tca att cac ttg tgg gat ttg ctg gaa ggg aaa gaa aag cct gtg tgt    850
Ser Ile His Leu Trp Asp Leu Leu Glu Gly Lys Glu Lys Pro Val Cys
        210                 215                 220 gga aca acc tat aaa gct cta aag gaa att gtt gag cgt gtt ttc cag    898
Gly Thr Thr Tyr Lys Ala Leu Lys Glu Ile Val Glu Arg Val Phe Gln
225                 230                 235                 240 tca aac tac ttt gat agc act cac aat cat caa aat ggg ttg tgt gag    946
Ser Asn Tyr Phe Asp Ser Thr His Asn His Gln Asn Gly Leu Cys Glu
                245                 250                 255 gag gaa gag gcg gct tca gcg ccc aca gtg gag gac cag gta gct gaa    994
Glu Glu Glu Ala Ala Ser Ala Pro Thr Val Glu Asp Gln Val Ala Glu
                260                 265                 270 gct gaa cct gag cca gcg gaa gaa tac aca gag caa agt gag gtt gaa   1042
Ala Glu Pro Glu Pro Ala Glu Glu Tyr Thr Glu Gln Ser Glu Val Glu
            275                 280                 285 tca aca gag tat gtc aat agg cag ttc atg gca gaa aca cag ttc agc   1090
Ser Thr Glu Tyr Val Asn Arg Gln Phe Met Ala Glu Thr Gln Phe Ser
        290                 295                 300 agt ggt gag aag gag caa gtg gat gag tgg aca gtt gaa aca gtt gag   1138
Ser Gly Glu Lys Glu Gln Val Asp Glu Trp Thr Val Glu Thr Val Glu
305                 310                 315                 320 gtt gta aac tca ctc cag cag caa cct cag gct gcg tcc cct tca gtc   1186
Val Val Asn Ser Leu Gln Gln Gln Pro Gln Ala Ala Ser Pro Ser Val
                325                 330                 335 cca gag ccc cac tct ttg act cca gtg gct cag tca gat cca ctt gtg   1234
Pro Glu Pro His Ser Leu Thr Pro Val Ala Gln Ser Asp Pro Leu Val
                340                 345                 350 aga agg cag cgt gta caa gat ctt atg gca caa atg caa ggg ccc tat   1282
```

```
Arg Arg Gln Arg Val Gln Asp Leu Met Ala Gln Met Gln Gly Pro Tyr
        355                 360                 365 aat ttc ata cag gat tca atg ttg gat ttt gaa aat cag acg ctt gat      1330
Asn Phe Ile Gln Asp Ser Met Leu Asp Phe Glu Asn Gln Thr Leu Asp
370                 375                 380 cct gcc att gta tcc gca cag cct atg aac cct acc cag aac atg gat      1378
Pro Ala Ile Val Ser Ala Gln Pro Met Asn Pro Thr Gln Asn Met Asp
385                 390                 395                 400 atg cct cag ctg gtt tgc cct cag gtt cat tct gaa tct aga ctt gcc      1426
Met Pro Gln Leu Val Cys Pro Gln Val His Ser Glu Ser Arg Leu Ala
            405                 410                 415 caa tct aat caa gtt cct gta caa cca gaa gcc aca cag gtt cct ttg      1474
Gln Ser Asn Gln Val Pro Val Gln Pro Glu Ala Thr Gln Val Pro Leu
            420                 425                 430 gtt tca tcc aca agt gag ggg tat aca gca tct cag ccc ttg tac cag      1522
Val Ser Ser Thr Ser Glu Gly Tyr Thr Ala Ser Gln Pro Leu Tyr Gln
            435                 440                 445 cca tct cat gct acg gag cag cgg ccg cag aaa gag cca atg gat cag      1570
Pro Ser His Ala Thr Glu Gln Arg Pro Gln Lys Glu Pro Met Asp Gln
450                 455                 460 att cag gca aca ata tct ttg aat aca gac cag act aca gca tcc tca      1618
Ile Gln Ala Thr Ile Ser Leu Asn Thr Asp Gln Thr Thr Ala Ser Ser
465                 470                 475                 480 tcc ctt cct gct gct tct cag cct caa gtg ttc cag gct ggg aca agt      1666
Ser Leu Pro Ala Ala Ser Gln Pro Gln Val Phe Gln Ala Gly Thr Ser
            485                 490                 495 aaa cct ttg cac agc agt gga atc aat gta aat gca gct cca ttc cag      1714
Lys Pro Leu His Ser Ser Gly Ile Asn Val Asn Ala Ala Pro Phe Gln
            500                 505                 510 tcc atg caa acg gtg ttc aat atg aat gct cca gtc cct cct gct aat      1762
Ser Met Gln Thr Val Phe Asn Met Asn Ala Pro Val Pro Pro Ala Asn
            515                 520                 525 gaa cca gaa acg tta aaa caa cag agt cag tac cag gcc act tat aac      1810
Glu Pro Glu Thr Leu Lys Gln Gln Ser Gln Tyr Gln Ala Thr Tyr Asn
530                 535                 540 cag agt ttt tcc agt cag cct cac caa gtg gaa caa aca gag ctt caa      1858
Gln Ser Phe Ser Ser Gln Pro His Gln Val Glu Gln Thr Glu Leu Gln
545                 550                 555                 560 caa gac caa ctg caa acg gtg gtt ggc act tac cat gga tcc cag gac      1906
Gln Asp Gln Leu Gln Thr Val Val Gly Thr Tyr His Gly Ser Gln Asp
            565                 570                 575 cag cct cat caa gtg cct ggt aac cac cag caa ccc cca cag cag aac      1954
Gln Pro His Gln Val Pro Gly Asn His Gln Gln Pro Pro Gln Gln Asn
            580                 585                 590 act ggc ttt cca cgt agc agt cag cct tat tac aac agt cgt ggg gta      2002
Thr Gly Phe Pro Arg Ser Ser Gln Pro Tyr Tyr Asn Ser Arg Gly Val
            595                 600                 605 tct cga gga ggg tct cgt ggt gcc aga ggc ttg atg aat gga tac agg      2050
Ser Arg Gly Gly Ser Arg Gly Ala Arg Gly Leu Met Asn Gly Tyr Arg
610                 615                 620 ggc cct gcc aat gga ttt aga gga gga tat gat ggt tac cgc cct tca      2098
Gly Pro Ala Asn Gly Phe Arg Gly Gly Tyr Asp Gly Tyr Arg Pro Ser
625                 630                 635                 640 ttc tcg aac act cca aac agt ggt tat tca cag tct cag ttc act gct      2146
Phe Ser Asn Thr Pro Asn Ser Gly Tyr Ser Gln Ser Gln Phe Thr Ala
            645                 650                 655 ccc cgg gac tac tct ggt tac cag cgg gat gga tat cag cag aat ttc      2194
Pro Arg Asp Tyr Ser Gly Tyr Gln Arg Asp Gly Tyr Gln Gln Asn Phe
            660                 665                 670
```

```
aag cga ggc tct ggg cag agt gga cca cgg gga gcc cca cga ggt aat    2242
Lys Arg Gly Ser Gly Gln Ser Gly Pro Arg Gly Ala Pro Arg Gly Asn
        675                 680                 685 ata ttg tgg tgg tga tcctagctcc tatgtggagc ttctgttctg gccttggaag    2297
Ile Leu Trp Trp
        690 aactgttcat agtccgcatg taggttacat gttaggaata catttatctt ttccagactt    2357
gttgctaaag attaaatgaa atgctctgtt tctaaaattt catcttgaat ccaaattta    2417
atttttgaat gactttccct gctgttgtct tcaaaatcag aacatttct ctgcctcaga    2477
aaagcgtttt tccaactgga aatttatttt tcaggtctta aaacctgcta atgttttta    2537
ggaagtacct actgaaactt tttgtaagac attttggaa cgagcttgaa catttatata    2597
aatttattac cctctttgat ttttgaaaca tgcatattat atttaggctg agaagccctt    2657
caaatggcca gataagccac agttttagct agagaaccat ttagaattga cataactaat    2717
ctaaacttga acacttttag gaccaatgtt agtgttctaa ataccaacat atttctgatg    2777
tttaaacaga tctcccaaat tcttaggacc ttgatgtcat taaaatttag aatgacaagc    2837
ttaagaggct ttagtttcat ttgttttca gtaatgaaa ataatttct tacatgggca    2897
gatagttaat ttgttgaaca attacaggta gcatttcatg taatctgatg ttctaaatgg    2957
ttctcttatt gaaggaggtt aaagaattag gtttcttaca gttttggct ggccatgaca    3017
tgtataaaat gtatattaag gaggaattat aaagtacttt aattgaatg ctagtggcaa    3077
ttgatcatta agaaagtact ttaaagcaaa aggttaatgg gtcatctggg aaaaatactg    3137
aagtatcaaa ggtatttgca tgtgaatgtg ggttatgttc ttctatccca ccttgtagca    3197
tattctatga agttgagtt aaatgatagc taaaatatct gtttcaacag catgtaaaaa    3257
gttattttaa ctgttacaag tcattataca attttgaatg ttctgtagtt tcttttaac    3317
agtttaggta caaaggtctg ttttcattct ggtgctttt attaattttg atagtatgat    3377
gtcacttcct attgaaatgt aagctagcgt gtaccttaga atgtgagctc catgagagca    3437
ggtaccttgt ttgtcttcac tgctgtatct attcccaacg cctcatgaca gtgcctggca    3497
catagtaggc actcaataaa tacttgttga atgaatgaaa aaaaaaaaa a             3548
```

<210> SEQ ID NO 26
<211> LENGTH: 692
<212> TYPE: PRT
<213> ORGANISM: Mus musculus

<400> SEQUENCE: 26

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110
```

```
Ser Phe Met Ala Leu Ser Gln Asp Ile Gln Lys Thr Ile Lys Lys Thr
            115                 120                 125

Ala Arg Arg Glu Gln Leu Met Arg Glu Ala Glu Gln Lys Arg Leu
130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
```

```
                  530                 535                 540
Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690

<210> SEQ ID NO 27
<211> LENGTH: 3508
<212> TYPE: DNA
<213> ORGANISM: Mus musculus
<220> FEATURE:
<221> NAME/KEY: CDS
<222> LOCATION: (139)..(2217)

<400> SEQUENCE: 27
cccaccgcgc gcgcgcgtag ccgcctgccc gcccgcccgc tgcgcgtttt gtcccgcgtc     60
tctccccgtc cgtctcctga cttgctggtc ttgtccttcc ctcccgcttt tttcctctcc    120
tctcttctcg gtctaaag atg ccc tcg gcc acc agc cac agc gga agc ggc      171
                    Met Pro Ser Ala Thr Ser His Ser Gly Ser Gly
                     1               5                   10 agc aaa tcg tcg gga ccg ccg ccg ccg tcc ggt tcc tcc ggg agt gag      219
Ser Lys Ser Ser Gly Pro Pro Pro Pro Ser Gly Ser Ser Gly Ser Glu
            15                  20                  25 gcg gcg gcc ggg gca gct gcg ccg gct tct cag cat ccg gca acc ggc      267
Ala Ala Ala Gly Ala Ala Ala Pro Ala Ser Gln His Pro Ala Thr Gly
        30                  35                  40 acc ggc gcc gtc cag acc gag gcc atg aag cag att ctc ggc gta atc      315
Thr Gly Ala Val Gln Thr Glu Ala Met Lys Gln Ile Leu Gly Val Ile
    45                  50                  55 gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75 tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90 gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                  100                 105 aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120
```

|  |  |
|---|---|
| aca ata aag aag aca gca cgt cgg gaa cag ctt atg aga gaa gaa gca<br>Thr Ile Lys Lys Thr Ala Arg Arg Glu Gln Leu Met Arg Glu Glu Ala<br>125                     130                     135 | 555 |
| gaa cag aag cgc tta aaa act gta ctt gag tta cag tat gta ttg gat<br>Glu Gln Lys Arg Leu Lys Thr Val Leu Glu Leu Gln Tyr Val Leu Asp<br>140                     145                     150                     155 | 603 |
| aag ctg gga gat gat gat gtg aga aca gat ctg aaa caa ggt ttg agt<br>Lys Leu Gly Asp Asp Asp Val Arg Thr Asp Leu Lys Gln Gly Leu Ser<br>                     160                     165                     170 | 651 |
| gga gtg cca ata ttg tct gag gag gag ttg tca ttg ctg gat gag ttc<br>Gly Val Pro Ile Leu Ser Glu Glu Glu Leu Ser Leu Leu Asp Glu Phe<br>                     175                     180                     185 | 699 |
| tac aag ctc gta gat cct gag cgt gac atg agt tta agg tta aat gag<br>Tyr Lys Leu Val Asp Pro Glu Arg Asp Met Ser Leu Arg Leu Asn Glu<br>                     190                     195                     200 | 747 |
| cag tat gaa cat gcc tca att cac ttg tgg gat ttg ctg gaa ggg aaa<br>Gln Tyr Glu His Ala Ser Ile His Leu Trp Asp Leu Leu Glu Gly Lys<br>205                     210                     215 | 795 |
| gaa aag cct gtg tgt gga aca acc tat aaa gct cta aag gaa att gtt<br>Glu Lys Pro Val Cys Gly Thr Thr Tyr Lys Ala Leu Lys Glu Ile Val<br>220                     225                     230                     235 | 843 |
| gag cgt gtt ttc cag tca aac tac ttt gat agc act cac aat cat caa<br>Glu Arg Val Phe Gln Ser Asn Tyr Phe Asp Ser Thr His Asn His Gln<br>                     240                     245                     250 | 891 |
| aat ggg ttg tgt gag gag gaa gag gcg gct tca gcg ccc aca gtg gag<br>Asn Gly Leu Cys Glu Glu Glu Glu Ala Ala Ser Ala Pro Thr Val Glu<br>                     255                     260                     265 | 939 |
| gac cag gta gct gaa gct gaa cct gag cca gcg gaa gaa tac aca gag<br>Asp Gln Val Ala Glu Ala Glu Pro Glu Pro Ala Glu Glu Tyr Thr Glu<br>                     270                     275                     280 | 987 |
| caa agt gag gtt gaa tca aca gag tat gtc aat agg cag ttc atg gca<br>Gln Ser Glu Val Glu Ser Thr Glu Tyr Val Asn Arg Gln Phe Met Ala<br>285                     290                     295 | 1035 |
| gaa aca cag ttc agc agt ggt gag aag gag caa gtg gat gag tgg aca<br>Glu Thr Gln Phe Ser Ser Gly Glu Lys Glu Gln Val Asp Glu Trp Thr<br>300                     305                     310                     315 | 1083 |
| gtt gaa aca gtt gag gtt gta aac tca ctc cag cag caa cct cag gct<br>Val Glu Thr Val Glu Val Val Asn Ser Leu Gln Gln Gln Pro Gln Ala<br>                     320                     325                     330 | 1131 |
| gcg tcc cct tca gtc cca gag ccc cac tct ttg act cca gtg gct cag<br>Ala Ser Pro Ser Val Pro Glu Pro His Ser Leu Thr Pro Val Ala Gln<br>                     335                     340                     345 | 1179 |
| tca gat cca ctt gtg aga agg cag cgt gta caa gat ctt atg gca caa<br>Ser Asp Pro Leu Val Arg Arg Gln Arg Val Gln Asp Leu Met Ala Gln<br>                     350                     355                     360 | 1227 |
| atg caa ggg ccc tat aat ttc ata cag gat tca atg ttg gat ttt gaa<br>Met Gln Gly Pro Tyr Asn Phe Ile Gln Asp Ser Met Leu Asp Phe Glu<br>365                     370                     375 | 1275 |
| aat cag acg ctt gat cct gcc att gta tcc gca cag cct atg aac cct<br>Asn Gln Thr Leu Asp Pro Ala Ile Val Ser Ala Gln Pro Met Asn Pro<br>380                     385                     390                     395 | 1323 |
| acc cag aac atg gat atg cct cag ctg gtt tgc cct cag gtt cat tct<br>Thr Gln Asn Met Asp Met Pro Gln Leu Val Cys Pro Gln Val His Ser<br>                     400                     405                     410 | 1371 |
| gaa tct aga ctt gcc caa tct aat caa gtt cct gta caa cca gaa gcc<br>Glu Ser Arg Leu Ala Gln Ser Asn Gln Val Pro Val Gln Pro Glu Ala<br>                     415                     420                     425 | 1419 |
| aca cag gtt cct ttg gtt tca tcc aca agt gag ggg tat aca gca tct<br>Thr Gln Val Pro Leu Val Ser Ser Thr Ser Glu Gly Tyr Thr Ala Ser<br>                     430                     435                     440 | 1467 |

```
cag ccc ttg tac cag cca tct cat gct acg gag cag cgg ccg cag aaa       1515
Gln Pro Leu Tyr Gln Pro Ser His Ala Thr Glu Gln Arg Pro Gln Lys
        445                 450                 455 gag cca atg gat cag att cag gca aca ata tct ttg aat aca gac cag       1563
Glu Pro Met Asp Gln Ile Gln Ala Thr Ile Ser Leu Asn Thr Asp Gln
460                 465                 470                 475 act aca gca tcc tca tcc ctt cct gct gct tct cag cct caa gtg ttc       1611
Thr Thr Ala Ser Ser Ser Leu Pro Ala Ala Ser Gln Pro Gln Val Phe
                480                 485                 490 cag gct ggg aca agt aaa cct ttg cac agc agt gga atc aat gta aat       1659
Gln Ala Gly Thr Ser Lys Pro Leu His Ser Ser Gly Ile Asn Val Asn
            495                 500                 505 gca gct cca ttc cag tcc atg caa acg gtg ttc aat atg aat gct cca       1707
Ala Ala Pro Phe Gln Ser Met Gln Thr Val Phe Asn Met Asn Ala Pro
        510                 515                 520 gtc cct cct gct aat gaa cca gaa acg tta aaa caa cag agt cag tac       1755
Val Pro Pro Ala Asn Glu Pro Glu Thr Leu Lys Gln Gln Ser Gln Tyr
    525                 530                 535 cag gcc act tat aac cag agt ttt tcc agt cag cct cac caa gtg gaa       1803
Gln Ala Thr Tyr Asn Gln Ser Phe Ser Ser Gln Pro His Gln Val Glu
540                 545                 550                 555 caa aca gag ctt caa caa gac caa ctg caa acg gtg gtt ggc act tac       1851
Gln Thr Glu Leu Gln Gln Asp Gln Leu Gln Thr Val Val Gly Thr Tyr
                560                 565                 570 cat gga tcc cag gac cag cct cat caa gtg cct ggt aac cac cag caa       1899
His Gly Ser Gln Asp Gln Pro His Gln Val Pro Gly Asn His Gln Gln
            575                 580                 585 ccc cca cag cag aac act ggc ttt cca cgt agc agt cag cct tat tac       1947
Pro Pro Gln Gln Asn Thr Gly Phe Pro Arg Ser Ser Gln Pro Tyr Tyr
        590                 595                 600 aac agt cgt ggg gta tct cga gga ggg tct cgt ggt gcc aga ggc ttg       1995
Asn Ser Arg Gly Val Ser Arg Gly Gly Ser Arg Gly Ala Arg Gly Leu
    605                 610                 615 atg aat gga tac agg ggc cct gcc aat gga ttt aga gga gga tat gat       2043
Met Asn Gly Tyr Arg Gly Pro Ala Asn Gly Phe Arg Gly Gly Tyr Asp
620                 625                 630                 635 ggt tac cgc cct tca ttc tcg aac act cca aac agt ggt tat tca cag       2091
Gly Tyr Arg Pro Ser Phe Ser Asn Thr Pro Asn Ser Gly Tyr Ser Gln
                640                 645                 650 tct cag ttc act gct ccc cgg gac tac tct ggt tac cag cgg gat gga       2139
Ser Gln Phe Thr Ala Pro Arg Asp Tyr Ser Gly Tyr Gln Arg Asp Gly
            655                 660                 665 tat cag cag aat ttc aag cga ggc tct ggg cag agt gga cca cgg gga       2187
Tyr Gln Gln Asn Phe Lys Arg Gly Ser Gly Gln Ser Gly Pro Arg Gly
        670                 675                 680 gcc cca cga ggt aat ata ttg tgg tgg tga cctagctcc tatgtggagc          2237
Ala Pro Arg Gly Asn Ile Leu Trp Trp
    685                 690 ttctgttctg gccttggaag aactgttcat agtccgcatg taggttacat gttaggaata    2297
catttatctt ttccagactt gttgctaaag attaaatgaa atgctctgtt tctaaaattt    2357
catcttgaat ccaaatttta atttttgaat gactttccct gctgttgtct tcaaaatcag    2417 aacatttct ctgcctcaga aaagcgtttt tccaactgga aatttatttt tcaggtctta    2477
aaacctgcta aatgttttta ggaagtacct actgaaactt tttgtaagac attttggaa    2537 cgagcttgaa catttatata aatttattac cctctttgat ttttgaaaca tgcatattat    2597
atttaggctg agaagcccctt caaatggcca gataagccac agtttagct agagaaccat    2657
```

```
ttagaattga cataactaat ctaaacttga acacttttag gaccaatgtt agtgttctaa    2717
ataccaacat atttctgatg tttaaacaga tctcccaaat tcttaggacc ttgatgtcat    2777
taaaatttag aatgacaagc ttaagaggct ttagtttcat ttgttttca agtaatgaaa     2837 aataatttct tacatgggca gatagttaat ttgttgaaca attacaggta gcatttcatg    2897
taatctgatg ttctaaatgg ttctcttatt gaaggaggtt aaagaattag gtttcttaca    2957 gttttttggct ggccatgaca tgtataaaat gtatattaag gaggaattat aaagtacttt   3017
aatttgaatg ctagtggcaa ttgatcatta agaaagtact ttaaagcaaa aggttaatgg    3077
gtcatctggg aaaaatactg aagtatcaaa ggtatttgca tgtgaatgtg ggttatgttc    3137
ttctatccca ccttgtagca tattctatga agttgagtt aaatgatagc taaaatatct     3197
gtttcaacag catgtaaaaa gttattttaa ctgttacaag tcattataca attttgaatg    3257
ttctgtagtt tcttttttaac agtttaggta caaaggtctg ttttcattct ggtgcttttt   3317
attaattttg atagtatgat gtcacttcct attgaaatgt aagctagcgt taccttaga    3377 atgtgagctc catgagagca ggtaccttgt ttgtcttcac tgctgtatct attcccaacg    3437
cctcatgaca gtgcctggca catagtaggc actcaataaa tacttgttga atgaatgaaa    3497
aaaaaaaaaa a                                                         3508
```

<210> SEQ ID NO 28
<211> LENGTH: 692
<212> TYPE: PRT
<213> ORGANISM: Mus musculus

<400> SEQUENCE: 28

```
Met Pro Ser Ala Thr Ser His Ser Gly Ser Gly Ser Lys Ser Gly
1               5                   10                  15

Pro Pro Pro Ser Gly Ser Ser Gly Ser Glu Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220
```

-continued

```
Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
            245                 250                 255

Glu Glu Glu Ala Ala Ser Ala Pro Thr Val Glu Asp Gln Val Ala Glu
        260                 265                 270

Ala Glu Pro Glu Pro Ala Glu Glu Tyr Thr Glu Gln Ser Glu Val Glu
    275                 280                 285

Ser Thr Glu Tyr Val Asn Arg Gln Phe Met Ala Glu Thr Gln Phe Ser
290                 295                 300

Ser Gly Glu Lys Glu Gln Val Asp Glu Trp Thr Val Glu Thr Val Glu
305                 310                 315                 320

Val Val Asn Ser Leu Gln Gln Pro Gln Ala Ala Ser Pro Ser Val
            325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
            405                 410                 415

Gln Ser Asn Gln Val Pro Val Gln Glu Ala Thr Gln Val Pro Leu
        420                 425                 430

Val Ser Ser Thr Ser Glu Gly Tyr Thr Ala Ser Gln Pro Leu Tyr Gln
            435                 440                 445

Pro Ser His Ala Thr Glu Gln Arg Pro Gln Lys Glu Pro Met Asp Gln
450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
            485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
            565                 570                 575

Gln Pro His Gln Val Pro Gly Asn His Gln Gln Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640
```

```
Phe Ser Asn Thr Pro Asn Ser Gly Tyr Ser Gln Ser Gln Phe Thr Ala
            645                 650                 655

Pro Arg Asp Tyr Ser Gly Tyr Gln Arg Asp Gly Tyr Gln Gln Asn Phe
        660                 665                 670

Lys Arg Gly Ser Gly Gln Ser Gly Pro Arg Gly Ala Pro Arg Gly Asn
            675                 680                 685

Ile Leu Trp Trp
    690

<210> SEQ ID NO 29
<211> LENGTH: 2109
<212> TYPE: DNA
<213> ORGANISM: Gallus gallus
<220> FEATURE:
<221> NAME/KEY: CDS
<222> LOCATION: (1)..(2109)

<400> SEQUENCE: 29
```

| | | | | | | | | | | | | | | | | |
|---|---|---|---|---|---|---|---|---|---|---|---|---|---|---|---|---|
| atg | ccc | tcg | gct | acc | aac | ggc | acc | atg | gcg | agc | agc | agc | ggg | aag | gcg | 48 |
| Met | Pro | Ser | Ala | Thr | Asn | Gly | Thr | Met | Ala | Ser | Ser | Ser | Gly | Lys | Ala | |
| 1 | | | | 5 | | | | | 10 | | | | | 15 | | |
| ggc | ccg | ggc | ggc | aac | gag | cag | gcc | ccg | gcg | gcg | gca | gcg | gcc | ccg | | 96 |
| Gly | Pro | Gly | Gly | Asn | Glu | Gln | Ala | Pro | Ala | Ala | Ala | Ala | Ala | Pro | | |
| | | | 20 | | | | | 25 | | | | | 30 | | | |
| cag | gcg | tcg | ggc | ggc | agc | atc | acc | tcg | gtt | cag | acc | gag | gcc | atg | aag | 144 |
| Gln | Ala | Ser | Gly | Gly | Ser | Ile | Thr | Ser | Val | Gln | Thr | Glu | Ala | Met | Lys | |
| | | 35 | | | | | 40 | | | | | 45 | | | | |
| cag | atc | ttg | gga | gtg | atc | gac | aaa | aag | ctc | cgc | aac | ctc | gag | aag | aaa | 192 |
| Gln | Ile | Leu | Gly | Val | Ile | Asp | Lys | Lys | Leu | Arg | Asn | Leu | Glu | Lys | Lys | |
| 50 | | | | | 55 | | | | | 60 | | | | | | |
| aag | agc | aaa | ctt | gac | gat | tac | cag | gaa | cga | atg | aac | aag | ggg | gaa | cgt | 240 |
| Lys | Ser | Lys | Leu | Asp | Asp | Tyr | Gln | Glu | Arg | Met | Asn | Lys | Gly | Glu | Arg | |
| 65 | | | | 70 | | | | | 75 | | | | | 80 | | |
| cta | aat | caa | gat | caa | ctg | gat | gca | gtg | tca | aaa | tac | cag | gaa | gtg | aca | 288 |
| Leu | Asn | Gln | Asp | Gln | Leu | Asp | Ala | Val | Ser | Lys | Tyr | Gln | Glu | Val | Thr | |
| | | | | 85 | | | | | 90 | | | | | 95 | | |
| aat | aac | ctg | gaa | ttc | gct | aaa | gaa | ctg | cag | agg | agc | ttt | atg | gca | ctg | 336 |
| Asn | Asn | Leu | Glu | Phe | Ala | Lys | Glu | Leu | Gln | Arg | Ser | Phe | Met | Ala | Leu | |
| | | | 100 | | | | | 105 | | | | | 110 | | | |
| agc | caa | gat | atc | cag | aaa | aca | ata | aaa | aag | acg | gct | cgc | agg | gag | cag | 384 |
| Ser | Gln | Asp | Ile | Gln | Lys | Thr | Ile | Lys | Lys | Thr | Ala | Arg | Arg | Glu | Gln | |
| | 115 | | | | | 120 | | | | | 125 | | | | | |
| ctg | atg | aga | gaa | gag | gct | gag | cag | aag | cgt | tta | aag | act | gtg | cta | gag | 432 |
| Leu | Met | Arg | Glu | Glu | Ala | Glu | Gln | Lys | Arg | Leu | Lys | Thr | Val | Leu | Glu | |
| 130 | | | | | 135 | | | | | 140 | | | | | | |
| ctg | cag | ttc | att | ttg | gac | aag | ttg | ggt | gac | gat | gaa | gtg | cgc | agt | gac | 480 |
| Leu | Gln | Phe | Ile | Leu | Asp | Lys | Leu | Gly | Asp | Asp | Glu | Val | Arg | Ser | Asp | |
| 145 | | | | | 150 | | | | | 155 | | | | | 160 | |
| ttg | aaa | caa | gga | tca | aat | gga | gta | ccg | gta | ctg | aca | gag | gag | gaa | ctg | 528 |
| Leu | Lys | Gln | Gly | Ser | Asn | Gly | Val | Pro | Val | Leu | Thr | Glu | Glu | Glu | Leu | |
| | | | | 165 | | | | | 170 | | | | | 175 | | |
| aca | atg | ctg | gat | gaa | ttt | tac | aag | cta | gtt | tac | cct | gaa | agg | gac | atg | 576 |
| Thr | Met | Leu | Asp | Glu | Phe | Tyr | Lys | Leu | Val | Tyr | Pro | Glu | Arg | Asp | Met | |
| | | | 180 | | | | | 185 | | | | | 190 | | | |
| aac | atg | agg | ttg | aat | gag | cag | tat | gag | caa | gca | tct | gtt | cac | ctg | tgg | 624 |
| Asn | Met | Arg | Leu | Asn | Glu | Gln | Tyr | Glu | Gln | Ala | Ser | Val | His | Leu | Trp | |
| | 195 | | | | | 200 | | | | | 205 | | | | | |
| gac | tta | ctg | gaa | ggg | aag | gaa | aaa | ccc | gtt | tgt | gga | aca | acc | tat | aaa | 672 |
| Asp | Leu | Leu | Glu | Gly | Lys | Glu | Lys | Pro | Val | Cys | Gly | Thr | Thr | Tyr | Lys | |
| 210 | | | | | 215 | | | | | 220 | | | | | | |

```
gcc ctg aag gag gtt gtt gaa cgt att ctt caa act agt tac ttt gat       720
Ala Leu Lys Glu Val Val Glu Arg Ile Leu Gln Thr Ser Tyr Phe Asp
225             230                 235                 240 agc acc cat aac cat cag aac ggg tta tgt gag gaa gaa gag gca gca       768
Ser Thr His Asn His Gln Asn Gly Leu Cys Glu Glu Glu Glu Ala Ala
                245                 250                 255 ccc aca cct gca gta gaa gac act gta gca gaa gct gag cct gat cca       816
Pro Thr Pro Ala Val Glu Asp Thr Val Ala Glu Ala Glu Pro Asp Pro
            260                 265                 270 gca gaa gaa ttt act gaa cct act gaa gtt gaa tcg act gag tat gta       864
Ala Glu Glu Phe Thr Glu Pro Thr Glu Val Glu Ser Thr Glu Tyr Val
        275                 280                 285 aac aga caa ttc atg gca gag act cag ttc agc agt agt gag aag gaa       912
Asn Arg Gln Phe Met Ala Glu Thr Gln Phe Ser Ser Ser Glu Lys Glu
    290                 295                 300 cag gta gat gag tgg aca gtt gaa acg gtt gag gtt gta aat tca ctg       960
Gln Val Asp Glu Trp Thr Val Glu Thr Val Glu Val Val Asn Ser Leu
305                 310                 315                 320 cag caa caa aca caa gct aca tct cct cca gtt cct gaa cct cat aca      1008
Gln Gln Gln Thr Gln Ala Thr Ser Pro Pro Val Pro Glu Pro His Thr
                325                 330                 335 ctc act act gtg gct caa gca gat cct ctt gtt aga aga cag aga gta      1056
Leu Thr Thr Val Ala Gln Ala Asp Pro Leu Val Arg Arg Gln Arg Val
            340                 345                 350 cag gac ctt atg gcc cag atg cag ggt cca tat aac ttc atg cag gac      1104
Gln Asp Leu Met Ala Gln Met Gln Gly Pro Tyr Asn Phe Met Gln Asp
        355                 360                 365 tct atg ctg gag ttt gag aac cag aca ctt gat cct gcc att gta tct      1152
Ser Met Leu Glu Phe Glu Asn Gln Thr Leu Asp Pro Ala Ile Val Ser
370                 375                 380 gca cag ccc atg aat cca gca cag aat ttg gac atg ccg caa atg gtc      1200
Ala Gln Pro Met Asn Pro Ala Gln Asn Leu Asp Met Pro Gln Met Val
385                 390                 395                 400 tgc cct cca gtt cat act gag tca aga ctt gcc cag cct aat caa gtt      1248
Cys Pro Pro Val His Thr Glu Ser Arg Leu Ala Gln Pro Asn Gln Val
                405                 410                 415 cct gtg caa cca gaa gct acg cag gtt ccc ttg gtt tca tct aca agt      1296
Pro Val Gln Pro Glu Ala Thr Gln Val Pro Leu Val Ser Ser Thr Ser
            420                 425                 430 gag gga tat aca gcc tcc cag ccc atg tat cag cct tct cat acc aca      1344
Glu Gly Tyr Thr Ala Ser Gln Pro Met Tyr Gln Pro Ser His Thr Thr
        435                 440                 445 gag caa cgg cca cag aag gaa tcc att gac cag att cag gct tca atg      1392
Glu Gln Arg Pro Gln Lys Glu Ser Ile Asp Gln Ile Gln Ala Ser Met
    450                 455                 460 tca ctg aat gca gac cag acc ccg tca tca tca ctt ccc act gca          1440
Ser Leu Asn Ala Asp Gln Thr Pro Ser Ser Ser Leu Pro Thr Ala
465                 470                 475                 480 tcc cag ccg caa gtt ttc caa gct gga tct agc aaa cct ttg cat agc      1488
Ser Gln Pro Gln Val Phe Gln Ala Gly Ser Ser Lys Pro Leu His Ser
                485                 490                 495 agc gga atc aat gtt aat gca gct cca ttc caa tcc atg caa aca gta      1536
Ser Gly Ile Asn Val Asn Ala Ala Pro Phe Gln Ser Met Gln Thr Val
            500                 505                 510 ttc aac atg aat gca cct gtt cct cct gtt aat gag cca gaa gcc ctt      1584
Phe Asn Met Asn Ala Pro Val Pro Pro Val Asn Glu Pro Glu Ala Leu
        515                 520                 525 aag caa caa aat cag tac cag gcc agt tac aac cag agt ttc tcc aat      1632
Lys Gln Gln Asn Gln Tyr Gln Ala Ser Tyr Asn Gln Ser Phe Ser Asn
    530                 535                 540
```

-continued

```
cag cca cac caa gta gaa caa tca gat ctt cag caa gaa cag ctc cag    1680
Gln Pro His Gln Val Glu Gln Ser Asp Leu Gln Gln Glu Gln Leu Gln
545                 550                 555                 560 aca gtg gtt ggt act tac cat ggt tct ccg gac cag acc cat caa gtg    1728
Thr Val Val Gly Thr Tyr His Gly Ser Pro Asp Gln Thr His Gln Val
                565                 570                 575 gca gga aac cac cag caa cct ccc cag cag aat act gga ttt cca cgc    1776
Ala Gly Asn His Gln Gln Pro Pro Gln Gln Asn Thr Gly Phe Pro Arg
            580                 585                 590 aac agt cag cct tat tac aac agt cgg gga gtg tct cgt ggt gga tca    1824
Asn Ser Gln Pro Tyr Tyr Asn Ser Arg Gly Val Ser Arg Gly Gly Ser
        595                 600                 605 cgt ggg act cgt gga ttg atg aat ggt tac agg gga cct gca aat gga    1872
Arg Gly Thr Arg Gly Leu Met Asn Gly Tyr Arg Gly Pro Ala Asn Gly
    610                 615                 620 ttt aga gga gga tat gat ggc tac cgt cct tca ttt tcc aac act ccg    1920
Phe Arg Gly Gly Tyr Asp Gly Tyr Arg Pro Ser Phe Ser Asn Thr Pro
625                 630                 635                 640 aac agt ggt tac acg cag ccc caa ttt aat gct cct cga gat tat tca    1968
Asn Ser Gly Tyr Thr Gln Pro Gln Phe Asn Ala Pro Arg Asp Tyr Ser
                645                 650                 655 aac tac cag cgg gat gga tat cag cag aac ttc aaa cgt ggt tct gga    2016
Asn Tyr Gln Arg Asp Gly Tyr Gln Gln Asn Phe Lys Arg Gly Ser Gly
            660                 665                 670 caa agt ggg cct cgg gga gct cct cga ggt cgt gga ggg ccc cca aga    2064
Gln Ser Gly Pro Arg Gly Ala Pro Arg Gly Arg Gly Gly Pro Pro Arg
        675                 680                 685 cca aac aga ggg atg cct caa atg aac gct cag caa gtg aat taa        2109
Pro Asn Arg Gly Met Pro Gln Met Asn Ala Gln Gln Val Asn
    690                 695                 700

<210> SEQ ID NO 30
<211> LENGTH: 702
<212> TYPE: PRT
<213> ORGANISM: Gallus gallus

<400> SEQUENCE: 30

Met Pro Ser Ala Thr Asn Gly Thr Met Ala Ser Ser Gly Lys Ala
1               5                   10                  15

Gly Pro Gly Gly Asn Glu Gln Ala Pro Ala Ala Ala Ala Ala Pro
                20                  25                  30

Gln Ala Ser Gly Gly Ser Ile Thr Ser Val Gln Thr Glu Ala Met Lys
            35                  40                  45

Gln Ile Leu Gly Val Ile Asp Lys Lys Leu Arg Asn Leu Glu Lys Lys
        50                  55                  60

Lys Ser Lys Leu Asp Asp Tyr Gln Glu Arg Met Asn Lys Gly Glu Arg
65                  70                  75                  80

Leu Asn Gln Asp Gln Leu Asp Ala Val Ser Lys Tyr Gln Glu Val Thr
                85                  90                  95

Asn Asn Leu Glu Phe Ala Lys Glu Leu Gln Arg Ser Phe Met Ala Leu
                100                 105                 110

Ser Gln Asp Ile Gln Lys Thr Ile Lys Lys Thr Ala Arg Arg Glu Gln
            115                 120                 125

Leu Met Arg Glu Glu Ala Glu Gln Lys Arg Leu Lys Thr Val Leu Glu
        130                 135                 140

Leu Gln Phe Ile Leu Asp Lys Leu Gly Asp Asp Glu Val Arg Ser Asp
145                 150                 155                 160
```

```
Leu Lys Gln Gly Ser Asn Gly Val Pro Val Leu Thr Glu Glu Leu
            165                 170                 175
Thr Met Leu Asp Glu Phe Tyr Lys Leu Val Tyr Pro Glu Arg Asp Met
        180                 185                 190
Asn Met Arg Leu Asn Glu Gln Tyr Glu Gln Ala Ser Val His Leu Trp
        195                 200                 205
Asp Leu Leu Glu Gly Lys Glu Lys Pro Val Cys Gly Thr Thr Tyr Lys
        210                 215                 220
Ala Leu Lys Glu Val Val Glu Arg Ile Leu Gln Thr Ser Tyr Phe Asp
225                 230                 235                 240
Ser Thr His Asn His Gln Asn Gly Leu Cys Glu Glu Glu Ala Ala
                245                 250                 255
Pro Thr Pro Ala Val Glu Asp Thr Val Ala Glu Ala Glu Pro Asp Pro
            260                 265                 270
Ala Glu Glu Phe Thr Glu Pro Thr Glu Val Glu Ser Thr Glu Tyr Val
        275                 280                 285
Asn Arg Gln Phe Met Ala Glu Thr Gln Phe Ser Ser Glu Lys Glu
        290                 295                 300
Gln Val Asp Glu Trp Thr Val Glu Thr Val Glu Val Val Asn Ser Leu
305                 310                 315                 320
Gln Gln Gln Thr Gln Ala Thr Ser Pro Pro Val Pro Glu Pro His Thr
                325                 330                 335
Leu Thr Thr Val Ala Gln Ala Asp Pro Leu Val Arg Arg Gln Arg Val
            340                 345                 350
Gln Asp Leu Met Ala Gln Met Gln Gly Pro Tyr Asn Phe Met Gln Asp
        355                 360                 365
Ser Met Leu Glu Phe Glu Asn Gln Thr Leu Asp Pro Ala Ile Val Ser
        370                 375                 380
Ala Gln Pro Met Asn Pro Ala Gln Asn Leu Asp Met Pro Gln Met Val
385                 390                 395                 400
Cys Pro Pro Val His Thr Glu Ser Arg Leu Ala Gln Pro Asn Gln Val
                405                 410                 415
Pro Val Gln Pro Glu Ala Thr Gln Val Pro Leu Val Ser Ser Thr Ser
            420                 425                 430
Glu Gly Tyr Thr Ala Ser Gln Pro Met Tyr Gln Pro Ser His Thr Thr
        435                 440                 445
Glu Gln Arg Pro Gln Lys Glu Ser Ile Asp Gln Ile Gln Ala Ser Met
        450                 455                 460
Ser Leu Asn Ala Asp Gln Thr Pro Ser Ser Ser Leu Pro Thr Ala
465                 470                 475                 480
Ser Gln Pro Gln Val Phe Gln Ala Gly Ser Ser Lys Pro Leu His Ser
                485                 490                 495
Ser Gly Ile Asn Val Asn Ala Ala Pro Phe Gln Ser Met Gln Thr Val
            500                 505                 510
Phe Asn Met Asn Ala Pro Val Pro Val Asn Glu Pro Glu Ala Leu
        515                 520                 525
Lys Gln Gln Asn Gln Tyr Gln Ala Ser Tyr Asn Gln Ser Phe Ser Asn
530                 535                 540
Gln Pro His Gln Val Glu Gln Ser Asp Leu Gln Glu Gln Leu Gln
545                 550                 555                 560
Thr Val Val Gly Thr Tyr His Gly Ser Pro Asp Gln Thr His Gln Val
                565                 570                 575
Ala Gly Asn His Gln Gln Pro Pro Gln Gln Asn Thr Gly Phe Pro Arg
```

-continued

```
                580                 585                 590
Asn Ser Gln Pro Tyr Tyr Asn Ser Arg Gly Val Ser Arg Gly Gly Ser
            595                 600                 605

Arg Gly Thr Arg Gly Leu Met Asn Gly Tyr Arg Gly Pro Ala Asn Gly
        610                 615                 620

Phe Arg Gly Gly Tyr Asp Gly Tyr Arg Pro Ser Phe Ser Asn Thr Pro
625                 630                 635                 640

Asn Ser Gly Tyr Thr Gln Pro Gln Phe Asn Ala Pro Arg Asp Tyr Ser
            645                 650                 655

Asn Tyr Gln Arg Asp Gly Tyr Gln Gln Asn Phe Lys Arg Gly Ser Gly
        660                 665                 670

Gln Ser Gly Pro Arg Gly Ala Pro Arg Gly Arg Gly Gly Pro Pro Arg
    675                 680                 685

Pro Asn Arg Gly Met Pro Gln Met Asn Ala Gln Val Asn
        690                 695                 700

<210> SEQ ID NO 31
<211> LENGTH: 20
<212> TYPE: DNA
<213> ORGANISM: Artificial
<220> FEATURE:
<223> OTHER INFORMATION: T3 primer

<400> SEQUENCE: 31
aattaaccct cactaaaggg                                              20

<210> SEQ ID NO 32
<211> LENGTH: 19
<212> TYPE: DNA
<213> ORGANISM: Artificial
<220> FEATURE:
<223> OTHER INFORMATION: T7 primer

<400> SEQUENCE: 32
taatacgact cactatagg                                               19

<210> SEQ ID NO 33
<211> LENGTH: 18
<212> TYPE: DNA
<213> ORGANISM: Artificial
<220> FEATURE:
<223> OTHER INFORMATION: primer

<400> SEQUENCE: 33
aaggtttgaa tggagtgc                                                18

<210> SEQ ID NO 34
<211> LENGTH: 18
<212> TYPE: DNA
<213> ORGANISM: Artificial
<220> FEATURE:
<223> OTHER INFORMATION: primer

<400> SEQUENCE: 34
tgctcctttt caccactg                                                18

<210> SEQ ID NO 35
<211> LENGTH: 18
<212> TYPE: DNA
<213> ORGANISM: Artificial
<220> FEATURE:
<223> OTHER INFORMATION: GAPDH primer
```

<400> SEQUENCE: 35
gggctgcttt taactctg                                                18

<210> SEQ ID NO 36
<211> LENGTH: 18
<212> TYPE: DNA
<213> ORGANISM: Artificial
<220> FEATURE:
<223> OTHER INFORMATION: GAPDH primer

<400> SEQUENCE: 36
ccaggaaatg agcttgac                                                18

<210> SEQ ID NO 37
<211> LENGTH: 14
<212> TYPE: PRT
<213> ORGANISM: Artificial
<220> FEATURE:
<223> OTHER INFORMATION: peptides

<400> SEQUENCE: 37

Arg Asn Leu Glu Lys Lys Lys Gly Lys Leu Asp Asp Tyr Gln
1               5                   10

<210> SEQ ID NO 38
<211> LENGTH: 22
<212> TYPE: DNA
<213> ORGANISM: Artificial
<220> FEATURE:
<223> OTHER INFORMATION: primer

<400> SEQUENCE: 38
aggtsharct gcagsagtcw gg                                           22

<210> SEQ ID NO 39
<211> LENGTH: 23
<212> TYPE: DNA
<213> ORGANISM: Artificial
<220> FEATURE:
<223> OTHER INFORMATION: primer

<400> SEQUENCE: 39
ctcgagttaa ttcacttgct gag                                          23

<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
ggtaccattc acttgctgag tg                                           22

<210> SEQ ID NO 41
<211> LENGTH: 23
<212> TYPE: DNA
<213> ORGANISM: Artificial Sequence
<220> FEATURE:
<223> OTHER INFORMATION: primer

<400> SEQUENCE: 41
gagctcatgc cctcggccac cag                                          23

<210> SEQ ID NO 42

<211> LENGTH: 23
<212> TYPE: DNA
<213> ORGANISM: Artificial Sequence
<220> FEATURE:
<223> OTHER INFORMATION: primer

<400> SEQUENCE: 42
ctcgagttaa ttcacttgct gag                                              23

<210> SEQ ID NO 43
<211> LENGTH: 14
<212> TYPE: PRT
<213> ORGANISM: Homo sapiens

<400> SEQUENCE: 43

Arg Asn Leu Gln Lys Lys Gly Lys Leu Asp Asp Tyr Gln
1               5                   10

<210> SEQ ID NO 44
<211> LENGTH: 148
<212> TYPE: PRT
<213> ORGANISM: Mus musculus

<400> SEQUENCE: 44

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145

<210> SEQ ID NO 45
<211> LENGTH: 132
<212> TYPE: PRT
<213> ORGANISM: Mus musculus

<400> SEQUENCE: 45

Ala Val Leu Arg Cys Ser Arg Gly Leu Leu Val Ile Trp Ile Ser Asp
1               5                   10                  15

Ile Gln Leu Thr Gln Ser Pro Ser Ser Leu Ala Val Thr Ala Gly Glu
            20                  25                  30

Lys Val Thr Met Ser Cys Lys Ser Ser Gln Ser Leu Leu Trp Ser Val
        35                  40                  45

Asn Gln Lys Asn Tyr Leu Ser Trp Tyr Gln Gln Lys Gln Arg Gln Pro
    50                  55                  60

```
Pro Lys Leu Leu Ile Tyr Gly Ala Ser Ile Arg Glu Ser Trp Val Pro
 65                  70                  75                  80

Asp Arg Phe Thr Gly Ser Gly Ser Gly Thr Asp Phe Thr Leu Thr Ile
                 85                  90                  95

Ser Asn Val His Ala Glu Asp Leu Ala Val Tyr Tyr Cys Gln His Asn
            100                 105                 110

His Gly Ser Phe Leu Pro Ser Arg Ser Glu Gln Val Pro Ser Trp Arg
        115                 120                 125

Ser Asn Asn Arg
    130

<210> SEQ ID NO 46
<211> LENGTH: 117
<212> TYPE: PRT
<213> ORGANISM: Mus musculus

<400> SEQUENCE: 46

Arg Thr Thr Ser His Met Asp Ser Asp Ile Gln Leu Thr Gln Ser Pro
 1               5                  10                  15

Ala Ser Leu Ser Ala Ser Val Gly Glu Thr Val Thr Ile Thr Cys Arg
             20                  25                  30

Ala Ser Gly Asn Ile His Asn Tyr Leu Ala Trp Tyr Gln Gln Lys Gln
         35                  40                  45

Gly Lys Ser Pro Gln Leu Leu Val Tyr Asn Ala Lys Thr Leu Ala Asp
 50                  55                  60

Gly Val Pro Ser Arg Phe Ser Gly Ser Gly Ser Gly Thr Gln Tyr Ser
 65                  70                  75                  80

Leu Lys Ile Asn Ser Leu Gln Pro Glu Asp Phe Gly Ser Tyr Tyr Cys
                 85                  90                  95

Gln His Phe Trp Ser Thr Leu Thr Phe Gly Gly Gly Thr Lys Leu Glu
            100                 105                 110

Ile Lys Gln Ser Asp
        115

<210> SEQ ID NO 47
<211> LENGTH: 94
<212> TYPE: PRT
<213> ORGANISM: Mus musculus

<400> SEQUENCE: 47

Ser Gly Asp Arg Val Ser Leu Ser Cys Arg Ala Ser Gln Ser Ile Ser
 1               5                  10                  15

Asn Tyr Leu His Trp Tyr Gln Gln Lys Ser His Glu Ser Pro Arg Leu
             20                  25                  30

Leu Ile Lys Tyr Ala Ser Gln Ser Ile Ser Gly Ile Pro Ser Arg Phe
         35                  40                  45

Ser Gly Ser Gly Ser Gly Thr Asp Phe Thr Leu Ser Ile Asn Ser Val
 50                  55                  60

Glu Thr Glu Asp Phe Gly Met Tyr Phe Cys Gln Gln Ser Asn Ser Trp
 65                  70                  75                  80

Pro Tyr Thr Phe Gly Ala Gly Thr Lys Leu Glu Ile Lys Gln
                 85                  90

<210> SEQ ID NO 48
<211> LENGTH: 105
<212> TYPE: PRT
<213> ORGANISM: Mus musculus
```

<400> SEQUENCE: 48

```
Gly Leu Phe Cys Ser Val Glu Arg Cys His Tyr Gln Leu Gln Ser Ser
1               5                   10                  15

Gln Asn Leu Leu Ser Ile Val Asn Arg Tyr His Tyr Met Ser Gly Asn
            20                  25                  30

Pro Pro Lys Leu Leu Val Tyr Pro Ala Leu Leu Ile Tyr Glu Ala Ser
        35                  40                  45

Ile Thr Lys Ser Cys Val Pro Asp Arg Phe Thr Arg Ser Gly Ser Gly
50                  55                  60

Thr Asn Phe Thr Leu Thr Ile Asn Phe Val His Ala Asp Asp Leu Ile
65                  70                  75                  80

Phe Tyr Tyr Cys Gln His Asn Arg Gly Ser Phe Leu Pro Ser Ser Ser
                85                  90                  95

Val Gln Val Pro Arg Arg Ser Asn
            100                 105
```

<210> SEQ ID NO 49
<211> LENGTH: 100
<212> TYPE: PRT
<213> ORGANISM: Mus musculus

<400> SEQUENCE: 49

```
Asp Ile Leu Gln Ala Ser Gly Tyr Ser Phe Thr Gly Tyr Thr Met Asn
1               5                   10                  15

Trp Val Lys Gln Ser His Gly Lys Asn Leu Glu Trp Ile Gly Leu Ile
            20                  25                  30

Asn Pro Tyr Asn Gly Gly Thr Ser Tyr Asn Gln Lys Phe Lys Gly Lys
        35                  40                  45

Ala Thr Leu Thr Val Asp Lys Ser Ser Ser Thr Ala Tyr Met Glu Leu
50                  55                  60

Leu Ser Leu Thr Ser Glu Asp Ser Ala Val Tyr Tyr Cys Ala Arg Trp
65                  70                  75                  80

Gly Val Trp Ser Ala Met Asp Tyr Trp Gly Gln Gly Thr Thr Val Thr
                85                  90                  95

Val Ser Ser Lys
            100
```

<210> SEQ ID NO 50
<211> LENGTH: 90
<212> TYPE: PRT
<213> ORGANISM: Mus musculus

<400> SEQUENCE: 50

```
Asp Arg Val Ser Ile Thr Cys Lys Ala Ser Gln Asn Val Arg Thr Ala
1               5                   10                  15

Val Ala Trp Tyr Gln Gln Lys Pro Arg Gln Ser Pro Lys Ala Leu Ile
            20                  25                  30

Tyr Leu Ala Ser Asn Arg Asp Thr Gly Leu Pro Asp Arg Phe Pro Gly
        35                  40                  45

Arg Gly Ser Gly Thr Asp Phe Thr Leu Asn Ile Thr Asn Val Gln Ser
50                  55                  60

Glu Asp Leu Glu Asp Tyr Phe Cys Leu Gln His Cys Asn Tyr Pro Asn
65                  70                  75                  80

Glu Phe Arg Gly Cys Thr Lys Val Pro Ile
                85                  90
```

```
<210> SEQ ID NO 51
<211> LENGTH: 116
<212> TYPE: PRT
<213> ORGANISM: Mus musculus

<400> SEQUENCE: 51

Leu Gln Glu Ser Gly Ala Glu Leu Ala Arg Pro Gly Ala Ser Val Lys
1               5                   10                  15

Leu Ser Cys Lys Ala Ser Gly Tyr Thr Phe Thr Ser Tyr Trp Met Gln
                20                  25                  30

Trp Val Lys Gln Arg Pro Gly Gln Gly Leu Glu Trp Ile Gly Ala Ile
            35                  40                  45

Tyr Pro Gly Asp Gly Asp Thr Arg Tyr Thr Gln Lys Phe Lys Gly Lys
    50                  55                  60

Ala Thr Leu Thr Ala Asp Lys Ser Ser Ser Thr Ala Tyr Met Gln Leu
65                  70                  75                  80

Ser Ser Leu Ala Ser Glu Asp Ser Ala Val Tyr Tyr Cys Ala Arg Gly
                85                  90                  95

Glu Tyr Gly Asn Tyr Phe Ala Tyr Trp Gly Gln Gly Thr Thr Val Thr
            100                 105                 110

Val Ser Ser Asn
        115

<210> SEQ ID NO 52
<211> LENGTH: 100
<212> TYPE: PRT
<213> ORGANISM: Mus musculus

<400> SEQUENCE: 52

Thr Ser Asp Ala Ser Leu Gly Glu Arg Val Thr Ile Thr Cys Lys Ala
1               5                   10                  15

Ser Gln Asp Ile Asn Ser Tyr Leu Ser Trp Phe Gln Gln Lys Pro Gly
                20                  25                  30

Lys Ser Pro Lys Thr Leu Ile Tyr Arg Ala Asn Arg Leu Val Asp Gly
            35                  40                  45

Val Pro Ser Arg Phe Ser Gly Ser Gly Ser Gln Asp Tyr Ser Leu
    50                  55                  60

Thr Ile Ser Ser Leu Glu Tyr Glu Asp Met Gly Ile Tyr Tyr Cys Leu
65                  70                  75                  80

Gln Tyr Asp Glu Phe Pro Leu Thr Phe Gly Gly Thr Lys Leu Glu
                85                  90                  95

Ile Lys Gln Lys
        100

<210> SEQ ID NO 53
<211> LENGTH: 108
<212> TYPE: PRT
<213> ORGANISM: Mus musculus

<400> SEQUENCE: 53

Ala Trp Leu Ser Gln Leu Ser Cys Thr Ala Ser Gly Phe Asn Ile Lys
1               5                   10                  15

Asp Thr Tyr Met His Trp Val Lys Gln Arg Pro Glu Gln Gly Leu Glu
                20                  25                  30

Trp Ile Gly Arg Ile Asp Pro Ala Asn Gly Asn Thr Lys Tyr Asp Pro
            35                  40                  45

Lys Phe Gln Gly Lys Ala Thr Ile Thr Ala Asp Thr Ser Ser Asn Thr
    50                  55                  60
```

```
Ala Tyr Leu Gln Leu Ser Ser Leu Thr Ser Glu Asp Thr Ala Val Tyr
65                  70                  75                  80

Tyr Cys Ala Arg Pro Ile His Tyr Tyr Tyr Gly Ser Ser Leu Ala Tyr
            85                  90                  95

Trp Gly Gln Gly Thr Thr Val Thr Val Ser Ser Lys
            100                 105
```

<210> SEQ ID NO 54
<211> LENGTH: 104
<212> TYPE: PRT
<213> ORGANISM: Mus musculus

<400> SEQUENCE: 54

```
Glu Phe His Ala Val Ser Leu Gly Gln Arg Ala Thr Ile Ser Cys Arg
1               5                   10                  15

Ala Ser Glu Ser Val Asp Ser Tyr Gly Asn Ser Phe Met His Trp Tyr
                20                  25                  30

Gln Gln Lys Pro Gly Gln Pro Pro Lys Leu Leu Ile Tyr Arg Ala Ser
            35                  40                  45

Asn Leu Glu Ser Gly Ile Pro Ala Arg Phe Ser Gly Ser Gly Ser Arg
50                  55                  60

Thr Asp Phe Thr Leu Thr Ile Asn Pro Val Glu Ala Asp Asp Val Ala
65                  70                  75                  80

Thr Tyr Tyr Cys Gln Gln Ser Asn Glu Asp Pro Gly Arg Ser Glu Val
                85                  90                  95

Val Pro Ser Trp Arg Ser Asn Lys
            100
```

<210> SEQ ID NO 55
<211> LENGTH: 109
<212> TYPE: PRT
<213> ORGANISM: Mus musculus

<400> SEQUENCE: 55

```
Pro Arg Ala Ser Leu Gly Val Ser Glu Thr Leu Leu Cys Thr Ser Gly
1               5                   10                  15

Phe Thr Phe Thr Asp Tyr Tyr Met Ser Trp Val Arg Gln Pro Pro Gly
                20                  25                  30

Lys Ala Leu Glu Trp Leu Gly Phe Ile Arg Asn Lys Ala Asn Gly Tyr
            35                  40                  45

Thr Thr Glu Tyr Ser Ala Ser Val Lys Gly Arg Phe Thr Ile Ser Arg
50                  55                  60

Asp Asn Ser Gln Ser Ile Leu Tyr Leu Gln Met Asn Thr Leu Arg Ala
65                  70                  75                  80

Glu Asp Ser Ala Thr Tyr Tyr Cys Ala Arg Ala Asn Trp Ala Phe Asp
                85                  90                  95

Tyr Trp Gly Gln Gly Thr Thr Val Thr Val Ser Ser Lys
            100                 105
```

<210> SEQ ID NO 56
<211> LENGTH: 94
<212> TYPE: PRT
<213> ORGANISM: Mus musculus

<400> SEQUENCE: 56

```
Ser Gly Asp Arg Val Ser Leu Ser Cys Arg Ala Ser Gln Ser Ile Ser
1               5                   10                  15
```

```
Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
 50                  55                  60

Glu Thr Glu Asp Phe Gly Met Tyr Phe Cys Gln Gln Ser Asn Ser Trp
 65                  70                  75                  80

Pro Tyr Thr Phe Gly Gly Gly Thr Lys Leu Glu Ile Lys Gln
                85                  90
```

<210> SEQ ID NO 57
<211> LENGTH: 111
<212> TYPE: PRT
<213> ORGANISM: Mus musculus

<400> SEQUENCE: 57

```
Pro Ala Cys Leu Pro Gly Gly Ser Leu Arg Leu Ser Cys Ala Thr Ser
 1               5                  10                  15

Gly Phe Thr Phe Thr Asp Tyr Tyr Met Ser Trp Val Arg Gln Pro Pro
            20                  25                  30

Gly Lys Ala Leu Glu Trp Leu Gly Phe Ile Arg Asn Lys Ala Asn Gly
        35                  40                  45

Tyr Thr Thr Glu Tyr Ser Ala Ser Val Lys Gly Arg Phe Thr Ile Ser
 50                  55                  60

Arg Asp Asn Ser Gln Ser Ile Leu Tyr Leu Gln Met Asn Thr Leu Arg
 65                  70                  75                  80

Ala Glu Asp Ser Ala Thr Tyr Tyr Cys Ala Arg Ala Pro Leu Leu Tyr
                85                  90                  95

Tyr Ala Met Asp Tyr Trp Gly Gln Gly Thr Thr Val Thr Val Ser
                100                 105                 110
```

<210> SEQ ID NO 58
<211> LENGTH: 102
<212> TYPE: PRT
<213> ORGANISM: Mus musculus

<400> SEQUENCE: 58

```
Arg Leu Pro Phe Tyr Ser Leu Glu Gln Arg Ala Thr Ile Ser Tyr Arg
 1               5                  10                  15

Ala Ser Lys Asn Val Ser Thr Ser Gly Tyr Ser Tyr Met His Trp Asn
            20                  25                  30

Gln Gln Lys Pro Gly Gln Pro Pro Lys Leu Leu Ile Tyr Leu Val Ser
        35                  40                  45

Asn Leu Glu Ser Gly Val Pro Ala Arg Phe Ser Gly Ser Gly Ser Gly
 50                  55                  60

Thr Asp Phe Thr Leu Asn Ile His Pro Val Glu Glu Asp Ala Ala
 65                  70                  75                  80

Thr Tyr Tyr Cys Gln His Ile Arg Glu Leu Thr Arg Ser Glu Leu Val
                85                  90                  95

Pro Ser Trp Lys Ser Asn
                100
```

<210> SEQ ID NO 59
<211> LENGTH: 109
<212> TYPE: PRT
<213> ORGANISM: Mus musculus

<400> SEQUENCE: 59

Pro Arg Ala Ser Leu Gly Val Ser Glu Thr Leu Leu Cys Thr Ser Gly
1               5                   10                  15

Phe Thr Phe Thr Asp Tyr Tyr Met Ser Trp Val Arg Gln Pro Pro Gly
            20                  25                  30

Lys Ala Leu Glu Trp Leu Gly Phe Ile Arg Asn Lys Ala Asn Gly Tyr
        35                  40                  45

Thr Thr Glu Tyr Ser Ala Ser Val Lys Gly Arg Phe Thr Ile Ser Arg
50                  55                  60

Asp Asn Ser Gln Ser Ile Leu Tyr Leu Gln Met Asn Thr Leu Arg Ala
65                  70                  75                  80

Glu Asp Ser Ala Thr Tyr Tyr Cys Ala Arg Ala Asn Trp Ala Phe Asp
                85                  90                  95

Tyr Trp Gly Gln Gly Thr Thr Val Thr Val Ser Ser Lys
            100                 105

<210> SEQ ID NO 60
<211> LENGTH: 94
<212> TYPE: PRT
<213> ORGANISM: Mus musculus

<400> SEQUENCE: 60

Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
50                  55                  60

Glu Thr Glu Asp Phe Gly Met Tyr Phe Cys Gln Gln Ser Asn Ser Trp
65                  70                  75                  80

Pro Tyr Thr Phe Gly Gly Gly Thr Lys Leu Glu Ile Lys Gln
                85                  90

<210> SEQ ID NO 61
<211> LENGTH: 58
<212> TYPE: PRT
<213> ORGANISM: Homo sapiens

<400> SEQUENCE: 61

Val Phe Gln Ser Asn Tyr Phe Asp Ser Thr His Asn His Gln Asn Gly
1               5                   10                  15

Leu Cys Glu Glu Glu Glu Ala Ala Ser Ala Pro Ala Val Glu Asp Gln
            20                  25                  30

Val Pro Glu Ala Glu Pro Glu Pro Ala Glu Glu Tyr Thr Glu Gln Ser
        35                  40                  45

Glu Val Glu Ser Thr Glu Tyr Val Asn Arg
    50                  55

<210> SEQ ID NO 62
<211> LENGTH: 15
<212> TYPE: PRT
<213> ORGANISM: Homo sapiens

<400> SEQUENCE: 62

Tyr Thr Glu Gln Ser Glu Val Glu Ser Thr Glu Tyr Val Asn Arg
1               5                   10                  15

<210> SEQ ID NO 63
<211> LENGTH: 12
<212> TYPE: PRT
<213> ORGANISM: Homo sapiens

<400> SEQUENCE: 63

Phe Thr Ser Gly Glu Lys Glu Gln Val Asp Glu Trp
1               5                   10

<210> SEQ ID NO 64
<211> LENGTH: 128
<212> TYPE: PRT
<213> ORGANISM: Gallus gallus

<400> SEQUENCE: 64

Ala Val Thr Leu Asp Glu Ser Gly Gly Leu Gln Met Ser Arg Gly
1               5                   10                  15

Gly Leu Ser Leu Val Cys Lys Ala Ser Gly Phe Asp Phe Ser Ser Tyr
            20                  25                  30

Gln Met Asn Trp Ile Arg Gln Ala Pro Gly Lys Gly Leu Glu Phe Val
        35                  40                  45

Ala Ala Ile Asn Lys Phe Gly Asn Ser Thr Gly His Gly Ala Ala Val
    50                  55                  60

Lys Gly Arg Val Thr Ile Ser Arg Asp Asn Gly Gln Ser Thr Val Arg
65                  70                  75                  80

Leu Gln Leu Asn Asn Leu Arg Ala Glu Asp Thr Ala Ile Tyr Phe Cys
                85                  90                  95

Thr Lys His Ala Tyr Gly Tyr Cys Gly Ser Gly Thr Trp Cys Ala Ala
            100                 105                 110

Gly Glu Ile Asp Ala Trp Gly His Gly Thr Glu Val Ile Val Ser Ser
        115                 120                 125

<210> SEQ ID NO 65
<211> LENGTH: 108
<212> TYPE: PRT
<213> ORGANISM: Gallus gallus

<400> SEQUENCE: 65

Gln Ala Ala Ser Thr Gln Pro Ser Ser Val Ser Ala Asn Pro Gly Glu
1               5                   10                  15

Thr Val Glu Ile Thr Cys Ser Gly Gly Gly Ser Tyr Ser Tyr Gly Trp
            20                  25                  30

Phe Gln Gln Lys Ser Pro Gly Ser Ala Pro Val Thr Val Ile Tyr Tyr
        35                  40                  45

Asn Asn Lys Arg Pro Ser Asp Ile Pro Ser Arg Phe Ser Gly Ser Lys
    50                  55                  60

Ser Gly Ser Thr Gly Thr Leu Thr Ile Thr Gly Val Gln Ala Asp Asp
65                  70                  75                  80

Glu Ala Val Tyr Tyr Cys Gly Ser Gly Asp Ser Thr Asp Thr Ala Val
                85                  90                  95

Phe Gly Ala Gly Thr Thr Leu Thr Val Leu Gly Gln
            100                 105

<210> SEQ ID NO 66
<211> LENGTH: 12
<212> TYPE: PRT
<213> ORGANISM: Homo sapiens

<400> SEQUENCE: 66

Gln Gln Pro Gln Ala Ala Ser Pro Ser Val Pro Glu
1               5                   10

<210> SEQ ID NO 67
<211> LENGTH: 240
<212> TYPE: DNA
<213> ORGANISM: Gallus gallus

<400> SEQUENCE: 67

| | | | | |
|---|---|---|---|---|
| accatgagcc cactcgtctc ctccctcctg ctcctggccg ccctgccagg tgagggcgct | 60 |
| gtggggctct atgggctct atggggtctc agcggggctc tgcgggctca atggggccca | 120 |
| aaggggggt ctgcgggctc tatggggggg tcaacggggg gtctcacggg gggccggctc | 180 |
| cgcgaggccg tgtggcggcg gctccgtcag cgctttctgt ccttccccac agggcgcgcc | 240 |

<210> SEQ ID NO 68
<211> LENGTH: 1807
<212> TYPE: DNA
<213> ORGANISM: Homo sapiens

<400> SEQUENCE: 68

| | |
|---|---|
| ctttctgggg caggccaggc ctgaccttgg ctttggggca gggaggggc taaggtgagg | 60 |
| caggtggcgc cagccaggtg cacacccaat gcccatgagc ccagacactg gacgctgaac | 120 |
| ctcgcggaca gttaagaacc caggggcctc tgcgccctgg gcccagctct gtcccacacc | 180 |
| gcggtcacat ggcaccacct ctcttgcagc ctccaccaag ggcccatcgg tcttcccct | 240 |
| ggcaccctcc tccaagagca cctctggggg cacagcggcc ctgggctgcc tggtcaagga | 300 |
| ctacttcccc gaaccggtga cggtgtcgtg gaactcaggc gccctgacca gcggcgtgca | 360 |
| caccttcccg gctgtcctac agtcctcagg actctactcc ctcagcagcg tggtgaccgt | 420 |
| gccctccagc agcttgggca cccagaccta catctgcaac gtgaatcaca agcccagcaa | 480 |
| caccaaggtg gacaagaaag ttggtgagag gccagcacag ggagggaggg tgtctgctgg | 540 |
| aagccaggct cagcgctcct gcctggacgc atcccggcta tgcagcccca gtccagggca | 600 |
| gcaaggcagg ccccgtctgc ctcttcaccc ggaggcctct gcccgcccca ctcatgctca | 660 |
| gggagagggt cttctggctt tttcccagg ctctgggcag gcacaggcta ggtgccccta | 720 |
| acccaggccc tgcacacaaa ggggcaggtg ctgggctcag acctgccaag agccatatcc | 780 |
| gggaggaccc tgccctgac ctaagcccac cccaaaggcc aaactctcca ctccctcagc | 840 |
| tcggacacct tctctcctcc cagattccag taactcccaa tcttctctct gcagagccca | 900 |
| aatcttgtga caaaactcac acatgcccac cgtgcccagg taagccagcc caggcctcgc | 960 |
| cctccagctc aaggcgggac aggtgcccta gagtagcctg catccaggga caggccccag | 1020 |
| ccgggtgctg acacgtccac ctccatctct cctcagcac ctgaactcct ggggggaccg | 1080 |
| tcagtcttcc tcttccccc aaaacccaag gacaccctca tgatctcccg gacccctgag | 1140 |
| gtcacatgcg tggtggtgga cgtgagccac gaagaccctg aggtcaagtt caactggtac | 1200 |
| gtggacggcg tggaggtgca taatgccaag acaaagccgc gggaggagca gtacaacagc | 1260 |
| acgtaccgtg tggtcagcgt cctcaccgtc ctgcaccagg actggctgaa tggcaaggag | 1320 |
| tacaagtgca aggtctccaa caaagccctc ccagccccca tcgagaaaac catctccaaa | 1380 |
| gccaaaggtg ggacccgtgg ggtgcgaggg ccacatggac agaggccggc tcggcccacc | 1440 |

```
ctctgccctg agagtgaccg ctgtaccaac ctctgtccct acagggcagc ccgagaacc     1500 acaggtgtac accctgcccc catcccggga tgagctgacc aagaaccagg tcagcctgac     1560
ctgcctggtc aaaggcttct atcccagcga catcgccgtg gagtgggaga gcaatgggca     1620
gccggagaac aactacaaga ccacgcctcc cgtgctggac tccgacggct ccttcttcct     1680
ctacagcaag ctcaccgtgg acaagagcag gtggcagcag gggaacgtct tctcatgctc     1740
cgtgatgcat gaggctctgc acaaccacta cacgcagaag agcctctccc tgtctccggg     1800
taaatga                                                               1807
```

<210> SEQ ID NO 69
<211> LENGTH: 567
<212> TYPE: DNA
<213> ORGANISM: Homo sapiens

<400> SEQUENCE: 69

```
cagaatggct gcaaagagct ccaacaaaac aatttagaac tttattaagg aatagggga      60 agctaggaag aaactcaaaa catcaagatt ttaaatacgc ttcttggtct ccttgctata    120
attatctggg ataagcatgc tgtttctgt ctgtccctaa catgccctgt gattatccgc     180
aaacaacaca cccaagggca gaactttgtt acttaaacac catcctgttt gcttctttcc    240
tcaggaactg tggctgcacc atctgtcttc atcttcccgc catctgatga gcagttgaaa    300
tctggaactg cctctgttgt gtgcctgctg ataacttct atcccagaga ggccaaagta     360
cagtggaagg tggataacgc cctccaatcg gtaactccc aggagagtgt cacagagcag     420
gacagcaagg acagcaccta cagcctcagc agcaccctga cgctgagcaa agcagactac    480
gagaaacaca agtctacgc ctgcgaagtc acccatcagg gcctgagctc gcccgtcaca     540
aagagcttca caggggaga gtgttag                                          567
```

<210> SEQ ID NO 70
<211> LENGTH: 106
<212> TYPE: PRT
<213> ORGANISM: Mus musculus

<400> SEQUENCE: 70

```
Gly Ala Glu Leu Val Lys Pro Gly Ala Ser Val Lys Leu Ser Cys Thr
1               5                   10                  15

Ala Ser Gly Leu Asn Ile Arg Asp Ile Tyr Met His Trp Val Lys Gln
            20                  25                  30

Arg Pro Glu Gln Gly Leu Glu Trp Ile Gly Lys Ile Asp Pro Ala Asn
        35                  40                  45

Gly Asn Thr Lys Tyr Asp Pro Lys Phe Gln Gly Lys Ala Thr Ile Thr
    50                  55                  60

Ala Asp Thr Ser Ser Asn Thr Ala Tyr Val Gln Leu Ser Ser Leu Thr
65                  70                  75                  80

Ser Glu Asp Thr Ala Val Tyr Tyr Cys Ala Gly Thr Gly Asp Tyr Trp
                85                  90                  95

Gly Gln Gly Thr Thr Val Thr Val Ser Ser
            100                 105
```

<210> SEQ ID NO 71
<211> LENGTH: 112
<212> TYPE: PRT
<213> ORGANISM: Mus musculus

```
<400> SEQUENCE: 71

Gly Thr Cys Gly Asp Ile Val Met Ser Gln Ser Pro Ser Ser Leu Ala
1               5                   10                  15

Val Ser Ala Gly Glu Lys Val Thr Met Ser Cys Lys Ser Ser Gln Ser
                20                  25                  30

Leu Leu Asn Ser Arg Thr Arg Lys Asn Tyr Leu Ala Trp Val Gln His
            35                  40                  45

Lys Pro Gly Gln Ser Pro Arg Leu Leu Ile Tyr Trp Ala Ser Thr Arg
        50                  55                  60

Glu Ser Gly Val Pro Asp Arg Phe Thr Gly Ser Gly Ser Gly Thr Asp
65                  70                  75                  80

Phe Thr Leu Thr Ile Ser Ser Val Gln Ala Glu Asp Leu Ala Val Tyr
                85                  90                  95

Tyr Cys Arg Gln Ser Tyr Asn Leu Val Thr Phe Gly Ala Gly Pro Ser
            100                 105                 110
```